(12) United States Patent
Oi et al.

(10) Patent No.: US 7,160,887 B1
(45) Date of Patent: Jan. 9, 2007

(54) AROMATIC AMINE DERIVATIVES, THEIR PRODUCTION AND USE

(75) Inventors: Satoru Oi, Nara (JP); Nobuhiro Suzuki, Tsukuba (JP); Kazuyoshi Aso, Takatsuki (JP); Yoshihiro Banno, Takatsuki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 09/807,081

(22) PCT Filed: Oct. 19, 1999

(86) PCT No.: PCT/JP99/05755

§ 371 (c)(1),
(2), (4) Date: Apr. 6, 2001

(87) PCT Pub. No.: WO00/23420

PCT Pub. Date: Apr. 27, 2000

(30) Foreign Application Priority Data

Oct. 20, 1998 (JP) ................... 10/298940

(51) Int. Cl.
- *A61K 31/497* (2006.01)
- *A61K 31/16* (2006.01)
- *C07C 331/00* (2006.01)
- *C07C 205/00* (2006.01)
- *C07D 241/04* (2006.01)

(52) U.S. Cl. ............... 514/252.12; 514/616; 568/77; 568/306; 544/400

(58) Field of Classification Search .......... 568/77, 568/306; 514/616, 252.12; 544/400
See application file for complete search history.

(56) References Cited

U.S. PATENT DOCUMENTS 4,668,757 A * 5/1987 Nichols .................... 528/88

FOREIGN PATENT DOCUMENTS

| GB | 2010818 A | 7/1979 |
|---|---|---|
| JP | 61-233741 | 10/1986 |
| JP | 62-173465 | 7/1987 |
| JP | 10-148905 | 6/1998 |
| WO | WO 97/43278 | 11/1997 |
| WO | WO 98/18786 | 5/1998 |
| WO | WO 98/44921 | 10/1998 |
| WO | WO 98/47882 | 10/1998 |

OTHER PUBLICATIONS

Patel et. al., "Minireview The Somatostatin Receptor Family", Life Sciences, vol. 57, No. 13, pp. 1249-1265, 1995.*
PubMed ID: 7605866.*
Ford et. al., "Review Article: colonic sensorimotor physiology in health, and its alteration in constipation and diarrhoeal disorders", Alimen. Pharmacol. Therapy 1998: 12: 287-302.*
Caplus 2003:435886.*

(Continued)

Primary Examiner—Thomas Mckenzie
Assistant Examiner—Binta Robinson
(74) Attorney, Agent, or Firm—Elaine M. Ramesh; Mark Chao

(57) ABSTRACT

Compounds of a formula:

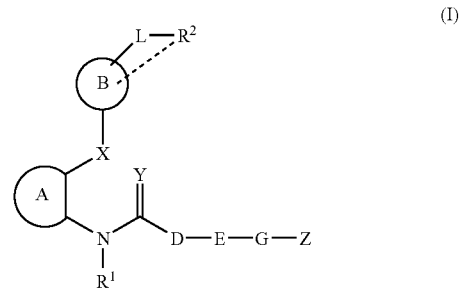

wherein Ring A represents an optionally-substituted aromatic ring; Ring B represents an optionally-substituted cyclic hydrocarbon group; Z represents an optionally-substituted cyclic group; $R^1$ represents a hydrogen atom, an optionally-substituted hydrocarbon group, an optionally-substituted heterocyclic group, or an acyl group; $R^2$ represents an optionally-substituted amino group; D represents a chemical bond or a divalent group; E represents —CO—, —CON($R^a$)—, —COO—, N($R^a$)CON($R^b$)—, —N($R^a$)COO—, —N($R^a$)SO$_2$—, N($R^a$)—, —O—, —S—, —SO— or —SO$_2$— (in which $R^a$ and $R^b$ each independently represent a hydrogen atom or an optionally-substituted hydrocarbon group); G represents a chemical bond or a divalent group; L represents (1) a chemical bond or (2) a divalent hydrocarbon group optionally having from 1 to 5 substituents selected from;

(i) a $C_{1-6}$ alkyl group,
(ii) a halogeno-$C_{1-6}$ alkyl group,
(iii) a phenyl group,
(iv) a benzyl group,
(v) an optionally-substituted amino group,
(vi) an optionally-substituted hydroxy group, and
(vii) a carbamoyl or thiocarbamoyl group optionally substituted by:
 <1> a $C_{1-6}$ alkyl group,
 <2> an optionally-substituted phenyl group, or
 <3> an optionally-substituted heterocyclic group, and optionally interrupted by —O— or —S—; X represents an oxygen atom, an optionally-oxidized sulfur atom, an optionally-substituted nitrogen atom, or an optionally-substituted divalent hydrocarbon group; Y represents two hydrogen atoms, an oxygen atom or a sulfur atom; . . . means that $R^2$ may be bonded to the atom on Ring B to form a ring, or their salts, and a method for producing them.

18 Claims, No Drawings

OTHER PUBLICATIONS

PubMed ID: 7997211.*
"Growth Factors in progressive renal disease", Johnson, David, Nephrology 2000;5, pp. 251-261.*

"Structure-activity relations in 2-aminodiphenyl sulfides against trypanothione reductase from Trypanosoma Cruzi", Girault et. al., Bioorganic & Medicinal Chemistry Letters (1998).*

* cited by examiner

AROMATIC AMINE DERIVATIVES, THEIR PRODUCTION AND USE

This application is the National Stage of International Application No. PCT/JP99/05755, filed on Oct. 19, 1999.

TECHNICAL FIELD

The present invention relates to novel aromatic amine derivatives having a somatostatin receptor function-regulating effect, and a method for producing them, as well as pharmaceutical compositions containing them.

BACKGROUND ART

Somatostatin was isolated from ovine hypothalmic tissue, as a peptide (SST-14) composed of 14 amino acids and having a growth hormone secretion-inhibiting effect. At present, somatostatin (SST-28) composed of 28 amino acids has been isolated and identified. These somatostatins are brain and enteric canal peptides broadly distributed not only in hypothalami but also, for example, cerebra, limbic systems, spinal cords, vagal nerves, autonomic ganglia, mucous membranes of digestive tubes, pancreatic Langerhans' islets, etc., and they inhibit the secretion of pituitary and digestive canal hormones such as growth hormone, thyrotropin, gastrin, insulin, glucagon, etc. In addition, they also inhibit gastric acid secretion, pancreatic exocretion, and digestive canal movement and blood streams. At present, type I to type V somatostatin receptors (SSTR1, SSTR2, SSTR3, SSTR4, SSTR5) are known, and it is recognized that they express different functions in central and peripheral sites of the body.

[1. Life Sciences, Vol. 57, No. 13, p. 1249, 1995;
2. Journal of Clinical Endocrinology and Metabolism, Vol. 80, No. 6, pp. 1789–1793;
3. The New England Journal of Medicine, Jan. 25, 1996;
4. Eur. J. Clin. Pharmacol., 1996, 51, 139–144;
5. Exp. Opin. Ther. Patents (1998) 8 (7): 855–870.]

At present, peptidic somatostatin analogues that inhibit specific hormone secretion have been clinically developed.

DISCLOSURE OF THE INVENTION

Compounds heretofore developed for somatostatin receptor function-regulating agents are peptidic compounds and have many problems in terms of their activity duration, administration route, specificity, side effects, etc. For solving these problems, it is extremely meaningful to create and develop non-peptidic compounds having an excellent somatostatin receptor function-regulating effect.

We, the present inventors, have assiduously investigated in consideration of the above-mentioned situation, and have first succeeded in producing compounds of the following formula (I) which are characterized by their chemical structure in that an amino group is bonded to the cyclic hydrocarbon B in formula (I) directly or via a divalent group, or their salts.

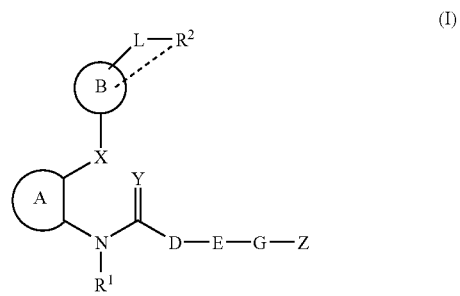

(I)

wherein Ring A represents an optionally-substituted aromatic ring; Ring B represents an optionally-substituted cyclic hydrocarbon group; Z represents an optionally-substituted cyclic group; $R^1$ represents a hydrogen atom, an optionally-substituted hydrocarbon group, an optionally-substituted heterocyclic group, or an acyl group; $R^2$ represents an optionally-substituted amino group; D represents a chemical bond or a divalent group; E represents —CO—, —CON($R^a$)—, COO—, N($R^a$)CON($R^b$)—, —N($R^a$)COO—, —N($R^a$)SO$_2$—, —N($R^a$)—, —O—, —S—, —SO— or —SO$_2$— (in which $R^a$ and $R^b$ each independently represent a hydrogen atom or an optionally-substituted hydrocarbon group); G represents a chemical bond or a divalent group; L represents (1) a chemical bond or (2) a divalent hydrocarbon group optionally having from 1 to 5 substituents selected from;
  (i) a $C_{1-6}$ alkyl group,
  (ii) a halogeno-$C_{1-6}$ alkyl group,
  (iii) a phenyl group,
  (iv) a benzyl group,
  (v) an optionally-substituted amino group,
  (vi) an optionally-substituted hydroxy group, and
  (vii) a carbamoyl or thiocarbamoyl group optionally substituted by:
    <1> a $C_{1-6}$ alkyl group,
    <2> an optionally-substituted phenyl group, or
    <3> an optionally-substituted heterocyclic group, and optionally interrupted by —O— or —S—; X represents an oxygen atom, an optionally-oxidized sulfur atom, an optionally-substituted nitrogen atom, or an optionally-substituted divalent hydrocarbon group; Y represents two hydrogen atoms, an oxygen atom or a sulfur atom; . . . means that $R^2$ may be bonded to the atom on Ring B to form a ring. We have found that the compounds have an excellent somatostatin receptor function-regulating effect, based on their peculiar chemical structure, and are non-toxic and therefore they have excellent properties suitable to medicines. On the basis of these findings, we have completed the present invention.

Specifically, the invention relates to the following:
(1) Compounds (I) or their salts;
(2) Compounds described in (1), wherein L is an alkylene group optionally interrupted by —O— and optionally substituted by a $C_{1-6}$ alkyl group;
(3) Compounds described in (1), wherein L is a $C_{1-6}$ alkylene group;
(4) Compounds described in (1), wherein $R^2$ is (1) an unsubstituted amino group, (2) a piperidyl group, or (3) an amino group optionally having one or two substituents selected from (i) a benzyl group, (ii) a $C_{1-6}$ alkyl group optionally substituted by an amino or phenyl group, (iii) a (mono- or di-$C_{1-6}$ alkyl)-carbamoyl or -thiocarbamoyl group, (iv) a $C_{1-6}$ alkoxy-carbonyl group, (v) a $C_{1-6}$ alkyl-sulfonyl group, (vi) a piperidylcarbonyl group, and (vii) a $C_{1-6}$ alkyl-carbonyl group optionally substituted by a halogen atom or an amino group;

(5) Compounds described in (1), wherein $R^2$ is an unsubstituted amino group;

(6) Compounds described in (1), wherein A is an optionally-substituted benzene or pyridine ring;

(7) Compounds described in (1), wherein B is an optionally-substituted benzene ring;

(8) Compounds described in (1), wherein E is —CON($R^a$)—;

(9) Compounds described in (1), wherein X is an oxygen atom;

(10) Compounds described in (1), wherein D is a $C_{1-6}$ alkylene group;

(11) Compounds described in (1), wherein G is a $C_{1-6}$ alkylene group;

(12) Compounds described in (1), wherein G is an optionally-substituted divalent hydrocarbon group, and Ring B along with $R^2$ does not form a nitrogen-containing hetero ring;

(13) Compounds described in (1), wherein E is —CON($R^a$)—, G is an optionally-substituted divalent hydrocarbon group, Y is two hydrogen atoms, $R^1$ is an acyl group, and Ring B along with $R^2$ does not form a nitrogen-containing hetero ring;

(14) Compounds described in (1), wherein Ring A is an optionally-substituted benzene or pyridine ring;

Ring B is a benzene or cyclohexane ring optionally substituted by a $C_{1-6}$ alkoxy group, or is a tetrahydroisoquinoline or isoindoline ring formed along with $R^2$ bonded thereto;

Z is a $C_{6-14}$ aryl, $C_{3-10}$ cycloalkyl, piperidyl, thienyl, furyl, pyridyl, thiazolyl, indanyl or indolyl group optionally having from 1 to 3 substituents selected from a halogen atom, a formyl group, a halogeno-$C_{1-6}$ alkyl group, a $C_{1-6}$ alkoxy group, a $C_{1-6}$ alkyl-carbonyl group, an oxo group and a pyrrolidinyl group;

D is a $C_{1-6}$ alkylene group;

G is a chemical bond, or a $C_{1-6}$ alkylene group optionally having a phenylene group and optionally substituted by a phenyl group;

$R^1$ is (a) a hydrogen atom, (b) a $C_{1-6}$ alkyl, $C_{2-6}$ alkenyl, $C_{6-14}$ aryl or $C_{7-14}$ aralkyl group optionally substituted by substituent(s) selected from (1) a halogen atom, (2) a nitro group, (3) an amino group optionally substituted by one or two substituents selected from a $C_{1-6}$ alkyl-carbonyl group, a $C_{6-14}$ aryl-carbonyl group, a $C_{1-6}$ alkyl group, a $C_{1-6}$ alkyloxy-carbonyl group, a $C_{7-14}$ aralkyloxy-carbonyl group, a $C_{1-6}$ alkyl-sulfonyl group and a $C_{6-14}$ aryl-sulfonyl group, (4) (i) a $C_{1-6}$ alkyl group optionally substituted by a hydroxy group, a $C_{1-6}$ alkyl-carbonyl group, a $C_{6-14}$ aryl-carbonyl group, a carboxyl group or a $C_{1-6}$ alkoxy-carbonyl group, (ii) a phenyl group optionally substituted by a hydroxy group, (iii) a benzoyl group, or (iv) a hydroxy group optionally substituted by a mono- or di-$C_{1-6}$ alkylamino-carbonyl group, (5) a $C_{3-6}$ cycloalkyl group, (6) a phenyl group optionally substituted by a hydroxy group or a halogeno-$C_{1-6}$ alkyl group, and (7) a thienyl group, a furyl group, a thiazolyl group, an indanyl group, an indolyl or a benzyloxycarbonylpiperidyl group, or (c) an acyl group;

$R^2$ is (1) an unsubstituted amino group, (2) a piperidyl group, or (3) an amino group optionally having one or two substituents selected from (i) a benzyl group, (ii) a $C_{1-6}$ alkyl group optionally substituted by an amino or phenyl group, (iii) a mono- or di-$C_{1-6}$ alkyl-carbamoyl or -thiocarbamoyl group, (iv) a $C_{1-6}$ alkoxy-carbonyl group, (v) a $C_{1-6}$ alkyl-sulfonyl group, (vi) a piperidylcarbonyl group, and (vii) a $C_{1-6}$ alkyl-carbonyl group optionally substituted by a halogen atom or an amino group;

E is —CO—, —CON($R^a$)—, —N($R^a$)CO (in which $R^a$ is a hydrogen atom or a $C_{1-6}$ alkyl group); and L is a $C_{1-6}$ alkylene group optionally interrupted by —O— and optionally substituted by a $C_{1-6}$ alkyl group;

(15) Compounds described in (1), wherein Z is a phenyl group optionally substituted by a halogen atom; D is a $C_{1-6}$ alkylene group; G is a $C_{1-6}$ alkylene group; $R^1$ is (a) a $C_{1-6}$ alkyl or $C_{7-14}$ aralkyl group optionally substituted by substituent(s) selected from (1) a hydroxy group, (2) a phenyl group, (3) a thienyl, furyl, thiazolyl, indanyl, indolyl or benzyloxycarbonylpiperidyl group, and (4) an amino group optionally substituted by a $C_{1-6}$ alkyl-carbonyl, $C_{6-14}$ aryl-carbonyl, $C_{1-6}$ alkyl-sulfonyl or $C_{6-14}$ aryl-sulfonyl group, or (b) an acyl group; $R^2$ is an unsubstituted amino group; E is —CON($R^a$)—; L is a $C_{1-6}$ alkylene group; and Y is two hydrogen atoms;

(16) A prodrug comprising a compound described in (1) or its salt;

(17) A method for producing compounds of a formula (I-a):

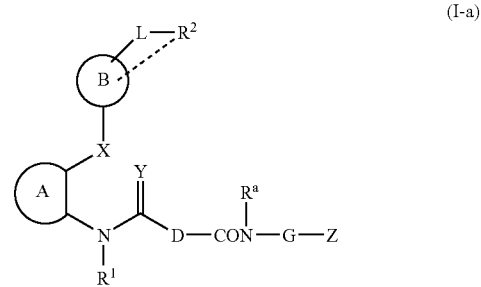

(I-a)

wherein the symbols have the same meanings as above, or their salts, which comprises reacting a compound of a formula (IIa):

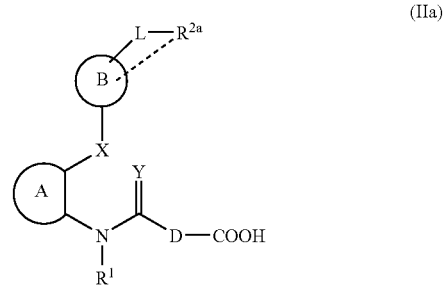

(IIa)

wherein $R^{2a}$ represents an optionally-protected, optionally-substituted amino group; and the other symbols have the same meanings as in (1), or its reactive derivative or salt with a compound of a formula (III):

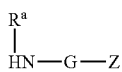

wherein the symbols have the same meanings as in (1), or its salt to give a compound of a formula (Ia-a):

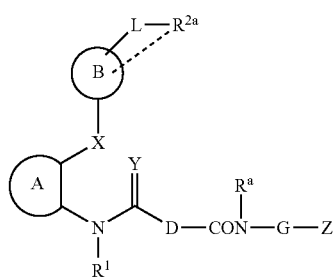

wherein the symbols have the same meanings as above, or its salt, optionally followed by de-protecting it;

(18) A pharmaceutical composition comprising a compound described in (1) or its salt;

(19) The pharmaceutical composition described in (18), which is a somatostatin receptor function-regulating agent;

(20) The pharmaceutical composition described in (18), of which the somatostatin receptor function-regulating agent is a somatostatin receptor agonist;

(21) The pharmaceutical composition described in (18), which is for preventing or treating diabetes, obesity, complications of diabetes, or intractable diarrhea;

(22) A method for regulating the somatostatin receptor function, which comprises administering a compound of a formula (I):

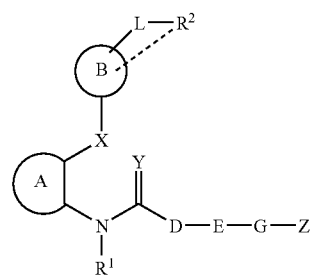

wherein Ring A represents an optionally-substituted aromatic ring; Ring B represents an optionally-substituted cyclic hydrocarbon group; Z represents an optionally-substituted cyclic group; $R^1$ represents a hydrogen atom, an optionally-substituted hydrocarbon group, an optionally-substituted heterocyclic group, or an acyl group; $R^2$ represents an optionally-substituted amino group; D represents a chemical bond or a divalent group; E represents —CO—, —CON($R^a$)—, COO—, N($R^a$)CON($R^b$)—, —N($R^a$) COO—, —N($R^a$)SO$_2$—, —N($R^a$)—, —O—, —S—, —SO— or —SO$_2$— (in which $R^a$ and $R^b$ each independently represent a hydrogen atom or an optionally-substituted hydrocarbon group); G represents a chemical bond or a divalent group; L represents (1) a chemical bond or (2) a divalent hydrocarbon group optionally having from 1 to 5 substituents selected from;
(i) a $C_{1-6}$ alkyl group,
(ii) a halogeno-$C_{1-6}$ alkyl group,
(iii) a phenyl group,
(iv) a benzyl group,
(v) an optionally-substituted amino group,
(vi) an optionally-substituted hydroxy group, and
(vii) a carbamoyl or thiocarbamoyl group optionally substituted by:
  <1> a $C_{1-6}$ alkyl group,
  <2> an optionally-substituted phenyl group, or
  <3> an optionally-substituted heterocyclic group, and optionally interrupted by —O— or —S—; X represents an oxygen atom, an optionally-oxidized sulfur atom, an optionally-substituted nitrogen atom, or an optionally-substituted divalent hydrocarbon group; Y represents two hydrogen atoms, an oxygen atom or a sulfur atom; . . . means that $R^2$ may be bonded to the atom on Ring B to form a ring, or its salt;

(23) Use of a compound of a formula (I):

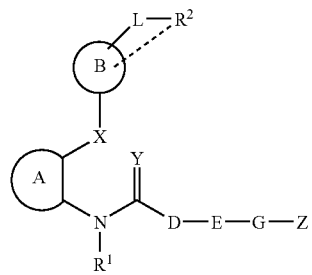

wherein Ring A represents an optionally-substituted aromatic ring; Ring B represents an optionally-substituted cyclic hydrocarbon group; Z represents an optionally-substituted cyclic group; $R^1$ represents a hydrogen atom, an optionally-substituted hydrocarbon group, an optionally-substituted heterocyclic group, or an acyl group; $R^2$ represents an optionally-substituted amino group; D represents a chemical bond or a divalent group; E represents —CO—, —CON($R^a$)—, COO—, N($R^a$)CON($R^b$)—, —N($R^a$) COO—, —N($R^a$)SO$_2$—, —N($R^a$)—, —O—, —S—, —SO— or —SO$_2$— (in which $R^a$ and $R^b$ each independently represent a hydrogen atom or an optionally-substituted hydrocarbon group); G represents a chemical bond or a divalent group; L represents (1) a chemical bond or (2) a divalent hydrocarbon group optionally having from 1 to 5 substituents selected from;
(i) a $C_{1-6}$ alkyl group,
(ii) a halogeno-$C_{1-6}$ alkyl group,
(iii) a phenyl group,
(iv) a benzyl group,
(v) an optionally-substituted amino group,
(vi) an optionally-substituted hydroxy group, and
(vii) a carbamoyl or thiocarbamoyl group optionally substituted by:
  <1> a $C_{1-6}$ alkyl group,
  <2> an optionally-substituted phenyl group, or
  <3> an optionally-substituted heterocyclic group, and optionally interrupted by —O— or —S—; X represents an oxygen atom, an optionally-oxidized sulfur atom, an optionally-substituted nitrogen atom, or an optionally-substituted divalent hydrocarbon group; Y represents two hydrogen atoms, an oxygen atom or a sulfur atom; . . . means that $R^2$ may be bonded to the atom on Ring B to form a ring, or its salt for producing a pharmaceutical composition for regulating the somatostatin receptor function.

In the above-mentioned formulae, Ring A represents an optionally-substituted aromatic ring. The aromatic ring includes 4- to 8-membered homocyclic or heterocyclic rings. Preferred are 5- to 7-membered cyclic groups; and more preferred are 5- or 6-membered cyclic groups. The homocyclic rings includes aromatic hydrocarbons; and the heterocyclic rings include those containing from 1 to 4 hetero atoms of, for example, nitrogen, sulfur and oxygen atoms. Preferably, the heterocyclic rings are those containing from 1 to 3 nitrogen atoms. Concretely, the aromatic ring includes benzene ring, pyridine ring, pyridazine ring, pyrimidine ring, triazine ring, furan ring, pyran ring, thiophene ring, etc. Especially preferred are benzene ring and pyridine ring.

The substituents which the aromatic ring of Ring A may have include, for example, a halogen atom (e.g., fluorine, chlorine, bromine, iodine, etc.), a $C_{1-6}$ alkyl group (e.g., methyl, ethyl, propyl, butyl, sec-butyl, t-butyl, isopropyl, etc.), a halogeno-$C_{1-6}$ alkyl group (e.g., a $C_{1-6}$ alkyl group substituted by from 1 to 5 halogen atoms such as those mentioned above, etc.; e.g., trifluoromethyl, etc.), a phenyl group, a benzyl group, a $C_{1-6}$ alkoxy group (e.g., methoxy, ethoxy, propoxy, butoxy, sec-butoxy, t-butoxy, isopropoxy, etc.), a halogeno-$C_{1-6}$ alkoxy group (e.g., a $C_{1-6}$ alkoxy group substituted by from 1 to 5 halogen atoms such as those mentioned above, etc.; e.g., trifluoromethoxy, chloropropyloxy, etc.), a phenoxy group, a $C_{7-14}$ aralkyloxy group (e.g., benzyloxy, phenethyloxy, phenylpropyloxy, biphenylmethyloxy, etc.), a formyloxy group, a $C_{1-6}$ alkyl-carbonyloxy group (e.g., acetyloxy, etc.), a $C_{1-6}$ alkylthio group (e.g., methylthio, ethylthio, propylthio, butylthio, sec-butylthio, t-butylthio, isopropylthio, etc.), a halogeno-$C_{1-6}$ alkylthio group (e.g., a $C_{1-6}$ alkylthio group substituted by from 1 to 5 halogen atoms such as those mentioned above; e.g., trifluoromethylthio, etc.), a hydroxy group, a mercapto group, a cyano group, a nitro group, a carboxyl group, a formyl group, a $C_{1-6}$ alkyl-carbonyl group (e.g., acetyl, propionyl, etc.), a benzoyl group, a $C_{1-6}$ alkoxy-carbonyl group (e.g., methoxycarbonyl, ethoxycarbonyl, propoxycarbonyl, etc.), a phenoxycarbonyl group, an amino group, a mono- or di-$C_{1-6}$ alkylamino group (e.g., methylamino, ethylamino, dimethylamino, diethylamino, etc.), a formylamino group, a $C_{1-6}$ alkyl-carbonylamino group (e.g., acetylamino, propionylamino, butyrylamino, etc.), a carbamoyl group, a thiocarbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl, etc.), a mono- or di-$C_{1-6}$ alkyl-thiocarbamoyl group (e.g., N-methylthiocarbamoyl, N-ethylthiocarbamoyl, N,N-dimethylthiocarbamoyl, N,N-diethylthiocarbamoyl, etc.), a sulfo group, a $C_{1-6}$ alkylsulfonyl group (e.g., methylsulfonyl, ethylsulfonyl, propylsulfonyl, etc.), a benzoyl-$C_{1-6}$ alkoxy group (e.g., benzoylmethyloxy, etc.), a hydroxy-$C_{1-6}$ alkoxy group (e.g., hydroxyethyloxy, etc.), a $C_{1-6}$ alkoxy-carbonyl-$C_{1-6}$ alkoxy group (e.g., methoxycarbonylmethyloxy, etc.), a $C_{3-14}$ cycloalkyl-$C_{1-6}$ alkoxy group (e.g., cyclohexylmethyloxy, etc.), an imidazol-1-yl-$C_{1-6}$alkoxy group (e.g., imidazol-1-ylpropyloxy, etc.), a $C_{7-14}$ aralkyloxy-carbonyl-$C_{1-6}$ alkoxy group (e.g., benzyloxycarbonylmethyloxy, etc.), a hydroxyphenyl-$C_{1-6}$ alkoxy group (e.g., [3-(4-hydroxyphenyl)propyl]oxy, etc.), a $C_{7-14}$ aralkyloxycarbonyl group (e.g., benzyloxycarbonyl, etc.), a mono- or di-$C_{1-6}$ alkylamino-$C_{1-6}$ alkoxy group (e.g., methylaminomethoxy, ethylaminoethoxy, dimethylaminomethoxy, etc.), a mono- or di-$C_{1-6}$ alkylamino-carbonyloxy group (e.g., methylaminocarbonyloxy, ethylaminocarbonyloxy, dimethylaminocarbonyloxy, etc.), etc. In particular, halogen atoms such as those mentioned above are much used for the substituents. The aromatic ring may have from 1 to 4 substituents selected from those mentioned above.

When Ring A is a 6-membered ring, and, for example, when its one carbon atom bonding to X is referred to as a 1-positioned carbon, and its another carbon atom bonding to N is referred to as a 2-positioned carbon, Ring A preferably has a substituent in the 4-position or 5-position, and the number of the substituents is preferably one or two.

Especially preferably, Ring A is an optionally-substituted benzene ring, more preferably a benzene ring optionally substituted by any of a halogen atom, a hydroxy group, a $C_{1-6}$ alkoxy group, a halogeno-$C_{1-6}$ alkoxy group, a $C_{7-14}$ aralkyloxy group, a benzoyl-$C_{1-6}$ alkoxy group, a hydroxy-$C_{1-6}$ alkoxy group, a $C_{1-6}$ alkoxy-carbonyl-$C_{1-6}$ alkoxy group, a $C_{3-14}$ cycloalkyl-$C_{1-6}$ alkoxy group, an imidazol-1-yl-$C_{1-6}$ alkoxy group, a $C_{7-14}$ aralkyloxy-carbonyl-$C_{1-6}$ alkoxy group or a hydroxyphenyl-$C_{1-6}$ alkoxy group, most preferably a benzene ring substituted by a halogen atom (preferably, chlorine), a hydroxy group or a $C_{1-6}$ alkoxy group (preferably, methoxy), or a non-substituted benzene ring.

In the above-mentioned formulae, Ring B is an optionally-substituted cyclic hydrocarbon group. The cyclic hydrocarbon group may be a 3- to 14-membered one, but preferably a 5- to 8-membered one, more preferably a 5- or 6-membered one. Preferably, Ring B is an optionally-substituted aromatic hydrocarbon group. In particular, an optionally-substituted phenyl group is much used for it. The cyclic hydrocarbon group for Ring B may be, for example, an alicyclic hydrocarbon group having from 3 to 14 carbon atoms, or an aromatic hydrocarbon group having from 6 to 14 carbon atoms. The alicyclic hydrocarbon group includes, for example, a $C_{3-14}$ cycloalkyl group (e.g., cyclopropyl, cyclobutyl, cyclopentyl, cyclohexyl, etc.), a $C_{3-14}$ cycloalkenyl group (e.g., cyclopentenyl, cyclohexenyl, etc.), a $C_{5-14}$ cycloalkadienyl group (e.g., 2,4-cyclopentadienyl, 1,3-cyclohexadienyl, etc.), an indanyl group, etc. Preferably, it is a 5- to 8-membered alicyclic hydrocarbon group. The aromatic hydrocarbon group for Ring B may be, for example, an aromatic hydrocarbon group having from 6 to 14 carbon atoms (e.g., a $C_{6-14}$ aryl group, such as phenyl, naphthyl, anthranyl, phenanthryl, etc.). Preferably, it is a 6- to 10-membered aromatic hydrocarbon group; and more preferred is a phenyl group.

The substituents which the alicyclic hydrocarbon group and the aromatic hydrocarbon group for Ring B may have include, for example, a halogen atom (e.g., fluorine, chlorine, bromine, iodine, etc.), a $C_{1-6}$ alkyl group (e.g., methyl, ethyl, propyl; butyl, sec-butyl, t-butyl, isopropyl, etc.), a halogeno-$C_{1-6}$ alkyl group (e.g., a $C_{1-6}$ alkyl group substituted by from 1 to 5 halogen atoms such as those mentioned above, etc.; e.g., trifluoromethyl, etc.), a phenyl group, a benzyl group, a $C_{1-4}$ alkoxy group (e.g., methoxy, ethoxy, propoxy, butoxy, sec-butoxy, t-butoxy, isopropoxy, etc.), a halogeno-$C_{1-4}$ alkoxy group (e.g., a $C_{1-6}$ alkoxy group substituted by from 1 to 5 halogen atoms such as those mentioned above, etc.; e.g., trifluoromethoxy, chloropropyloxy, etc.), a phenoxy group, a $C_{7-14}$ aralkyloxy group (e.g., benzyloxy, phenethyloxy, phenylpropyloxy, etc.), a formyloxy group, a $C_{1-6}$ alkyl-carbonyloxy group (e.g., acetyloxy, etc.), a $C_{1-6}$ alkylthio group (e.g., methylthio, ethylthio, propylthio, butylthio, sec-butylthio, t-butylthio, isopropylthio, etc.), a halogeno-$C_{1-6}$ alkylthio group (e.g., a $C_{1-6}$ alkylthio group substituted by from 1 to 5 halogen atoms such as those mentioned above; e.g., trifluoromethylthio, etc.), a hydroxy group, a mercapto group, a cyano group, a nitro group, a carboxyl group, a formyl group, a $C_{1-6}$ alkyl-carbonyl group (e.g., acetyl, propionyl, etc.), a benzoyl group, a $C_{1-6}$ alkoxy-carbonyl group (e.g., methoxycarbonyl, ethoxycarbonyl, propoxycarbonyl, etc.), a phenoxycarbonyl group, an amino group, a mono- or di-$C_{1-6}$ alkylamino group (e.g., methylamino, ethylamino, dimethylamino, diethylamino, etc.), a formylamino group, a $C_{1-6}$ alkyl-carbonylamino group (e.g., acetylamino, propionylamino, butyrylamino, etc.), a carbamoyl group, a thiocarbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl, etc.), a mono- or di-$C_{1-6}$alkyl-thiocarbamoyl group (e.g., N-methylthiocarbamoyl, N-ethylthiocarbamoyl, N,N-dimethylthiocarbamoyl, N,N-diethylthiocarbamoyl, etc.), a sulfo group, a $C_{1-6}$ alkylsulfonyl group (e.g., methylsulfonyl, ethylsulfonyl, propylsulfonyl, etc.), a benzoyl-$C_{1-6}$ alkoxy group (e.g., benzoylmethyloxy, etc.), a hydroxy-$C_{1-6}$alkoxy group (e.g., hydroxyethyloxy, etc.), a $C_{1-6}$ alkoxy-carbonyl-$C_{1-6}$ alkoxy group (e.g., methoxycarbonylmethyloxy, etc.), a $C_{3-14}$ cycloalkyl-$C_{1-6}$ alkoxy group (e.g., cyclohexylmethyloxy, etc.), an imidazol-1-yl-$C_{1-4}$ alkoxy group (e.g., imidazol-1-ylpropyloxy, etc.), a $C_{7-14}$ aralkyloxy-carbonyl-$C_{1-6}$ alkoxy group (e.g., benzyloxycarbonylmethyloxy, etc.), a hydroxyphenyl-$C_{1-4}$ alkoxy group (e.g., [3-(4-hydroxyphenyl)propyl]oxy, etc.), a $C_{7-14}$ aralkyloxy-carbonyl group (e.g., benzyloxycarbonyl, phenethyloxycarbonyl, phenylpropyloxycarbonyl, etc.), a mono- or di-$C_{1-6}$ alkylamino-$C_{1-6}$ alkoxy group (e.g., methylaminomethoxy, ethylaminoethoxy, dimethylaminomethoxy, etc.), a mono- or di-$C_{1-6}$ alkylamino-carbonyloxy group (e.g., methylaminocarbonyloxy, ethylaminocarbonyloxy, dimethylaminocarbonyloxy, etc.), etc. The alicyclic hydrocarbon group and the aromatic hydrocarbon group may have from 1 to 4 substituents selected from those mentioned above.

Especially preferably, Ring B is an optionally-substituted benzene or cycloalkane ring; more preferred for it is a benzene or cyclohexane ring optionally substituted by a $C_{1-6}$ alkoxy group (preferably, methoxy, etc.); and most preferred is an unsubstituted benzene or cyclohexane ring. $R^2$ may be bonded to the atom on Ring B to form a ring. For example, the atom of Ring B adjacent to the atom thereof to which L is bonded may be bonded to the amino group of $R^2$ or to the substituent of the amino group to form an optionally-substituted, nitrogen-containing hetero ring. When Ring B forms such a nitrogen-containing hetero ring, the nitrogen atom of the amino group of $R^2$ may be bonded to the atom of Ring B either directly or via a spacer. The spacer means a part or all of the substituent of the amino group.

The nitrogen-containing hetero ring to be formed by the adjacent atoms of Ring B and L and $R^2$ bonded thereto may be, for example, a bicyclic, condensed, nitrogen-containing hetero ring (preferably, a bicyclic, non-aromatic, condensed, nitrogen-containing hetero ring) formed through condensation of an optionally-substituted cyclic hydrocarbon group (e.g., benzene ring, 4 etc.) of Ring B and a 5- or 6-membered monocyclic hetero ring (preferably, a monocyclic non-aromatic hetero ring) having at least one nitrogen atom and additionally having one or two hetero atoms selected from nitrogen, oxygen and sulfur atoms, etc. Concretely, it includes tetrahydroisoquinolines (e.g., 1,2,3,4-tetrahydroisoquinoline), tetrahydroquinolines (e.g., 1,3,4-tetrahydroquinoline), isoindolines, indolines, 2,3-dihydrobenzothiazoles, 2,3-dihydrobenzoxazoles, 3,4-dihydro-2H-1,4-benzothiazines, 3,4-dihydro-2H-1,4-benzoxazines, 1,2,3,4-tetrahydroquinoxalines, 2,3,4,5-tetrahydro-1,4-benzoxazepines, etc. Of those, preferred are tetrahydroisoquinolines. For the substituents which the optionally-substituted nitrogen-containing hetero ring may have, referred to are the same as those mentioned hereinabove for the alicyclic hydrocarbon group and the aromatic hydrocarbon group for Ring B. The optionally-substituted nitrogen-containing hetero ring may have from 1 to 4 substituents selected from the above-mentioned ones.

In the above-mentioned formulae, Z represents an optionally-substituted cyclic group. The cyclic group for Z includes, for example, a cyclic hydrocarbon group, a heterocyclic group, etc. For Z, for example, preferred are an optionally-substituted aromatic hydrocarbon group, an optionally-substituted aromatic heterocyclic group, etc.; and more preferred are an optionally substituted phenyl group, etc.

The cyclic hydrocarbon group for Z includes, for example, an alicyclic hydrocarbon group having from 3 to 14 carbon atoms, an aromatic hydrocarbon group having from 6 to 14 carbon atoms, etc. The alicyclic hydrocarbon group for Z includes, for example, a $C_{3-14}$ cycloalkyl group (e.g., cyclopropyl, cyclobutyl, cyclopentyl, cyclohexyl, etc.), a $C_{3-14}$ cycloalkenyl group (e.g., cyclopentenyl, cyclohexenyl, etc.), a $C_{5-14}$ cycloalkadienyl group (e.g., 2,4-cyclopentadienyl, 1,3-cyclohexadienyl, etc.), an indanyl group, etc. Preferably, it is a 5- to 8-membered alicyclic hydrocarbon group. The aromatic hydrocarbon group for Z includes, for example, a $C_{6-14}$ aryl group (e.g., phenyl, naphthyl, anthranyl, phenanthryl, etc.), etc. Preferably, it is a 6- to 10-membered aromatic hydrocarbon group.

The heterocyclic group for Z includes, for example, a monocyclic heterocyclic group, a polycyclic, condensed heterocyclic group, etc. The monocyclic heterocyclic group may be, for example, a 5- or 6-membered monocyclic heterocyclic group having from 1 to 4 hetero atoms selected from nitrogen, oxygen and sulfur atoms, in addition to carbon atoms. Concretely, it includes, for example, a monocyclic aromatic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyl, etc.), a monocyclic non-aromatic heterocyclic group (e.g., oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.), etc. The polycyclic condensed heterocyclic group includes, for example, a di- or tri-cyclic aromatic condensed heterocyclic group to be formed through condensation of two or three monocyclic aromatic hetero rings such as those mentioned hereinabove, a di- or tri-cyclic aromatic condensed heterocyclic group to be formed through condensation of one or two monocyclic aromatic hetero rings such as those mentioned above along with a benzene ring (preferably, a di- or tri-cyclic aromatic condensed heterocyclic group to be formed through condensation of one or two monocyclic aromatic hetero rings such as those mentioned above along with a benzene ring), and their partially reduced groups, etc. Concretely, it includes a polycyclic aromatic condensed heterocyclic group (e.g., benzofuryl, isobenzofuryl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolyl, quinazolinyl, quinoxalinyl, phthalazinyl, naphthyridinyl, purinyl, pteridinyl, dibenzofuryl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl, etc.), a polycyclic non-aromatic condensed heterocyclic group (e.g., isochromanyl, chromanyl, indolyl, isoindolyl, 1,2,3,4-tetrahydroisoquinolyl, 1,2,3,4-tetrahydroquinolyl, etc.), etc.

For the substituents which the cyclic group for Z may have, referred to are the same as those mentioned hereinabove for the cyclic hydrocarbon group for Ring B. In addition to these, the substituents for the cyclic group for Z further include oxo groups, thioxo groups, etc. The cyclic group for Z may have from 1 to 5 substituents selected from them.

Preferably, for example, Z is a $C_{6-14}$ aryl (more preferably, phenyl), $C_{3-10}$ cycloalkyl, piperidyl, thienyl, furyl, pyridyl, thiazolyl, indanyl or indolyl group optionally having from 1 to 3 substituents selected from halogens and formyl, halogeno-$C_{1-6}$ alkyl, $C_{1-6}$ alkoxy, $C_{1-6}$ alkyl-carbonyl, oxo and pyrrolidinyl groups. Especially preferred is a halogen (preferably, fluorine)-substituted phenyl group.

Regarding the site of the substituents in the cyclic group for Z, when Z is a phenyl group, it is substituted preferably at the ortho-position. Also preferably, it is substituted by one substituent.

In the above-mentioned formulae, D represents a chemical bond, or a divalent group. The divalent group may be optionally substituted, and may be interrupted by —O—, —S— or —N($R^a$)— (in which $R^a$ indicates a hydrogen atom, o an optionally-substituted hydrocarbon group). Especially preferred for D is a divalent group bonding to a ring via a carbon atom; and more preferred is an optionally-substituted divalent hydrocarbon group.

The divalent group for D may be, for example, an optionally-substituted, linear divalent hydrocarbon group having from 1 to 10 carbon atoms. Concretely, it includes, for example, a $C_{1-10}$ alkylene group (e.g., methylene, ethylene, propylene, butylene, pentamethylene, hexamethylene, heptamethylene, octamethylene, etc.), etc. Especially preferred is a $C_{1-6}$ alkylene group (e.g., methylene, ethylene, propylene, butylene, pentamethylene, hexamethylene, etc.). The divalent group may optionally contain, for example, a $C_{3-6}$ cycloalkylene group (e.g., 1,4-cyclohexylene, etc.), a phenylene group (e.g., 1,4-phenylene, 1,2-phenylene, etc.) or the like in any desired site.

The substituents which the divalent group for D may have include, for example, a $C_{1-6}$ alkyl group (e.g., methyl, ethyl, propyl, isopropyl, etc.), a halogeno-$C_{1-6}$ alkyl group (e.g., a $C_{1-6}$ alkyl group substituted by from 1 to 5 halogen atoms such as those mentioned above; e.g., trifluoromethyl, etc.), a phenyl group, a benzyl group, an optionally-substituted amino group, an optionally-substituted hydroxy group, an optionally-substituted carbamoyl group, an optionally-substituted thiocarbamoyl group, etc. The divalent group for D may have from 1 to 3 such substituents. Especially preferably, D is a $C_{1-6}$ alkylene group (e.g., methylene, ethylene, propylene, etc., more preferably, methylene).

In the above-mentioned formulae, G represents a chemical bond or a divalent group. For the divalent group for G, for example, referred to are the same as those mentioned hereinabove for the divalent group for D.

G may have, for example, a chemical bond or a phenylene group; and it is preferably a $C_{1-6}$ alkylene group optionally substituted by a phenyl group, etc. For it, for example, preferred is a $C_{1-6}$ alkylene group (e.g., methylene, ethylene, propylene, etc.). The $C_{1-6}$ alkylene group for G may have a phenylene group between the $C_{1-6}$ alkylene group and E or Z, or may have a phenylene group inside the $C_{1-6}$ alkylene group.

In the above-mentioned formulae, $R^1$ represents a hydrogen atom, an optionally-substituted hydrocarbon group, an optionally-substituted heterocyclic group, or an acyl group. Preferably, $R^1$ is an optionally-substituted hydrocarbon group or an acyl group.

The hydrocarbon group for $R^1$ includes, for example, an aliphatic hydrocarbon group, an alicyclic hydrocarbon group, an aryl group, an aralkyl group, a polycyclic condensed hydrocarbon group, etc. Especially preferably, it is an aliphatic hydrocarbon group.

The aliphatic hydrocarbon group for $R^1$ may have from 1 to 10 carbon atoms, including, for example, a $C_{1-10}$ alkyl group, a $C_{2-10}$ alkenyl group, a $C_{2-10}$ alkynyl group, etc. The $C_{1-10}$ alkyl group includes, for example, methyl, ethyl, propyl, isopropyl, butyl, isobutyl, sec-butyl, t-butyl, pentyl, isopentyl, neopentyl, 1-methylpropyl, hexyl, isohexyl, 1,1-dimethylbutyl, 2,2-dimethylbutyl, 3,3-dimethylbutyl, 3,3-dimethylpropyl, 2-ethylbutyl, heptyl, etc. Preferably, for example, it is a $C_{3-5}$ alkyl group (e.g., propyl, isopropyl, isobutyl, neopentyl, etc.), more preferably, isobutyl or neopentyl. The $C_{2-10}$ alkenyl group includes, for example, vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc. Especially preferred for it is a $C_{2-6}$ alkenyl group (e.g., vinyl, allyl, isopropenyl, 2-methylallyl, 2-methyl-1-propenyl, 2-methyl-2-propenyl, 3-methyl-2-butenyl, etc.). The $C_{2-10}$ alkynyl group includes, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc. Especially preferred for it is a $C_{2-6}$ alkynyl group (e.g., ethynyl, 1-propynyl, 2-propynyl, etc.).

The alicyclic hydrocarbon group for $R^1$ may have, for example, from 3 to 10 carbon atoms, including, for example, a $C_{3-10}$ cycloalkyl group, a $C_{3-10}$ cycloalkenyl group, a $C_{5-10}$ cycloalkadienyl group, etc. The $C_{3-10}$ cycloalkyl group includes, for example, cyclopropyl, cyclobutyl, cyclopentyl, cyclohexyl, cycloheptyl, cyclooctyl, cyclononyl, etc. The $C_{3-10}$ cycloalkenyl group includes, for example, 1-cyclobuten-1-yl, 1-cyclopenten-1-yl, 2-cyclopenten-1-yl, 3-cyclopenten-1-yl, 2-cyclohexen-1-yl, 3-cyclohexen-1-yl, etc. The $C_{5-10}$ cycloalkadienyl group includes, for example, 2,4-cyclopentadien-1-yl, 2,5-cyclohexadien-1-yl, etc.

The aryl group for $R^1$ may be, for example, a $C_{6-14}$ aryl group (e.g., phenyl, naphthyl, anthryl, phenanthryl, acenaphthylenyl, etc.), etc.

The aralkyl group for $R^1$ may be, for example, a $C_{7-14}$ aralkyl group (e.g., benzyl, phenethyl, 3-phenylpropyl, 4-phenylbutyl, 2-naphthylmethyl, etc.), etc.

The polycyclic condensed hydrocarbon group for $R^1$ includes, for example, an indanyl group, a fluorenyl group, etc.

The substituents which the hydrocarbon group for $R^1$ may have include, for example, a halogen atom, a nitro group, a cyano group, an imino group, an optionally-substituted amino group, an optionally-substituted hydroxy group, an optionally-esterified carboxyl group, an optionally-substituted carbamoyl group, an optionally-substituted thiocarbamoyl group, a cycloalkyl group, a cycloalkenyl group, an optionally-substituted heterocyclic group, an alkyl group, a halogenoalkyl group, an optionally-substituted aryl group, an indanyl group, a fluorenyl group, etc. The hydrocarbon group may have from 1 to 5 (preferably, from 1 to 3) such substituents.

The halogen atom, one of the substituents for the hydrocarbon group for $R^1$, includes, for example, fluorine, chlorine, bromine and iodine atoms, etc.

The optionally-substituted amino group, one of the substituents for the hydrocarbon group for $R^1$ and for D, G and L, includes, for example, (1) an amino group optionally having one or two substituents selected from (i) a $C_{1-6}$ alkyl group optionally substituted by from 1 to 5 halogen atoms such as those mentioned above, or by a $C_{1-6}$ alkoxy group (e.g., methyl, ethyl, propyl, isopropyl, trifluoromethyl, etc.), a $C_{6-10}$ aryl group (e.g., phenyl, etc.), a $C_{7-14}$ aralkyl group (e.g., benzyl, etc.), (ii) a formyl group, a $C_{1-6}$ alkyl-carbonyl group (e.g., acetyl, propionyl, butyryl, etc.), a $C_{6-14}$ arylcarbonyl group (e.g., benzoyl, etc.), (iii) a $C_{1-6}$ alkoxycarbonyl group (e.g., methoxycarbonyl, ethoxycarbonyl, propoxycarbonyl, sec-propoxycarbonyl, butoxycarbonyl, etc.), a $C_{7-14}$ aralkyloxy-carbonyl group (e.g., benzyloxycarbonyl, phenethyloxycarbonyl, phenylpropyloxycarbonyl, etc.), (iv) a sulfo group, a $C_{1-6}$ alkylsulfonyl group (e.g., methylsulfonyl, ethylsulfonyl, propylsulfonyl, sec-propylsulfonyl, butylsulfonyl, t-butylsulfonyl, etc.), a $C_{6-14}$ arylsulfonyl group (e.g., benzenesulfonyl, naphthalenesulfonyl, anthracenesulfonyl, etc.) and (v) a $C_{1-6}$ alkylamino-carbonyl group (e.g., methylaminocarbonyl, ethylaminocarbonyl, propylaminocarbonyl, butylaminocarbonyl, dimethylaminocarbonyl, etc.), etc., and (2) a 5- or 6-membered, optionally-substituted cyclic amino group such as a pyrrolidinyl group, a piperidyl group, a morpholinyl group, a thiomorpholinyl group, a 4-methylpiperidyl group, a 4-phenylpiperidyl group, etc.

The substituents which the optionally-substituted hydroxy group, one of the substituents for the hydrocarbon group for $R^1$ and for D, G and L, may have include, for example, (i) an optionally-substituted $C_{1-6}$ alkyl group, (ii) an optionally-substituted $C_{6-10}$ aryl group, (iii) an optionally-substituted $C_{7-14}$ aralkyl group, and (iv) an acyl group, etc.

The $C_{1-6}$ alkyl group of the optionally-substituted $C_{1-6}$ alkyl group includes, for example, methyl, ethyl, isopropyl, butyl, pentyl, etc. The $C_{1-6}$ alkyl group may have from 1 to 3 substituents selected from, for example, a halogen atom (e.g., fluorine, chlorine, bromine, iodine, etc.), a hydroxy group, a $C_{1-6}$alkoxy group (e.g., methoxy, ethoxy, propoxy, isopropoxy, etc.), a formyl group, a $C_{1-6}$ alkyl-carbonyl group (e.g., acetyl, propionyl, butyryl, etc.), a carboxyl group, a $C_{1-6}$ alkoxy-carbonyl group (e.g., methoxycarbonyl, ethoxycarbonyl, propoxycarbonyl, sec-propoxycarbonyl, butoxycarbonyl, etc.), an amino group, a mono- or di-$C_{1-6}$ alkylamino group (e.g., methylamino, ethylamino, dimethylamino, diethylamino, etc.), a pyrrolidyl group, a piperidyl group, a morpholinyl group, a thiomorpholinyl group, a 4-methylpiperidyl group, a 4-phenylpiperidyl group, a carbamoyl group, a thiocarbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl, etc.), a mono- or di-$C_{1-6}$ alkyl-thiocarbamoyl group (e.g., N-methylthiocarbamoyl, N-ethylthiocarbamoyl, N,N-dimethylthiocarbamoyl, N,N-diethylthiocarbamoyl, etc.), a phenoxy group, a mono- or di-$C_{1-6}$ alkyl-carbamoyloxy group (e.g., N-methylcarbamoyloxy, N-ethylcarbamoyloxy, N,N-dimethylcarbamoyloxy, N,N-diethylcarbamoyloxy, etc.), a mono- or di-$C_{1-6}$ alkyl-thiocarbamoyloxy group (e.g., N-methylthiocarbamoyloxy, N-ethylthiocarbamoyloxy, N,N-dimethylthiocarbamoyloxy, N,N-diethylthiocarbamoyloxy, etc.), a formylamino group, a $C_{1-6}$ alkyl-carbonylamino group (e.g., acetylamino, propionylamino, butyrylamino, etc.), a formyloxy group, a $C_{1-6}$ alkyl-carbonyloxy group (e.g., acetoxy, etc.), etc.

The $C_{6-10}$ aryl group of the optionally-substituted $C_{6-10}$ aryl group includes, for example, phenyl, naphthyl, etc. The $C_{6-10}$ aryl group may have from 1 to 5 substituents selected from those mentioned hereinabove for the substituents which the $C_{1-6}$ alkyl group may have, and, in addition to these, from a $C_{1-6}$ alkyl group (e.g., methyl, ethyl, propyl, isopropyl, etc.), a halogeno-$C_{1-6}$ alkyl group (e.g., a $C_{1-6}$ alkyl group substituted by from 1 to 5 halogen atoms such as those mentioned hereinabove, e.g., trifluoromethyl, etc.), etc.

The $C_{7-14}$ aralkyl group of the optionally-substituted $C_{7-14}$ aralkyl group includes, for example, benzyl, phenethyl, phenylpropyl, etc. For the substituents which the $C_{7-14}$ aralkyl group may have, referred to are the same as those mentioned hereinabove for the optionally-substituted $C_{6-10}$ aryl group. The number of the substituents which the group may have is from 1 to 5.

For the substituents which the optionally-substituted phenyl group for L may have, referred to are the same as those mentioned hereinabove for the optionally-substituted $C_{6-10}$ aryl group.

The acyl group may be represented by any of the following formula:

—$COR^3$, —$COOR^4$, —$SO_2R^5$, —$CONR^6R^7$, —$CSNR^8R^9$, —$SOR^{10}$ or —$PO_3R^{11}R^{12}$

[in which $R^3$, $R^4$, $R^5$, $R^6$, $R^7$, $R^8$, $R^9$, $R^{10}$, $R^{11}$ and $R^{12}$ may be the same or different, and each represents a hydrogen atom, an optionally-substituted hydrocarbon group, or an optionally-substituted heterocyclic group].

For examples of the hydrocarbon group of the optionally-substituted hydrocarbon group for $R^3$, $R^4$, $R^5$, $R^6$, $R^7$, $R^8$, $R^9$, $R^{10}$, $R^{11}$ and $R^{12}$, referred to are the same as those mentioned hereinabove for the hydrocarbon group for $R^1$. The substituents which the hydrocarbon group for $R^3$, $R^4$, $R^5$, $R^6$, $R^7$, $R^8$, $R^9$, $R^{10}$, $R^{11}$ and $R^{12}$ may have include, for example, a halogen atom, a nitro group, a cyano group, an imino group, an optionally-substituted amino group, an optionally-substituted hydroxy group, an optionally-esterified carboxyl group, an optionally-substituted carbamoyl group, an optionally-substituted thiocarbamoyl group, a cycloalkyl group, a cycloalkenyl group, an optionally-substituted heterocyclic group, an alkyl group, a halogenoalkyl group, an optionally-substituted aryl group, an indanyl group, a fluorenyl group, etc. For the optionally-substituted amino group, the optionally-esterified carboxyl group, the optionally-substituted carbamoyl group, the optionally-substituted thiocarbamoyl group, the cycloalkyl group, the cycloalkenyl group, the optionally-substituted heterocyclic group, the alkyl group, the halogenoalkyl group and the optionally-substituted aryl group, referred to are the same as those mentioned hereinabove for the substituents which the hydrocarbon group for $R^1$ may have, or that is, those mentioned for the optionally-substituted amino group, the optionally-esterified carboxyl group, the optionally-substituted carbamoyl group, the optionally-substituted thiocarbamoyl group, the cycloalkyl group, the cycloalkenyl group, the optionally-substituted heterocyclic group, the alkyl group, the halogenoalkyl group and the optionally-substituted aryl group for $R^1$. The substituents for the optionally-substituted hydroxy group include, for example, (i) a $C_{1-6}$ alkyl group, (ii) a $C_{6-10}$ aryl group, (iii) a $C_{7-14}$ aralkyl group, (iv) a formyl group, (v) a $C_{1-6}$ alkyl-carbonyl group (e.g., acetyl, propionyl, butyryl, t-butylcarbonyl, etc.), (vi) a $C_{6-14}$ aryl-carbonyl group (e.g., benzoyl, naphthalenecarbonyl, anthracenecarbonyl, etc.), (vii) a $C_{1-6}$ alkoxy-carbonyl group (e.g., methoxycarbonyl, ethoxycarbonyl, propoxycarbonyl, sec-propoxycarbonyl, butoxycarbonyl, t-butoxycarbonyl, etc.), (viii) a $C_{7-14}$ aralkyloxy-carbonyl group (e.g., benzyloxycarbonyl, phenethyloxycarbonyl, phenylpropyloxycarbonyl, etc.), (ix) a $C_{6-14}$ cyclic hydrocarbon-carbonyl group (e.g., benzenecarbonyl, fluorenecarbonyl, etc.), (x) a heterocyclic-carbonyl group (e.g., furancarbonyl, thiophenecarbonyl, pyridinecarbonyl, benzofurancarbonyl, benzothiophenecarbonyl, carbazolecarbonyl, dibenzofurancarbonyl, etc.), (xi) a $C_{1-6}$ alkylsulfonyl group (e.g., methylsulfonyl, ethylsulfonyl, propylsulfonyl, sec-propylsulfonyl, butylsulfonyl, t-butylsulfonyl, etc.), (xii) a $C_{6-14}$ aryl-sulfonyl group (e.g., benzenesulfonyl, naphthalenesulfonyl, anthracenesulfonyl, etc.), (xiii) a carbamoyl group, (xiv) a thiocarbamoyl group, (xv) a mono- or di-$C_{1-6}$ alkyl-carbamoyl group (e.g., N-methylcarbamoyl, N-ethylcarbamoyl, N,N-dimethylcarbamoyl, N,N-diethylcarbamoyl, etc.), (xvi) a mono- or di-$C_{1-6}$ alkyl-thiocarbamoyl group (e.g., N-methylthiocarbamoyl, N-ethylthiocarbamoyl, N,N-dimethylthiocarbamoyl, N,N-diethylthiocarbamoyl, etc.), etc. These (i) to (xvi) may have from 1 to 3 substituents selected from, for example, a halogen atom (e.g., fluorine, chlorine, bromine, iodine, etc.), a hydroxy group, a $C_{1-6}$ alkoxy group (e.g., methoxy, ethoxy, propoxy, isopropoxy, etc.), a formyl group, a $C_{1-6}$ alkyl-carbonyl group (e.g., acetyl, propionyl, butyryl, etc.), a carboxyl group, a $C_{1-6}$ alkoxy-carbonyl group (e.g., methoxycarbonyl, ethoxycarbonyl, propoxycarbonyl, sec-propoxycarbonyl, butoxycarbonyl, etc.), an amino group, a mono- or di-$C_{1-6}$ alkylamino group (e.g., methylamino, ethylamino, dimethylamino, diethylamino, etc.), a pyrrolidinyl group, a piperidyl group, a morpholinyl group, a thiomorpholinyl group, a 4-methylpiperidyl group, a 4-phenylpiperidyl group, a 4-benzyloxycarbonylpiperidyl group, a carbamoyl group, a thiocarbamoyl group, a mono- or di-$C_{1-6}$ alkyl-carbamoyl group (e.g., methylcarbamoyl, ethylcarbamoyl, dimethylcarbamoyl, diethylcarbamoyl, etc.), a mono- or di-$C_{1-6}$ alkyl-thiocarbamoyl group (e.g., ethylthiocarbamoyl, ethylthiocarbamoyl, dimethylthiocarbamoyl, diethylthiocarbamoyl, etc.), a phenoxy group, a mono- or di-$C_{1-6}$ alkyl-carbamoyloxy group (e.g., methylcarbamoyloxy, ethylcarbamoyloxy, dimethylcarbamoyloxy, diethylcarbamoyloxy, etc.), a mono- or di-$C_{1-6}$ alkyl-thiocarbamoyloxy group (e.g., methylthiocarbamoyloxy, ethylthiocarbamoyloxy, dimethylthiocarbamoyloxy, diethylthiocarbamoyloxy, etc.), a formylamino group, a $C_{1-6}$ alkyl-carbonylamino group (e.g., acetylamino, propionylamino, butyrylamino, etc.), a formyloxy group, a $C_{1-6}$ alkyl-carbonyloxy group (e.g., acetoxy, etc.), etc.

For examples of the heterocyclic group of the optionally-substituted heterocyclic group for $R^3$, $R^4$, $R^5$, $R^6$, $R^7$, $R^8$, $R^9$, $R^{10}$, $R^{11}$ and $R^{12}$, referred to are the same as those mentioned hereinabove for the heterocyclic group for Z. For the substituents which the heterocyclic group for $R^3$, $R^4$, $R^5$, $R^6$, $R^7$, $R^8$, $R^9$, $R^{10}$, $R^{11}$ and $R^{12}$ may have, referred to are the same as those mentioned hereinabove for the substituents for the cyclic group for Z.

Concretely, for example, the heterocyclic group for them may have from 1 to 3 substituents selected from a formyl group, a $C_{1-6}$ alkyl-carbonyl group (e.g., acetyl, propionyl, butyryl, 5-butylcarbonyl, etc.), a $C_{6-14}$ aryl-carbonyl group (e.g., benzoyl, naphthalenecarbonyl, anthracenecarbonyl, etc.), a $C_{1-6}$ alkoxy-carbonyl group (e.g., methoxycarbonyl, ethoxycarbonyl, propoxycarbonyl, sec-propoxycarbonyl, butoxycarbonyl, t-butoxycarbonyl, etc.), a $C_{7-14}$ aralkyloxycarbonyl group (e.g., benzyloxycarbonyl, phenethyloxycarbonyl, phenylpropyloxycarbonyl, etc.), a $C_{6-14}$ cyclic hydrocarbon-carbonyl group (e.g., benzenecarbonyl, fluorenecarbonyl, etc.), a heterocyclic-carbonyl group (e.g., furancarbonyl, thiophenecarbonyl, pyridinecarbonyl, benzofurancarbonyl, benzothiophenecarbonyl, carbazolecarbonyl, dibenzofurancarbonyl, etc.), a $C_{1-6}$ alkylsulfonyl group (e.g., methylsulfonyl, ethylsulfonyl, propylsulfonyl, sec-propylsulfonyl, butylsulfonyl, t-butylsulfonyl, etc.), a $C_{6-14}$ aryl-sulfonyl group (e.g., benzenesulfonyl, naphthalenesulfonyl, anthracenesulfonyl, etc.), a carbamoyl group, a thiocarbamoyl group, a mono- or di-$C_{1-6}$ alkyl-carbamoyl group (e.g., N-methylcarbamoyl, N-ethylcarbamoyl, N,N-dimethylcarbamoyl, N,N-diethylcarbamoyl, etc.), a mono- or di-$C_{1-6}$ alkyl-thiocarbamoyl group (e.g., N-methylthiocarbamoyl, N-ethylthiocarbamoyl, N,N-dimethylthiocarbamoyl, N,N-diethylthiocarbamoyl, etc.). These may have from 1 to 3 substituents selected from, for example, a halogen atom (e.g., fluorine, chlorine, bromine, iodine, etc.), a hydroxy group, a $C_{1-6}$ alkoxy group (e.g., methoxy, ethoxy, propoxy, isopropoxy, etc.), a formyl group, a $C_{1-6}$ alkyl-carbonyl group (e.g., acetyl, propionyl, butyryl, etc.), a carboxyl group, a $C_{1-6}$ alkoxy-carbonyl group (e.g., methoxycarbonyl, ethoxycarbonyl, propoxycarbonyl, sec-propoxycarbonyl, butoxycarbonyl, etc.), an amino group, a mono- or di-$C_{1-6}$ alkylamino group (e.g., methylamino, ethylamino, dimethylamino, diethylamino, etc.), a pyrrolidinyl group, a piperidyl group, a morpholinyl group, a thiomorpholinyl group, a 4-methylpiperidyl group, a 4-phenylpiperidyl group, a 4-benzyloxycarbonylpiperidyl group, a carbamoyl group, a thiocarbamoyl group, a mono- or di-$C_{1-6}$ alkyl-carbamoyl group (e.g., methylcarbamoyl, ethylcarbamoyl, dimethylcarbamoyl, diethylcarbamoyl, etc.), a mono- or di-$C_{1-6}$ alkyl-thiocarbamoyl group (e.g., methylthiocarbamoyl, ethylthiocarbamoyl, dimethylthiocarbamoyl, diethylthiocarbamoyl, etc.), a phenoxy group, a mono- or di-$C_{1-6}$ alkyl-carbamoyloxy group (e.g., methylcarbamoyloxy, ethylcarbamoyloxy, dimethylcarbamoyloxy, diethylcarbamoyloxy, etc.), a mono- or di-$C_{1-6}$ alkyl-thiocarbamoyloxy group (e.g., methylthiocarbamoyloxy, ethylthiocarbamoyloxy, dimethylthiocarbamoyloxy, diethylthiocarbamoyloxy, etc.), a formylamino group, a $C_{1-6}$ alkyl-carbonylamino group (e.g., acetylamino, propionylamino, butyrylamino, etc.), a formyloxy group, a $C_{1-6}$ alkyl-carbonyloxy group (e.g., acetoxy, etc.), etc.

Preferably, the acyl group includes (1) an optionally-substituted 5- or 6-membered aromatic ring such as benzene, furan, thiophene or pyridine ring, or (2) an optionally-substituted, bicyclic or tricyclic condensed ring that contains one or two 5- or 6-membered aromatic rings such as benzene, furan, thiophene or pyridine ring (e.g., benzofuran, benzothiophene, quinoline, carbazole, dibenzofuran, fluorene, etc.), bonded to a carbonyl group directly or via a linear or branched $C_{1-6}$ alkylene group.

The optionally-esterified carboxyl group, one of the substituents for the hydrocarbon group for $R^1$, may be, for example, a group represented by a formula, —$COOR^c$ (in which $R^c$ represents a hydrogen atom, a $C_{1-6}$ alkyl group (e.g., methyl, ethyl, propyl, isopropyl, butyl, t-butyl, etc.), a benzyl group or the like).

The substituents which the optionally-substituted carbamoyl group, one of the substituents for the hydrocarbon group for $R^1$ and for D, G and L, may have include, for example, a $C_{1-6}$ alkyl group (e.g., methyl, ethyl, propyl, isopropyl, butyl, t-butyl, etc.), a benzyl group, an optionally-substituted phenyl group (e.g., a phenyl group optionally having substituent(s) such as those that the optionally-substituted aryl group, one of the substituents for the hydrocarbon group for $R^1$, may have, etc.), an optionally-substituted heterocyclic group (e.g., those of the optionally-substituted heterocyclic group, one of the substituents for the hydrocarbon group for $R^1$, etc.), etc.

For the substituents which the optionally-substituted thiocarbamoyl group, one of the substituents for the hydrocarbon group for $R^1$ and for D, G and L, may have, referred to are the same as those mentioned above for the optionally-substituted carbamoyl group.

The cycloalkyl group, one of the substituents for the hydrocarbon group for $R^1$, may be, for example, a $C_{3-6}$ cycloalkyl group that includes, for example, cyclopropyl, cyclobutyl, cyclopentyl, cyclohexyl, etc.

The cycloalkenyl group, one of the substituents for the hydrocarbon group for $R^1$, may be, for example, a $C_{3-6}$ cycloalkenyl group that includes, for example, 1-cyclobuten-1-yl, 1-cyclopenten-1-yl, 2-cyclopenten-1-yl, 3-cyclopenten-1-yl, 2-cyclohexen-1-yl, 3-cyclohexen-1-yl, etc.

The heterocyclic group of the optionally-substituted heterocyclic group, one of the substituents for the hydrocarbon group for $R^1$ and for L, includes, for example, a 5- or 6-membered monocyclic heterocyclic group having from 1 to 4 hetero atoms selected from nitrogen, oxygen and sulfur atoms, in addition to carbon atoms (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, triazinyl, oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc.); as well as a di- or tri-cyclic condensed heterocyclic group to be formed through condensation of 5- or 6-membered monocyclic hetero rings such as those mentioned hereinabove, and a di- or tri-cyclic condensed heterocyclic group to be formed through condensation of such 5- or 6-membered monocyclic hetero rings along with a benzene ring (preferably, a benzene ring-containing, di- or tri-cyclic condensed heterocyclic group) (e.g., benzofuryl, isobenzofuryl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnolyl, quinazolinyl, quinoxalinyl, phthalazinyl, naphthyridinyl, purinyl, pteridinyl, dibenzofuryl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-a]pyridazinyl, imidazo[1,2-a]pyrimidinyl, 1,2,4-triazolo[4,3-a]pyridyl, 1,2,4-triazolo[4,3-b]pyridazinyl, isochromanyl, chromanyl, indolyl, isoindolyl, etc.), etc. For the substituents which the heterocyclic group may have, referred to are those mentioned hereinabove for the substituents for the aromatic ring for Ring A. In addition to those, the substituents for the heterocyclic group further include an oxy group, a pyrrolidinyl group, etc. The heterocyclic group may have from 1 to 5 substituents selected from them.

The alkyl group, one of the substituents for the hydrocarbon group for $R^1$, may be a $C_{1-6}$ alkyl group, including, for example, methyl, ethyl, propyl, isopropyl, butyl, isobutyl, sec-butyl, t-butyl, etc.

The halogenoalkyl group, one of the substituents for the hydrocarbon group for $R^1$, may be a $C_{1-6}$ alkyl group substituted by from 1 to 5 halogen atoms (e.g., fluorine, chlorine, bromine, iodine, etc.), including, for example, trifluoromethyl, trichloromethyl, etc.

The aryl group of the optionally-substituted aryl group, one of the substituents for the hydrocarbon group for $R^1$, may be a $C_{6-14}$ aryl group, including, for example, phenyl, naphthyl, 2-biphenyl, 3-biphenyl, 4-biphenyl, anthryl, phenanthryl, acenaphthylenyl, etc. The aryl group may have from 1 to 5 substituents selected from, for example, a halogen atom (e.g., fluorine, chlorine, bromine, iodine, etc.), a $C_{1-6}$ alkyl group (e.g., methyl, ethyl, propyl, isopropyl, butyl, t-butyl, etc.), a halogeno-$C_{1-6}$ alkyl group (e.g., a $C_{1-6}$ alkyl group substituted by from 1 to 5 halogen atoms such as those mentioned above; e.g., trifluoromethyl, etc.), a $C_{1-6}$ alkoxy group (e.g., methoxy, ethoxy, propoxy, isopropoxy, t-butoxy, etc.), a $C_{7-14}$ aralkyloxy group (e.g., benzyloxy, etc.), a hydroxy group, an amino group, a mono- or di-$C_{1-6}$ alkylamino group (e.g., methylamino, ethylamino, dimethylamino, diethylamino, etc.), a carboxyl group, a $C_{1-6}$ alkyl-carbonyl group (e.g., acetyl, propionyl, butyryl, etc.), a $C_{1-6}$ alkoxy-carbonyl group (e.g., methoxycarbonyl, ethoxycarbonyl, propoxycarbonyl, sec-propoxycarbonyl, butoxycarbonyl, etc.), a nitro group and a cyano group.

For the optionally-substituted heterocyclic group for $R^1$, referred to are the same as those mentioned hereinabove for the optionally-substituted heterocyclic group given as an example of the substituents for the hydrocarbon group for $R^1$.

For the acyl group for $R^1$, referred to are the same as those mentioned hereinabove for the acyl group for the substituent of the optionally-substituted hydroxy group given as an example of the substituents for the optionally-substituted hydrocarbon group for $R^1$.

Preferred examples of $R^1$ are (a) a hydrogen atom, (b) a $C_{1-6}$ alkyl, $C_{2-6}$ alkenyl, $C_{6-14}$ aryl or $C_{7-14}$ aralkyl group optionally substituted by substituent(s) selected from (1) a halogen atom, (2) a nitro group, (3) an amino group optionally substituted by one or two substituents selected from a $C_{1-6}$ alkyl-carbonyl group, a $C_{6-14}$ aryl-carbonyl group, a $C_{1-6}$ alkyl group, a $C_{1-6}$ alkyloxy-carbonyl group, a $C_{7-14}$ aralkyloxy-carbonyl group, a $C_{1-6}$ alkyl-sulfonyl group and a $C_{6-14}$ aryl-sulfonyl group, (4) (i) a $C_{1-6}$ alkyl group optionally substituted by a hydroxy group, a $C_{1-6}$ alkyl-carbonyl group, a $C_{6-14}$ aryl-carbonyl group, a carboxyl group or a $C_{1-6}$ alkoxy-carbonyl group, (ii) a phenyl group optionally substituted by a hydroxy group, (iii) a benzoyl group, or (iv) a hydroxy group optionally substituted by a mono- or di-$C_{1-6}$ alkylamino-carbonyl group, (5) a $C_{3-6}$ cycloalkyl group, (6) a phenyl group optionally substituted by a hydroxy group or a halogeno-$C_{1-6}$ alkyl group, and (7) a thienyl group, a furyl group, a thiazolyl group, an indanyl group, an indolyl or a benzyloxycarbonylpiperidyl group, or (c) an acyl group. More preferably, $R^1$ is (a) a $C_{1-6}$ alkyl or $C_{7-14}$ aralkyl group optionally substituted by substituent(s) selected from (1) a hydroxy group, (2) a phenyl group, (3) a thienyl, furyl, thiazolyl, indanyl, indolyl or benzyloxycarbonylpiperidyl group, and (4) an amino group optionally substituted by a $C_{1-6}$ alkyl-carbonyl, $C_{6-14}$ aryl-carbonyl, $C_{1-6}$ alkyl-sulfonyl or $C_{6-14}$ aryl-sulfonyl group, or (b) an acyl group. Preferably, the substituent on the aralkyl group for $R^1$ is in the para-position.

In the above-mentioned formulae, $R^2$ is an optionally-substituted amino group. The optionally-substituted amino group includes, for example (i) an unsubstituted amino group, (ii) an amino group having one or two substituents selected from an optionally-substituted hydrocarbon group, an optionally-substituted heterocyclic group and an acyl group, and (iii) an optionally-substituted nitrogen-containing heterocyclic group, etc.

For the optionally-substituted hydrocarbon group, one example of the substituents for $R^2$, referred to are the same as those mentioned hereinabove for the optionally-substituted hydrocarbon group for $R^1$.

For the optionally-substituted heterocyclic group, one example of the substituents for $R^2$, referred to are the same as those mentioned hereinabove for the optionally-substituted heterocyclic group for $R^1$.

For the acyl group, one example of the substituents for $R^2$, referred to are the same as those mentioned hereinabove for the acyl group for the substituent of the optionally-substituted hydroxy group given as an example of the substituents for the optionally-substituted hydrocarbon group for $R^1$.

The nitrogen-containing heterocyclic group of the optionally-substituted nitrogen-containing heterocyclic group for $R^2$ includes, for example, a 5- to 7-membered nitrogen-containing heterocyclic group having from 1 to 4 hetero atoms selected from nitrogen, oxygen and sulfur atoms, in addition to the chemical bond-having nitrogen atom (e.g., 1-imidazolyl, 1-pyrazolyl, 1-pyrrolyl, 1-pyrrolidinyl, 1-piperazinyl, 1-piperidyl, morpholinyl, thiomorpholinyl, etc.), as well as a condensed cyclic group formed through condensation of such a 5- to 7-membered nitrogen-containing heterocyclic group and benzene, pyridine or the like (e.g., 1-benzimidazolyl, 1,2,3,4-tetrahydroisoquinolin-2-yl, 1,2,3,4-tetrahydroquinolin-1-yl, 1-indolyl, etc.), etc.

For the substituents which the nitrogen-containing heterocyclic group for $R^2$ may have, for example, referred to are those mentioned hereinabove for the substituents which the cyclic hydrocarbon for Ring B may have. Preferably, the substituents are any of a halogen atom (e.g., fluorine, chlorine, bromine, iodine, etc.), a $C_{1-6}$ alkyl group (e.g., methyl, ethyl, propyl, butyl, sec-butyl, t-butyl, isopropyl, etc.), and a $C_{1-6}$ alkoxy group (e.g., methoxy, ethoxy, propoxy, butoxy, sec-butoxy, t-butoxy, isopropoxy, etc.); and the number of the substituents which the group may have is from 1 to 5.

Preferably, $R^2$ is, for example, (1) an unsubstituted amino group, (2) a piperidyl group, or (3) an amino group optionally having one or two substituents selected from (i) a benzyl group, (ii) a $C_{1-6}$ alkyl group optionally substituted by an amino or phenyl group, (iii) a mono- or di-$C_{1-6}$ alkyl-carbamoyl group, (iv) a mono- or di-$C_{1-6}$ alkyl-thiocarbamoyl group, (v) a $C_{1-6}$ alkoxy-carbonyl group, (vi) a $C_{1-6}$ alkyl-sulfonyl group, (vii) a piperidylcarbonyl group and (viii) a $C_{1-6}$ alkyl-carbonyl group optionally substituted by a halogen atom or an amino group. More preferably, $R^2$ is an unsubstituted amino group.

In the above-mentioned formulae, E represents —CO—, CON($R^a$)—, COO—, —N($R^a$)CON($R^b$)—, —N($R^a$)COO—, —N($R^a$)SO$_2$—, N($R^a$)—, —O—, —S—, —SO— or —SO$_2$— (in which $R^a$ and $R^b$ each independently represent a hydrogen atom or an optionally-substituted hydrocarbon group). Preferably, E is —CON($R^a$)— or —N($R^a$)CON($R^b$)—; and $R^a$ and $R^b$ are preferably hydrogen atoms. More preferred is —CONH—.

For the optionally-substituted hydrocarbon group for $R^a$ and $R^b$, referred to are the same as those mentioned hereinabove for the optionally-substituted hydrocarbon group for $R^1$.

In the above-mentioned formulae, L represents (1) a chemical bond or (2) a divalent hydrocarbon group optionally having from 1 to 5 substituents selected from;
(i) a $C_{1-6}$ alkyl group,
(ii) a halogeno-$C_{1-6}$ alkyl group,
(iii) a phenyl group,
(iv) a benzyl group,
(v) an optionally-substituted amino group,
(vi) an optionally-substituted hydroxy group, and
(vii) a carbamoyl or thiocarbamoyl group optionally substituted by:
<1> a $C_{1-6}$ alkyl group,
<2> an optionally-substituted phenyl group, or
<3> an optionally-substituted heterocyclic group, and optionally interrupted by —O— or —S—.

Preferably, L is a $C_{1-6}$ alkylene group having any of the substituents (i) to (vii).

For the divalent hydrocarbon group for L, for example, referred to are the same as those mentioned hereinabove for the divalent hydrocarbon group, one example of the divalent group for D. The $C_{1-6}$ alkylene group of the optionally-substituted $C_{1-6}$ alkylene group includes, for example, methylene, ethylene, propylene, butylene, etc. The $C_{1-6}$ alkylene group may be substituted by from 1 to 5 $C_{1-6}$ alkyl groups (e.g., methyl, ethyl, propyl, isopropyl, butyl, etc.), etc.

Preferably, L is a $C_{1-6}$ alkylene group optionally substituted by $C_{1-6}$ alkyl group(s) and optionally interrupted by —O—; more preferably a $C_{1-6}$ alkylene group (even more preferably, methylene, etc.).

In the above-mentioned formulae, X represents an oxygen atom, an optionally-oxidized sulfur atom, an optionally-substituted nitrogen atom, or an optionally-substituted divalent hydrocarbon group. Preferably, X is an oxygen atom, or an optionally-substituted nitrogen atom.

For the substituents which the nitrogen atom for X may have, referred to are the same as those mentioned hereinabove for the substituents which Ring A may have.

For the divalent hydrocarbon group for X, for example, referred to are the same as those mentioned hereinabove for the divalent hydrocarbon group, one example of the divalent group for D. For the substituents which the divalent hydrocarbon group for X may have, referred to are the same as those mentioned hereinabove for the substituents for $R^1$.

In the above-mentioned formulae, Y represents two hydrogen atoms, or an oxygen atom or a sulfur atom. Preferably, Y is two hydrogen atoms or an oxygen atom. When Y is two hydrogen atoms, $R^1$ is preferably an acyl group; and when Y is an oxygen atom, $R^1$ is preferably an optionally-substituted hydrocarbon group or an optionally-substituted heterocyclic group.

Preferably, in the compounds of formula (1), Ring A is an optionally-substituted benzene or pyridine ring;

Ring B is a benzene or cyclohexane ring optionally substituted by a $C_{1-6}$ alkoxy group, or is a tetrahydroisoquinoline or isoindoline ring formed along with $R^2$ bonded thereto;

Z is a $C_{6-14}$ aryl, $C_{3-10}$ cycloalkyl, piperidyl, thienyl, furyl, pyridyl, thiazolyl, indanyl or indolyl group optionally having from 1 to 3 substituents selected from a halogen atom, a formyl group, a halogeno-$C_{1-6}$ alkyl group a $C_{1-6}$ alkoxy group, a $C_{1-6}$ alkyl-carbonyl group, an oxo group and a pyrrolidinyl group;

D is a $C_{1-6}$ alkylene group;

G is a chemical bond, or a $C_{1-6}$ alkylene group optionally having a phenylene group and optionally substituted by a phenyl group;

$R^1$ is (a) a hydrogen atom, (b) a $C_{1-6}$ alkyl, $C_{2-6}$ alkenyl, $C_{6-14}$ aryl or $C_{7-14}$ aralkyl group optionally substituted by substituent(s) selected from (1) a halogen atom, (2) a nitro group, (3) an amino group optionally substituted by one or two substituents selected from a $C_{1-6}$ alkyl-carbonyl group, a $C_{6-14}$ aryl-carbonyl group, a $C_{1-6}$ alkyl group, a $C_{1-6}$ alkyloxy-carbonyl group, a $C_{7-14}$ aralkyloxy-carbonyl group, a $C_{1-6}$ alkyl-sulfonyl group and a $C_{6-14}$ aryl-sulfonyl group, (4) (i) a $C_{1-6}$ alkyl group optionally substituted by a hydroxy group, a $C_{1-6}$ alkyl-carbonyl group, a $C_{6-14}$ aryl-carbonyl group, a carboxyl group or a $C_{1-6}$ alkoxy-carbonyl group, (ii) a phenyl group optionally substituted by a hydroxy group, (iii) a benzoyl group, or (iv) a hydroxy group optionally substituted by a mono- or di-$C_{1-6}$ alkylamino-carbonyl group, (5) a $C_{3-6}$ cycloalkyl group, (6) a phenyl group optionally substituted by a hydroxy group or a halogeno-$C_{1-6}$ alkyl group, and (7) a thienyl group, a furyl group, a thiazolyl group, an indanyl group, an indolyl or a benzyloxycarbonylpiperidyl group, or (c) an acyl group;

$R^2$ is (1) an unsubstituted amino group, (2) a piperidyl group, or (3) an amino group optionally having one or two substituents selected from (i) a benzyl group, (ii) a $C_{1-6}$ alkyl group optionally substituted by an amino or phenyl group, (iii) a mono- or di-$C_{1-6}$ alkyl-carbamoyl or mono- or di-$C_{1-6}$ alkyl-thiocarbamoyl group, (iv) a $C_{1-6}$ alkoxy-carbonyl group, (v) a $C_{1-6}$ alkyl-sulfonyl group, (vi) a piperidylcarbonyl group, and (vii) a $C_{1-6}$ alkyl-carbonyl group optionally substituted by a halogen atom or an amino group;

E is —CO—, —CON($R^a$), —N($R^a$)CO (in which $R^a$ is a hydrogen atom or a $C_{1-6}$ alkyl group); and L is a $C_{1-6}$ alkylene group optionally interrupted by —O— and optionally substituted by a $C_{1-6}$ alkyl group;

More preferably, Z is a phenyl group optionally substituted by a halogen atom; D is a $C_{1-6}$ alkylene group; G is a $C_{1-6}$ alkylene group; $R^1$ is (a) a $C_{1-6}$ alkyl or $C_{7-14}$ aralkyl group optionally substituted by substituent(s) selected from (1) a hydroxy group, (2) a phenyl group, (3) a thienyl, furyl, thiazolyl, indanyl, indolyl or benzyloxycarbonylpiperidyl group, and (4) an amino group optionally substituted by a $C_{1-6}$ alkyl-carbonyl, $C_{6-14}$ aryl-carbonyl, $C_{1-6}$ alkyl-sulfonyl or $C_{6-14}$ aryl-sulfonyl group, or (b) an acyl group; $R^2$ is an unsubstituted amino group; E is —CON($R^a$)—; L is a $C_{1-6}$ alkylene group; and Y is two hydrogen atoms.

Of the compounds of formula (I), those of formula (Ia-a) or their salts may be produced, for example, by reacting an intermediate compound of formula (IIa), or its reactive derivative or salt with a compound of formula (III) or its salt, as in the following reaction scheme 1.

Scheme 1

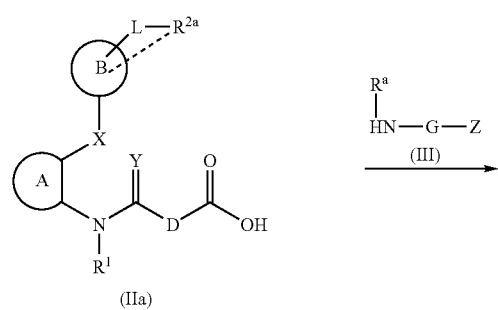

(IIa)

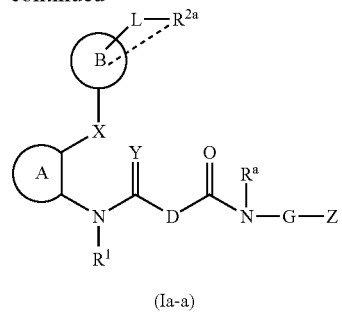

(Ia-a)

In Scheme 1, $R^{2a}$ corresponds to $R^2$ and may be optionally protected (for example, with t-butoxycarbonyl, benzyloxycarbonyl, trityl, etc.); and the other symbols have the same meanings as above.

Compounds of formula (Ia-a) or their salts may be produced by reacting a compound of formula (IIa) or its salt with a compound of formula (III) or its salt in a solvent, optionally in the presence of a base, and by the use of a condensation agent. The reactive derivative of the compound of formula (IIa) includes, for example, acid anhydrides, acid halides (acid chlorides, acid bromides), imidazolides, mixed acid anhydrides (e.g., anhydrides with methyl carbonate, anhydrides with ethyl carbonate, etc.), etc. Their specific examples are compounds of formula (IIa) where COOH has been converted into COQ (in which Q indicates a leaving group, such as a halogen atom, e.g., fluorine, chlorine, bromine, iodine, etc., or a methanesulfonyl, benzenesulfonyl, p-toluenesulfonyl group or the like). The solvent to be used in the reaction of Scheme 1 includes, for example, ether solvents (e.g., diethyl ether, tetrahydrofuran, dioxane, etc.), hydrocarbon solvents (e.g., benzene, toluene, hexane, heptane, etc.), halogen-containing solvents (e.g., dichloromethane, dichloroethane, chloroform, carbon tetrachloride, etc.), acetonitrile, dimethylformamide, etc. The base usable therein includes triethylamine, 4-dimethylaminopyridine, triethylenediamine, tetramethylethylenediamine, etc. The condensation agent also usable therein may be any one employable for peptide production. Concretely, it includes, for example, dicyclohexylcarbodiimide, diethyl cyanophosphate, 1-ethyl-3-(3-dimethylaminopropyl)carbodiimide, etc. For the reaction, for example, from 0.5 to 2 molar equivalents, preferably from 1 to 1.2 molar equivalents of a compound (III) or its salt is reacted with one mol of a compound (IIa) or its salt in the presence of from 0.5 to 5 molar equivalents, preferably from 1 to 2 molar equivalents of a condensation agent. The reaction temperature may fall between 0 and 100° C., but preferably between 20 and 50° C.; and the reaction time may fall between 0.5 and 24 hours, but preferably between 1 and 5 hours.

Of the compounds of formula (IIa), those with Y being an oxygen atom or their salts (IIa-7) may be produced, for example, according to the process of the following Scheme 2. On the other hand, those with Y being two hydrogen atoms or their salts (IIa-10) may be produced, for example, according to the process of the following Scheme 3.

(IIa-7)
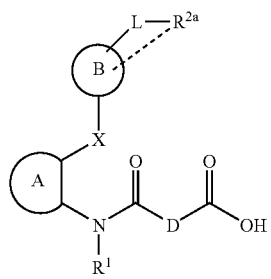
(IIa-10)
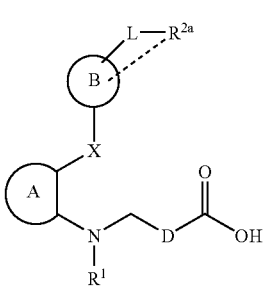
Scheme 2
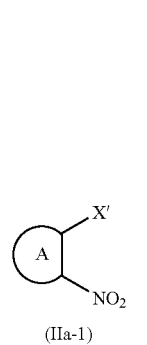
(IIa-1)
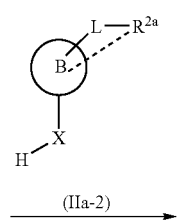
(IIa-3)
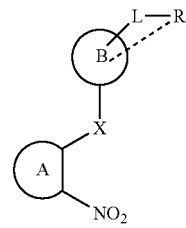
(IIa-4)
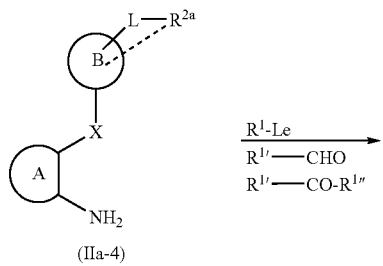
-continued
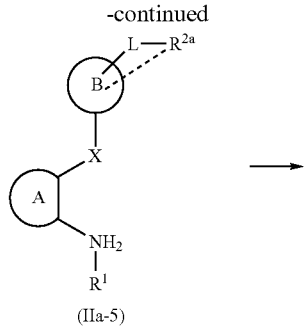
(IIa-5)
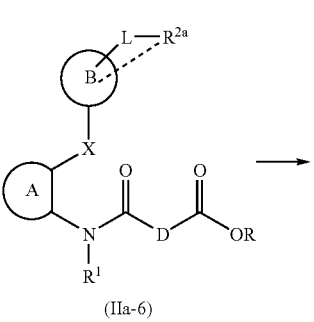
(IIa-6)
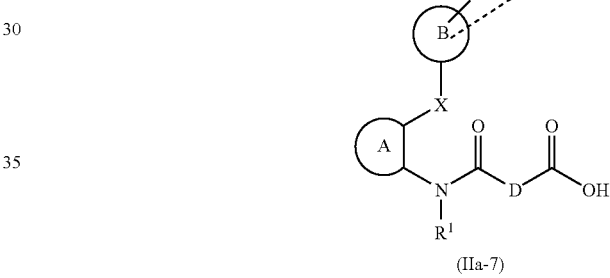
(IIa-7)
Scheme 3
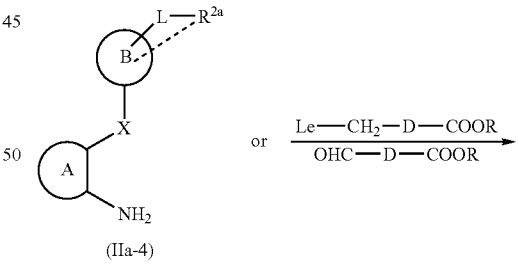
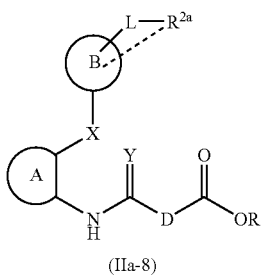
(IIa-8)

-continued

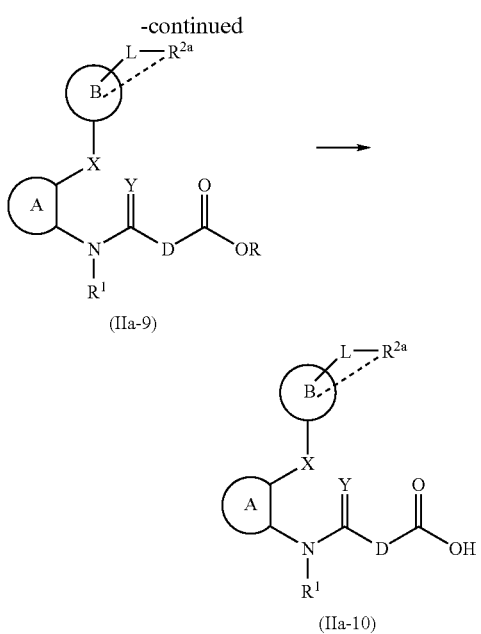

(IIa-9)

(IIa-10)

In Scheme 2 and Scheme 3, X' indicates a halogen atom (e.g., fluorine, chlorine, bromine, iodine, etc.); Le indicates a leaving group (e.g., chlorine, bromine, iodine, methanesulfonyloxy, toluenesulfonyloxy, etc.); $R^{1'}$ and $R^{1'''}$ each indicate a group derived from the optionally-substituted hydrocarbon group of $R^1$ by removing one methylene chain from it; R indicates a $C_{1-6}$ alkyl, $C_{7-14}$ aralkyl or phenyl group optionally substituted by a halogen atom or a $C_{1-6}$ alkoxy group; and the other symbols have the same meanings as above.

As in Scheme 2, a compound of formula (IIa-1) or its salt is reacted with a compound of formula (IIa-2) to give a compound of formula (IIa-3) or its salt. The reaction may be effected in the absence or presence of a solvent, and optionally in the presence of a base. The solvent includes, for example, ether solvents (e.g., diethyl ether, tetrahydrofuran, dioxane, etc.), halogen-containing solvents (e.g., dichloromethane, dichloroethane, chloroform, carbon tetrachloride, etc.), hydrocarbon solvents (e.g., benzene, toluene, hexane, heptane, etc.), dimethylformamide, dimethylsulfoxide, ester solvents (e.g., ethyl acetate, methyl acetate, etc.), etc. The base includes, for example, sodium hydrogencarbonate, potassium hydrogencarbonate, sodium carbonate, potassium carbonate, sodium hydride, potassium hydride, etc. For example, from 0.5 to 5 molar equivalents, preferably from 0.8 to 2 molar equivalents of the compound (II-a) is reacted with one mol of the compound (IIa-1) or its salt. The reaction temperature may fall between 0 and 200° C., but preferably between 80 and 150° C. The amount of the base, if used, may fall between 0.5 and 5 molar equivalents, but preferably between 1 and 1.5 molar equivalents, relative to one mol of the compound (IIa-2). The reaction time may fall between 0.5 and 48 hours, but preferably between 0.5 and 24 hours.

In Scheme 2, the reaction to convert the compound (IIa-3) or its into a compound (IIa-4) or its salt may be catalytic reduction that requires hydrogen and a metal catalyst such as a palladium catalyst (e.g., metal palladium, palladium held on carbon, etc.), a Raney nickel, platinum or the like, or simple reduction that requires a metal or a metal salt such as iron chloride, tin chloride or the like; and it may be effected in a solvent. The solvent includes, for example, ether solvent (e.g., diethyl ether, tetrahydrofuran, dioxane, etc.), hydrocarbon solvents (e.g., benzene, toluene, hexane, heptane, etc.), alcohol solvents (e.g., methanol, ethanol, propanol, etc.), acetone, dimethylformamide, etc. The hydrogen pressure may fall between 1 and 100 atmospheres, but preferably between 1 and 10 atmospheres; the reaction temperature may fall between 0 and 200° C., but preferably between 10 and 50° C.; and the reaction time may fall between 0.5 and 100 hours, but preferably between 0.5 and 24 hours.

In Scheme 2, the reaction to convert the compound (IIa-4) or its salt to a compound (IIa-5) or its salt may be nitrogen-carbon bonding reaction of the compound (IIa-4) or its salt with a halogenohydrocarbon, a sulfonate or the like, or reductive alkylation thereof with an aldehyde or a ketone. The nitrogen-carbon bonding reaction may be effected, for example, in a solvent, such as an ether solvent (e.g., diethyl ether, tetrahydrofuran, dioxane, etc.), a halogen-containing solvent (e.g., dichloromethane, dichloroethane, chloroform, carbon tetrachloride, etc.), a hydrocarbon solvent (e.g., benzene, toluene, hexane, heptane, etc.), an alcohol solvent (e.g., methanol, ethanol, propanol, butanol, etc.), acetonitrile, dimethylformamide, dimethylsulfoxide, an ester solvent (e.g., ethyl acetate, methyl acetate, etc.) or the like, or a mixed solvent of any of them, optionally in the presence of a phase-transfer catalyst (e.g., quaternary ammonium salts such as tetrabutylammonium bromide, benzyltriethylammonium chloride, etc.; crown ethers such as 18-Crown-6, etc.) or a base (e.g., sodium hydrogencarbonate, potassium hydrogencarbonate, sodium carbonate, potassium carbonate, sodium hydroxide, potassium hydroxide, etc.), or optionally in the presence of such a phase-transfer catalyst and such a base. For example, from 0.5 to 5 molar equivalents, preferably from 0.8 to 2 molar equivalents of a compound of a formula $R^1$-Le is reacted with one mol of the compound (IIa-4) or its salt. The reaction temperature may fall between 0° C. and 200° C., but preferably between 20 and 80° C. The amount of the base, if used, may fall between 0.5 and 5 molar equivalents, but preferably between 1 and 1.5 molar equivalents, relative to one mol of the compound (IIa-4). The reaction time may fall between 0.5 and 24 hours.

For its reductive alkylation, for example, the compound (IIa-4) or its salt may be reacted with a compound of a formula $R^{1'}$—CHO or $R^{1'}$—CO—$R^{1'''}$ or its salt, for example, through catalytic reduction or in the presence of a metal hydride complex compound (e.g., sodium borohydride, sodium borocyanohydride, etc.), in a solvent such as an ether solvent (e.g., diethyl ether, tetrahydrofuran, dioxane, etc.), a halogen-containing solvent (e.g., dichloromethane, dichloroethane, chloroform, carbon tetrachloride, etc.), a hydrocarbon solvent (e.g., benzene, toluene, hexane, heptane, etc.), an alcohol solvent (e.g., methanol, ethanol, propanol, butanol, etc.) or the like, or a mixed solvent of any of them. For example, from 1 to 10 molar equivalents, preferably from 1 to 2 molar equivalents of the compound of $R^{1'}$—CHO or $R^{1'}$—CO—$R^{1'''}$ or its salt is reacted with one mol of the compound (IIa-4) or its salt, in the presence of from 0.5 to 5 molar equivalents, preferably from 0.3 to 1.5 molar equivalents of the reducing agent. The reaction temperature may fall between 0 and 100° C., but preferably between 10 and 70° C.; and the reaction time may fall between 1 and 24 hours, preferably between 3 and 15 hours.

To convert the compound (IIa-5) or its salt into a compound (IIa-6) or its salt in Scheme 2, for example, the compound (IIa-5) may be reacted with a dicarboxylic acid monoester chloride (e.g., ethylmalonyl chloride, ethylsuccinyl chloride, ethylglutaryl chloride, etc.) in a solvent such as an ether solvent (e.g., diethyl ether, tetrahydrofuran, dioxane, etc.), a halogen-containing solvent (such as dichloromethane, dichloroethane, chloroform, carbon tetrachloride, etc.), a hydrocarbon solvent (e.g., benzene, toluene, hexane, heptane, etc.), dimethylformamide, dimethylsulfoxide, an ester solvent (e.g., ethyl acetate, methyl acetate, etc.), acetonitrile, water or the like. For example, from 1 to 10 molar equivalents, preferably from 1 to 2 molar equivalents of a dicarboxylic acid monoester chloride is reacted with one mol of the compound (IIa-5); the reaction temperature may fall between −20 and 100° C., but preferably between 0 and 50° C.; and the reaction time may fall between 0.5 and 24 hours, preferably between 1 and 3 hours.

The reaction to convert the compound (IIa-4) or its salt into a compound (IIa-8) or its salt in Scheme 3 may be nitrogen-carbon bonding reaction of the compound (IIa-4) or its salt with a halogenohydrocarbon, a sulfonate or the like, or reductive alkylation thereof with an aldehyde. The nitrogen-carbon bonding reaction may be effected, for example, in a solvent, such as an ether solvent (e.g., diethyl ether, tetrahydrofuran, dioxane, etc.), a halogen-containing solvent (e.g., dichloromethane, dichloroethane, chloroform, carbon tetrachloride, etc.), a hydrocarbon solvent (e.g., benzene, toluene, hexane, heptane, etc.), an alcohol solvent (e.g., methanol, ethanol, propanol, butanol, etc.), acetonitrile, dimethylformamide, dimethylsulfoxide, an ester solvent (e.g., ethyl acetate, methyl acetate, etc.) or the like, or a mixed solvent of any of them, optionally in the presence of a phase-transfer catalyst or a base (e.g., sodium hydrogencarbonate, potassium hydrogencarbonate, sodium carbonate, potassium carbonate, sodium hydroxide, potassium hydroxide, etc.), or optionally in the presence of a phase-transfer catalyst (e.g., quaternary ammonium salts such as tetrabutylammonium bromide, benzyltriethylammonium chloride, etc.; crown ethers such as 18-Crown-6, etc.) and a base. For example, from 0.5 to 5 molar equivalents, preferably from 0.8 to 2 molar equivalents of a compound of a formula Le-CH$_2$-D-COOR is reacted with one mol of the compound (IIa-4) or its salt. The reaction temperature may fall between 0 and 200° C., but preferably between 20 and 80° C. The amount of the base, if used, may fall between 0.5 and 5 molar equivalents, but preferably between 1 and 1.5 molar equivalents, relative to one mol of the compound (IIa-4). The reaction time may fall between 0.5 and 24 hours, but preferably between 0.5 and 24 hours.

For its reductive alkylation, for example, the compound (IIa-4) or its salt may be reacted with a compound of a formula OHC-D-COOR or its salt, for example, through catalytic reduction or in the presence of sodium borohydride, sodium borocyanohydride, in a solvent such as an ether solvent (e.g., diethyl ether, tetrahydrofuran, dioxane, etc.), a hydrocarbon solvent (e.g., benzene, toluene, hexane, heptane, etc.), an alcohol solvent (e.g., methanol, ethanol, propanol, butanol, etc.) or the like, or a mixed solvent of any of them. For example, from 1 to 10 molar equivalents, preferably from 1 to 2 molar equivalents of the compound of OHC-D-COOR or its salt is reacted with one mol of the compound (IIa-4) or its salt, in the presence of from 0.3 to 5 molar equivalents, preferably from 0.5 to 1.5 molar equivalents of the reducing agent. The reaction temperature may fall between 0 and 100° C., but preferably between 10 and 70° C.; and the reaction time may fall between 1 and 24 hours, preferably between 3 and 15 hours.

To convert the compound (IIa-8) or its salt into a compound (IIa-9) or its salt in Scheme 3, for example, the compound (IIa-8) may be reacted with an acyl chloride (e.g., a carboxylic acid chloride, a sulfonic acid chloride, etc.), an isocyanate, a carboxylic acid or the like, in a solvent such as an ether solvent (e.g., diethyl ether, tetrahydrofuran, dioxane, etc.), a halogen-containing solvent (e.g., dichloromethane, dichloroethane, chloroform, carbon tetrachloride, etc.), a hydrocarbon solvent (e.g., benzene, toluene, hexane, heptane, etc.), dimethylformamide, dimethylsulfoxide, an ester solvent (e.g., ethyl acetate, methyl acetate, etc.), acetonitrile, water or the like. For example, from 1 to 10 molar equivalents, preferably from 1 to 2 molar equivalents of an acyl chloride or an isocyanate may be reacted with one mol of the compound (IIa-8); the reaction temperature may fall between −20 and 100° C., but preferably between 0 and 50° C.; and the reaction time may fall between 0.5 and 24 hours, preferably between 1 and 3 hours. If desired, a base may be present in the reaction.

The compound (IIa-7) or its salt in Scheme 2, and the compound (IIa-10) or its salt in Scheme 3 may be produced by processing the compound (IIa-6) or its salt, or the compound (IIa-9) or its salt with an acid or a base, respectively. Concretely, the intended compounds may be produced by processing the compound (IIa-6) or (IIa-9) or its salt in an aqueous solution of, for example, a mineral acid (e.g., nitric acid, hydrochloric acid, hydrobromic acid, hydroiodic acid, sulfuric acid, etc.) or an alkali metal hydroxide (e.g., sodium hydroxide, potassium hydroxide, barium hydroxide, lithium hydroxide, etc.) or the like, at a temperature falling between 0 and 150° C., preferably between 20 and 50° C. Regarding their strength, the acid and the base to be used may have from 1 to 10 normalities or so, but preferably from 4 to 10 normalities. The reaction time may fall between 1 and 24 hours, but preferably between 2 and 10 hours.

The compound (IIa-9) or its salt in Scheme 3 may also be produced by converting a compound (IIa-4) or its salt into a compound (IIa-5) or its salt followed by further converting the resulting compound (IIa-5) or its salt into the compound (IIa-9) or its salt, as in Scheme 4 mentioned below. The reaction to convert the compound (IIa-4) or its salt into the compound (IIa-5) or its salt may be effected under the same condition as that for the reaction to convert the compound (IIa-8) or its salt into the compound (IIa-9) or its salt in Scheme 3. The reaction of the compound (IIa-5) or its salt with a compound, Le-CH$_2$-D-COOR may be effected under the same condition as that for the reaction of the compound (IIa-4) or its salt with the compound Le-CH$_2$-D-COOR in Scheme 3.

Scheme 4

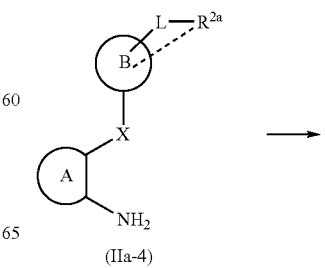

(IIa-4)

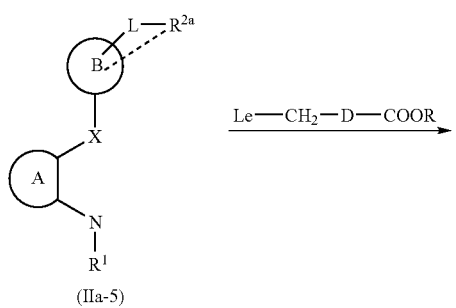
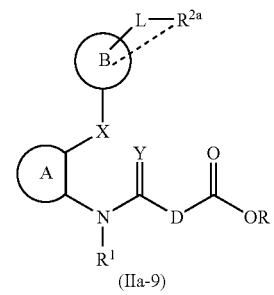
wherein the symbols all have the same meanings as above. Of the compounds of formula (I), those of formulae (Ia-b), (Ia-c), (Ia-d), (Ia-e) and their salts may be produced according to the process of the following Scheme 5.
Scheme 5
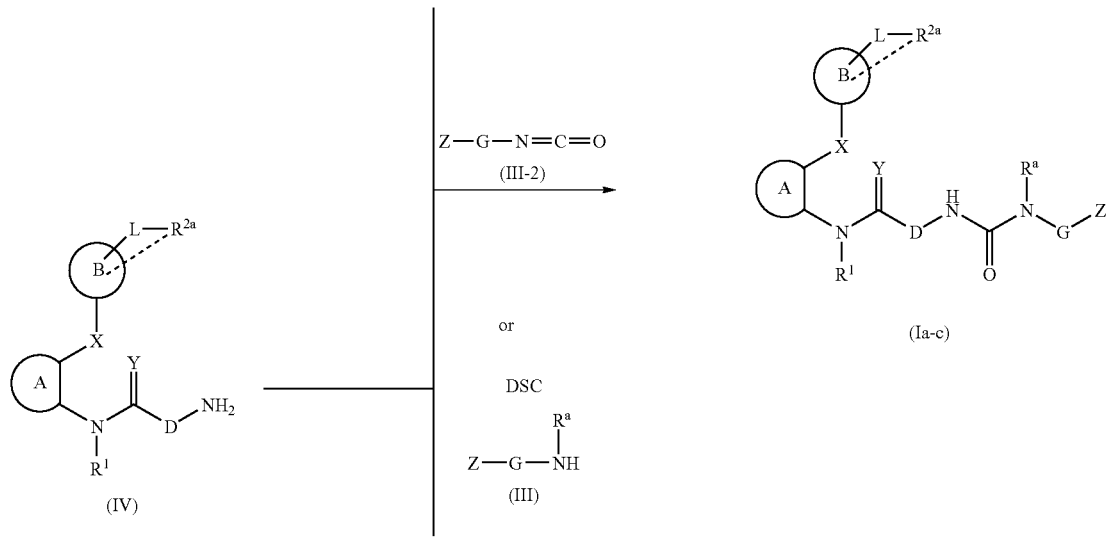

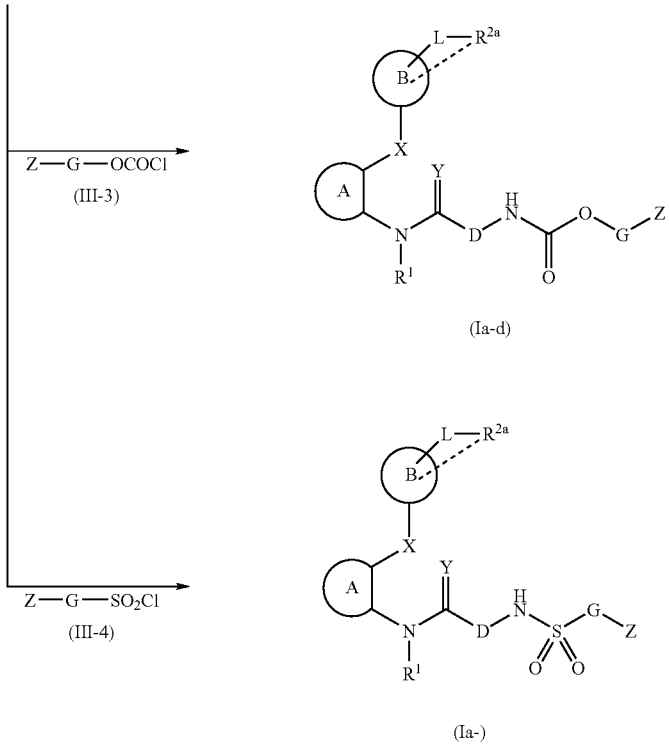

In Scheme 5, the symbols all have the same meanings as above.

Compounds of formula (Ia-b) or their salts in Scheme 5 may be produced by reacting a compound of formula (IV) or its salt with a compound of formula (III-1) or its salt. The reaction is condensation, for which the condition may be the same as that for the condensation of the compound (IIa) or its salt with the compound (III) or its salt to give the compound (Ia-a) or its salt in Scheme 1.

In Scheme 5, compounds of formula (Ia-c) or their salts may be produced by reacting the compound (IV) or its salt with a compound (III) or its salt along with a reagent of DSC (N,N'-disuccinimidyl carbonate) or the like, or by reacting it with a compound (III-2) or its salt. The reaction may be effected in a solvent optionally in the presence of a base. The solvent includes, for example, ether solvents (e.g., diethyl ether, tetrahydrofuran, dioxane, etc.), halogen-containing solvents (e.g., dichloromethane, dichloroethane, chloroform, etc.), acetonitrile, dimethylformamide, etc. The base includes, for example, triethylamine, 4-dimethylaminopyridine, triethylenediamine, tetramethylethylenediamine, etc. The amount of the compound (III) to be used for the reaction along with a reagent of N,N'-disuccinimidyl carbonate or the like, or that of the compound (III-2) or its salt also to be used may fall between 1 and 10 molar equivalents, but preferably between 1 and 2 molar equivalents, relative to one mol of the compound (IV) or its salt to be reacted therewith. The reaction temperature may fall between 0 and 100° C., but preferably between 20 and 50° C.; and the reaction time may fall between 1 and 24 hours, preferably between 3 and 10 hours.

In Scheme 5, compounds of formula (Ia-d) or their salts may be produced by reacting a compound (IV) or its salt with a compound (III-3) or its salt. The reaction may be effected in a solvent optionally in the presence of a base. The solvent includes, for example, ether solvents (e.g., diethyl ether, tetrahydrofuran, dioxane, etc.), halogen-containing solvents (e.g., dichloromethane, dichloroethane, chloroform, etc.), acetonitrile, dimethylformamide, etc. The base includes, for example, triethylamine, 4-dimethylaminopyridine, triethylenediamine, tetramethylethylenediamine, etc. For example, from 1 to 10 molar equivalents, preferably from 1 to 2 molar equivalents of the compound (III-3) or its salt may be reacted with one mol of the compound (IV) or its salt. The reaction temperature may fall between 0 and 100° C., but preferably between 20 and 50° C.; and the reaction time may fall between 1 and 24 hours, preferably between 3 and 10 hours.

In Scheme 5, compounds of formula (Ia-e) or their salts may be produced by reacting a compound (IV) or its salt with a compound (III-4) or its salt. The reaction may be effected in a solvent optionally in the presence of a base. The solvent includes, for example, ether solvents (e.g., diethyl ether, tetrahydrofuran, dioxane, etc.), alcohol solvents (e.g., methanol, ethanol, propanol, butanol, etc.), acetone, dimethylformamide, etc. The base includes, for example, sodium hydrogencarbonate, potassium hydrogencarbonate, sodium carbonate, potassium carbonate, sodium hydride, potassium hydride, triethylamine, etc. For example, from 1 to 10 molar equivalents, preferably from 1 to 2 molar equivalents of the compound (III-4) or its salt may be reacted with one mol of the compound (IV) or its salt. The reaction temperature may fall between 0 and 100° C., but preferably between 20 and 50° C.; and the reaction time may fall between 1 and 24 hours, preferably between 3 and 10 hours.

Compounds (IV) or their salts for Scheme 5 may be produced according to the process of Scheme 6 mentioned below. Briefly, a compound of formula (IIa) or its salt is reacted with diphenylphosphorylazide or the like in a solvent in the presence of a base, the resulting acylazide product is subjected to Curtius transfer reaction in a solvent to give an intermediate of an isocyanic acid derivative (V), and thereafter the intermediate is processed with an acid to give the intended compound (IV) or its salt. Alternatively, the compounds (IV) or their salts may also be produced according to the process of Scheme 6 mentioned below. Briefly, an isocyanic acid derivative (V) is converted into the corresponding carbamate derivative (VI), which is further converted into the intended compound (IV) or its salt.

Scheme 6

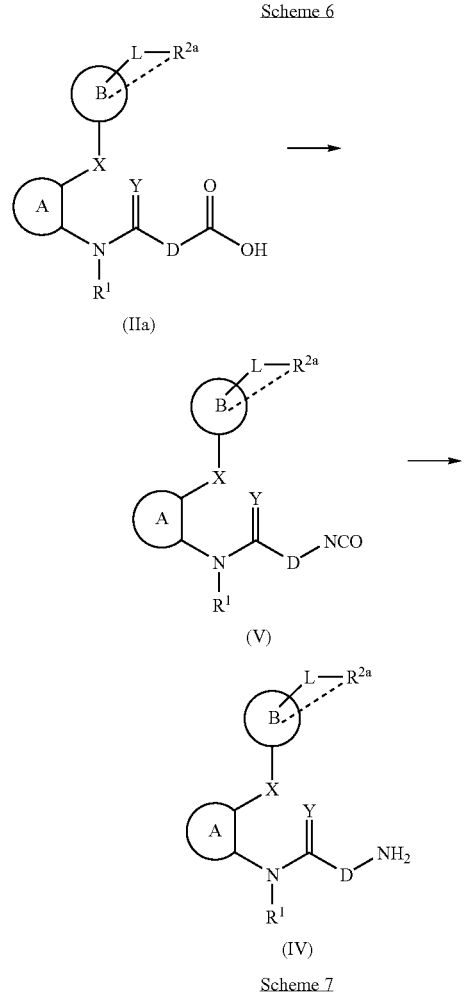

Scheme 7

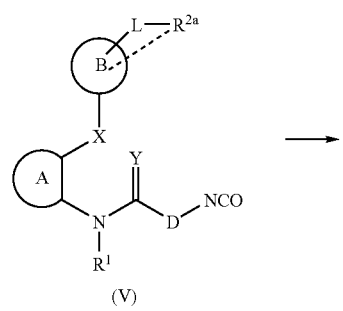

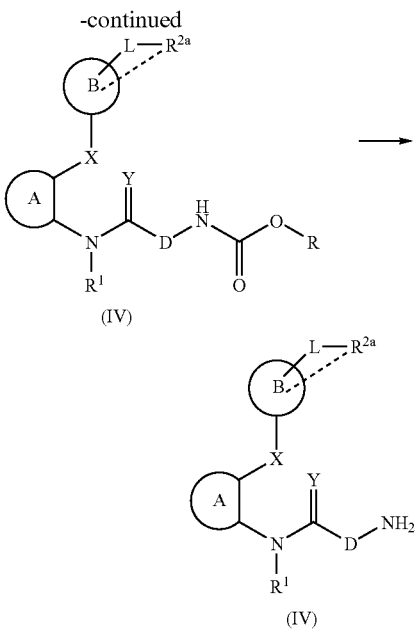

In Scheme 6 and Scheme 7, the symbols all have the same meanings as above.

The solvent which may be used in the reaction of the compound (IIa) or its salt with diphenylphosphorylazide includes, for example, ether solvents (e.g., diethyl ether, tetrahydrofuran, dioxane, etc.), halogen-containing solvents (e.g., dichloromethane, dichloroethane, chloroform, etc.), dimethylformamide, etc. The solvent also usable in the reaction includes, for example, triethylamine, 4-dimethylaminopyridine, triethylenediamine, tetramethylethylenediamine, etc. For example, from 1 to 10 molar equivalents, preferably from 1.5 to 3 molar equivalents of diphenylphosphorylazide is reacted with one mol of the compound (IIa) or its salt. The reaction temperature may fall between −20 and 50° C., but preferably between 0 and 20° C.; and the reaction time may fall between 0.5 and 5 hours, preferably between 1 and 2 hours.

The solvent which may be used in the Curtius transfer reaction of the product obtained through the reaction as above includes, for example, hydrocarbon solvents (e.g., benzene, toluene, xylene, etc.), ether solvents (e.g., diethyl ether, tetrahydrofuran, dioxane, etc.), halogen-containing solvents (e.g., dichloromethane, dichloroethane, chloroform, etc.), dimethylformamide, etc. The reaction temperature may fall between 50 and 200° C., but preferably between 80 and 150° C.; and the reaction time may fall between 0.5 and 12 hours, preferably between 1 and 3 hours.

The solvent which may be used in the step or processing the resulting product with an acid includes, for example, water, dioxane, dimethylformamide, etc. The acid to be used may be a mineral acid, including, for example, sulfuric acid, hydrochloric acid, nitric acid, hydrobromic acid, etc. The reaction temperature may fall between 20 and 200° C., but preferably between 50 and 100° C.; and the reaction time may fall between 0.5 and 5 hours, preferably between 1 and 2 hours.

Apart from the process of Scheme 5, the compounds (Ia-c) or (Ia-d) or their salts may also be produced by reacting the isocyanic acid derivative (V) in Scheme 6 with a compound of formula (III) or (VII), for example, as in Scheme 8 mentioned below. In this case, the reaction of the isocyanic acid derivative (V) with the compound (III) or (VII) may be effected under the same condition as that for the reaction of the compound (IV) or its salt with the compound (III-2) in Scheme 5.

Scheme 8

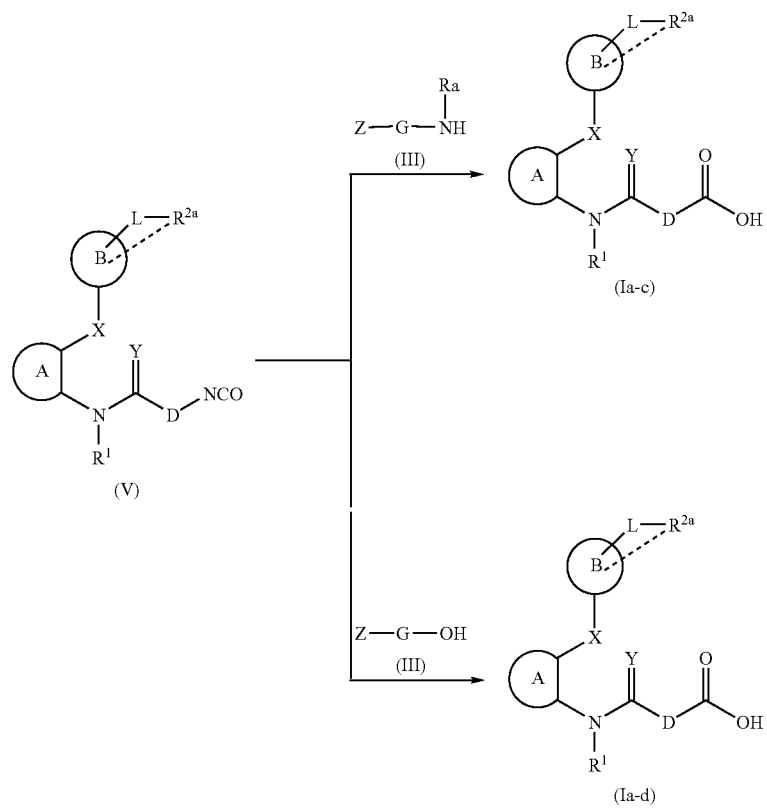

In Scheme 8, the symbols all have the same meanings as above.

Of compounds of formula (I) or salts, those of formula (Ia-f) or their salts may be produced by reacting a compound (IIa) or its salt with a compound (VII) or its salt, for example, according to the process of Scheme 9 mentioned below.

Scheme 9

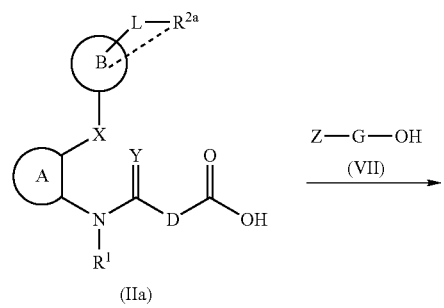

-continued

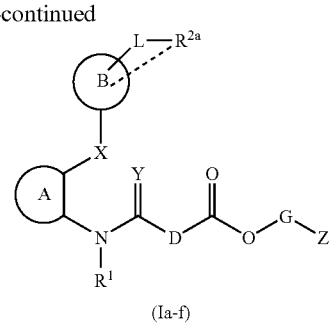

In Scheme 9, the symbols all have the same meanings as above

The compounds (Ia-f) or their salts may be produced, for example, by reacting a compound (IIa) or its salt with a compound (VII) or its salt in a solvent, optionally in the presence of a base, by the use of a condensation agent. The solvent usable in the reaction includes, for example, ether solvent (e.g., diethyl ether, tetrahydrofuran, dioxane, etc.), halogen-containing solvent (e.g., dichloromethane, dichloroethane, chloroform, carbon tetrachloride, etc.), acetonitrile, dimethylformamide, etc. The base usable therein includes, for example, triethylamine, 4-dimethylaminopyridine, triethylenediamine, tetramethylethylenediamine, etc. The condensation agent usable therein may be any ordinary one generally employed in peptide production. Concretely, it includes, for example, dicyclohexylcarbodiimide, diethyl cyanophosphate, 1-ethyl-3-(3-dimethylaminopropyl)carbodiimide, etc. For example, from 0.5 to 2 molar equivalents, preferably from 1 to 1.2 molar equivalents of the compound (VII) or its salt is reacted with one mol of the compound (IIa) or its salt, and the amount of the condensation agent to be used in the reaction may fall between 0.5 and 5 molar equivalents, preferably between 1 and 2 molar equivalents. The reaction temperature may fall between 0 and 100° C., but preferably between 20 and 50° C.; and the reaction time may fall between 0.5 and 24 hours, preferably between 1 and 5 hours.

Of compounds of formula (I) or their salts, those of formula (Ia-g) or their salts may be produced according to the process of Scheme 10 mentioned below. Briefly, a compound (VIII) or its salt is reacted with a compound (IX) or its salt to give the intended compound (Ia-g) or its salt.

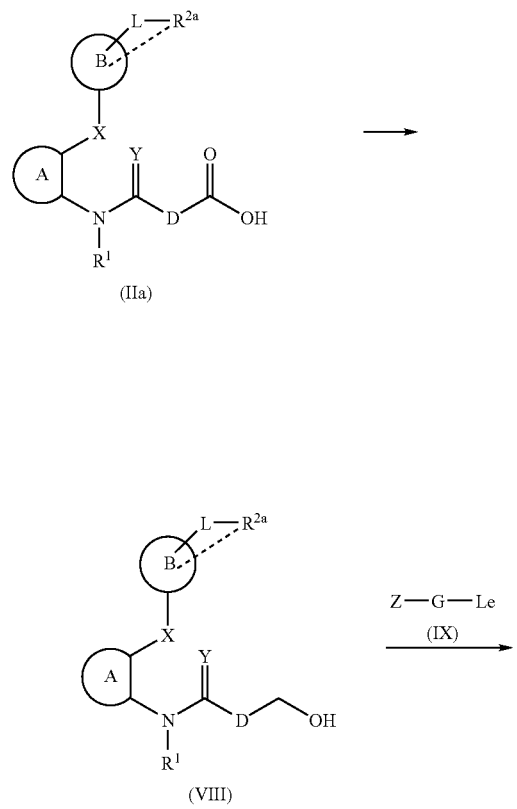

Scheme 10

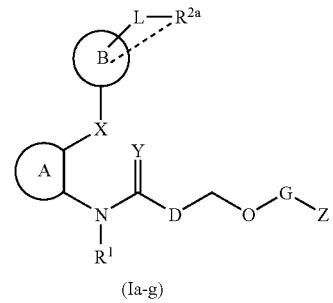

(Ia-g)

In Scheme 10, the symbols all have the same meanings as above.

Compounds (VIII) or their salts may be produced by reacting a compound (IIa) or its salt with ethyl chlorocarbonate or the like to give a mixed acid anhydride, followed by processing the resulting anhydride with, for example, a metal hydride complex (e.g., lithiumaluminium hydride, sodiumaluminium hydride, sodium borohydride, etc.) in a protic solvent (e.g., methanol, ethanol, propanol, butanol, etc.) or an aprotic solvent (e.g., ethyl ether, tetrahydrofuran, dioxane, etc.). For example, from 0.3 to 5 molar equivalents, preferably from 0.5 to 2 molar equivalents of such a metal hydride complex may be reacted with one mol of the compound (IIa) or its salt. The reaction temperature may fall between −20 and 100° C., preferably between 0 and 20° C.; and the reaction time may fall between 0.5 and 10 hours, preferably between 1 and 3 hours.

The reaction of the compound (VIII) with the compound (IX) or its salt may be effected in a solvent optionally in the presence of a base. The solvent may be an aprotic solvent, including, for example, ethyl ether, tetrahydrofuran, dioxane, acetonitrile, dimethylformamide, etc.; and the base includes, for example, inorganic bases (e.g., sodium hydrogencarbonate, potassium hydrogencarbonate, sodium carbonate, potassium carbonate, etc.), organic bases (e.g., triethylamine, 4-dimethylaminopyridine, triethylenediamine, tetramethylethylenediamine, etc.), sodium hydride, cesium fluoride, etc. For example, from 0.5 to 5 molar equivalents, preferably from 1 to 2 molar equivalents of the compound (IX) or its salt is reacted with one mol of the compound (VIII) or its salt. The reaction temperature may fall between 0 and 200° C., preferably between 20 and 100° C.; and the reaction time may fall between 10 minutes and 5 hours, preferably between 30 minutes and 2 hours.

Of compounds (I) or their salts, those of a formula (Ia-h) or (Ia-i) or their salts may be produced according to the process of Scheme 11 mentioned below. Briefly, a compound (X) or its salt is reacted with a compound (VII) or (XI) or its salt to give the intended compound or its salt.

Scheme 11

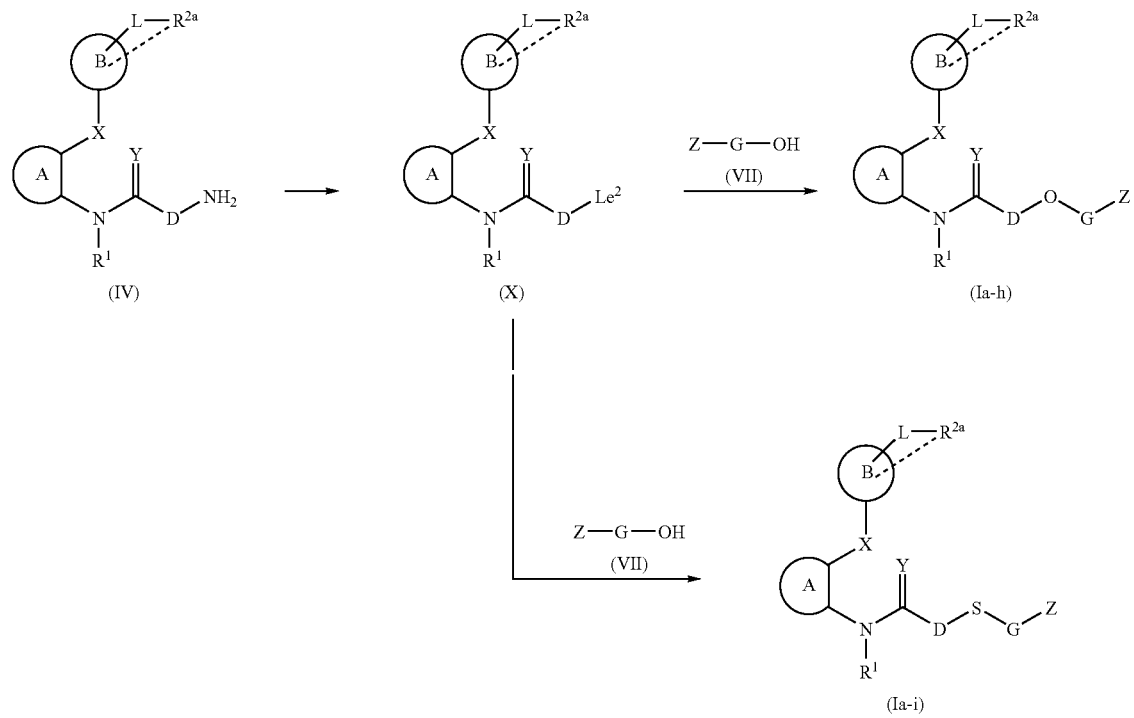

wherein Le² indicates a halogen atom (e.g., chlorine, bromine, iodine, etc.); and the other symbols have the same meanings as above.

Compounds (X) or their salts may be produced by diazoating a compound (IV) or its salt with from 1 to 5 molar equivalents, preferably from 1 to 3 molar equivalents, relative to the compound (IV) or its salt, of sodium nitrite in, for example, hydrochloric acid, hydrobromic acid or hydroiodic acid, followed by heating the resulting diazo product. The reaction temperature may fall between 20 and 200° C., but preferably between 50 and 100° C.; and the reaction time may fall between 5 minutes and 2 hours, preferably between 15 and 30 minutes or so. The reaction of the compound (X) or its salt with a compound (VII) or (XI) or its salt may be effected under the same condition as that for the reaction of the compound (VIII) or its salt with the compound (IX) or its salt to give the compound (Ia-g) or its salt.

Of compounds (I) or their salts, those of formula (Ia-j) or their salts may be produced according to the process of Scheme 12 mentioned below. Briefly, a compound (Ia-i) or its salt is oxidized to give the intended compound or its salt.

Scheme 12

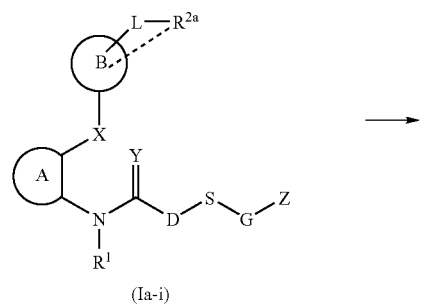

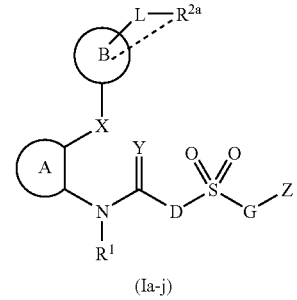

In Scheme 12, the symbols all have the same meanings as above.

Concretely, for example, from 1 to 5 molar equivalents, preferably from 2 to 3 molar equivalents of metachloroperbenzoic acid is reacted with one mol of a compound (Ia-i) or its salt in a solvent. The solvent includes, for example, ether solvents (e.g., diethyl ether, tetrahydrofuran, dioxane, etc.), hydrocarbon solvents (e.g., benzene, toluene, hexane, heptane, etc.), halogen-containing solvents (e.g., dichloromethane, dichloroethane, chloroform, etc.), acetonitrile, dimethylformamide, etc. The reaction temperature may fall between 0 and 100° C., but preferably between 0 and 30° C.; and the reaction time may fall between 1 and 10 hours, preferably between 1 and 2 hours.

Compounds (I) or their salts, and compounds (Ib) or their salts may be produced according to the process of Scheme 13 mentioned below. Briefly, a compound (Ia) or its salt is de-protected in any known manner to give a compound (Ib) or its salt. The resulting compound (Ib) or its salt is then reacted with a compound (XII) or (XIII) or its salt to give the intended compound (I) or its salt.

Scheme 13

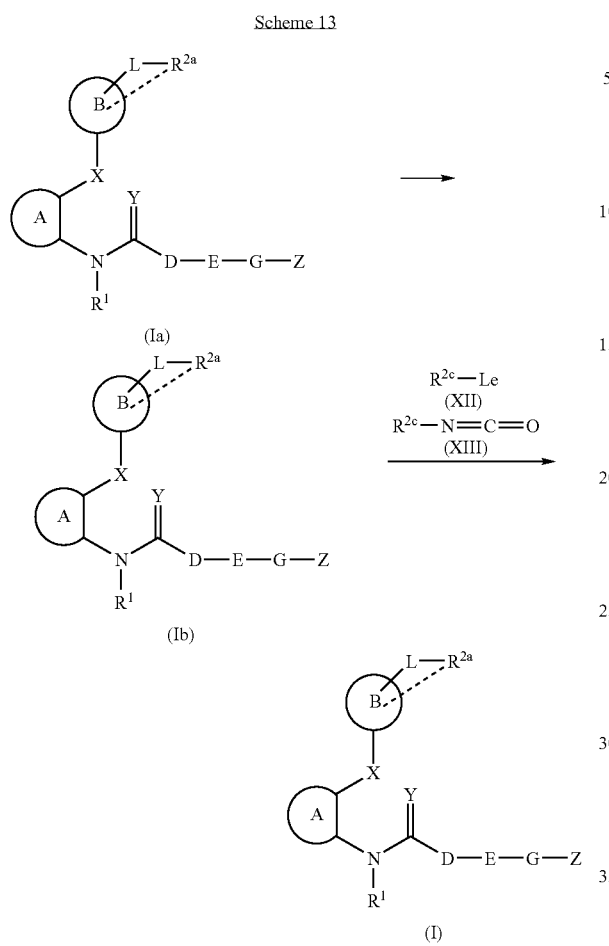

In Scheme 13, $R^{2b}$ indicates a de-protected $R^{2a}$; $R^{2c}$ and $R^{2d}$ each indicate an optionally-substituted hydrocarbon group, an optionally-substituted heterocyclic group, a hydrogen atom, or an acyl group; and the other symbols have the same meanings as above.

The reaction for de-protecting the compound (Ia) is described. When the protective group is a t-butoxycarbonyl, trityl or benzyloxycarbonyl group, for example, the protected compound is processed with an acid (e.g., hydrogen chloride, hydrogen bromide, hydrochloric acid, hydrobromic acid, nitric acid, sulfuric acid, trifluoroacetic acid, etc.) in a solvent to remove the protective group. The solvent includes, for example, ether solvents (e.g., diethyl ether, tetrahydrofuran, dioxane, etc.), alcohol solvents (e.g., methanol, ethanol, propanol, etc.), halogen-containing solvents (e.g., dichloromethane, dichloroethane, chloroform, etc.), etc. When the protective group is a benzyloxycarbonyl group, for example, the protected compound is hydrolyzed in a solvent in the presence of a palladium catalyst (e.g., metal palladium, palladium/carbon, etc.) to remove the protective group. The solvent includes, for example, ether solvents (e.g., diethyl ether, tetrahydrofuran, dioxane, etc.), alcohol solvents (e.g., methanol, ethanol, propanol, etc.), dimethylformamide, ethyl acetate, acetic acid, etc. For the acid treatment, the reaction temperature may fall between –20 and 100° C., but preferably between 0 and 30° C.; and the reaction time may fall between 0.1 and 5 hours, preferably between 0.5 and 1 hour. For the hydrolysis, the reaction temperature may fall between –20 and 150° C., but preferably between 0 and 50° C.; the reaction time may fall between 0.1 and 10 hours, preferably between 0.5 and 3 hours; and the hydrogen pressure may fall between 1 and 100 atmospheres, preferably between 1 and 3 atmospheres. The amount of the catalyst for the reaction may fall between 0.001 and 0.5 molar equivalents, but preferably between 0.01 and 0.1 molar equivalents, relative to one mol of the compound (Ia) or its salt.

The reaction of the compound (Ib) or its salt with the compound (XII) or its salt may be effected under the same condition as that for the reaction of the compound (IIa-4) or its salt with the compound, $R^1$-Le or its salt in the above-mentioned Scheme 2. The reaction of the compound (Ib) or its salt with the compound (XIII) or its salt may be effected under the same condition as that for the reaction of the compound (IV) or its salt with the compound (III-2) or its salt to give the compound (Ia-c) or its salt in the above-mentioned Scheme 5.

Of compounds (I) or their salts, those of the following formula (Ik):

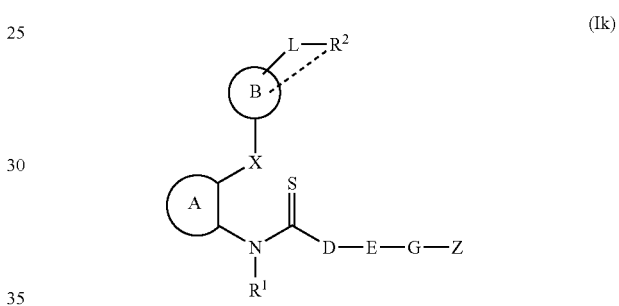

wherein the symbols all have the same meanings as above, or their salts may be obtained by processing a compound of formula (I) wherein X is an oxygen atom or its salt, with a Lawson reagent or phosphorus pentasulfide in a solvent. The solvent includes, for example, ether solvents (e.g., diethyl ether, tetrahydrofuran, dioxane, etc.), hydrocarbon solvents (e.g., benzene, toluene, hexane, heptane, etc.), alcohol solvents (e.g., methanol, ethanol, propanol), halogen-containing solvents (e.g., dichloromethane, chloroform, etc.), hexamethylphosphoric triamide, dimethylsulfoxide, etc. The amount of the Lawson reagent or phosphorus pentasulfide to be used in the reaction may fall between 1 and 10 molar equivalents, but preferably between 1 and 3 molar equivalents, relative to one mol of the compound (I) having an oxygen atom for X or its salt. The reaction temperature may fall between 0 and 150° C., but preferably between 50 and 100° C.; and the reaction time may fall between 1 and 24 hours, preferably between 3 and 10 hours.

The compound (IIa-2) or its salt in the above-mentioned Scheme 2 may be produced by protecting a compound (IIb-1) or its salt according to a method known in the field of organic synthesis, or by converting the substituent $X^a$ in a compound (IIb-4) or its salt into a substituent H—X according to a method known in the field of organic synthesis, for example, as in Scheme 14 mentioned below. The compound (IIb-1) or its salt may be produced by converting the substituent $X^a$ in a compound (IIb-2) or its salt into a substituent H—X according to a method known in the field of organic synthesis. The compound (IIb-2) or its salt may be produced by converting the substituent $R^{2e}$ in a compound (IIb-3) or its salt into a substituent $R^{2b}$ according to a method known in the field of organic synthesis.

The compound (IIb-4) or its salt may be produced by converting the substituent $R^{2e}$ in a compound (IIb-3) or its salt into a substituent $R^{2a}$ according to a method known in the field of organic synthesis.

Scheme 14

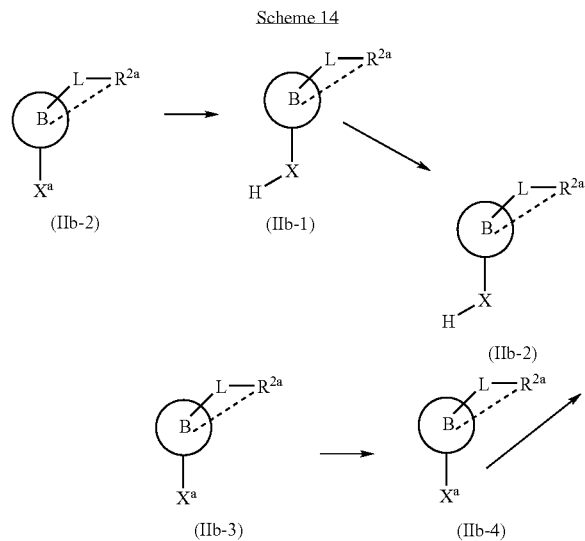

wherein $R^{2b}$ indicates a de-protected $R^{2a}$; $R^{2e}$ indicates a substituent convertible into $R^{2a}$ or $R^{2b}$; $X^a$ indicates a substituent convertible into H—X; and the other symbols have the same meanings as above.

The starting compounds and the process intermediates in the invention may form salts, and are not specifically defined so far as they are processed to give the intended products. Salts of the compounds includes, for example, inorganic acid salts (e.g., hydrochlorides, sulfates, hydrobromides, phosphates, etc.), organic acid salts (e.g., acetates, trifluoroacetates, succinates, maleates, fumarates, propionates, citrates, tartrates, malates, lactates, oxalates, methanesulfonates, o-toluenesulfonates, etc.), alkali metal salts (e.g., sodium salts, potassium salts, etc.), alkaline earth metal salts (e.g., calcium salts, magnesium salts, etc.), organic base salts (e.g., trimethylamine salts, triethylamine salts, pyridine salts, piperidine salts, ethanolamine salts, etc.), aluminium salts, ammonium salts, etc. The starting compounds and the process intermediates in the invention may be isolated in any known manner, but may be directly used in the next reaction without being isolated.

In the reaction processes of the invention mentioned above, when the compounds have an amino group, a carboxyl group or a hydroxy group as their substituent, the group may be protected in any ordinary manner generally employed in the field of peptide chemistry, and the protected group may be removed, if desired, after the reaction of the compounds to give the intended products.

The protective group for amino groups includes, for example, a formyl group, a $C_{1-6}$ alkyl-carbonyl group (e.g., acetyl, ethylcarbonyl, etc.), a benzyl group, a t-butyloxycarbonyl group, a benzyloxycarbonyl group, a 9-fluorenylmethyloxycarbonyl group, an allyloxycarbonyl group, a phenylcarbonyl group, a $C_{1-6}$ alkyloxy-carbonyl group (e.g., methoxycarbonyl, ethoxycarbonyl, etc.), a $C_{7-10}$ aralkyl-carbonyl group (e.g., benzylcarbonyl, etc.), a trityl group, a phthaloyl group, an N,N-dimethylaminomethylene group, etc. These groups may be substituted by from 1 to 3 substituents selected from a halogen atom (e.g., fluorine, chlorine, bromine, etc.), a nitro group, etc.

The protective group for carboxyl groups includes, for example, a $C_{1-6}$ alkyl group (e.g., methyl, ethyl, propyl, isopropyl, butyl, t-butyl, etc.), a phenyl group, a silyl group, a benzyl group, an allyl group, etc. These groups may be substituted by from 1 to 3 substituents selected from a halogen atom (e.g., fluorine, chlorine, bromine, etc.), a nitro group, etc.

The protective group for hydroxy groups includes, for example, a methoxymethyl group, an allyl group, a t-butyl group, a $C_{7-10}$ aralkyl group (e.g., benzyl, etc.), a formyl group, a $C_{1-6}$alkyl-carbonyl group (e.g., acetyl, ethylcarbonyl, etc.), a benzoyl group, a $C_{7-10}$ aralkyl-carbonyl group (e.g., benzylcarbonyl, etc.), a pyranyl group, a furanyl group, a trialkylsilyl group, etc. These groups may be substituted by from 1 to 3 substituents selected from a halogen atom (e.g., fluorine, chlorine, bromine, etc.), a $C_{1-6}$ alkyl group (e.g., methyl, ethyl, propyl, isopropyl, butyl, t-butyl, etc.), a phenyl group, a $C_{7-10}$ aralkyl group (e.g., benzyl, etc.), a nitro group, etc.

Removing the protective group may be effected in any known method or in accordance with such a known method. For example, the protected compounds may be reduced or may be exposed to UV rays, or may be processed with any of acids, bases, hydrazine, phenylhydrazine, sodium N-methyldithiocarbamate, tetrabutylammonium fluoride, palladium acetate or the like.

When free compounds are obtained in any step of the above-mentioned reactions for the invention, they may be converted into salts in any known method; or when salts are obtained therein, they may be converted into free compounds or any other salts in any known method.

The compounds (I) or their salts of the invention thus obtained may be isolated from the reaction solvent used and may be purified in any known method, for example, through trans-solvation, concentration, solvent extraction, distillation, crystallization, recrystallization, chromatography, etc.

When the compounds (I) or their salts of the invention include different types of diastereomers, conformers, etc., they may be separated into individual ones through known isolation or purification, if desired. When the compounds (I) or their salts of the invention are racemates, they may be separated into d- and l-forms through known optical resolution.

The compounds and their prodrugs having a somatostatin receptor function-regulating effect for use in the invention may be as they are or may also be in the form of their pharmaceutically-acceptable salts. For example, when the compounds having a somatostatin receptor function-regulating effect have an acidic group such as a carboxyl group or the like, they may form salts with inorganic bases (e.g., alkali metals such as sodium, potassium, etc.; alkaline earth metals such as calcium, magnesium, etc.; transition metals such as zinc, iron, copper, etc.), or with organic bases (e.g., organic amines such as trimethylamine, triethylamine, pyridine, picoline, ethanolamine, diethanolamine, triethanolamine, dicyclohexylamine, N,N'-dibenzylethylenediamine, etc.; basic amino acids such as arginine, lysine, ornithine, etc.).

When the compounds having a somatostatin receptor function-regulating effect have a basic group such as an amino group or the like, they may form salts with inorganic acids or organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.), or with acidic amino acids such as aspartic acid, glutamic acid, etc.

Prodrugs of the compounds having a somatostatin receptor function-regulating effect for use in the invention are meant to indicate compounds capable of being converted into the intended compounds having a somatostatin receptor function-regulating effect through reaction with enzymes, gastric acids or the like in vivo or under physiological conditions, including, for example, those capable of being enzymatically oxidized, reduced or hydrolyzed to give the intended compounds having a somatostatin receptor function-regulating effect, those capable of being hydrolyzed with gastric acids to give the intended compounds having a somatostatin receptor function-regulating effect. Concretely, such prodrugs of the compounds having a somatostatin receptor function-regulating effect include those derived from the compounds having a somatostatin receptor function-regulating effect by acylating, alkylating of phosphorylating the amino group of the compounds (e.g., those derived from the compounds having a somatostatin receptor function-regulating effect by eicosanoylating, alanylating, pentylaminocarbonylating, (5-methyl-2-oxo-1,3-dioxolen-1-yl)methoxycarbonylating, tetrahydrofuranylating, pyrrolidylmethylating, pivaloyloxymethylating or tert-butylating the amino group of the compounds, etc.); those derived from the compounds having a somatostatin receptor function-regulating effect by acylating, alkylating, phosphorylating or borylating the hydroxy group of the compounds (e.g., those derived from the compounds having a somatostatin receptor function-regulating effect by acetylating, palmitoylating, propanoylating, pivaloylating, succinylating, fumarylating, alanylating or dimethylaminomethylcarbonylating the hydroxy group of the compounds, etc.); those derived from the compounds having a somatostatin receptor function-regulating effect by esterifying or amidating the carboxyl group of the compounds (e.g., those derived from the compounds having a somatostatin receptor function-regulating effect by ethyl-esterifying, phenyl-esterifying, carboxymethyl-esterifying, dimethylaminomethyl-esterifying, pivaloyloxymethyl-esterifying, ethoxycarbonyloxyethyl-esterifying, phthalidyl-esterifying, (5-methyl-2-oxo-1,3-dioxolen-4-yl)methyl-esterifying, cyclohexyloxycarbonylethyl-esterifying or methyl-amidating the carboxyl group of the compounds, etc.), etc. These compounds may be derived from the compounds having a somatostatin receptor function-regulating effect in any per-se known method.

In addition, the prodrugs of the compounds having a somatostatin receptor function-regulating effect may be those capable of being converted into the intended compounds having a somatostatin receptor function-regulating effect under physiological conditions, for example, as in Development of Medicines, Vol. 7, Molecular Planning, pp. 163–198 (published by Hirokawa Shoten, 1990).

The compounds having a somatostatin receptor function-regulating effect may be in any form of hydrates or non-hydrates. In addition, the compounds having a somatostatin receptor function-regulating effect may be labeled with isotopes (e.g., $^3$H, $^{14}$C, $^{35}$S, $^{125}$I, etc.), etc.

The somatostatin receptor function-regulating (controlling) referred to herein is meant to indicate that the compounds activate or suppress the function of somatostatin receptors. The somatostatin receptor function activation means that the compounds activate the somatostatin receptor transmission system. Substances having the activity are usable as somatostatin receptor ligands, somatostatin receptor ligand agonists, somatostatin receptor agonists, somatostatin receptor co-activator agonists, etc.; and they all enjoy the same response as that to be produced by somatostatin receptors acting on ligands.

The somatostatin receptor function suppression means that the compounds suppress the somatostatin receptor transmission system. Substances having the activity are usable as somatostatin receptor antagonists, etc.; and they all suppress the response to be produced by somatostatin receptors acting on ligands.

Of the somatostatin receptor function-regulating effect mentioned above, the compounds (I) or their salts of the invention preferably have the somatostatin receptor agonistic effect.

The compounds (I) or their salts of the invention are non-toxic and have few side effects, and are therefore usable as various preventive agents, diagnostic agents or treating agents for mammals (e.g., humans, bovines, equines, dogs, cats, monkeys, mice, rats, etc.; especially humans). The compounds (I) or their salts of the invention suppress or regulate the production or secretion of various hormones, growth factors, physiologically-active substances, etc. The hormones include, for example, growth hormone (GH), thyroid-stimulating hormone (TSH), prolactin, insulin, glucagon, etc. The growth factors include, for example, IGF-1, etc. The physiologically-active substances include, for example, vasoactive intestinal polypeptide (VIP), gastrin, glucagon-like peptide-1, amylin, substance-P, CGRP, CCK (cholecystokinin), amylase, etc. The physiologically-active substances further include interleukins and cytokines such as TNF-α, etc. These compounds act via various somatostatin-related intracellular information transmission systems. Various transfer factors participate in the intracellular information transmission systems, including, for example, adenylate cyclase, $K^+$ channel, $Ca^{2+}$ channel, protein dephosphorylation, phospholipase C/inositol-3-phosphorylation, MAP kinase, $Na^+/H^+$ exchange, phospholipase A2, NF-κB, etc. These compounds and their salts regulate direct or indirect cell growth suppression or apoptosis.

Accordingly, the compounds (I) or their salts of the invention are effective for disorders accompanied by abnormal production or secretion of these hormones, growth factors, physiologically-active substances, etc.; disorders accompanied by the abnormality of these intracellular information transmission systems (for example, excessive promotion or suppression of the systems); or disorders accompanied by abnormal cell growth control. Concretely, the compounds (I) or their salts of the invention can be used for (1) treating medicines for acromegaly and for various tumors such as TSH-producing tumor, non-secreting (non-functional) pituitary tumor, ectopic ACTH (adrenocorticotropin)-producing tumor, medullary thyroid carcinoma, VIP-producing tumor, glucagon-producing tumor, gastrin-producing tumor, insulinoma, carcinoid, etc.; (2) treating medicines for insulin-dependent or independent diabetes, or various disorders associated with such diabetes, for example, diabetic retinopathy, diabetic nephropathy, diabetic neuropathy, Down's syndrome, orthostatic hypotension, etc.; (3) treating medicines for obesity caused by relief of hyperinsulinemia or suppression of appetite, or for hyperphagia, etc.; (4) treating medicines for acute pancreatitis, chronic pancreatitis, pancreatic and intestinal fistulae, hematoid ulcer, digestive ulcer, gastritis, gastroxynsis, etc. (because the compounds (I) or their salts suppress or regulate exocretion in digestive tubes); (5) medicines for relieving various disorders caused by *Helicobacter pylori* infections, for example, suppressants for gastrin hypersecretion; (6) amylase secretion suppressants after endoscopic cholangiopancreatography, and treating medicines after surgical operation of pancreas; (7) treating medicines for diarrhea caused by intestinal malabsorption or hypersecretion, or by digestive hypokinesis (e.g., short bowel syndrome, etc.), diarrhea caused by internal chemotherapy of cancers, diarrhea caused by congenital intestinal atrophy, diarrhea caused by neuroendocrine tumors such as VIP-producing tumor, etc., diarrhea caused by AIDS, diarrhea caused by host-to-implant reaction after marrow implantation, etc., diarrhea caused by diabetes, diarrhea caused by celiac plexus blocking, diarrhea caused by systemic scleroma, diarrhea caused by eosinophilia, etc.; (8) treating medicines for dumping syndrome, irritable bowel syndrome, Crone's disease, inflammatory enteropathy, etc.; (9) treating medicines for various cancers of which the growth depends on insulin or IGF-1 or on other growth factors, and for other tumors or cancers owing to cell growth suppression insufficiency caused by any other reasons (e.g., thyroid cancer, colon cancer, breast cancer, prostate cancer, microcytic lung cancer, non-microcytic lung cancer, pancreas cancer, stomach cancer, cholangiocarcinoma, liver cancer, bladder cancer, ovary cancer, uterine cancer, melanoma, osteosarcoma, chondrosarcoma, malignant pheochromocytoma, neuroblastoma, brain tumor, thymoma, kidney cancer, etc.), leukemia (e.g., basophilic leukemia, chronic lymphocytic leukemia, chronic myelocytic leukemia, Hodgkin's disease, non-Hodgkinic lymphoma, etc.), etc. (the treating medicines for these cancers may be used singly or as combined with any other carcinostatics such as, for example, tamoxifen, LHRH agonist, LHRH antagonist, interferon-$\alpha$, interferon-$\beta$, interferon-$\gamma$, interleukin-2, etc.); (10) preventive and treating medicines for hypergenic myocardosis, arteriosclerosis, cardiovalvulitis, myocardial infarction (especially, myocardial infarction after percutaneous intravascular coronary arteriplasty), and revascularization; (11) treating medicines for esophageal varices hemorrhage, hepatocirrhosis, and distal angiopathy; (12) treating medicines for disorders caused by systemic or local inflammations, for example, polyarteritis, rheumatic arthritis, lepra, sunburn, eczema, allergy (e.g., asthma, atopic dermatitis, allergic rhinitis, etc.), etc. (as the compounds (I) or their salts suppress or regulate the secretion of physiologically-active substances acting on immune systems, such as substance P, taphykinin, cytokine, etc.); (13) treating medicines for dementia (e.g., Alzheimer's disease, Alzheimer-type senile dementia, vascular polydementia, etc.), headache, migraine, schizophrenia, epilepsy, melancholia, general anxiety neurosis, sleep disorder, polyscleroma, etc. (as the compounds (I) or their salts have influences on the production and secretion of nerve regulating factors); (14) sedatives; (15) treating medicines for acute bacterial meningitis, acute viral encephalitis, adult hyper-respiration syndrome, bacterial pneumonia, grave systemic mycosepsis, tuberculosis, spinal marrow damage, fracture, hepatic insufficiency, pneumonia, alcoholic hepatitis, hepatitis type A, hepatitis type B, hepatitis type C, AIDS infectious diseases, human papilloma virus infectious diseases, influenza infectious diseases, cancer metastasis, polymyeloma, osteomalacia, osteoporosis, Paget's disease (osteitis deformans), retrograde esophagitis, nephritis, renal insufficiency, septicemia, septic shock, hypercalcemia, hypercholesterolemia, hyperglyceridemia, hyperlipemia, systemic lupus erythematosus, transient ischemic attack, alcoholic hepatitis, etc.; (16) treatment of organ transplants, burns, wounds, alopecia, etc.; (17) treating medicines for ophthalmopathy (e.g., glaucoma, etc.); (18) imaging of somatostatin receptor-having tumors, for which a radioactive substance (e.g., $^{123}$I, $^{125}$I, $^{111}$In, etc.) is introduced into the compounds (I) or their salts directly or via a suitable spacer; and (19) targeting of somatostatin receptor-having tumors, for which a carcinostatic is introduced into the compounds (I) or their salts directly or via a suitable spacer, etc.

The compounds (I) or their salts of the invention may be used directly as they are, but, in general, they may be formulated into pharmaceutical compositions along with suitable doses of pharmaceutical carriers in some known manner. The pharmaceutical carriers include vehicles (e.g., calcium carbonate, kaolin, sodium hydrogencarbonate, lactose, D-mannitol, starches, crystalline cellulose, talc, granular sugar, porous substances, etc.), binders (e.g., dextrin, rubbers, alpha starch, gelatin, hydroxypropyl cellulose, hydroxypropylmethyl cellulose, pullulan, etc.), thickeners (e.g., natural gums, cellulose derivatives, acrylic acid derivatives, etc.), disintegrators (e.g., calcium carboxymethyl cellulose, sodium cross-carmellose, cross-povidone, low-substitution hydroxypropyl cellulose, partial-alpha starch, etc.), solvents (e.g., water for injection, alcohol, propylene glycol, macrogol, sesame oil, corn oil, etc.), dispersants (e.g., Tween 80, HCO 60, polyethylene glycol, carboxymethyl cellulose, sodium alginate, etc.), dissolution promoters (e.g., polyethylene glycol, propylene glycol, D-mannitol, benzyl benzoate, ethanol, trisaminomethane, triethanolamine, sodium carbonate, sodium citrate, etc.), suspending agents (e.g., stearyltriethanolamine, sodium laurylsulfate, benzalkonium chloride, polyvinyl alcohol, polyvinyl pyrrolidone, hydroxymethyl cellulose, etc.), analgesics (e.g., benzyl alcohol, etc.), isotonic agents (e.g., sodium chloride, glycerin, etc.), buffers (e.g., phosphates, acetates, carbonates, citrates, etc.), lubricants (e.g., magnesium stearate, calcium stearate, talc, starch, sodium benzoate, etc.), colorants (e.g., tar dye, caramel, iron sesquioxide, titanium oxide, riboflavins, etc.), flavorings (e.g., sweeteners, aromatics, etc.), stabilizers (e.g., sodium sulfite, ascorbic acid, etc.), preservatives (e.g., parabens, sorbic acid, etc.), etc. The preventive and treating medicines of the invention that optionally contain pharmaceutical carriers such as those mentioned above contain a necessary amount of any of the compounds (I) or their pharmaceutically-acceptable salts of the invention for preventing and treating the intended disorders. The amount of the compounds (I) or their pharmaceutically-acceptable salts of the invention in the pharmaceutical compositions of the invention may be generally from 0.1 to 100% by weight of the total composition. Specific examples of the pharmaceutical compositions are tablets (including sugar-coated tablets, film-coated tablets), pills, capsules (including microcapsules), granules, powdery granules, powders, intravenous drip injections, syrups, emulsions, suspensions, injections, inhalations, ointments, suppositories, troches, cataplasms, etc. These pharmaceutical compositions may be prepared in any known manner (for example, according to the methods described in Japanese Pharmacopoeia, Ed. 12).

Methods for preparing typical pharmaceutical compositions of the invention are described below, which, however, are not limitative.

(1) Tablets:

The compound of the invention is directly or after having been uniformly mixed with a vehicle, a binder, a disintegrator or any other suitable additives, formulated into granules in a suitable manner, to which is added a lubricant, etc. The resulting mixture is shaped into tablets under pressure.

Next, if desired, they may be coated with a coating agent for taste masking, for enteric disintegration or for duration.

(2) Injections:

A predetermined amount of the compound of the invention is optionally mixed with a stabilizer, a dissolution promoter, a suspending agent, an emulsifier, a buffer, a preservative, etc., and dissolved, suspended or emulsified in water for injection, etc. to be a predetermined dose.

(3) Suppositories:

An oily or fatty base, a water-soluble base or any other suitable base is prepared, to which an emulsifier, a suspending agent or the like is optionally added. This is uniformly mixed with the compound of the invention, and shaped into suppositories.

(4) Capsules:

The compound of the invention is uniformly mixed with a suitable vehicle and other additives, or is granulated in any suitable manner, or the resulting granules are coated with a suitable coating agent. They are directly or lightly encapsulated.

The pharmaceutical compositions of the invention are non-toxic and are safe, and have an excellent somatostatin receptor agonistic effect. Therefore, they are useful as preventive and treating agents for the above-mentioned disorders.

The dose of the compound of the invention to be in the pharmaceutical compositions varies, depending on the compound selected, the type of animals (including men) to which the compositions are administered, and the dosage frequency, but is efficacious in a broad range. For example, when the pharmaceutical composition is orally administered to adult cases of acromegaly, diabetic complications, intractable diarrhea, diabetes or obesity, its dose per day may fall generally between about 0.001 and 20 mg/kg body weight, but preferably between about 0.2 and 3 mg/kg body weight, in terms of the effective dose of the compound (I) of the invention; but when it is non-orally administered or when it is combined with any other active ingredient or any other pharmaceutical composition, its dose will be smaller than its oral dose mentioned above. However, the clinical dose shall be determined, depending on the compound selected, the form of the composition, the age, the body weight, the sex and the condition of the patient, the administration route, the administration period and frequency, and other various parameters. In any case, it can be varied by the doctor for each patient.

The administration route of the pharmaceutical compositions of the invention is not specifically defined, as varying depending on various conditions. For example, the compositions may be orally or non-orally administered. The non-oral administration includes intravenous, intramuscular, subcutaneous, intranasal, intrarectal, intravaginal and intra-abdominal administration, etc. The administration period and frequency of the pharmaceutical compositions shall be varied in various conditions, and shall be suitably determined by the doctor for each patient. For example, the composition may be divided into plural portions for plural times of administration, or may be continuously administered every day, or may be administered intermittently; or a large amount thereof may be administered within a short period of time, or it may be administered repeatedly. For example, for oral administration, it is desirable that the composition is administered once a day, or in a few portions a day (especially, once a day or in two or three portions a day). Long-term intravenous dripping injection can apply to the pharmaceutical compositions of the invention.

The invention is described in more detail with reference to the following Examples and Experimental Examples, which, however, are to merely demonstrate the preferred embodiments of the invention and are therefore not intended to restrict the scope of the invention. Various changes and modifications can be made in the invention without departing from the spirit and scope of the invention. The meanings of the abbreviations referred to in the following Reference Examples and Examples are described below.

s: singlet d: doublet t: triplet q: quartet dd: double doublet dt: double triplet m: multiplet bs: broad singlet tt: triple triplet J: coupling constant room temperature: 0 to 30° C.

Some acid chlorides used in the following experiments are commercially-available ones; and some others are prepared by processing commercially-available carboxylic acids with oxalyl chloride in the same manner as in Example 184-(1) mentioned below. They are used directly as they are without being specifically purified.

EXAMPLE 1

N-[2-(3-aminomethylphenoxy)-4-chlorophenyl]-N-(4-biphenylmethyl)-N'-(2-fluorobenzyl)succinamide hydrochloride (1) A mixture of 3-methoxybenzylamine (81 g, 590 mmols) and 47% hydrobromic acid (300 ml) was stirred, while heated under reflux, for 10 hours. The reaction mixture was cooled, the solvent was evaporated away, and the residue was poured into water. To the resulting mixture, added was an aqueous solution (200 ml) of potassium hydroxide (34 g, 600 mmols), and stirred at room temperature for 30 minutes. Next, a diethyl ether solution (100 ml) of di-tert-butyl dicarbonate (129 g, 0.59 mmols) was dropwise added thereto at 0° C. over a period of 2 hours. The reaction mixture was stirred at 0° C. for 12 hours, and then extracted with diethyl ether. The extract was washed with brine, and then dried with anhydrous magnesium sulfate. This was concentrated under reduced pressure to give a crystal of N-tert-butoxycarbonyl-3-hydroxybenzylamine (111 g, 84%).

m.p. 73–74° C.

$^1$H-NMR (CDCl$_3$) δ: 1.46(9H,s), 4.24(2H,d,J=6 Hz), 4.95 (1H,bs), 6.59(1H,bs), 6.71–6.79(3H,m), 7.12–7.20(1H,m)

(2) A mixture of 4-chloro-2-fluoronitrobenzene (8,78 g, 50 mmols), N-tert-butoxycarbonyl-3-hydroxybenzylamine (11.2 g, 50 mmols), potassium carbonate (6.95 g, 50 mmols) and N,N-dimethylformamide (70 ml) was stirred at 100° C. for 12 hours. The reaction mixture was cooled, then poured into water, and extracted with ethyl acetate. The extract was washed with water, and then dried with anhydrous magnesium sulfate, and the solvent was evaporated away. The crystal precipitated was taken out through filtration. This is tert-butyl[3-(5-chloro-2-nitrophenoxy)benzyl]carbamate (15.8 g, 83.4%).

m.p. 122–123° C.

Elemental Analysis for $C_{18}H_{19}N_2O_5Cl$:

Calcd.: C, 57.07; H, 5.06; N, 7.40

Found: C, 57.18; H, 4.92; N, 7.33

$^1$H-NMR (CDCl$_3$) δ: 1.45(9H,s), 4.33(2H,d,J=6 Hz), 4.91 (1H,bs), 6.94–7.01(3H,m), 7.12–7.19(2H,m), 7.30(1H,t, J=7.7 Hz), 7.90(1H,d,J=8.6 Hz)

(3) 5% carbon-palladium (3.4 g) was added to an ethyl acetate (200 ml) solution of tert-butyl[3-(5-chloro-2-nitrophenoxy)benzyl]carbamate (11.4 g, 30 mmols). The resulting mixture was hydrogenated at room temperature under atmospheric pressure. The catalyst was removed through filtration, and the filtrate was concentrated under reduced pressure. The crystal precipitated was taken out through filtration. This is tert-butyl[3-(2-amino-5-chlorophenoxy) benzyl]carbamate (10.1 g, 96.2%).

m.p. 115–116° C.

Elemental Analysis for $C_{18}H_{21}N_2O_3Cl$:

Calcd.: C, 61.98; H, 6.07; N, 8.03

Found: C, 62.07, H, 5.99; N, 8.07

$^1$H-NMR (CDCl$_3$) δ: 1.45(9H,s), 3.41(2H,bs), 4.29(2H, d,J=5.8 Hz), 4.86(1H,bs), 6.75(1H,d,J=8.2 Hz), 6.81(1H,d, J=2.2 Hz), 6.85–6.92(2H,m), 6.96(1H,d,J=2.2 Hz), 7.02(1H, d,J=7.2 Hz), 7.29(1H,t,J=7.7 Hz)

(4) A mixture of tert-butyl[3-(2-amino-5-chlorophenoxy) benzyl]carbamate (3.48 g, 10 mmols), 4-phenylbenzaldehyde (2.19 g, 12 mmols), acetic acid (1 ml) and methanol (40 ml) was stirred at room temperature for 1 hour, to which was added sodium cyanoborohydride (0.75 g, 12 mmols). Next, this was stirred at room temperature for 3 hours. The reaction mixture was poured into water, and extracted with ethyl acetate. The extract was washed with water, then dried with anhydrous magnesium sulfate, and concentrated under reduced pressure. The residue was purified through silica gel column chromatography to give a prism crystal of tert-butyl [3-[2-(4-biphenylmethylamino)-5-chlorophenoxy]benzyl] carbamate (2.92 g, 56.7%).

m.p. 104–105° C.

Elemental Analysis for $C_{31}H_{31}N_2O_3Cl$:

Calcd.: C, 72.29; H, 6.07; N, 5.44

Found: C, 72.54; H, 6.07; N, 5.31

$^1$H-NMR (CDCl$_3$) δ: 1.45(9H,s), 4.30(2H,d,J=5.6 Hz), 4.40(2H,s), 4.68(1H,bs), 4.88(1H,bs), 6.61(1H,d,J=8.4 Hz), 6.79(1H,d,J=2.4 Hz), 6.87–6.98(3H,m), 7.03(1H,d,J=7.6 Hz), 7.30–7.48(6H,m), 7.55–7.60(4H,m)

(5) A mixture of tert-butyl[3-[2-(4-biphenylmethylamino)-5-chlorophenoxy]benzyl]carbamate (2.58 g, 5 mmols), ethylsuccinyl chloride (1.1 ml, 7.5 mmols), 4-dimethylaminopyridine (0.92 g, 7.5 mmols) and tetrahydrofuran (30 ml) was stirred at room temperature for 3 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-biphenylmethyl)-N-[2-[3-(tert-butoxycarbonylaminomethyl)phenoxy]-4-chlorophenyl]succinamate (2.65 g, 82.6%).

Elemental Analysis for $C_{37}H_{39}N_2O_6Cl$:

Calcd.: C, 69.09; H, 6.11; N, 4.36

Found: C, 68.97; H, 6.16; N, 4.39

$^1$H-NMR (CDCl$_3$) δ: 1.26(3H,t,J=7.4 Hz), 1.44(9H,s), 2.41–2.81(4H,m), 4.17(2H,q,J=7.4 Hz), 4.21(2H,d,J=5.6 Hz), 4.75(1H,d,J=14.3 Hz), 4.84(1H,bs), 5.03(1H,d,J=14.3 Hz), 6.68(3H,m), 7.22–7.57(1H,m)

(6) To a solution of ethyl N-(4-biphenylmethyl)-N-[2-[3-(tert-butoxycarbonylaminomethyl)phenoxy]-4-chlorophenyl]succinamate (2.57 g, 4 mmols) in tetrahydrofuran (10 ml) and ethanol (10 ml), added was aqueous 1 N sodium hydroxide solution (8 ml, 8 mmols). The resulting mixture was stirred at room temperature for 2 hours. Water was added to the reaction mixture, which was then acidified with 1 N hydrochloric acid added thereto. This was extracted with ethyl acetate. The extract was washed with water, and then dried with anhydrous magnesium sulfate. This was concentrated under reduced pressure to give an amorphous solid of N-(4-biphenylmethyl)-N-[2-[3-(tert-butoxycarbonylaminomethyl)phenoxy]-4-chlorophenyl]succinamic acid (2.4 g, 97.6%).

Elemental Analysis for $C_{35}H_{35}N_2O_6Cl.1/4H_2O$:

Calcd.: C, 67.85; H, 5.77; N, 4.52

Found: C, 67.89; H, 5.88; N, 4.44

$^1$H-NMR (CDCl$_3$) δ: 1.43(9H,s), 2.42–2.53(2H,m), 2.63–2.81(2H,m), 4.20(2H,q,J=6.0 Hz), 4.76(1H,d,J=14.8 Hz), 4.88(1H,bs), 5.03(1H,d,J=14.8 Hz), 6.72–6.78(2H,m), 7.00–7.08(3H,m), 7.22–7.57(11H,m)

(7) A mixture of N-(4-biphenylmethyl)-N-[2-[3-(tert-butoxycarbonylaminomethyl)phenoxy]-4-chlorophenyl]succinamic acid (0.92 g, 1.5 mmols), 2-fluorobenzylamine (0.21 ml, 1.8 mmols), diethyl cyanophosphate (0.25 ml, 1.8 mmols), triethylamine (0.25 ml, 1.8 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(4-biphenylmethyl)-N-[2-[3-(tert-butoxycarbonylaminomethyl)phenoxy]-4-chlorophenyl]-N'-(2-fluorobenzyl)succinamide (1.02 g, 94.4%).

Elemental Analysis for $C_{42}H_{41}N_3O_6ClF$:

Calcd.: C, 69.84; H, 5.72; N, 5.82

Found: C, 69.82; H, 5.55; N, 5.60

$^1$H-NMR (CDCl$_3$) δ: 1.42(9H,s), 2.47–2.61(4H,m), 4.19 (2H,d,J=7.4 Hz), 4.45(2H,d,J=6.0 Hz), 4.73(1H,d,J=14.4 Hz), 5.03(1H,d,J=14.4 Hz), 5.06(1H,bs), 6.48(1H,bs), 6.68–6.76(3H,m), 6.97–7.56(12H,m)

(8) A 2 N hydrochloric acid/ethyl acetate solution (10 ml) of N-(4-biphenylmethyl)-N-[2-[3-(tert-butoxycarbonylaminomethyl)phenoxy]-4-chlorophenyl]-N'-(2-fluorobenzyl) succinamide was stirred at room temperature for 1 hour. The reaction mixture was concentrated under reduced pressure. The solid precipitated was taken out through filtration, and washed with ethyl ether to give an amorphous solid of N-[2-(3-aminomethylphenoxy)-4-chlorophenyl]-N-(4-biphenylmethyl)-N'-(2-fluorobenzyl)succinamide hydrochloride (0.62 g, 95.4%).

Elemental Analysis for $C_{37}H_{34}N_3O_3Cl_2F.1/2H_2O$:

Calcd.: C, 66.57; H, 5.28; N, 6.29

Found: C, 66.29; H, 5.13; N, 6.11

$^1$H-NMR (DMSO-d$_6$) δ: 2.34–2.58(4H,m), 4.01(2H,s), 4.29(2H,s), 4.53(1H,d,J=14.9 Hz), 5.133(1H,d,J=14.9 Hz), 6.82(1H,d,J=1.8 Hz), 6.95(1H,d,J=8 Hz), 7.10(18H,m), 8.32–8.47(3H,m)

EXAMPLE 2

N-[2-(3-aminomethylphenoxy)-4-chlorophenyl]-N-(4-hydroxybenzyl)-N'-(2-fluorobenzyl)succinamide hydrochloride (1) A mixture of tert-butyl[3-(2-amino-5-chlorophenoxy) benzyl]carbamate (3.48 g, 10 mmols), 4-tert-butyldimethylsilyloxybenzaldehyde (2.19 g, 12 mmols), acetic acid (1 ml) and methanol (40 ml) was stirred at room temperature for 1 hour, to which was added sodium cyanoborohydride (0.75 g, 12 mmols). Next, this was stirred at room temperature for 3 hours. The reaction mixture was poured into water, and extracted with ethyl acetate. The extract was washed with water, then dried with anhydrous magnesium sulfate, and concentrated under reduced pressure. The residue was purified through silica gel column chromatography to give an oil of tert-butyl[3-[2-(4-tert-butyldimethylsilyloxybenzylamino)-5-chlorophenoxy]benzyl]carbamate (2.40 g, 42.4%).

Elemental Analysis for $C_{31}H_{41}N_2O_4ClSi \cdot 1/2H_2O$:
Calcd.: C, 64.39; H, 7.32; N, 4.84
Found: C, 64.82; H, 7.38; N, 4.53
$^1$H-NMR (CDCl$_3$) δ: 0.18(6H,m), 0.97(9H,s), 1.45(9H,s), 4.27–4.31(4H,m), 4.53(1H,bs), 4.83(1H,bs), 6.70–7.05(7H,m), 7.14–7.33(4H,m)

(2) A mixture of tert-butyl[3-[2-(4-tert-butyldimethylsilyloxybenzylamino)-5-chlorophenoxy]benzyl]carbamate (2.58 g, 5 mmols), ethylsuccinyl chloride (1.1 ml, 7.5 mmols), 4-dimethylaminopyridine (0.92 g, 7.5 mmols) and tetrahydrofuran (30 ml) was stirred at room temperature for 3 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-tert-butyldimethylsilyloxybenzyl)-N-[2-[3-(tert-butoxycarbonylaminomethyl)phenoxy]-4-chlorophenyl]succinamate (2.18 g, 31.3%).

Elemental Analysis for $C_{37}H_{49}N_2O_7ClSi \cdot 1/2H_2O$:
Calcd.: C, 62.92; H, 7.13; N, 3.97
Found: C, 63.21; H, 7.25; N, 3.70
$^1$H-NMR (CDCl$_3$) δ: 0.16(6H,s), 0.96(9H,s), 1.22(3H,t,J=7.0 Hz), 1.44(9H,s), 2.38–2.78(4H,m), 4.12(2H,q,J=7.0 Hz), 4.27(2H,d,J=6.2 Hz), 4.60(1H,d,J=14.2 Hz), 4.96(1H,d,J=14.2 Hz), 5.16(1H,bs), 6.60–6.81(4H,m), 6.97–7.11(5H,m), 7.26–7.34(2H,m)

(3) A mixture in tetrahydrofuran (20 ml) of ethyl N-(4-tert-butyldimethylsilyloxybenzyl)-N-[2-[3-(tert-butoxycarbonylaminomethyl)phenoxy]-4-chlorophenyl]succinamate (2.09 g, 3 mmols) and tetrabutylammonium fluoride trihydrate (0.95 g, 3 mmols) was stirred at room temperature for 2 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an amorphous solid of ethyl N-[2-[3-(tert-butoxycarbonylaminomethyl)phenoxy]-4-chlorophenyl]-N-(4-hydroxybenzyl) succinamate (1.68 g, 97%).

Elemental Analysis for $C_{31}H_{35}N_2O_7Cl$:
Calcd.: C, 63.86; H, 6.05; N, 4.80
Found: C, 63.66; H, 5.95; N, 4.53
$^1$H-NMR (CDCl$_3$) δ: 1.25(3H,t,J=7.2 Hz), 1.47(9H,s), 2.47–2.84(4H,m), 4.11(2H,q,J=7.2 Hz), 4.20–4.32(3H,m), 5.18(1H,t,J=6.4 Hz), 5.43(1H,d,J=13.2 Hz), 6.12(1H,bs), 6.63(2H,d,J=7.8 Hz), 6.78–7.07(5H,m), 7.27–7.32(3H,m)

(4) Aqueous 1 N sodium hydroxide solution (8 ml, 8 mmols) was added to a solution of ethyl N-[2-[3-(tert-butoxycarbonylaminomethyl)phenoxy]-4-chlorophenyl]-N-(4-hydroxybenzyl)succinamate (2.57 g, 4 mmols) in tetrahydrofuran (10 ml) and ethanol (10 ml). The resulting mixture was stirred at room temperature for 2 hours. Water was added to the reaction mixture, which was then acidified with 1 N hydrochloric acid added thereto. Then, this was extracted with ethyl acetate. The extract was washed with water, and then dried with anhydrous magnesium sulfate. This was concentrated under reduced pressure to give an amorphous solid of N-[2-[3-(tert-butoxycarbonylaminomethyl)phenoxy]-4-chlorophenyl]-N-(4-hydroxybenzyl) succinamic acid (1.47 g, 99%).

Elemental Analysis for $C_{29}H_{31}N_2O_7Cl \cdot 1/2H_2O$:
Calcd.: C, 61.75; H, 5.72; N, 4.97
Found: C, 61.99; H, 5.66; H, 4.78
$^1$H-NMR (CDCl$_3$) δ: 1.46(9H,s), 2.45–2.58(2H,m), 2.70–2.82(2H,m), 4.22(2H,d,J=6.0 Hz), 4.25–4.39(1H,m), 5.22(1H,bs), 5.55(1H,bs), 6.16(1H,s), 6.47(1H,s), 6.64(2H,d,J=8.4 Hz), 6.76–7.79(1H,m), 6.93–7.31(4H,m)

(5) A mixture of N-[2-[3-(tert-butoxycarbonylaminomethyl)phenoxy]-4-chlorophenyl]-N-(4-hydroxybenzyl)succinamic acid (0.67 g, 1.2 mmols), 2-fluorobenzylamine (0.16 ml, 1.4 mmols), diethyl cyanophosphate (0.20 ml, 1.4 mmols), triethylamine (0.20 ml, 1.4 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[2-[3(tert-butoxycarbonylaminomethyl)phenoxy]-4-chlorophenyl]-N-(4-hydroxybenzyl)-N'-(2-fluorobenzyl)succinamide (0.69 g, 97%).

Elemental Analysis for $C_{36}H_{37}N_3O_6ClF$:
Calcd.: C, 65.30; H, 5.63; H, 6.35
Found: C, 65.04; H, 5.80; N, 6.60
$^1$H-NMR (CDCl$_3$) δ: 1.46(9H,s), 2.54(4H,s), 4.21(2H,d,J=5.8 Hz), 4.23–4.28(1H,m), 4.45(2H,d,J=6.0 Hz), 5.26–5.37(1H,m), 6.13(1H,s), 6.61–6.65(4H,m), 6.78–6.34(12H,m)

(6) A 2 N hydrochloric acid/ethyl acetate solution (10 ml) of N-[2-[3-(tert-butoxycarbonylaminomethyl)phenoxy]-4-chlorophenyl]-N-(4-hydroxybenzyl)-N'-(2-fluorobenzyl) succinamide was stirred at room temperature for 1 hour. The reaction mixture was concentrated under reduced pressure. The solid precipitated was taken out through filtration, and washed with ethyl ether to give an amorphous solid of N-[2-(3-aminomethylphenoxy)-4-chlorophenyl]-N-(4-biphenylmethyl)-N'-(2-fluorobenzyl)succinamide hydrochloride (0.49 g, 83%).

Elemental Analysis for $C_{31}H_{30}N_3O_4ClF \cdot 1/2H_2O$:
Calcd.: C, 61.29; H, 5.14; N, 6.92
Found: C, 61.59; H, 5.10; N, 6.92
$^1$H-NMR (DMSO-d$_6$) δ: 2.28–2.45(4H,m), 4.03(2H,d,J=6.0 Hz), 4.26–4.33(3H,m), 5.03(1H,d,J=14 Hz), 6.63(2H,d,J=8.4 Hz), 6.79(1H,d,J=1.6 Hz), 6.97(2H,d,J=8.4 Hz), 6.99–7.46(10H,m), 8.43(3H,bs)

EXAMPLE 3

N-[2-(3-aminomethylphenoxy)-4-chlorophenyl]-N-(3,4-dichlorobenzyl)-N'-(2-fluorobenzyl)succinamide hydrochloride (1) A mixture of tert-butyl[3-(2-amino-5-chlorophenoxy)benzyl]carbamate (3.49 g, 10 mmols), 3,4-dichlorobenzyl chloride (2.1 ml, 15 mmols), potassium carbonate (1.38 g. 10 mmols) and N,N-dimethylformamide (30 ml) was stirred at room temperature for 12 hours. The reaction mixture was poured into water, and extracted with ethyl acetate. The extract was washed with brine, then dried with anhydrous magnesium sulfate, and concentrated under reduced pressure. The residue was purified through silica gel column chromatography to give an oil of tert-butyl[3-[5-chloro-2-(3,4-dichlorobenzylamino)phenoxy]benzyl]carbamate (3.03 g, 59.8%).

m.p. 104–105° C.

Elemental Analysis for $C_{25}H_{25}N_3O_3Cl_3$:

Calcd.: C, 59.13; H, 4.96; N, 5.52

Found: C, 59.03; H, 4.99; N, 5.34

$^1$H-NMR (CDCl$_3$) δ: 1.45(9H,s), 4.29–4.34(4H,m), 4.68 (2H, bs), 4.89(1H, bs), 6.47(1H,d,J=8.4 Hz), 6.80(1H,d,J=2 Hz), 6.86–6.95(3H,m), 7.03–7.07(1H,m), 7.23–7.48(6H,m), 7.19- (1H,dd,J=2, 8.4 Hz), 7.31–7.41(3H,m)

(2) A mixture of tert-butyl 3-[5-chloro-2-(3,4-dichlorobenzylamino)phenoxy]benzylcarbamate (2.79 g, 5.5 mmols), ethylsuccinyl chloride (1.2 ml, 8.3 mmols), 4-dimethylaminopyridine (1.01 g, 8.3 mmols) and tetrahydrofuran (30 ml) was stirred at room temperature for 1 hour, and then at 60° C. for 3 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-[2-[3-(tert-butoxycarbonylaminomethyl)phenoxy]-4-chlorophenyl]-N-(3,4-dichlorobenzyl)succinamate (3.34 g, 95.7%).

Elemental Analysis for $C_{31}H_{33}N_2O_6Cl_3.2H_2O$:

Calcd.: C, 55.41; H, 5.55; N, 4.17

Found: C, 55.16; H, 5.57; N, 4.45

$^1$H-NMR (CDCl$_3$) δ: 1.25(3H,t,J=7.0 Hz), 1.45(9H,s), 2.54–2.84(4H,m), 4.13(2H,q,J=7.0 Hz), 4.29(2H,d,J=5.8 Hz), 4.72(1H,d,J=14.8 Hz), 4.86(1H,d,J=14.8 Hz), 5.00(1H, bs), 6.71–6.82(2H,m), 7.01–7.13(4H,m), 7.25–7.35(4H,m)

(3) Aqueous 1 N sodium hydroxide solution (10 ml, 10 mmols) was added to a solution of ethyl N-[2-[3-(tert-butoxycarbonylaminomethyl)phenoxy]-4-chlorophenyl]-N-(2,3-dichlorobenzyl)succinamate (3.18 g, 5 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of N-[2-[3-(tert-butoxycarbonylaminomethyl)phenoxy]-4-chlorophenyl]-N-(3,4-dichlorobenzyl) succinamic acid (2.46 g, 81.2%).

Elemental Analysis for $C_{29}H_{29}N_3O_6Cl.3/4H_2O$:

Calcd.: C, 56.05; H, 4.78; H, 4.50

Found: C, 56.21; H, 4.79; N, 4.40

$^1$H-NMR (CDCl$_3$) δ: 1.44(9H,s), 2.45(2H,bs), 2.68(2H, bs), 4.28(2H,d,J=5.6 Hz), 4.59–4.92(2H,m), 5.04(1H,bs), 6.71–6.83(3H,m), 7.03–7.12(4H,m), 7.26–7.35(3H,m)

(4) A mixture of N-[2-[3-(tert-butoxycarbonylaminomethyl)phenoxy]-4-chlorophenyl]-N-(3,4-dichlorobenzyl) succinamic acid (0.91 g, 1.5 mmols), 2-fluorobenzylamine (0.23 g, 1.8 mmols), diethyl cyanophosphate (0.25 ml, 1.8 mmols), triethylamine (0.25 ml, 1.8 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[2-[3-(tert-butoxycarbonylaminomethyl)phenoxy]-4-chlorophenyl]-N-(3,4-dichlorobenzyl)-N'-(2-fluorobenzyl)succinamide (0.61 g, 57%).

Elemental Analysis for $C_{36}H_{35}N_3O_5Cl_3F$:

Calcd.: C, 60.47; H, 4.93; N, 5.88

Found: C, 60.26; H, 4.93; N, 5.78

$^1$H-NMR (CDCl$_3$) δ: 1.43(9H,s), 2.44–2.60(4H,m), 4.27 (2H,d,J=6.2 Hz), 4.45(2H,d,J=6.0 Hz), 4.71(1H,d,J=14.2 Hz), 4.85(2H,d,J=14.2 Hz), 5.17(1H,bs), 6.32(1H,bs), 6.71–6.81(3H,m), 6.97–7.19(5H,m), 7.22–7.33(6H,m)

(5) A 2 N hydrochloric acid/ethyl acetate solution (10 ml) of N-[2-[3-(tert-butoxycarbonylaminomethyl)phenoxy]-4-chlorophenyl]-N-(3,4-dichlorobenzyl)-N'-(2-fluorobenzyl) succinamide (0.50 g, 0.7 mmols) was stirred at room temperature for 1 hour. The reaction mixture was concentrated under reduced pressure. The solid precipitated was taken out through filtration, and washed with ethyl ether to give an amorphous solid of N-[2-(3-aminomethylphenoxy)-4-chlorophenyl]-N-(3,4-dichlorobenzyl)-N'-(2-fluorobenzyl)succinamide hydrochloride (0.37 g, 82.2%).

Elemental Analysis for $C_{31}H_{28}N_3O_3Cl_4F$:

Calcd.: C, 57.16; H, 4.33; N, 6.45

Found: C, 56.99; H, 4.39; N, 6.30

$^1$H-NMR (DMSO-d$_6$) δ: 2.23–2.52(4H,m), 4.03(2H,s), 4.29(2H,s), 4.54(1H,d,J=15.3 Hz), 5.00(1H,d,J=15.3 Hz), 6.85(1H,d,J=2.2 Hz), 6.99(1H,d,J=8.2 Hz), 7.13–7.50(12H, m), 8.41(3H,bs)

EXAMPLE 4

N-[2-(3-aminomethylphenoxy)-4-hydroxyphenyl]-N-(4-biphenylmethyl)-N'-(2-fluorobenzyl)succinamide hydrochloride (1) A mixture of 3-fluoro-4-nitrophenol (5.03 g, 32 mmols), benzyl bromide (4.5 ml, 38.4 mmols), potassium carbonate (4.42 g, 32 mmols) and N,N-dimethylformamide (50 ml) was stirred at room temperature for 1.5 hours. The reaction mixture was poured into water, and extracted with ethyl acetate. The extract was washed with water, and then dried with anhydrous magnesium sulfate, and the solvent was evaporated away. The crystal precipitated was taken out through filtration. This is 4-benzyloxy-2-fluoronitrobenzene (6.47 g, 81.8%).

m.p. 83–84° C.

Elemental Analysis for $C_{13}H_{10}NO_3F$:

Calcd.: C, 63.16; H, 4.08; N, 5.67

Found: C, 63.07; H, 4.01; N, 5.68

$^1$H-NMR (CDCl$_3$) δ: 5.15(2H,s), 6.76–6.86(2H,m), 7.40–7.43(5H,m), 8.05–8.16(1H,m)

(2) A mixture of 4-benzyloxy-2-fluoronitrobenzene (6.43 g, 26 mmols), N-tert-butoxycarbonyl-3-hydroxybenzylamine (5.78 g, 26 mmols), potassium carbonate (3.59 g, 26 mmols) and N,N-dimethylformamide (70 ml) was stirred at 100° C. for 12 hours. The reaction mixture was cooled, then poured into water, and extracted with ethyl acetate. The extract was washed with water, and then dried with anhydrous magnesium sulfate, and the solvent was evaporated away to give an yellow oil of tert-butyl[3-(5-benzyloxy-2-nitrophenoxy)benzyl]carbamate (11.2 g, 95.0%).

Elemental Analysis for $C_{25}H_{26}N_2O_6$:

Calcd.: C, 66.65; H, 5.82; N, 6.22

Found: C, 66.30; H, 5.79; N, 6.00

$^1$H-NMR (CDCl$_3$) δ: 1.44(9H, s), 4.31(2H,d,J=6.2 Hz), 4.90(1H,bs), 5.02(2H,s), 6.47(1H,d,J=2.6 Hz), 6.74(1H,dd, J=2.6,9.2 Hz), 6.88–6.96(2H,m), 7.11(1H,d,J=7.8 Hz), 7.26–7.41(6H,m), 8.06(1H,d,J=9.2 Hz)

(3) 5% carbon-palladium (3.2 g) was added to an ethyl acetate (300 ml) solution of tert-butyl[3-(5-benzyloxy-2-nitrophenoxy)benzyl]carbamate (10.5 g, 23.3 mmols). The resulting mixture was hydrogenated at room temperature under atmospheric pressure. The catalyst was removed through filtration, and the filtrate was concentrated under reduced pressure to give a brown oil of tert-butyl[3-(2-amino-5-hydroxyphenoxy)benzyl]carbamate (7.6 g, 98.8%).

$^1$H-NMR (CDCl$_3$) δ: 1.43(9H,s), 4.23(2H,d,J=6.2 Hz), 5.06(1H,bs), 6.31(1H,d,J=2.4 Hz), 6.44(1H,dd,J-=2.4,8.4 Hz), 6.66(1H,d,J=8.4 Hz), 6.79–6.84(2H,m), 6.94(1H,d, J=7.6 Hz), 7.20(1H,d,J=7.6 Hz)

(4) A mixture of tert-butyl[3-(2-amino-5-hydroxyphenoxy)benzyl]carbamate (3.30 g, 10 mmols), 4-phenylbenzaldehyde (2.18 g, 12 mmols), acetic acid (1 ml), methanol (15 ml) and tetrahydrofuran (15 ml) was stirred at room temperature for 1 hour, to which was added sodium borocyanohydride (0.75 g, 12 mmols). Then, this was stirred at room temperature for 5 hours. The reaction mixture was poured into water, and extracted with ethyl acetate. The extract was washed with brine, then dried with anhydrous magnesium sulfate, and concentrated under reduced pressure. The residue was purified through silica gel column chromatography to give a prism crystal of tert-butyl[3-[2-(4-biphenyl)methylamino-5-hydroxyphenoxy]benzyl]carbamate (3.37 g, 67.9%).

m.p. 168–169° C.

Elemental Analysis for C$_{31}$H$_{32}$N$_2$O$_4$:

Calcd.: C, 74.98; H, 6.50; N, 5.64

Found: C, 75.03; H, 6.23, N, 5.45

$^1$H-NMR (CDCl$_3$) δ: 1.43(9H,s), 4.25(2H,d,J=6.2 Hz), 4.35(3H,s), 4.90(1H,bs), 5.33(1H,bs), 6.37(1H,bs), 6.47–6.64(2H,m), 6.83–6.99(3H,m), 7.20–7.60(10H,m)

(5) A mixture of tert-butyl[3-[2-(4-biphenyl)methylamino-5-hydroxyphenoxy]benzyl]carbamate (2.98 g, 6 mmols), ethylsuccinyl chloride (2.6 ml, 18 mmols), 4-dimethylaminopyridine (2.2 g, 18 mmols) and tetrahydrofuran (30 ml) was stirred at room temperature for 3 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-biphenylmethyl)-N-[2-[3-(tert-butoxycarbonylaminomethyl)phenoxy]-4-[3-(ethoxycarbonyl)propionyloxy]phenyl]succinamate (4.5 g, 100%).

Elemental Analysis for C$_{43}$H$_{48}$N$_2$O$_{10}$.1/2H$_2$O:

Calcd.: C, 67.79; H, 6.48; N, 3.68

Found: C, 67.61; H, 6.51; N, 3.63

$^1$H-NMR (CDCl$_3$) δ: 1.19–1.30(6H,m), 1.44(9H,s), 2.41–2.84(8H,m), 4.08–4.21(6H,m), 4.75(1H,d,J=14.5 Hz), 4.87(1H,bs), 5.04(1H,d,J=14.5 Hz), 6.57(1H,d,J=2.2 Hz), 6.71(2H,d,J=7.4 Hz), 6.81(1H,dd,J=2.6,8.4 Hz), 7.04(1H,d, J=7.8 Hz), 7.13(1H,d,J=7.8 Hz), 7.21–7.56(10H,m)

(6) Aqueous 1 N sodium hydroxide solution (23 ml, 23 mmols) was added to a solution of ethyl N-(4-biphenylmethyl)-N-[2-[3-(tert-butoxycarbonylaminomethyl)phenoxy]-4-[3-(ethoxycarbonyl)propionyloxy]phenyl]succinamate (4.51 g, 6 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of N-(4-biphenylmethyl)-N-[2-[3-(tert-butoxycarbonylaminomethyl)phenoxy]-4-hydroxyphenyl]succinamic acid (3.5 g, 97.8%).

Elemental Analysis for C$_{35}$H$_{36}$N$_2$O$_7$.1/2H$_2$O.1/2 ethyl acetate:

Calcd.: C, 68.40; H, 6.36; N, 4.31

Found: C, 68.37; H, 6.14; N, 4.08

$^1$H-NMR (CDCl$_3$) δ: 1.39(9H, s), 2.45–2.48(2H,m), 2.57–2.61(2H,m), 4.02–4.04(2H,m), 4.71–4.94(3H,m), 6.18 (1H,s), 6.45–6.61(3H,m), 6.85–6.92(2H,m), 7.10–7.52(11H, m)

(7) A mixture of N-(4-biphenylmethyl)-N-[2-[3-(tert-butoxycarbonylaminomethyl)phenoxy]-4-hydroxyphenyl]succinamic acid (1.19 g, 2 mmols), 2-fluorobenzylamine (0.27 ml, 2.4 mmols), diethyl cyanophosphate (0.33 ml, 2.4 mmols), triethylamine (0.33 ml, 2.4 mmols) and N,N-diethylformamide (10 ml) was stirred at room temperature for 2 hours. The reaction mixture was poured into water, and extracted with ethyl acetate. The extract was washed with water, and the dried with anhydrous magnesium sulfate. This was concentrated under reduced pressure, and the residue was purified through silica gel column chromatography to give an amorphous solid of N-(4-biphenylmethyl)-N-[2-[3-(tert-butoxycarbonylaminomethyl)phenoxy]-4-hydroxyphenyl]-N'-(2-fluorobenzyl)succinamide (0.75 g, 53.6%).

Elemental Analysis for C$_{42}$H$_{42}$N$_3$O$_6$F.1/2H$_2$O:

Calcd.: C, 70.77; H, 6.08; N, 5.90

Found: C, 71.08; H, 6.06; N, 6.14

$^1$H-NMR (CDCl$_3$) δ: 1.40(9H,s), 2.47(4H,bs), 4.06–4.07 (1H,m), 4.40(2H,d,J=5.4 Hz), 4.68(1H,d,J=14.3 Hz), 4.92 (1H,d,J=14.3 Hz), 4.98(1H,bs), 6.26(1H,d,J=3 Hz), 6.43 (1H,dd,J=2.8,8.6 Hz), 6.60–6.65(2H,m), 6.76–7.53(16H,m), 8.42(1H,bs)

(8) A 2 N hydrochloric acid/ethyl acetate solution (10 ml) of N-(4-biphenylmethyl)-N-[2-[3-(tert-butoxycarbonylaminomethyl)phenoxy]-4-hydroxyphenyl]-N'-(2-fluorobenzyl) succinamide (0.70 g, 1 mmols) was stirred at room temperature for 1 hour. The reaction mixture was concentrated under reduced pressure. The solid precipitated was taken out through filtration, and washed with ethyl ether to give an amorphous solid of N-[2-[3-(aminomethyl)phenoxy]-4-hydroxyphenyl]-N-(4-biphenylmethyl)-N'-(2-fluorobenzyl) succinamide hydrochloride (0.40 g, 62.5%).

Elemental Analysis for C$_{37}$H$_{35}$N$_3$O$_4$ClF.1/2H$_2$O:

Calcd.: C, 68.46; H, 5.59; N, 6.47

Found: C, 68.14; H, 5.37; N, 6.49

$^1$H-NMR (DMSO-d$_6$) δ: 2.33–2.51(4H,m), 4.01(2H,s), 4.40(2H,s), 4.40(1H,d,J=14.8 Hz), 5.13(1H,d,J=14.8 Hz), 6.29(1H,s), 6.50(1H,dd,J=2.1,8.5 Hz), 6.89–7.01(2H,m), 7.10–7.64(16H,m), 8.43(3H,bs)

EXAMPLE 5

N-(2-fluorobenzyl)-4-[N'-[4-chloro-2-(1,2,3,4-tetrahydroisoquinolin-5-yloxy)phenyl]-N'-(4-phenylbenzoyl)]aminobutylamide hydrochloride (1) Platinum oxide (100 mg) was added to an acetic acid (30 ml) solution of 5-hydroxyisoquinoline (2.9 g, 20 mmols), and this was hydrogenated at room temperature under atmospheric pressure. After the reaction, the catalyst was removed through filtration, and the filtrate was concentrated under reduced pressure. The residue was crystallized from toluene (20 ml) and taken out through filtration. The resulting crystal was dissolved in a mixture of aqueous 1 N sodium hydroxide solution (40 ml) and tetrahydrofuran (40 ml), to which was added di-tert-butyl dicarbonate (4.8 g, 22 mmols). The reaction mixture was stirred at room temperature for 1 hour, to which was added 1 N hydrochloric acid (40 ml). This was extracted with diethyl ether. The extract was dried with anhydrous magnesium sulfate, and the solvent was evaporated away under reduced pressure. The crystal precipitated was recrystallized from diisopropyl ether to give a colorless crystal of 2-tert-butoxycarbonyl-5-hydroxy-tetrahydroisoquinoline (2.9 g, 58%).

m.p. 163–164° C.

$^1$H-NMR (CDCl$_3$) δ: 1.49(9H,s), 2.76(2H,t,J=6.0 Hz), 3.67(1H,t,J=6.0 Hz), 4.56(2H,s), 5.50–5.90(1H,bs), 6.67–6.70(2H,m), 6.98–7.10(1H,m)

(2) A mixture of 4-chloro-2-fluoronitrobenzene (1.93 g, 11 mmols), 2-tert-butoxycarbonyl-5-hydroxy-tetrahydroisoquinoline (2.74 g, 11 mmols), potassium carbonate (1.53 g, 11 mmols) and N,N-dimethylformamide (20 ml) was stirred at 60° C. for 24 hours. The reaction mixture was cooled, then poured into water, and extracted with ethyl acetate. The extract was washed with water, and then dried with anhydrous magnesium sulfate, and the solvent was evaporated away. The residue was purified through silica gel column chromatography to give an oil of 2-tert-butoxycarbonyl-5-(5-chloro-2-nitrophenoxy)-1,2,3,4-tetrahydroisoquinoline (4.35 g, 97.7%).

Elemental Analysis for $C_{20}H_{21}N_2O_5Cl$:
Calcd.: C, 59.33; H, 5.23; N, 6.92
Found: C, 59.06; H, 5.22; N, 7.00

$^1$H-NMR (CDCl$_3$) δ: 1.49(9H,s), 2.74(2H,t,J=6 Hz), 3.64 (2H,t,J=6.0 Hz), 4.64(2H,s), 6.81–6.87(2H,m), 7.04(1H,t, J=7.2 Hz), 7.13(1H,dd,J=2,8.8 Hz), 7.24(1H,d,J=7.8 Hz), 7.94(1H,d,J=8.8 Hz)

(3) 5% carbon-palladium (1.3 g) was added to an ethyl acetate (100 ml) solution of 2-tert-butoxycarbonyl-5-(5-chloro-2-nitrophenoxy)-1,2,3,4-tetrahydroisoquinoline (4.25 g, 10.5 mmols). The resulting mixture was hydrogenated at room temperature under atmospheric pressure. The catalyst was removed through filtration, and the filtrate was concentrated under reduced pressure. The residue was purified through silica gel column chromatography to give an oil of 5-(2-amino-5-chlorophenoxy)-2-tert-butoxycarbonyl-1,2,3,4-tetrahydroisoquinoline (2.95 g, 75%).

Elemental Analysis for $C_{20}H_{23}N_2O_3Cl$:
Calcd.: C, 64.08; H, 6.18; N, 7.47
Found: C, 64.09; H, 6.31; N, 7.48

$^1$H-NMR (CDCl$_3$) δ: 1.50(9H,s), 2.79(2H,t,J=5.8 Hz), 3.65(2H,t,J=5.8 Hz), 3.84(2H,bs), 4.71(2H,s), 6.63(1H,d, J=2.2 Hz), 6.70–6.75(2H,m), 6.87–6.94(2H,m), 7.15(1H,t, J=7.8 HZ)

(4) A mixture of 5-(2-amino-5-chlorophenoxy)-2-tert-butoxycarbonyl-1,2,3,4-tetrahydroisoquinoline (2.92 g, 7.8 mmols), ethyl 4-bromobutyrate (2.2 ml, 15.6 mmols), potassium carbonate (1.08 g, 10 mmols) and N,N-dimethylformamide (10 ml) was stirred at 60° C. for 3 hours. The reaction mixture was cooled, then poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[2-[2-(tert-butoxycarbonyl)-1,2,3,4-tetrahydroisoquinolin-5-yloxy]-4-chlorophenyl]aminobutyrate (2.47 g, 64.8%).

Elemental Analysis for $C_{26}H_{33}N_2O_5Cl$:
Calcd.: C, 63.86; H, 6.80; N, 5.73
Found: C, 63.73; H, 6.84; N, 5.52

$^1$H-NMR (CDCl$_3$) δ: 1.24(3H,t,J=7.4 Hz), 1.50(9H,s), 1.89–2.03(2H,m), 2.40(2H,t,J=7.2 Hz), 2.77(2H,t,J=5.9 Hz), 3.22(2H,t,J=6.9 Hz), 3.65(2H,t,J=6.9 Hz), 4.11(2H,q, J=7.4 Hz), 4.28(1H,bs), 4.62(2H,s), 6.57–6.73(3H,m), 6.90–6.97(2H,m), 7.19(1H,t,J=7.9 Hz)

(5) 4-Phenylbenzoyl chloride (1.6 g, 7.5 mmols) was added to a tetrahydrofuran (30 ml) solution of ethyl 4-[2-[2-(tert-butoxycarbonyl)-1,2,3,4-tetrahydroisoquinolin-5-yloxy]-4-chlorophenyl]aminobutyrate (2.45 g, 5 mmols) and 4-dimethylaminopyridine (1.22 g, 10 mmols). The reaction mixture was stirred at room temperature for 5 hours, then poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[N-[2-[2-(tert-butoxycarbonyl)-1,2,3,4-tetrahydroisoquinolin-5-yloxy]-4-chlorophenyl]-N-(4-phenylbenzoyl)]aminobutyrate (2.04 g, 58.5%).

Elemental Analysis for $C_{39}H_{41}N_2O_6Cl$:
Calcd.: C, 70.00; H, 6.18; N, 4.19
Found: C, 70.23; H, 6.24; N, 4.34

$^1$H-NMR (CDCl$_3$) δ: 1.24(3H,t,J=7.0 Hz), 1.48(9H,s), 2.04(2H,bs), 2.43–2.50(4H,m), 3.56(2H,bs), 3.90(1H,bs), 4.04(1H,bs), 4.12(2H,q,J=7 Hz), 4.59(2H,s), 6.10(1H,bs), 6.92–7.07(3H,m), 7.27–7.48(8H,m), 7.53–7.58(2H,m)

(6) Aqueous 1 N sodium hydroxide solution (4.5 ml, 4.5 mmols) was added to a solution of ethyl 4-[N-[2-[2-(tert-butoxycarbonyl)-1,2,3,4-tetrahydroisoquinolin-5-yloxy]-4-chlorophenyl]-N-(4-phenylbenzoyl)]aminobutyrate (2.01 g, 3 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of 4-[N-[2-[2-(tert-butoxycarbonyl)-1,2,3,4-tetrahydroisoquinolin-5-yloxy]-4-chlorophenyl]-N-(4-phenylbenzoyl)]aminobutyric acid (1.90 g, 99.0%).

Elemental Analysis for $C_{37}H_{37}N_2O_6Cl.1/2H_2O$:
Calcd.: C, 68.35; H, 5.89; N, 4.31
Found: C, 68.66; H, 5.90; N, 4.10

$^1$H-NMR (CDCl$_3$) δ: 1.47(9H,s), 1.95–2.09(2H,m), 3.54 (2H,bs), 3.84–3.89(1H,m), 4.11–4.18(1H,m), 4.59(2H,s), 6.06(1H,bs), 6.41(1H,s), 6.92–7.07(3H,m), 7.28–7.58(10H, m)

(7) A mixture of 4-[N-[2-[2-(tert-butoxycarbonyl)-1,2,3,4-tetrahydroisoquinolin-5-yloxy]-4-chlorophenyl]-N-(4-phenylbenzoyl)]aminobutyric acid (0.83 g, 1.3 mmols), 2-fluorobenzylamine (0.18 ml, 1.6 mmols), diethyl cyanophosphate (0.22 ml, 1.3 mmols), triethylamine (0.22 ml, 1.3 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[2-(tert-butoxycarbonyl)-1,2,3,4-tetrahydroisoquinolin-5-yloxy]-4-chlorophenyl]-N'-(4-phenylbenzoyl)]aminobutylamide (0.70 g, 72.2%).

Elemental Analysis for $C_{44}H_{43}N_3O_5ClF$:
Calcd.: C, 70.62; H, 5.79; N, 5.62
Found: C, 70.33; H, 5.61; H, 5.47

$^1$H-NMR (CDCl$_3$) δ: 1.47(9H,s), 1.97–2.05(2H,m), 2.36–2.49(4H,m), 3.53(2H,bs), 3.81–3.92(1H,m), 4.07–4.17 (1H,m), 4.53(2H,d,J=5.2 Hz), 4.58(2H,bs), 6.90(1H,bs), 6.39(1H,d,J=2 Hz), 6.92–7.13(5H,m), 7.23–7.58(13H,m)

(8) A 2 N hydrochloric acid/ethyl acetate solution (10 ml) of N-(2-fluorobenzyl)-4-[N'-[2-[2-(tert-butoxycarbonyl)-1,2,3,4-tetrahydroisoquinolin-5-yloxy]-4-chlorophenyl]-N'-

(4-phenylbenzoyl)]aminobutylamide (0.6 g, 0.8 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[4-chloro-2-(1,2,3,4-tetrahydroisoquinolin-5-yloxy) phenyl]-N'-(4-phenylbenzoyl)]aminobutylamide hydrochloride (0.46 g, 85.2%).

Elemental Analysis for $C_{39}H_{36}N_3O_3Cl_2F \cdot 1/2H_2O$:
Calcd.: C, 67.53; H, 5.38; N, 6.06
Found: C, 67.69; H, 5.32; N, 6.00
$^1$H-NMR (DMSO-$d_6$) δ: 1.87(2H,bs), 2.27(2H,s), 2.63 (2H,s), 3.28(2H,s), 3.82(2H,bs), 3.97(2H,bs), 4.29(2H,s), 6.40(1H,s), 7.10–7.67(18H,m), 8.37(1H,bs), 9.28(1H,bs)

EXAMPLE 6

N-(2-fluorobenzyl)-4-[N'-[2-(3-aminomethylphenoxy)-4-chlorophenyl]-N'-(4-phenylbenzoyl)]aminobutylamide hydrochloride (1) A mixture of tert-butyl[3-(2-amino-5-chlorophenoxy) benzylcarbamate (3.5 g, 10 mmols), ethyl 4-bromobutyrate (2.9 ml, 20 mmols), potassium carbonate (1.4 g, 10 mmols) and N,N-dimethylformamide (30 ml) was stirred at 60° C. for 3 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[2-[3-(tert-butoxycarbonylaminomethyl)phenoxy]-4-chlorophenyl]aminobutyrate (2.74 g, 59.3%).

Elemental Analysis for $C_{24}H_{31}N_2O_5Cl$:
Calcd.: C, 62.26; H, 6.75; N, 6.05
Found: C, 62.32; H, 6.84; N, 5.84
$^1$H-NMR (CDCl$_3$) δ: 1.24(3H,t,J=7.4 Hz), 1.45(9H,s), 1.85–1.99(2H,m), 2.37(2H,t,J=7.1 Hz), 3.19(2H,q,J=6.6 Hz), 4.11(2H,q,J=7.4 Hz), 4.20(2H,bs), 4.29(2H,d,J=6.2 Hz), 4.90(1H,bs), 6.64(1H,d,J=8.8 Hz), 6.76(1H,d,J=2.6 Hz9, 6.84–7.05(4H,m), 7.24–7.32(1H,m)

(2) 4-Phenylbenzoyl chloride (2.2 g, 10 mmols) was added to a tetrahydrofuran (20 ml) solution of ethyl 4-[2-[3-(tert-butoxycarbonylaminomethyl)phenoxy]-4-chlorophenyl]aminobutyrate (2.3 g, 5.0 mmols) and 4-dimethylaminopyridine (1.1 g, 1.8 mmols). The reaction mixture was stirred at room temperature for 3 hours, then poured into water, and extracted with ethyl acetate. The extract was washed with water, and then dried with anhydrous magnesium sulfate. This was concentrated under reduced pressure, and the residue was purified through silica gel column chromatography to give an amorphous solid of ethyl 4-[N-[2-[3-(tert-butoxycarbonylaminomethyl)phenoxy]-4-chlorophenyl]-N-(4-phenylbenzoyl)]aminobutyrate (2.06 g, 64.2%).

Elemental Analysis for $C_{37}H_{39}N_2O_6Cl$:
Calcd.: C, 69.09, H, 6.11; N, 4.36
Found: C, 68.86; H, 6.35; N, 4.21
$^1$H-NMR (CDCl$_3$) δ: 1.23(3H,t,J=7.2 Hz), 1.44(9H,s), 1.99(2H,t,J=7.4 Hz), 2.46(2H,t,J=7.4 Hz), 3.83–3.94(1H, m), 4.20–4.18(3H,m), 4.22(2H,d,J=5.8 Hz), 4.91(1H,bs), 6.47–6.64(3H,m), 6.98–7.10(2H,m), 7.19–7.28(2H,m), 7.31–7.48(7H,m), 7.55–7.59(2H,m)

(3) Aqueous 1 N sodium hydroxide solution (6 ml, 6 mmols) was added to a solution of ethyl 4-[N-[2-[3-(tert-butoxycarbonylaminomethyl)phenoxy]-4-chlorophenyl]-N-(4-phenylbenzoyl)]aminobutyrate (1.9 g, 3.0 mmols) in tetrahydrofuran (5 ml) and ethanol (5 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of 4-[N-[2-[3-(tert-butoxycarbonylaminomethyl)phenoxy]-4-chlorophenyl]-N-(4-phenylbenzoyl)]aminobutyric acid (1.73 g, 94,0%).

Elemental Analysis for $C_{35}H_{35}N_2O_6Cl \cdot 1/2H_2O$:
Calcd.: C, 67.35; H, 5.81; N, 4.49
Found: C, 67.68; H, 5.80; N, 4.44
$^1$H-NMR (CDCl$_3$) δ: 1.44(9H,s), 1.97(2H,bs), 2.50(2H, bs), 3.61(1H,bs), 3.96(1H,bs), 4.25(2H,d,J=6.2 Hz), 5.13 (1H,bs), 6.63–7.07(5H,m), 7.31–7.58(11H,m)

(4) A mixture of 4-[N-[2-[3-(tert-butoxycarbonylaminomethyl)phenoxy]-4-chlorophenyl]-N-(4-phenylbenzoyl)]aminobutyric acid (0.80 g, 1.3 mmols), 2-fluorobenzylamine (0.18 ml, 1.6 mmols), diethyl cyanophosphate (0.22 ml, 1.3 mmols), triethylamine (0.22 ml, 1.3 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-(4-phenylbenzoyl)]aminobutylamide (0.85 g, 90.4%).

Elemental Analysis for $C_{42}H_{41}N_3O_5ClF \cdot 1/4H_2O$:
Calcd.: C, 69.41; H, 5.76; N, 5.78
Found: C, 69.41; H, 5.72; N, 5.65
$^1$H-NMR (CDCl$_3$) δ: 1.43(9H,s), 1.94–2.01(2H,m), 2.34–2.44(2H,m), 3.77–3.83(1H,m), 4.07–4.17(1H,m), 4.19 (2H,d,J=7.8 Hz), 4.51(2H,d,J=5.4 Hz), 4.98(1H,bs), 6.44 (1H,d,J=8 Hz), 6.58(2H,d,J=9.8 Hz), 6.87(1H,bs), 6.99–7.12(11H,m), 7.54–7.59(2H,m)

(5) A 2 N hydrochloric acid/ethyl acetate solution (10 ml) of N-(2-fluorobenzyl)-4-[N'-[2-[3-(tert-butoxycarbonylaminomethyl)phenoxy]-4-chlorophenyl]-N'-(4-phenylbenzoyl)] aminobutylamide (0.72 g, 1.0 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-(3-aminomethylphenoxy)-4-chlorophenyl]-N'-(4-phenylbenzoyl)]aminobutylamide hydrochloride (0.61 g, 93.8%).

Elemental Analysis for $C_{37}H_{34}N_3O_3Cl_2F \cdot 1/2H_2O$:
Calcd.: C, 66.57; H, 5.28; N, 6.29
Found: C, 66.92; H, 5.27; N, 6.20
$^1$H-NMR (DMSO-$d_6$) δ: 1.75–1.88(2H,m), 2.21–2.35(2H,m), 3.68–3.81(2H,m), 4.00(2H,s), 4.29(2H,s), 5.50(1H,bs), 6.59(1H,bs), 6.63–6.72(1H,m), 7.15–7.68(18H,m), 8.44(2H,bs)

EXAMPLE 7

N-(2-fluorobenzyl)-5-[N'-[2-(3-aminomethylphenoxy)-4-chlorophenyl]-N'-(4-phenylbenzoyl)]aminovaleramide hydrochloride (1) A mixture of tert-butyl[3-(2-amino-5-chlorophenoxy) benzyl]carbamate (10.5 g. 30 mmols), ethyl 5-bromovalerate (10.2 ml, 60 mmols), potassium carbonate (4.2 g, 30 mmols) and N,N-dimethylformamide (100 ml) was stirred at 60° C. for 96 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 5-[2-[3-(tert-butoxycarbonylaminomethyl)phenoxy]-4-chlorophenyl]aminovalerate (8.65 g, 60.4%).

Elemental Analysis for $C_{25}H_{33}N_2O_5Cl.1/2H_2O$:
Calcd.: C, 61.75; H, 7.05; N, 5.76
Found: C, 62.14; H, 6.95; N, 5.64
$^1$H-NMR (CDCl$_3$) δ: 1.24(3H,t,J=7.0 Hz), 1.45(9H,s), 1.64–1.75(4H,m), 2.32(2H,t,J=6.6 Hz), 3.14(2H,t,J=6.3 Hz), 4.08(2H,q,J=7.0 Hz), 4.12(1H,bs), 4.29(2H,d,J=6.2 Hz), 4.93(1H,bs), 6.61(1H,d,J=8.8 Hz), 6.76(1H,d,J=2.2 Hz), 6.84–7.05(4H,m), 7.28(1H,t,J=7.9 Hz)

(2) 4-Phenylbenzoyl chloride (7.6 g, 35 mmols) was added to a tetrahydrofuran (50 ml) solution of ethyl 5-[2-[3-(tert-butoxycarbonylaminomethyl)phenoxy]-4-chlorophenyl]aminovalerate (8.40 g, 17.6 mmols). The reaction mixture was stirred at room temperature for 5 hours, then poured into water, and extracted with ethyl acetate. The extract was washed with water, and then dried with anhydrous magnesium sulfate. This was concentrated under reduced pressure, and the residue was purified through silica gel column chromatography to give a prism crystal of ethyl 5-[N-[2-[3-(tert-butoxycarbonylaminomethyl)phenoxy]-4-chlorophenyl]-N-(4-phenylbenzoyl)]aminovalerate (8.81 g, 76.2%).

m.p. 133–134° C.
Elemental Analysis for $C_{38}H_{41}N_2O_6Cl$:
Calcd.: C, 69.45; H, 6.29; N, 4.26
Found: C, 69.41; H, 6.39; N, 4.35
$^1$H-NMR (CDCl$_3$) δ: 1.23(3H,t,J=7.4 Hz), 1.44(9H,s), 1.92(4H,m), 2.34(2H,bs), 3.87(2H,bs), 4.11(1H,q,J=7.0 Hz), 4.23(2H,d,J=6.0 Hz), 4.94(1H,bs), 6.50–6.67(3H,m), 6.97–7.09(2H,m), 7.20–7.46(8H,m), 7.4–7.58(3H,m)

(3) Aqueous 1 N sodium hydroxide solution (6 ml, 6 mmols) was added to a solution of ethyl 5-[N-[2-[3-(tert-butoxycarbonylaminomethyl)phenoxy]-4-chlorophenyl]-N-(4-phenylbenzoyl)]aminovalerate (2.0 g, 3.0 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give a prism crystal of 5-[N-[2-[3-(tert-butoxycarbonylaminomethyl)phenoxy]-4-chlorophenyl]-N-(4-phenylbenzoyl)]aminovaleric acid (1.83 g, 96.8%).

m.p. 141–142° C.
Elemental Analysis for $C_{36}H_{37}N_2O_6Cl$:
Calcd.: C, 68.73; H, 5.93; N, 4.45
Found: C, 68.71; H, 5.86; N, 4.61
$^1$H-NMR (CDCl$_3$) δ: 1.43(9H,s), 1.70(4H,bs), 2.67(2H,bs), 3.35–3.67(1H,m), 4.24–4.29(1H,m), 4.28(2H,s), 5.18(1H,bs), 6.43–6.58(2H,m), 6.91–7.06(3H,m), 7.21–7.59(11H,m)

(4) A mixture of 5-[N-[2-[3-(tert-butoxycarbonylaminomethyl)phenoxy]-4-chlorophenyl]-N-(4-phenylbenzoyl)]aminovaleric acid (0.82 g, 1.3 mmols), 2-fluorobenzylamine (0.18 ml, 1.6 mmols), diethyl cyanophosphate (0.22 ml, 1.3 mmols), triethylamine (0.22 ml, 1.3 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-5-[N'-[2-[3-(tert-butoxycarbonylaminomethyl)phenoxy]-4-chlorophenyl]-N'-(4-phenylbenzoyl)]aminovaleramide (0.67 g, 70.5%).

Elemental Analysis for $C_{43}H_{43}N_3O_6ClF.1/2H_2O$:
Calcd.: C, 69.30; H, 5.95; N, 5.64
Found: C, 69.60; H, 5.94; N, 5.67
$^1$H-NMR (CDCl$_3$) δ: 1.42(9H,s), 1.67(4H,bs), 2.27–2.30(2H,m), 3.81(1H,bs), 3.98(1H,bs), 4.20(2H,d,J=6.4 Hz), 4.47(2H,d,J=5.8 Hz), 5.00(1H,bs), 6.36(1H,bs), 6.48–6.65(3H,m), 6.94–7.09(4H,m), 7.18–7.47(11H,m), 7.53–7.58(2H,m)

(5) A 2 N hydrochloric acid/ethyl acetate solution (10 ml) of N-(2-fluorobenzyl)-5-[N'-[2-[3-(tert-butoxycarbonylaminomethyl)phenoxy]-4-chlorophenyl]-N'-(4-phenylbenzoyl)]aminovaleramide (0.59 g, 0.8 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-5-[N'-[2-(3-aminomethylphenoxy)-4-chlorophenyl]-N'-(4-phenylbenzoyl)]aminovaleramide hydrochloride (0.46 g, 86.8%).

Elemental Analysis for $C_{38}H_{36}N_3O_3Cl_2F.1/2H_2O$:
Calcd.: C, 66.96; H, 5.47; N, 6.16
Found: C, 67.22; H, 5.50; N, 6.28
$^1$H-NMR (DMSO-d$_6$) δ: 1.58(4H,bs), 2.19(2H,bs), 3.76(2H,s), 4.01(2H,s), 4.28(2H,d,J=4.8 Hz), 6.58–6.68(2H,m), 7.09–7.67(18H,m), 8.36(3H,bs)

EXAMPLE 8

N-(2-fluorobenzyl)-6-[N'-[2-(3-aminomethylphenoxy)-4-chlorophenyl]-N'-(4-phenylbenzoyl)]aminohexanamide hydrochloride (1) A mixture of tert-butyl[3-(2-amino-5-chlorophenoxy)benzyl]carbamate (3.5 g, 10 mmols), ethyl 6-bromohexanoate (3.6 ml, 21 mmols), potassium carbonate (4.2 g, 10 mmols) and N,N-dimethylformamide (30 ml) was stirred at 60° C. for 24 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 6-[2-[3-(tert-butoxycarbonylaminomethyl)phenoxy]-4-chlorophenyl]aminohexanoate (2.29 g, 46.6%).

Elemental Analysis for $C_{26}H_{35}N_2O_5Cl$:
Calcd.: C, 63.60, H, 7.18; N, 5.71
Found: C, 63.83; H, 7.23; N, 5.59
$^1$H-NMR (CDCl$_3$) δ: 1.24(3H,t,J=7.4 Hz), 1.33–1.45(12H,m), 1.55–1.72(4H,m), 2.28(2H,t,J=7.4 Hz), 3.04–3.19(2H,m), 4.08(2H,q,J=7.4 Hz), 4.29(2H,d,J=5.8 Hz), 4.92(1H,bs), 6.61(1H,d,J=8.8 Hz), 6.75(1H,dd,J=2.2 Hz), 6.84–7.04(4H,m), 7.24–7.32(1H,m)

(2) 4-Phenylbenzoyl chloride (7.6 g, 35.2 mmols) was added to a tetrahydrofuran (50 ml) solution of ethyl 6-[2-[3-(tert-butoxycarbonylaminomethyl)phenoxy]-4-chlorophenyl]aminohexanoate (8.40 g, 17.6 mmols) and 4-dimethylaminopyridine (4.3 g, 35.2 mmols). The reaction mixture was stirred at room temperature for 12 hours, and then at 60° C. for 96 hours. This was poured into water, and extracted with ethyl acetate. The extract was washed with water, and then dried with anhydrous magnesium sulfate.

This was concentrated under reduced pressure, and the residue was purified through silica gel column chromatography to give an oil of ethyl 6-[N-[2-[3-(tert-butoxycarbonylaminomethyl)phenoxy]-4-chlorophenyl]-N-(4-phenylbenzoyl)]aminohexanoate (2.47 g, 81.8%).

Elemental Analysis for $C_{39}H_{43}N_2O_6Cl.1/2H_2O$:
Calcd.: C, 69.79; H, 6.46; N, 4.17
Found: C, 69.59; H, 6.77; N, 4.14
$^1$H-NMR (CDCl$_3$) δ: 1.17–1.30(7H,m), 1.44(9H,s), 1.54–1.72(1H,m), 2.28(2H,t,J=7.3 Hz), 3.78–3.87(2H,m), 4.12(2H,q,J=7.0 Hz), 4.23(2H,d,J=6.0 Hz), 4.92(1H,bs), 6.54–6.66(3H,m), 6.98–7.09(2H,m), 7.21(2H,d,J=8.2 Hz), 7.34–7.47(7H,m), 7.54–7.59(2H,m)

(3) Aqueous 1N sodium hydroxide solution (7 ml, 7 mmols) was added to a solution of ethyl 6-[N-[2-[3-(tert-butoxycarbonylaminomethyl)phenoxy]-4-chlorophenyl]-N-(4-phenylbenzoyl)]aminohexanoate (2.3 g, 3.4 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of 6-[N-[2-[3-(tert-butoxycarbonylaminomethyl)phenoxy]-4-chlorophenyl]-N-(4-phenylbenzoyl)]aminohexanoic acid (1.96 g, 89.9%).

Elemental Analysis for $C_{37}H_{39}N_2O_6Cl.1/2H_2O$:
Calcd.: C, 68.14; H, 6.18, N, 4.30
Found: C, 68.51; H, 6.06; N, 4.34
$^1$H-NMR (CDCl$_3$) δ: 1.44(11H,s), 1.64(4H,bs), 2.31–2.37 (2H,m), 3.70(1H,bs), 4.07(1H,bs), 4.25(2H,d,J=6.0 Hz), 5.03(1H,bs), 6.56(1H,bs), 6.74(1H,bs), 6.97–7.01(3H,m), 7.18–7.22(3H,m), 7.31–7.58(9H,m)

(4) A mixture of 6-[N-[2-[3-(tert-butoxycarbonylaminomethyl)phenoxy]-4-chlorophenyl]-N-(4-phenylbenzoyl)]aminohexanoic acid (0.84 mg, 1.3 mmols), 2-fluorobenzylamine (0.18 ml, 1.6 mmols), diethyl cyanophosphate (0.22 ml, 1.3 mmols), triethylamine (0.22 ml, 1.3 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-6-[N'-[2-[3-(tert-butoxycarbonylaminomethyl)phenoxy]-4-chlorophenyl]-N'-(4-phenylbenzoyl)]aminohexanamide (0.65 g, 67.0%).

Elemental Analysis for $C_{44}H_{45}N_3O_5ClF$:
Calcd.: C, 70.43; H, 6.05; N, 5.60
Found: C, 70.29; H, 6.11; N, 5.52
$^1$H-NMR (CDCl$_3$) δ: 1.42(9H,s), 1.52–1.77(6H,m), 2.19 (2H,t,J=7.8 Hz), 3.73(1H,bs), 3.95(1H,bs), 4,21(2H,d,J=6.6 Hz), 4.46(2H,d,J=6.2 Hz), 5.17(1H,bs), 6.07(1H,bs), 6.48 (1H,bs), 6.58(1H,s), 6.69(1H,s), 6.98–7.47(15H,m), 7.53–7.58(2H,m)

(5) A 2 N hydrochloric acid/ethyl acetate solution (10 ml) of N-(2-fluorobenzyl)-6-[N'-[2-[3-(tert-butoxycarbonylaminomethyl)phenoxy]-4-chlorophenyl]-N'-(4-phenylbenzoyl)] aminohexanamide (0.53 g, 0.7 mmols) was stirred at room temperature for 1 hour. The reaction mixture was concentrated under reduced pressure. The solid precipitated was taken out through filtration, and then washed with ethyl ether to give an amorphous solid of N-(2-fluorobenzyl)-6-[N'-[2-(3-aminomethylphenoxy)-4-chlorophenyl]-N'-(4-phenylbenzoyl)]aminohexanamide hydrochloride (0.40 g, 83.3%).

Elemental Analysis for $C_{39}H_{38}N_3O_3Cl_2F.1/2H_2O$:
Calcd.: C, 67.34; H, 5.64; N, 6.04
Found: C, 67.55; H, 5.63; N, 6.00
$^1$H-NMR (DMSO-d$_6$) δ: 1.30(2H,bs), 1.53(4H,bs), 2.13 (2H,s), 3.74(2H,bs), 4.02(2H,s), 4.96(2H,s), 6.59–6.71(2H, m), 7.14–7.63(18H,m), 8.34(3H,bs)

EXAMPLE 9

N-(2-fluorobenzyl)-3-[N'-[2-(3-aminomethylphenoxy)-4-chlorophenyl]-N'-(4-phenylbenzoyl)]aminopropionamide hydrochloride (1) A mixture of tert-butyl[3-(2-amino-5-chlorophenoxy) benzyl]carbamate (2.8 g, 8.0 mmols), ethyl 3-bromopropionate (2.1 ml, 16 mmols), potassium carbonate (1.1 g, 8.0 mmols) and N,N-dimethylformamide (30 ml) was stirred at 60° C. for 72 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 3-[2-[3-(tert-butoxycarbonylaminomethyl)phenoxy]-4-chlorophenyl]aminopropionate (1.42 g, 39.6%).

Elemental Analysis for $C_{23}H_{29}N_2O_5Cl$:
Calcd.: C, 61.53; H, 6.51; N, 6.24
Found: C, 61.25; H, 6.43; N, 6.37
$^1$H-NMR (CDCl$_3$) δ: 1.21(3H,t,J=7.0 Hz), 1.45(9H,s), 2.59(2H,t,J=6.6 Hz), 3.47(2H,t,J=6.6 Hz), 4.09(2H,q,J=7.0 Hz), 4.29(2H,d,J=6.0 Hz), 4.93(1H,bs), 6.66(1H,d,J=8.6 Hz), 6.77(1H,d,J=2.4 Hz), 6.82–6.89(2H,m), 6.98–7.05(2H, m), 7.28(1H,t,J=7.8 Hz)

(2) 4-Phenylbenzoyl chloride (1.3 g, 6.0 mmols) was added to a tetrahydrofuran (30 ml) solution of ethyl 3-[2-[3-(tert-butoxycarbonylaminomethyl)phenoxy]-4-chlorophenyl]aminopropionate (1.4 g, 3.0 mmols) and 4-dimethylaminopyridine (0.74 g, 6.0 mmols). The reaction mixture was stirred at room temperature for 3 hours, then poured into water, and extracted with ethyl acetate. The extract was washed with water, and then dried with anhydrous magnesium sulfate. This was concentrated under reduced pressure, and the residue was purified through silica gel column chromatography to give an oil of ethyl 3-[N-[2-[3-(tert-butoxycarbonylaminomethyl)phenoxy]-4-chlorophenyl]-N-(4-phenylbenzoyl)]aminopropionate (1.52 g, 80.9%).

Elemental Analysis for $C_{36}H_{37}N_2O_6Cl.1/2H_2O$:
Calcd.: C, 67.76; H, 6.00; N, 4.39
Found: C, 67.95; H, 5.90; N, 4.35
$^1$H-NMR (CDCl$_3$) δ: 1.22(3H,t,J=7.1 Hz), 1.44(9H,s), 2.73(1H,bs), 2,84(1H,bs), 4.03–4.17(4H,m), 4.23(2H,d, J=5.9 Hz), 4.85(1H,bs), 6.47–6.67(3H,m), 6.96–7.10(2H, m), 7.19–7.27(2H,m), 7.31–7.47(7H,m), 7.54–7.58(2H,m)

(3) Aqueous 1 N sodium hydroxide solution (5 ml, 5 mmols) was added to a solution of ethyl 3-[N-[2-[3-(tert-butoxycarbonylaminomethyl)phenoxy]-4-chlorophenyl]-N-(4-phenylbenzoyl)]aminopropionate (1.5 g, 2.3 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of 3-[N-[2-[3-(tert-butoxycarbonylaminomethyl)phenoxy]-4-chlorophenyl]-N-(4-phenylbenzoyl)]aminopropionic acid (1.35 g, 97.8%).

Elemental Analysis for $C_{34}H_{33}N_2O_6Cl$:
Calcd.: C, 67.94; H, 5.53; N, 4.66
Found: C, 67.56; H, 5.52; N, 4.51
$^1$H-NMR (CDCl$_3$) δ: 1.43(9H,s), 2.78–2.92(2H,m), 3.99–4.15(5H,m), 4.98(1H,bs), 6.47–6.56(2H,m), 6.72(1H, s), 6.96–7.08(2H,m), 7.23–7.26(2H,m), 7.35–7.60(2H,m)

(4) A mixture of 3-[N-[2-[3-(tert-butoxycarbonylaminomethyl)phenoxy]-4-chlorophenyl]-N-(4-phenylbenzoyl)]aminopropionic acid (0.42 g, 0.70 mmols), 2-fluorobenzylamine (0.10 ml, 0.90 mmols), diethyl cyanophosphate (0.13 ml, 0.90 mmols), triethylamine (0.13 ml, 0.90 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-3-[N'-[2-[3-(tert-butoxycarbonylaminomethyl)phenoxy]-4-chlorophenyl]-N'-(4-phenylbenzoyl)]aminopropionamide (0.39 g, 79.6%).

Elemental Analysis for $C_{41}H_{39}N_3O_5ClF \cdot H_2O$:
Calcd.: C, 67.81; H, 5.69; N, 5.79
Found: C, 67.83; H, 5.44; N, 5.59
$^1$H-NMR (CDCl$_3$) δ: 1.42(9H,s), 2.51–2.82(2H,m), 4.01–4.34(4H,m), 4.47(2H,d,J=5.6 Hz), 4.93(1H,bs), 6.41–6.59(3H,m), 6.88(1H,bs), 6.96–7.08(4H,m), 7.17–7.48 (11H,m), 7.53–7.58(2H,m)

(5) A 2 N hydrochloric acid/ethyl acetate solution (10 ml) of N-(2-fluorobenzyl)-3-[N'-[2-[3-(tert-butoxycarbonylaminomethyl)phenoxy]-4-chlorophenyl]-N'-(4-phenylbenzoyl)]aminopropionamide (0.35 g, 0.50 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-3-[N'-[2-(3-aminomethylphenoxy)-4-chlorophenyl]-N'-(4-phenylbenzoyl)]aminopropionamide hydrochloride (0.25 g, 78.1%).

Elemental Analysis for $C_{36}H_{32}N_3O_3Cl_2F \cdot 1/2H_2O$:
Calcd.: C, 66.16; H, 5.09; N, 6.43
Found: C, 65.98; H, 5.12; N, 6.35
$^1$H-NMR (DMSO-d$_6$) δ: 2.41–2.79(2H,m), 3.87–4.00(2H,m), 4.28(2H,d,J=4.8 Hz), 4.57(2H,s), 6.58 (1H,s), 6.72–6.76(1H,m), 7.12–7.20(3H,m), 7.26–7.68(15H,m), 8.50(2H,bs), 8.60(1H,s)

EXAMPLE 10

N-(2-fluorobenzyl)-4-[N'-[2-[3-(2-aminoethyl)phenoxy]-3-pyridyl]-N'-(4-phenylbenzoyl)]aminobutylamide hydrochloride (1) A mixture of 3-methoxyphenethylamine (21.9 ml, 150 mmols) and 47% hydrobromic acid (100 ml) was stirred, while being heated under reflux, for 10 hours. The reaction mixture was cooled, and the solvent was evaporated away under reduced pressure. The residue was poured into water. To the resulting mixture, added was an aqueous solution (100 ml) of sodium hydroxide (6 g, 150 mmols), and stirred at room temperature for 30 minutes. Next, a diethyl ether solution (100 ml) of di-tert-butyl dicarbonate (32.7 g, 0.15 mmols) was dropwise added thereto at 0° C. over a period of 2 hours. The reaction mixture was stirred at 0° C. for 12 hours, and then extracted with diethyl ether. The extract was washed with brine, and then dried with anhydrous magnesium sulfate. This was concentrated under reduced pressure, and the residue was purified through silica gel column chromatography to give a crystal of N-tert-butoxycarbonyl-3-hydroxyphenethylamine (33.4 g, 95.3%).

m.p. 84–85° C.
$^1$H-NMR (CDCl$_3$) δ: 1.44(9H,s), 2,72(2H,t,J=6.8 Hz), 3.32–3.42(2H,m), 4.65(1H,bs), 6.56(1H,bs), 6.70–6.76(3H, m), 7.11–7.19(1H,m)

(2) A mixture of 2-chloro-3-nitropyridine (4.76 g, 30 mmols), N-tert-butoxycarbonyl-3-hydroxyphenethylamine (7.11 g, 30 mmols), potassium carbonate (4.14 g, 30 mmols) and N,N-dimethylformamide (50 ml) was stirred at 100° C. for 12 hours. The reaction mixture was cooled, then poured into water, and then extracted with ethyl acetate. The extract was washed with water, and then dried with anhydrous magnesium sulfate, and the solvent was evaporated away. The residue was purified through silica gel column chromatography to give an yellow oil of tert-butyl[2-[3-(3-nitro-2-pyridyloxy)phenyl]ethyl]carbamate (10.1 g, 92.5%).

Elemental Analysis for $C_{18}H_{21}N_3O_5$:
Calcd.: C, 60.16; H, 5.89; N, 11.69
Found: C, 60.11; H, 5.98; N, 11.58
$^1$H-NMR (CDCl$_3$) δ: 1.43(9H,s), 2.83(2H,t,J=6.6 Hz), 3.39(2H,q,J=6.6 Hz), 4.60(1H,bs), 7.03–7.19(4H,m), 7.34–7.42(1H,m), 7.32–8.39(2H,m)

(3) 5% carbon-palladium (3.0 g) was added to an ethanol (100 ml) solution of tert-butyl[2-[3-(3-nitro-2-pyridyloxy)phenyl]ethyl]carbamate (10.1 g, 28 mmols). The resulting mixture was hydrogenated at room temperature under atmospheric pressure. The catalyst was removed through filtration, and the filtrate was concentrated under reduced pressure. Thus was obtained an oil of tert-butyl[2-[3-(3-amino-2-pyridyloxy)phenyl]ethyl]carbamate (7.09 g, 76.9%).

Elemental Analysis for $C_{18}H_{23}N_3O_3 \cdot 1/4H_2O$:
Calcd.: C, 64.75; H, 7.09; N, 12.58
Found: C, 65.10; H, 6.83; N, 12.22
$^1$H-NMR (CDCl$_3$) δ: 1.43(9H,s), 2.80(2H,t,J=7.0 Hz), 3.33–3.43(2H,m), 3.92(2H,bs), 4.65(1H,bs), 6.84(1H,dd, J=2.7,7.7 Hz), 6.98–7.06(4H,m), 7.27–7.36(1H,m), 7.56 (1H,dd,J=1.5,4.7 Hz)

(4) A mixture of tert-butyl[2-[3-(3-amino-2-pyridyloxy)phenyl]ethyl]carbamate (3.3 g, 10 mmols), ethyl 4-bromobutyrate (2.8 ml, 20 mmols), potassium carbonate (1.4 g, 10 mmols) and N,N-dimethylformamide (30 ml) was stirred at 60° C. for 72 hours. The reaction mixture was cooled, then poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[2-[3-[2-(tert-butoxycarbonylamino)ethyl]phenoxy]-3-pyridyl]aminobutyrate (2.41 g, 54.4%).

Elemental Analysis for $C_{24}H_{33}N_3O_5$:
Calcd.: C, 64.99; H, 7.50; N, 9,47
Found: C, 64.80; H, 7.39; N, 9.22
$^1$H-NMR (CDCl$_3$) δ: 1.26(3H,t,J=7.2 Hz), 1.43(9H,s), 1.94–2.08(2H,m), 2.46(2H,t,J=7.0 Hz), 2.80(2H,t,J=7.0 Hz), 3.24(2H,bs), 3.33–3.43(2H,m), 4.11(2H,q,J=7.2 Hz), 4.42(1H,bs), 4.65(1H,bs), 6.89–7.02(5H,m), 7.31(1H,t, J=7.9 Hz), 7.46(1H,t,J=3.3 Hz)

(5) 4-Phenylbenzoyl chloride (1.6 g, 7.5 mmols) was added to a tetrahydrofuran (30 ml) solution of ethyl 4-[2-[3-[2-(tert-butoxycarbonylamino)ethyl]phenoxy]-3-pyridyl]aminobutyrate (2.2 g, 5.0 mmols) and 4-dimethylaminopyridine (1.2 g, 10 mmols). The reaction mixture was stirred at room temperature for 5 hours, then poured into water, and extracted with ethyl acetate. The extract was washed with water, and then dried with anhydrous magnesium sulfate. This was concentrated under reduced pressure, and the residue was purified through silica gel column chromatography to give an amorphous solid of ethyl 4-[N-[2-[3-[2-(tert-butoxycarbonylamino)ethyl]phenoxy]-3-pyridyl]-N-(4-phenylbenzoyl)]aminobutyrate (2.54 g, 81.7%).

Elemental Analysis for $C_{37}H_{41}N_3O_6 \cdot 1/2H_2O$:
Calcd.: C, 70.23; H, 6.69; N, 6.64
Found: C, 70.53; H, 6.79; N, 6.70
$^1$H-NMR (CDCl$_3$) δ: 1.24(3H,t,J=7.0 Hz), 1.43(9H,s), 1.97–2.12(2H,m), 2.50(2H,t,J=7.4 Hz), 2.69(2H,t,J=6.8 Hz), 3.27(2H,bs), 4.12(2H,q,J=7.0 Hz), 4.50(1H,bs), 6.63 (1H,d,J=7.8 Hz), 6.96–7.02(2H,m), 7.25–7.31(1H,m), 7.35–7.57(9H,m), 7.63(1H,dd,J=1.8,7.8 Hz), 7.97(1H,dd, J=4,4.8 HZ)

(6) Aqueous 1 N sodium hydroxide solution (7 ml, 7 mmols) was added to a solution of ethyl 4-[N-[2-[3-[2-(tert-butoxycarbonylamino)ethyl]phenoxy]-3-pyridyl]-N-(4-phenylbenzoyl)]aminobutyrate (2.4 g, 3.8 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of 4-[N-[2-[3-[2-(tert-butoxycarbonylamino)ethyl]phenoxy]-3-pyridyl]-N-(4-phenylbenzoyl)]aminobutyric acid (2.19 g, 96.9%).

Elemental Analysis for $C_{35}H_{37}N_3O_6 \cdot 1/2H_2O$:
Calcd.: C, 69.52; H, 6.33; N, 6.95
Found: C, 69.41; H, 6.26; N, 6.81
$^1$H-NMR (CDCl$_3$) δ: 1.43(9H,s), 1.96(2H,bs), 2.55(2H, bs), 3.31(2H,bs), 3.93(1H,bs), 4.20(1H,bs), 4.73(1H,bs), 6.42(1H,s), 6.77–7.06(4H,m), 7.30–7.57(10H,m), 7.98(1H, dd,J=1.7,4.9 Hz)

(7) A mixture of 4-[N-[2-[3-[2-(tert-butoxycarbonylamino)ethyl]phenoxy]-3-pyridyl]-N-(4-phenylbenzoyl)] aminobutyric acid (1.0 g, 1.7 mmols), 2-fluorobenzylamine (0.23 ml, 2.0 mmols), diethyl cyanophosphate (0.28 ml, 2.0 mmols), triethylamine (0.28 ml, 2.0 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-[2-(tert-butoxycarbonylamino)ethyl]phenoxy]-3-pyridyl]-N'-(4-phenylbenzoyl)]aminobutylamide (0.92 g, 77.3%).

Elemental Analysis for $C_{42}H_{43}N_4O_5 \cdot 1/2H_2O$:
Calcd.: C, 70.87; H, 6.23; N, 7.87
Found: C, 70.99; H, 6.12; N, 7.87
$^1$H-NMR (CDCl$_3$) δ: 1.42(9H,s), 2.05(2H,bs), 2.43–2.47 (2H,m), 2.67(2H,t,J=7.0 Hz), 3.26(2H,bs), 3.97(1H,bs), 4.11 (1H,bs), 4.50(1H,bs), 4.52(2H,d,J=5.4 Hz), 6.46(1H,s), 6.56–6.60(1H,m), 6.82(1H,bs), 6.97–7.56(16H,m), 7.67 (1H,dd,J=1.8,7.6 Hz), 7.97(1H,dd,J=1.8,5.0 Hz)

(8) A 2 N hydrochloric acid/ethyl acetate solution (10 ml) of N-(2-fluorobenzyl)-4-[N'-[2-[3-[2-(tert-butoxycarbonylamino)ethyl]phenoxy]-3-pyridyl]-N'-(4-phenylbenzoyl)] aminobutylamide (0.84 g, 1.2 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(2-aminoethyl)phenoxy]-3-pyridyl]-N'-(4-phenylbenzoyl)] aminobutylamide hydrochloride (0.75 g, 92.6%).

Elemental Analysis for $C_{37}H_{36}N_4O_3ClF \cdot H_2O$:
Calcd.: C, 67.62; H, 5.83; N, 8.53
Found: C, 67.83; H, 5.86; N, 8.46
$^1$H-NMR (DMSO-d$_6$) δ: 1.81–1.92(2H,m), 2.27–2.34(2H,m), 2.91–3.05(4H,m), 3.85(2H,bs), 4.29(2H, s), 6.35–6.62(1H,m), 6.87(1H,s), 7.11–7.66(16H,m), 7.94–7.98(2H,m), 8.10(2H,bs), 8.41(1H,bs)

EXAMPLE 11

N-[2-(3-aminomethylphenoxy)phenyl]-N-(4-biphenylmethyl)-N'-(2-fluorobenzyl)succinamide hydrochloride (1) An oil was prepared from 2-fluoronitrobenzene and N-tert-butoxycarbonyl-3-hydroxybenzylamine in the same manner as in (1) and (2) in Example 1.
$^1$H-NMR (CDCl$_3$) δ: 1.44(9H,s), 3,78(2H,bs), 4.27(2H, d,J=5.8 Hz), 4.88(1H,bs), 6.67–6.78(1H,m), 6.79–7.03(6H, m), 7.25(1H,t,J=7.6 Hz)

(2) A mixture of tert-butyl[3-(2-amino-5-chlorophenoxy) benzyl]carbamate (6.3 g, 20 mmols), 4-phenylbenzaldehyde (4.4 g, 24 mmols), acetic acid (2 ml) and methanol (50 ml) was stirred at room temperature for 1 hour, to which was added sodium borocyanohydride (1.6 g, 24 mmols). Next, this was stirred at room temperature for 1 hour. The reaction mixture was poured into water, and extracted with ethyl acetate. The extract was washed with water, then dried with anhydrous magnesium sulfate, and concentrated under reduced pressure. The residue was purified through silica gel column chromatography to give an oil of tert-butyl[3-[2-(4-biphenylmethylamino)phenoxy]benzyl]carbamate (8.40 g, 87.4%).

Elemental Analysis for $C_{31}H_{32}N_2O_3 \cdot 3/4H_2O$:
Calcd.: C, 75.36; H, 6.83; N, 5.67
Found: C, 75.32; H, 6.86; N, 5.52
$^1$H-NMR (CDCl$_3$) δ: 1.44(9H,s), 4.29(2H,d,J=5.8 Hz), 4.41(2H,s), 4.66(1H,bs), 4.83(1H,bs), 6.61–7.06(7H,m), 7.22–7.60(10H,m)

(3) A mixture of tert-butyl[3-[2-(4-biphenylmethylamino) phenoxy]benzyl]carbamate (7.7 g, 16 mmols), ethylsuccinyl chloride (2.7 ml, 19 mmols), sodium hydrogencarbonate (4.0 g, 48 mmols), ethyl acetate (70 ml) and water (20 ml) was stirred at room temperature for 2 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-biphenylmethyl)-N-[2-[3-(tert-butoxycarbonylaminomethyl)phenoxy]phenyl]succinamate (8.33 g, 85.6. %).

Elemental Analysis for $C_{37}H_{40}N_2O_6 \cdot 1/2H_2O$:
Calcd.: C, 71.94; H, 6.69; N, 4.53
Found: C, 71.75; H, 6.75; N, 4.36
$^1$H-NMR (CDCl$_3$) δ: 1.25(3H,t,J=7.2 Hz), 1.43(9H,s), 2.42–2.75(4H,m), 4.07–4.20(4H,m), 4.73(1H,d,J=14.2 Hz), 4.81(1H,bs), 5.07(1H,d,J=14.2 Hz), 6.70–6.72(2H,m), 6.86 (1H,d,J=8.0 Hz), 6.98–7.55(14H,m)

(4) Aqueous 1 N sodium hydroxide solution (20 ml, 20 mmols) was added to a solution of ethyl N-(4-biphenylmethyl)-N-[2-[3-(tert-butoxycarbonylaminomethyl)phenoxy] phenyl]succinamate (7.9 g, 13 mmols) in tetrahydrofuran (40 ml) and ethanol (40 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of N-(4-biphenylmethyl)-N-[2-[3-(tert-butoxycarbonylaminomethyl)phenoxy]phenyl]succinamic acid (7.34 g, 97.3%).

Elemental Analysis for $C_{35}H_{36}N_2O_6 \cdot 1/2H_2O$:
Calcd.: C, 71.29; H, 6.32; N, 4.75
Found: C, 71.35; H, 6.29; N, 4.66
$^1$H-NMR (CDCl$_3$) δ: 1.43(9H,s), 2.50–2.53(2H,m), 2.66–2.69(2H,m), 4.18(2H,d,J=3.8 Hz), 4.72–4.85(2H,m), 5.06(1H,d,J=13.2 Hz), 6.70(3H,m), 6.84–7.10(3H,m), 7.20–7.55(1H,m)

(5) A mixture of N-(4-biphenylmethyl)-N-[2-[3-(tert-butoxycarbonylaminomethyl)phenoxy]phenyl]succinamic acid (1.16 g, 2 mmols), 2-fluorobenzylamine (0.27 ml, 2.4 mmols), diethyl cyanophosphate (0.35 ml, 2.4 mmols), triethylamine (0.33 ml, 2.4 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(4-biphenylmethyl)-N-[2-[3-(tert-butoxycarbonylaminomethyl)phenoxy]phenyl]-N'-(2-fluorobenzyl)succinamide (1.08 g, 78.8%).

Elemental Analysis for $C_{42}H_{42}N_3O_5 \cdot 1/2H_2O$:
Calcd.: C, 72.39; H, 6.22; N, 6.03
Found: C, 72.60; H, 6.21; N, 6.01
$^1$H-NMR (CDCl$_3$) δ: 1.40(9H,s), 2.55(4H,s), 4.17(2H,d,J=3.6 Hz), 4.43(2H,d,J=5.2 Hz), 5.07(1H,d,J=14.2 Hz), 5.11(1H,bs), 6.56(1H,bs), 6.69–6.73(2H,m), 6.85(1H,d,J=8.2 Hz), 6.97–7.08(4H,m), 7.19–7.55(14H,m)

(6) A 2 N hydrochloric acid/ethyl acetate solution (20 ml) of N-(4-biphenylmethyl)-N-[2-[3-(tert-butoxycarbonylaminomethyl)phenoxy]phenyl]-N'-(2-fluorobenzyl)succinamide (0.83 g, 1.2 mmols) was stirred at room temperature for 1 hour. The reaction mixture was concentrated under reduced pressure. The solid precipitated was taken out through filtration, and washed with ethyl ether to give an amorphous solid of N-[2-(3-aminomethylphenoxy)phenyl]-N-(4-biphenylmethyl)-N'-(2-fluorobenzyl)succinamide hydrochloride (0.70 g, 94.6%).

Elemental Analysis for $C_{37}H_{35}N_3O_3ClF$:
Calcd.: C, 71.20; H, 5.65; N, 6.73
Found: C, 71.38; H, 5.76; N, 6.31
$^1$H-NMR (DMSO-d$_6$) δ: 2.36–2.49(4H,m), 4.00(2H,s), 4.28(2H,s), 4.48(1H,d,J=14.8 Hz), 5.17(1H,d,J=14.8 Hz), 6.91(2H,d,J=8.0 Hz), 7.10–7.63(19H,m), 8.42(2H,bs)

EXAMPLE 12

N-[2-(3-aminomethylphenoxy)phenyl]-N-(4-biphenylmethyl)-N'-(2-fluorobenzyl)malonamide hydrochloride (1) A mixture of tert-butyl[3-[3-(4-biphenylmethylamino)phenoxy]benzyl]carbamate (1.4 g, 3.0 mmols), ethylmalonyl chloride (0.58 ml, 4.5 mmols), sodium hydrogencarbonate (0.76 g, 9.0 mmols), ethyl acetate (15 ml) and water (5 ml) was stirred at room temperature for 3 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-biphenylmethyl)-N-[2-[3-(tert-butoxycarbonylaminomethyl)phenoxy]phenyl]malonamate (1.55 g, 88.8%).

$^1$H-NMR (CDCl$_3$) δ: 1.19–1.33(3H,m), 1.44(9H,s), 3.32(2H,s), 4.07–4.19(4H,m), 4.74(1H,bs), 4.77(1H,d,J=14.7 Hz), 5.08(1H,d,J=14.7 Hz), 6.67–6.69(1H,d,J=8.4 Hz), 6.97–7.55(14H,m)

(2) Aqueous 1 N sodium hydroxide solution (5 ml, 5 mmols) was added to a solution of ethyl N-(4-biphenylmethyl)-N-[2-[3-(tert-butoxycarbonylaminomethyl)phenoxy]phenyl]malonamate (1.6 g, 2.6 mmols) in tetrahydrofuran (5 ml) and ethanol (5 ml). The resulting mixture was stirred at room temperature for 3 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of N-(4-biphenylmethyl)-N-[2-[3-(tert-butoxycarbonylaminomethyl)phenoxy]phenyl]malonamidic acid (1.40 g, 95.2%).

Elemental Analysis for $C_{34}H_{34}N_2O_6 \cdot 1/2H_2O$:
Calcd.: C, 70.94; H, 6.13; N, 4.87
Found: C, 71.04; H, 6.05; N, 4.83
$^1$H-NMR (CDCl$_3$) δ: 1.43(9H,s), 3.20(1H,d,J=19.4 Hz), 3.33(1H,d,J=19.4 Hz), 4.16(2H,d,J=5.0 Hz), 4.76(1H,bs), 4.97(2H,s), 6.60–6.63(2H,m), 6.83(1H,d,J=8.4 Hz), 7.01–7.09(3H,m), 7.19–7.55(11H,m)

(3) A mixture of N-(4-biphenylmethyl)-N-[2-[3-(tert-butoxycarbonylaminomethyl)phenoxy]phenyl]malonamidic acid (0.57 g, 1.0 mmol), 2-fluorobenzylamine (0.14 ml, 1.2 mmols), diethyl cyanophosphate (0.17 ml, 1.2 mmols), triethylamine (0.17 ml, 1.2 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(4-biphenylmethyl)-N-[2-[3-(tert-butoxycarbonylaminomethyl)phenoxy]phenyl]-N'-(2-fluorobenzyl)malonamide (0.54 g, 81%).

Elemental Analysis for $C_{41}H_{40}N_3O_5F \cdot 1/4H_2O$:
Calcd.: C, 72.60; H, 6.02; N, 6.20
Found: C, 72.62; H, 5.98; N, 6.10
$^1$H-NMR (CDCl$_3$) δ: 1.42(9H,s), 3.23(2H,s), 4.15(2H,d,J=4.4 Hz), 4.51(2H,d,J=5.8 Hz), 4.85(1H,d,J=14.4 Hz), 4.89(1H,bs), 5.01(1H,d,J=14.4 Hz), 6.63–6.67(2H,m), 6.82(1H,d,J=8.0 Hz), 6.94–7.06(5H,m), 7.16–7.56(13H,m), 8.45(1H, bs)

(4) A 2 N hydrochloric acid/ethyl acetate solution (20 ml) of N-(4-biphenylmethyl)-N-[2-[3-(tert-butoxycarbonylaminomethyl)phenoxy]phenyl]-N'-(2-fluorobenzyl)malonamide (0.47 g, 0.70 mmols) was stirred at room temperature for 1 hour. The reaction mixture was concentrated under reduced pressure. The solid precipitated was taken out through filtration, and washed with ethyl ether to give an amorphous solid of N-[2-(3-aminomethylphenoxy)phenyl]-N-(4-biphenylmethyl)-N'-(2-fluorobenzyl)malonamide hydrochloride (0.37 g, 88%).

Elemental Analysis for $C_{36}H_{33}N_3O_3ClF \cdot 1/2H_2O$:
Calcd.: C, 69.84; H, 5.54; N, 6.79
Found: C, 69.47; H, 5.39; N, 6.59
$^1$H-NMR (DMSO-d$_6$) δ: 3.07(1H,d,J=15.4 Hz), 3.28(1H,d,J=15.4 Hz), 4.00(2H,s), 4.28(2H,s), 4.49(1H,d,J=15.2 Hz), 5.22(1H,d,J=15.2 Hz), 6.91–6.97(2H,m), 7.06–7.65(19H,m), 8.46(2H,bs)

EXAMPLE 13

N-[2-(3-aminomethylphenoxy)phenyl]-N-(4-biphenylmethyl)-N'-(2-fluorobenzyl)glutaramide hydrochloride (1) A mixture of tert-butyl[3-[2-(4-biphenylmethylamino)phenoxy]benzyl]carbamate (1.4 g, 3.0 mmols), ethylglutaryl chloride (0.56 ml, 3.6 mmols), sodium hydrogencarbonate (0.76 g, 9.0 mmols), ethyl acetate (15 ml) and water (5 ml) was stirred at room temperature for 3 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-biphenylmethyl)-N-[2-[3-(tert-butoxycarbonylaminomethyl)phenoxy]phenyl]glutaramate (1.33 g, 71.5%).

$^1$H-NMR (CDCl$_3$) δ: 1.26(3H,t,J=7.0 Hz), 1.43(9H,s), 1.92–1.99(2H,m), 4.87(1H,bs), 5.06(1H,d,J=14.3 Hz), 6.68–6.71(2H,m), 6.84(1H,d,J=8.0 Hz), 6.99–7.06(3H,m), 7.18–7.56(12H,m)

(2) Aqueous 1 N sodium hydroxide solution (5 ml, 5 mmols) was added to a solution of ethyl N-(4-biphenylmethyl)-N-[2-[3-(tert-butoxycarbonylaminomethyl)phenoxy]phenyl]glutaramate (1.6 g, 2.6 mmols) in tetrahydrofuran (5 ml) and ethanol (5 ml). The resulting mixture was stirred at room temperature for 3 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of N-(4-biphenylmethyl)-N-[2-[3-(tert-butoxycarbonylaminomethyl)phenoxy]phenyl]glutaramidic acid (1.41 g, 91.9%).

Elemental Analysis for C$_{36}$H$_{38}$N$_2$O$_6$·1/2H$_2$O:
Calcd.: C, 71.62; H, 6.51; N, 4.64
Found: C, 71.80; H, 6.33; N, 4.51

$^1$H-NMR (CDCl$_3$) δ: 1.43(9H,s), 1.87–2.54(6H,m), 4.22–4.28(2H,m), 4.73(1H,d,J=13.9 Hz), 5.17(1H,d,J=13.9 Hz), 6.68–6.81(2H,m), 6.98–7.02(3H,m), 7.24–7.59(12H,m)

(3) A mixture of N-(4-biphenylmethyl)-N-[2-[3-(tert-butoxycarbonylaminomethyl)phenoxy]phenyl]glutaramidic acid (0.57 g, 1.0 mmol), 2-fluorobenzylamine (0.14 ml, 1.2 mmols), diethyl cyanophosphate (0.17 ml, 1.2 mmols), triethylamine (0.17 ml, 1.2 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(4-biphenylmethyl)-N-[2-[3-(tert-butoxycarbonylaminomethyl)phenoxy]phenyl]-N'-(2-fluorobenzyl)glutaramide (1.14 g, 91.9%).

Elemental Analysis for C$_{43}$H$_{44}$N$_3$O$_5$F·1/2H$_2$O:
Calcd.: C, 72.66; H, 6.38; N, 5.91
Found: C, 72.56; H, 6.23; N, 5.91

$^1$H-NMR (CDCl$_3$) δ: 1.41(9H,s), 1.90–2.01(4H,m), 2.19–2.28(4H,m), 4.17(2H,d,J=5.4 Hz), 4.43(2H,d,J=5.8 Hz), 4.67(1H,d,J=14.2 Hz), 5.05(1H,bs), 5.09(1H,d,J=14.2 Hz), 6.26(1H,bs), 6.68–6.71(2H,m), 6.85(1H,d,J=8.2 Hz), 6.97–7.10(5H,m), 7.18–7.56(13H,m)

(4) A 2 N hydrochloric acid/ethyl acetate solution (20 ml) of N-(4-biphenylmethyl)-N-[2-[3-(tert-butoxycarbonylaminomethyl)phenoxy]phenyl]-N'-(2-fluorobenzyl)glutaramide (0.47 g, 0.7 mmols) was stirred at room temperature for 1 hour. The reaction mixture was concentrated under reduced pressure. The solid precipitated was taken out through filtration, and washed with ethyl ether to give an amorphous solid of N-[2-(3-aminomethylphenoxy)phenyl]-N-(4-biphenylmethyl)-N'-(2-fluorobenzyl)glutaramide hydrochloride (0.33 g, 86.8%).

Elemental Analysis for C$_{38}$H$_{37}$N$_3$O$_3$ClF·H$_2$O:
Calcd.: C, 69.55; H, 5.99; N, 6.40
Found: C, 69.63; H, 5.89; C, 6.33

$^1$H-NMR (DMSO-d$_6$) δ: 1.76–1.87(2H,m), 2.10–2.16(4H,m), 3.99(2H,s), 4.25(2H,d,J=4.4 Hz), 4.51(1H,d,J=15.1 Hz), 5.14(1H,d,J=15.1 Hz), 6.83–6.90(2H,m), 7.1–7.63(18H,m), 8.32–8.43(3H,m)

EXAMPLE 14

N-[2-[3-(2-aminoethyl)phenoxy]-4-chlorophenyl]-N-(4-biphenylmethyl)-N'-(2-fluorobenzyl)succinamide hydrochloride (1) A mixture of 4-chloro-2-fluoronitrobenzene (7.0 g, 40 mmols), N-tert-butoxycarbonyl-3-hydroxyphenethylamine (9.5 g, 40 mmols), potassium carbonate (5.5 g, 40 mmols) and N,N-dimethylformamide (100 ml) was stirred at 100° C. for 12 hours. The reaction mixture was cooled, then poured into water, and extracted with ethyl acetate. The extract was washed with water, and then dried with anhydrous magnesium sulfate, and the solvent was evaporated away. The residue was purified through silica gel column chromatography to give an oil of tert-butyl 2-[3-(5-chloro-2-nitrophenoxy)phenyl]ethylcarbamate (15.2 g, 96.6%).

Elemental Analysis for C$_{19}$H$_{21}$N$_2$O$_5$Cl:
Calcd.: C, 58.09; H, 5.39; N, 7.13
Found: C, 57.93; H, 5.42; N, 6.84

$^1$H-NMR (CDCl$_3$) δ: 1.43(9H,s), 2.82(2H,t,J=7.2 Hz), 3.38(2H,q,J=7.2 Hz), 4.58(1H,bs), 6.92–6.96(3H,m), 7.08(1H,d,J=7.6 Hz), 7.15(1H,dd,J=2.2,8.8 Hz), 7.18(1H,m), 7.94(1H,d,J=8.8 Hz)

(2) 5% carbon-palladium (4.5 g) was added to an ethyl acetate (300 ml) solution of tert-butyl 2-[3-(5-chloro-2-nitrophenoxy)phenyl]ethylcarbamate (14.7 g, 37.5 mmols). The resulting mixture was hydrogenated at room temperature under atmospheric pressure. The catalyst was removed through filtration, and the filtrate was concentrated under reduced pressure. The solid precipitated was taken out through filtration. This is tert-butyl 2-[3-(2-amino-5-chlorophenoxy)phenyl]ethylcarbamate (13.6 g, 100%).

Elemental Analysis for C$_{19}$H$_{23}$N$_2$O$_3$Cl:
Calcd.: C, 62.89; H, 6.39; N, 7.72
Found: C, 62.79; H. 6.51; N, 7.48

$^1$H-NMR (CDCl$_3$) δ: 1.43(9H,s), 2.77(2H,t,J=7.0 Hz), 3.31–3.39(2H,m), 4.10(2H,bs), 4.59(1H,bs), 6.76–6.85(4H,m), 6.90–6.96(2H,m), 7.21–7.30(1H,m)

(3) A mixture of tert-butyl 2-[3-(2-amino-5-chlorophenoxy)phenyl]ethylcarbamate (3.6 g, 10 mmols), 4-phenylbenzyl chloride (2.0 g, 10 mmols), potassium carbonate (1.0 g, 7.5 mmols) and N,N-dimethylformamide (30 ml) was stirred at room temperature for 12 hours, and then the reaction mixture was poured into water and extracted with ethyl acetate. The extract was washed with water, then dried with anhydrous magnesium sulfate, and concentrated under reduced pressure. The residue was purified through silica gel column chromatography to give a prism crystal of tert-butyl 2-[3-[2-(4-biphenylmethylamino)-5-chlorophenoxy]phenyl]ethylcarbamate (2.14 g, 40.5%).

m.p. 108–109° C.

Elemental Analysis for C$_{32}$H$_{33}$N$_2$O$_3$Cl:

Calcd.: C, 72.65; H, 6.29; N, 5.29
Found: C, 72.93; H, 6.01; N, 5.36
¹H-NMR (CDCl₃) δ: 1.43(9H,s), 2.78(2H,t,J=7.1 Hz), 3.36(2H,q,J=7.1 Hz), 4.40(2H,d,J=5.2 Hz), 4.54(1H,bs), 4.68(1H,bs), 6.62(1H,d,J=8.8 Hz), 6.80(1H,d,J=2.2 Hz), 6.85–6.92(2H,m), 6.95(2H,dd,J=2.2,8.8 Hz), 7.23–7.48(6H, m), 7.55–7.60(4H,m)

(4) A mixture of tert-butyl 2-[3-[2-(4-biphenylmethylamino)-5-chlorophenoxy]phenyl]ethylcarbamate (3.7 g, 7.0 mmols), ethylsuccinyl chloride (1.5 ml, 10.5 mmols), 4-dimethylaminopyridine (1.28 g, 10.5 mmols) and tetrahydrofuran (30 ml) was stirred at room temperature for 12 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an oil of ethyl N-(4-biphenylmethyl)-N-[2-[3-(2-tert-butoxycarbonylaminoethyl)phenoxy]-4-chlorophenyl]succinamate (4.38 g, 95.2%).

Elemental Analysis for $C_{38}H_{41}N_2O_6Cl\cdot1/2H_2O$:
Calcd.: C, 68.51; H, 6.35; N, 4.20
Found: C, 68.48; H, 6.52; N, 4.00
¹H-NMR (CDCl₃) δ: 1.25(3H,t,J=7.0 Hz), 1.43(9H,s), 2.40–2.76(6H,m), 3.27–3.30(2H,m), 4.07–4.19(2H,m), 4.60 (1H,bs), 4.73(1H,d,J=14.6 Hz), 5.05(1H,d,J=14.6 Hz), 6.64–6.67(2H,m), 6.77(1H,d,J=2.2 Hz), 6.97–7.04(3H,m), 7.08–7.59(10H,m)

(5) Aqueous 1 N sodium hydroxide solution (12 ml, 12 mmols) was added to a solution ethyl N-(4-biphenylmethyl)-N-[2-[3-(2-tert-butoxycarbonylaminoethyl)phenoxy]-4-chlorophenyl]succinamate (3.9 g, 6.0 mmols) in tetrahydrofuran (10 ml) and ethanol (10 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of N-(4-biphenylmethyl)-N-[2-[3-(2-tert-butoxycarbonylaminoethyl)phenoxy]-4-chlorophenyl]succinamic acid (3.75 g, 99.5%).

Elemental Analysis for $C_{38}H_{37}N_2O_6Cl\cdot1/4H_2O$:
Calcd.: C, 68.24; H, 5.97; N, 4.42
Found: C, 68.27; H, 5.96; N, 4.46
¹H-NMR (CDCl₃) δ: 1.43(9H,s), 2.29–2.70(6H,m), 3.20–3.42(2H,m), 4.52(2H,d,J=14.6 Hz), 4.71(1H,bs), 4.74 (1H,d,J=14.6 Hz), 6.30(1H,bs), 6.68–7.10(5H,m), 7.26–7.59 (11H,m)

(6) A mixture of N-(4-biphenylmethyl)-N-[2-[3-(2-tert-butoxycarbonylaminoethyl)phenoxy]-4-chlorophenyl]succinamic acid (1.3 g, 2.0 mmols), 2-fluorobenzylamine (0.27 ml, 2.4 mmols), diethyl cyanophosphate (0.33 ml, 2.4 mmols), triethylamine (0.33 ml, 2.4 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(4-biphenylmethyl)-N-[2-[3-(2-tert-butoxycarbonylaminoethyl)phenoxy]-4-chlorophenyl]-N'-(2-fluorobenzyl)succinamide (1.10 g, 74.8%).

Elemental Analysis for $C_{43}H_{43}N_3O_5ClF$:
Calcd.: C, 70.15; H, 5.89; N, 5.71
Found: C, 70.09; H, 5.82; N, 5.50

¹H-NMR (CDCl₃) δ: 1.41(9H,s), 2.41–2.73(6H,m), 3.26–3.29(2H,m), 4.46(2H,d,J=6.0 Hz), 4.65–4.78(2H,m), 5.01(1H,d,J=13.6 Hz), 6.46(1H,bs), 6.62–6.74(3H,m), 7.00–7.08(5H,m), 7.18–7.58(12H,m)

(7) A 2 N hydrochloric acid/ethyl acetate solution (10 ml) of N-(4-biphenylmethyl)-N-[2-[3-(2-tert-butoxycarbonylaminoethyl)phenoxy]-4-chlorophenyl]-N'-(2-fluorobenzyl) succinamide (0.74 g, 1.0 mmol) was stirred at room temperature for 1 hour. The reaction mixture was concentrated under reduced pressure. The crystal precipitated was taken out through filtration, and washed with ethyl ether to give a prism crystal of N-[2-[3-(2-aminoethyl)phenoxy]-4-chlorophenyl]-N-(4-biphenylmethyl)-N'-(2-fluorobenzyl)succinamide hydrochloride (0.66 g, 98.5%).

m.p. 123–125° C.
Elemental Analysis for $C_{38}H_{36}N_3O_3Cl_2F$:
Calcd.: C, 67.86; H, 5.39; N, 6.25
Found: C, 67.55; H, 5.59; N, 6.29
¹H-NMR (DMSO-d₆) δ: 2.30–2.52(4H,m), 2.88–3.09(4H,m), 4.36(2H,s), 4.55(1H,d,J=14.8 Hz), 5.12 (1H,d,J=14.8 Hz), 6.79–6.87(2H,m), 6.94–7.63(18H,m), 8.04(2H,bs), 8.42(1H,bs)

EXAMPLE 15

N-[2-(4-aminomethylphenoxy)phenyl]-N-(4-biphenylmethyl)-N'-(2-fluorobenzyl)succinamide hydrochloride (1) A mixture of 2-fluoronitrobenzene (1.1 g, 10 mmols), methyl p-hydroxyphenylacetate (1.7 g, 10 mmols) and potassium carbonate (1.4 g, 10 mmols) was stirred at 140° C. for 1 hour. The reaction mixture was diluted with ethyl acetate, then washed with water, and thereafter dried with anhydrous magnesium sulfate. This was concentrated under reduced pressure to give an oil of methyl 4-(2-nitrophenoxy) phenylacetate (2.78 g, 96.9%).

¹H-NMR (CDCl₃) δ: 3.67(2H,s), 3.70(3H,s), 6.99(2H,d, J=8.0 Hz), 7.02(1H,d,J=8.0 Hz), 7.19(1H,t,J=8.0 Hz), 7.28 (2H,d,J=8.4 Hz), 7.50(1H,t,J=8.0 Hz), 7.94(1H,d,J=8.0 Hz)

(2) Aqueous 1 N sodium hydroxide solution (41.7 ml, 41.7 mmols) was added to a solution of methyl 4-(2-nitrophenoxy)phenylacetate (2.7 g, 9.3 mmols) in tetrahydrofuran (50 ml) and methanol (50 ml). The resulting mixture was stirred at 40° C. for 1 hour. Water and potassium hydrogensulfate (5.68 g, 41.7 mmols) were added to the reaction mixture, which was then extracted with ethyl acetate. The extract was washed with water, and then dried with anhydrous magnesium sulfate. This was concentrated under reduced pressure, and the resulting solid was recrystallized from ethyl acetate/hexane to give a crystal of 4-(2-nitrophenoxy)phenylacetic acid (1.83 g, 71.8%).

m.p. 109–111° C.
Elemental Analysis for $C_{14}H_{11}NO_5$:
Calcd.: C, 61.54; H, 4.06; N, 5.13
Found: C, 61.54; H, 4.08; N, 5.03
¹H-NMR (CDCl₃) δ: 3.62(2H,s), 7.01(2H,d,J=8.8 Hz), 7.04(1H,d,J=8.2 Hz), 7.20(1H,t,J=8.2 Hz), 7.30(2H,d,J=8.8 Hz), 7.50(1H,t,J=8.2 Hz), 7.92(1H,d,J=8.2 Hz)

(3) Diphenylphosphorylazide (0.398 ml, 1.85 mmols) was added to a tert-butanol (4 ml) solution of [4-(2-nitrophenoxy) phenyl]acetic acid (0.42 g, 1.5 mmols). The reaction mixture was stirred at room temperature, and then at 90° C. for 2 hours. This was cooled, then poured into water, and extracted with ethyl acetate. The extract was washed with water, aqueous 1 N sodium hydroxide solution, and water in that order, and then dried with anhydrous magnesium sulfate, and the solvent was evaporated away. The residue was purified through silica gel column chromatography, and then recrystallized from ethyl acetate/hexane to give a crystal of tert-butyl[4-(2-nitrophenoxy)benzyl]carbamate (0.128 g, 24.2%).

m.p. 89–90° C.

Elemental Analysis for $C_{18}H_{20}N_2O_5$:

Calcd.: C, 62.78; H, 5.85; N, 8.13

Found: C, 62.71; H, 5.77; N, 8.43

$^1$H-NMR (CDCl$_3$) δ: 1.47(9H,s), 4.30(2H,d,J=6.4 Hz), 4,85(1H,bs), 6.98–7.03(3H,m), 7.20(1H,t,J=7.6 Hz), 7.30 (2H,t,J=8.6 Hz), 7.50(1H,d,J=7.6 Hz), 7.95(1H,d,J=7.6 Hz)

(4) 10% carbon-palladium (0.2 g) was added to an ethanol (20 ml) solution of tert-butyl[4-(2-nitrophenoxy)benzyl]carbamate (1.43 g, 4.15 mmols). The resulting mixture was hydrogenated at room temperature under atmospheric pressure. The catalyst was removed through filtration, and the filtrate was concentrated under reduced pressure. An oil of tert-butyl[4-(2-aminophenoxy)benzyl]carbamate (1.13 g, 86.9%) was obtained.

$^1$H-NMR (CDCl$_3$) δ: 1.45(9H,s), 3.78(2H,bs), 4.25(2H, d,J=5.8 Hz), 4.84(1H,bs), 6.66–7.35(8H,m)

(5) A mixture of tert-butyl[4-(2-aminophenoxy)benzyl]carbamate (2.10 g, 6.66 mmol), 4-phenylbenzaldehyde (1.21 g, 6.66 mmols), acetic acid (0.458 ml) and ethanol (30 ml) was stirred at room temperature for 30 minutes, to which was added sodium borocyanohydride (1.8 g, 10 mmols). This was stirred at 60° C. for 1 hour. Sodium borocyanohydride (1.8 g. 10 mmols) was further added thereto, and stirred at 60° C. for 1 hour. The reaction mixture was poured into water, and extracted with ethyl acetate. The extract was washed with water, then dried with anhydrous magnesium sulfate, and concentrated under reduced pressure. The residue was purified through silica gel column chromatography to give a crystal of tert-butyl[4-[2-(4-biphenylmethylamino)phenoxy]benzyl]carbamate (0.488 g, 15.3%).

m.p. 138–140° C.

$^1$H-NMR (CDCl$_3$) δ: 1.46(9H,s), 4.27(2H,d,J=5.8 Hz), 4.42(2H,d,J=5.8 Hz), 4.65(1H,t,J=5.8 Hz), 4.80(1H,bs), 6.62–7.60(17H,m).

(6) Aqueous 1 N sodium hydroxide solution (5.14 ml, 5.14 mmols) and ethylsuccinyl chloride (0.357 g, 2.17 mmols) were added to an ethyl acetate (5 ml) solution of tert-butyl [4-[2-(4-biphenylmethylamino)phenoxy]benzyl]carbamate (0.411 g, 0.855 mmols). This was stirred at room temperature for 1 hour. The reaction mixture was poured into water, and extracted with ethyl acetate. The extract was washed with water, and then dried with anhydrous magnesium sulfate. This was concentrated under reduced pressure, and the residue was purified through silica gel column chromatography to give an oil of ethyl N-(4-biphenylmethyl)-N-[2-[4-(tert-butoxycarbonylaminomethyl)phenoxy]phenyl]succinamate (0.426 g, 81.9%).

$^1$H-NMR (CDCl$_3$) δ: 1.28(3H,t,J=7.0 Hz), 1.47(9H,s), 2.46–2.76(4H,m), 4.13(2H,q,J=7.0 Hz), 4.23(2H,d,J=6.6 Hz), 4.78(1H,d,J=14.2 Hz), 4.80(1H,bs), 5.04(1H,d,J=14.2 Hz), 6.73–7.55(17H,m)

(7) Aqueous 1 N sodium hydroxide solution (2.71 ml, 2.71 mmols) was added to a solution of ethyl N-(4-biphenylmethyl)-N-[2-[4-(tert-butoxycarbonylaminomethyl)phenoxy]phenyl]succinamate (0.37 g. 0.61 mmols) in tetrahydrofuran (4 ml) and methanol (12 ml). The resulting mixture was stirred at 60° C. for 2 hours. Water and potassium hydrogensulfate (0.37 g, 2.7 mmols) were added to the reaction mixture, which was then extracted with ethyl acetate. The extract was washed with water, and then dried with anhydrous magnesium sulfate. This was concentrated under reduced pressure to give an amorphous solid of N-(4-biphenylmethyl)-N-[2-[4-(tert-butoxycarbonylaminomethyl)phenoxy]phenyl]succinamic acid (0.35 g, 99.4%).

$^1$H-NMR (CDCl$_3$) δ: 1.46(9H,s), 2.46–2.71(4H,m), 4.22 (2H,d,J=5.6 Hz), 4.78(1H,d,J=14.6 Hz), 4.82(1H,bs), 5.05 (1H,d,J=14.6 Hz), 6.71–7.55(17H,m)

(8) A mixture of N-(4-biphenylmethyl)-N-[2-[4-(tert-butoxycarbonylaminomethyl)phenoxy]phenyl]succinamic acid (0.25 g, 0.43 mmols), 2-fluorobenzylamine (0.0542 ml, 0.474 ml), diethyl cyanophosphate (0.0774 ml, 0.517 mmols), triethylamine (0.0721 ml, 0.517 mmols) and N,N-dimethylformamide (3 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(4-biphenylmethyl)-N-[2-[4-(tert-butoxycarbonylaminomethyl)phenoxy]phenyl]-N'-(2-fluorobenzyl)succinamide (50 mg, 17%).

$^1$H-NMR (CDCl$_3$) δ: 1.45(9H,s), 2.47–2.62(4H,m), 4.21 (2H,d,J=5.8 Hz), 4.46(2H,d,J=6.0 Hz), 4.75(1H,d,J=14.4 Hz), 4.85(1H,bs), 5.01(1H,d,J=14.4 Hz), 6.71–7.54(22H,m)

(9) A 2 N hydrochloric acid/ethyl acetate solution (2 ml) of N-(4-biphenylmethyl)-N-[2-[4-(tert-butoxycarbonylaminomethyl)phenoxy]phenyl]-N'-(2-fluorobenzyl)succinamide (50 mg, 0.073 mmols) was stirred at room temperature for 1 hour. The reaction mixture was concentrated under reduced pressure to give an amorphous solid of N-[2-(4-aminomethylphenoxy)phenyl]-N-(4-biphenylmethyl)-N'-(2-fluorobenzyl)succinamide hydrochloride (23 mg, 45%).

$^1$H-NMR (DMSO-d$_6$) δ: 2.06–2.30(4H,m), 3.75–3.83(3H,m), 4.08(2H,d,J=6.0 Hz), 4.30(1H,d,J=15.0 Hz), 4.90(1H,d,J=15.0 Hz), 6.63–7.42(21H,m), 8.20(3H,bs)

In the following Examples, the condition for HPLC is as follows:

Apparatus used: Shimadzu's LC-10Avp System

Column: CAPCELL PAK C18UG120, S-3 μm, 2.0×50 mm solvent

Liquid A: 0.1% trifluoroacetic acid-containing water

Liquid B: 0.1% trifluoroacetic acid-containing acetonitrile

Gradient cycle with A/B: 0.00 min (A/B=90/10), 4.00 min (A/B=5/95), 5.50 min (A/B=5/95), 5.51 min (A/B=90/10), 8.00 min (A/B=90/10)

Sample amount: 2 μl

Flow rate: 0.5 ml/min

Detection: UV 220 nm

In the following Examples, the condition for mass-spectrometry (MASS) is as follows:

Apparatus used: Micromass' Platform II

Ionization: Atmospheric pressure chemical ionization (APCI)

EXAMPLE 16

1N-[2-(3-aminomethylphenoxy)phenyl]-N-benzyl-N'-benzylsuccinamide trifluoroacetate (1) P-nitrophenoxycarbonyl-Wang:

P-hydroxymethylphenoxymethylpolystyrene (hereinafter referred to as Wang—Polymer Laboratories, 250–300 μm, 1.7 mmols/g) (1.00 g, 1.7 mmols) was suspended in a mixture of dichloromethane (15 ml) and pyridine (1.65 ml), to which were added p-nitrophenyl chloroformate (1.03 g, 5.11 mmols) and N,N-diisopropylethylamine (0.86 ml, 5.11 mmols). The resulting mixture was stirred at room temperature for 20 hours, and the solvent was removed through filtration. The resulting resin was washed with N,N-dimethylformamide, tetrahydrofuran and methanol three times each, and then dried under reduced pressure to give p-nitrophenoxycarbonyl-Wang (1.44 g).

Elemental Analysis: N, 1.77 (found)

From the data found, the amount of the compound per gram of the resin, Wang was 1.26 mmols/g.

IR (KBr): 1767 cm$^{-1}$ (2) 3-(2-Nitrophenoxy)benzylcarbamate-Wang:

A mixture of p-nitrophenoxycarbonyl-Wang (1.35 g, 1.70 mmols), 3-(2-nitrophenoxy)benzylamine (1.16 g, 4.75 mmols), N,N-diisopropylethylamine (0.8 ml, 4.75 mmols) and N,N-dimethylformamide (10 ml) was stirred at room temperature for 67 hours, and then the solvent was removed through filtration. The resulting resin was washed with N,N-dimethylformamide, tetrahydrofuran and methanol three times each, and then dried under reduced pressure to give 3-(2-nitrophenoxy)benzylcarbamate-Wang (1.5 g). The thus-obtained 3-(2-nitrophenoxy)benzylcarbamate-Wang (5 beads) was processed with trifluoroacetic acid/dichloromethane (3/1, 50 µl) to cut 3-(2-nitrophenoxy)benzylamine out of it. This was analyzed through HPLC.

HPLC analysis (220 nm): purity 92% (retention time: 2.271 min)

(3) 3-(2-Aminophenoxy)benzylcarbamate-Wang:

3-(2-Nitrophenoxy)benzylcarbamate-Wang (1.3 g, 1.4 mmols) was suspended in 2 M tin(II) chloride/N,N-dimethylformamide solution (20 ml), and stirred for 14 hours. The solvent was removed through filtration, and the resulting resin was washed with N,N-dimethylformamide, tetrahydrofuran and methanol three times each, and dried under reduced pressure to give 3-(2-aminophenoxy)benzylcarbamate-Wang (1.4 g). The thus-obtained 3-(2-aminophenoxy)benzylcarbamate-Wang (5 beads) was processed with trifluoroacetic acid/dichloromethane (3/1, 50 µl) to cut 3-(2-aminophenoxy)benzylamine out of it. This was analyzed through HPLC.

HPLC analysis (220 nm): purity 94% (retention time: 0.642 min)

(4) 3-(2-Benzylaminophenoxy)benzylcarbamate-Wang:

3-(2-Aminophenoxy)benzylcarbamate-Wang (100 mg, 0.11 mmols) was suspended in 1% acetic acid-containing N,N-dimethylformamide solution (3 ml), to which was added benzaldehyde (0.56 ml, 5.5 mmols). This was then stirred at room temperature for 1 hour. Sodium borocyanohydride (346 mg, 55 mmols) was added thereto, and further stirred at room temperature for 15 hours. The solvent was removed through filtration, and the resulting resin was washed with 1% acetic acid-containing N,N-di-methylformamide, tetrahydrofuran and methanol three times each, and then dried under reduced pressure to give 3-(2-benzylaminophenoxy)benzylcarbamate-Wang (100 mg). The thus-obtained 3-(2-benzylaminophenoxy)benzylcarbamate-Wang (5 beads) was processed with trifluoroacetic acid/dichloromethane (3/1, 50 µl) to cut 3-(2-benzylaminophenoxy)benzylamine out of the resin. This was analyzed through HPLC and mass-spectrometry.

HPLC analysis (220 nm): purity 93% (retention time: 2.772 min)

MASS (APCI$^-$): 303 (M−1)

(5) Ethyl N-benzyl-N-[2-(3-Wang-carbonylaminomethyl)phenoxy]phenylsuccinamate:

A mixture of 3-(2-benzylaminophenoxy)benzylcarbamate-Wang (200 mg, 0.22 mmols), ethylsuccinyl chloride (362 mg, 2.2 mmols), pyridine (348 mg. 14.4 mmols) and N,N-dimethylformamide (3 ml) was stirred at room temperature for 15 hours. The solvent was removed through filtration, and the resulting resin was washed with N,N-dimethylformamide, N,N-dimethylformamide/water (1/1 mixture), N,N-dimethylformamide, tetrahydrofuran and methanol three times each, and dried under reduced pressure to give ethyl N-benzyl-N-[2-(3-Wang-carbonylaminomethyl)phenoxy]phenylsuccinamate (200 mg). The thus-obtained ethyl N-benzyl-N-[2-(3-Wang-carbonylaminomethyl)phenoxy]phenylsuccinamate (5 beads) was processed with trifluoroacetic acid/dichloromethane (3/1, 50 µl) to cut ethyl N-benzyl-N-[2-(3-aminomethyl)phenoxy]phenylsuccinamate out of the resin. This was analyzed through HPLC and mass-spectrometry.

HPLC analysis (220 nm): purity 90% (retention time: 2.984 min)

MASS (APCI$^+$): 433 (M+1)

(6) N-benzyl-N-[2-(3-Wang-carbonylaminomethyl)phenoxy]phenylsuccinamic acid:

A mixture of ethyl N-benzyl-N-[2-(3-Wang-carbonylaminomethyl)phenoxy]phenylsuccinamate (200 mg, 0.22 mmols), aqueous 1 N sodium hydroxide solution (2.2 ml, 2.2 mmols) and tetrahydrofuran (2.2 ml) was stirred at room temperature for 17 hours. The solvent was removed through filtration, and the resulting resin was washed with tetrahydrofuran, tetrahydrofuran/acetic acid (1/1 mixture), tetrahydrofuran/water (1/1 mixture), tetrahydrofuran and methanol three times each, and dried under reduced pressure to give N-benzyl-N-[2-(3-Wang-carbonylaminomethyl)phenoxy]phenylsuccinamic acid (200 mg). The thus-obtained N-benzyl-N-[2-(3-Wang-carbonylaminomethyl)phenoxy]phenylsuccinamic acid (5 beads) was processed with trifluoroacetic acid/dichloromethane (3/1, 50 µl) to cut N-benzyl-N-[2-(3-aminomethyl)phenoxy]phenylsuccinamic acid out of the resin. This was analyzed through HPLC and mass-spectrometry.

HPLC analysis (220 nm): purity 92% (retention time: 2.623 min)

MASS (APCI$^+$): 405 (M+1)

(7) N-[2-(3-aminomethylphenoxy)phenyl]-N-benzyl-N'-benzylsuccinamide trifluoroacetate:

A mixture of N-benzyl-N-[2-(3-Wang-carbonylaminomethyl)phenoxy]phenylsuccinamic acid (100 mg), benzylamine (0.12 ml, 1.1 mmols), BOP reagent (487 mg, 1.1 mmols), N,N-diisopropylethylamine (0.19 ml, 1.1 mmols), N,N-dimethylformamide (1 ml) was stirred at room temperature for 17 hours. The solvent was removed through filtration, and the resulting resin was washed with N,N-dimethylformamide, N,N-dimethylformamide/water (1/1 mixture), N,N-dimethylformamide, tetrahydrofuran and methanol three times each, and dried under reduced pressure to give N-[2-(3-Wang-carbonylaminomethylphenoxy)phenyl]-N-benzyl-N'-benzylsuccinamide (100 mg). The thus-obtained N-[2-(3-Wang-carbonylaminomethylphenoxy)phenyl]-N-benzyl-N'-benzylsuccinamide (47 mg) was processed with trifluoroacetic acid/dichloromethane (3/1, 1 ml) to give N-[2-(3-aminomethylphenoxy)phenyl]-N-benzyl-N'-benzylsuccinamide trifluoroacetate (15 mg).

HPLC analysis (220 nm): purity 91% (retention time: 3.022 min)

MASS (APCI$^+$): 494 (M+1)

¹H-NMR (CDCl₃) δ: 2.40–2.60(4H,m), 3.83(2H,s), 4.37 (2H,d,J=5.8 Hz), 4.55(1H,d,J=14.4 Hz), 5.17(1H,14.4 Hz), 6.60–6.70(1H,m), 6.70–7.30(18H,m)

The following compounds were produced in the same manner as in Example 16.

EXAMPLE 17

N-[2-(3-aminomethylphenoxy)phenyl]-N-benzyl-N'-(2-fluorobenzyl)succinamide trifluoroacetate Yield: 26 mg
HPLC analysis (220 nm): purity 87% (retention time: 3.189 min)
MASS (APCI⁺): 512 (M+1)

EXAMPLE 18

N-[2-(3-aminomethylphenoxy)phenyl]-N-benzyl-N'-(2,6-difluorobenzyl)succinamide trifluoroacetate Yield: 25 mg
HPLC analysis (220 nm): purity 88% (retention time: 3.186 min)
MASS (APCI⁺): 530 (M+1)

EXAMPLE 19

N-[2-(3-aminomethylphenoxy)phenyl]-N-benzyl-N'-(3,4-difluorobenzyl)succinamide trifluoroacetate Yield: 25 mg
HPLC analysis (220 nm): purity 89% (retention time: 3.261 min)
MASS (APCI⁺): 530 (M+1)

EXAMPLE 20

N-[2-(3-aminomethylphenoxy)phenyl]-N-benzyl-N'-(2-trifluoromethylbenzyl)succinamide trifluoroacetate Yield: 25 mg
HPLC analysis (220 nm): purity 86% (retention time: 3.369 min)
MASS (APCI⁺): 562 (M+1)

EXAMPLE 21

N-[2-(3-aminomethylphenoxy)phenyl]-N-benzyl-N'-(4-methoxybenzyl)succinamide trifluoroacetate Yield: 23 mg
HPLC analysis (220 nm): purity 86% (retention time: 3.160 min)
MASS (APCI⁺): 524 (M+1)

EXAMPLE 22

N-[2-(3-aminomethylphenoxy)phenyl]-N-benzyl-N'-[2-(2,4-dichlorophenethyl)]succinamide trifluoroacetate Yield: 28 mg
HPLC analysis (220 nm): purity 86% (retention time: 3.490 min)
MASS (APCI⁺): 576 (M+1), 578 (M+3)

EXAMPLE 23

N-[2-(3-aminomethylphenoxy)phenyl]-N-benzyl-N'-(1-naphthylmethyl)succinamide trifluoroacetate Yield: 26 mg
HPLC analysis (220 nm): purity 88% (retention time: 3.374 min)
MASS (APCI⁺): 544 (M+1)

EXAMPLE 24

N-[2-(3-aminomethylphenoxy)phenyl]-N-benzyl-N'-(1-indanyl)succinamide trifluoroacetate Yield: 25 mg
HPLC analysis (220 nm): purity 81% (retention time: 3.296 min)
MASS (APCI⁺): 520 (M+1)

EXAMPLE 25

N-[2-(3-aminomethylphenoxy)phenyl]-N-benzyl-N'-(3-pyridylmethyl)succinamide trifluoroacetate Yield: 28 mg
HPLC analysis (220 nm): purity 84% (retention time: 2.497 min)
MASS (APCI⁺): 495 (M+1)

EXAMPLE 26

N-[2-(3-aminomethylphenoxy)phenyl]-N-benzyl-N'-(1,2,3,4-tetrahydroisoquinolino)succinamide trifluoroacetate Yield: 23 mg
HPLC analysis (220 nm): purity 79% (retention time: 3.309 min)
MASS (APCI⁺): 520 (M+1)

EXAMPLE 27

N-[2-(3-aminomethylphenoxy)phenyl]-N-benzyl-N'-(4-phenylpiperazino)succinamide trifluoroacetate Yield: 28 mg
HPLC analysis (220 nm): purity 85% (retention time: 3.011 min)
MASS (APCI⁺): 549 (M+1)

EXAMPLE 28

N-[2-(3-aminomethylphenoxy)phenyl]-N-benzyl-N'-[2-(1-pyrrolidinoethyl)]succinamide trifluoroacetate Yield: 27 mg
HPLC analysis (220 nm): purity 71% (retention time: 3.548 min)
MASS (APCI⁺): 501 (M+1)

EXAMPLE 29

N-[2-(3-aminomethylphenoxy)phenyl]-N-(4-phenoxybenzyl)-N'-(2-fluorobenzyl)succinamide trifluoroacetate Yield: 8.7 mg
HPLC analysis (220 nm): purity 100% (retention time: 3.742 min)
MASS (APCI$^+$): 604 (M+1)

EXAMPLE 30

N-[2-(3-aminomethylphenoxy)phenyl]-N-(4-phenoxybenzyl)-N'-(2,6-difluorobenzyl)succinamide trifluoroacetate Yield: 7.9 mg
HPLC analysis (220 nm): purity 100% (retention time: 3.736 min)
MASS (APCI$^+$): 622 (M+1)

EXAMPLE 31

N-[2-(3-aminomethylphenoxy)phenyl]-N-(4-phenoxybenzyl)-N'-(3,4-difluorobenzyl)succinamide trifluoroacetate Yield: 8.8 mg
HPLC analysis (220 nm): purity 100% (retention time: 3.778 min)
MASS (APCI$^+$): 604 (M+1)

EXAMPLE 32

N-[2-(3-aminomethylphenoxy)phenyl]-N-(4-phenoxybenzyl)-N'-(2-trifluoromethylbenzyl)succinamide trifluoroacetate Yield: 11 mg
HPLC analysis (220 nm): purity 99% (retention time: 3.864 min)
MASS (APCI$^+$): 654 (M+1)

EXAMPLE 33

N-[2-(3-aminomethylphenoxy)phenyl]-N-(4-phenoxybenzyl)-N'-(2-methoxybenzyl)succinamide trifluoroacetate Yield: 4.6 mg
HPLC analysis (220 nm): purity 100% (retention time: 3.154 min)
MASS (APCI$^+$): 616 (M+1)

EXAMPLE 34

N-[2-(3-aminomethylphenoxy)phenyl]-N-(4-phenoxybenzyl)-N'-[2-(2,4-dichlorophenethyl)]succinamide trifluoroacetate Yield: 10 mg
HPLC analysis (220 nm): purity 100% (retention time: 3.367 min)
MASS (APCI$^+$): 668 (M+1), 670 (M+3)

EXAMPLE 35

N-[2-(3-aminomethylphenoxy)phenyl]-N-(4-phenoxybenzyl)-N'-(1-naphthylmethyl)succinamide trifluoroacetate Yield: 11 mg
HPLC analysis (220 nm): purity 100% (retention time: 3.873 min)
MASS (APCI$^+$): 636 (M+1)

EXAMPLE 36

N-[2-(3-aminomethylphenoxy)phenyl]-N-(4-phenoxybenzyl)-N'-(1-indanyl)succinamide trifluoroacetate Yield: 10 mg
HPLC analysis (220 nm): purity 99% (retention time: 3.813 min)
MASS (APCI$^+$): 612 (M+1)

EXAMPLE 37

N-[2-(3-aminomethylphenoxy)phenyl]-N-(4-phenoxybenzyl)-N'-(2-pyridylmethyl)succinamide trifluoroacetate Yield: 7.1 mg
HPLC analysis (220 nm): purity 99% (retention time: 3.147 min)
MASS (APCI$^+$): 587 (M+1)

EXAMPLE 38

N-[2-(3-aminomethylphenoxy)phenyl]-N-(4-phenoxybenzyl)-N'-(1,2,3,4-tetrahydroisoquinolino)succinamide trifluoroacetate Yield: 9.1 mg
HPLC analysis (220 nm): purity 98% (retention time: 3.392 min)
MASS (APCI$^+$): 612 (M+1)

EXAMPLE 39

N-[2-(3-aminomethylphenoxy)phenyl]-N-(4-phenoxybenzyl)-N'-(4-phenylpiperazino)succinamide trifluoroacetate Yield: 7.8 mg
HPLC analysis (220 nm): purity 99% (retention time: 3.824 min)
MASS (APCI$^+$): 641 (M+1)

EXAMPLE 40

N-[2-(3-aminomethylphenoxy)phenyl]-N-(4-phenoxybenzyl)-N'-[2-(1-pyrrolidinoethyl)]succinamide trifluoroacetate Yield: 6.5 mg
HPLC analysis (220 nm): purity 98% (retention time: 3.175 min)
MASS (APCI$^+$): 593 (M+1)

EXAMPLE 41

N-[2-(3-aminomethylphenoxy)phenyl]-N-(4-tert-butylbenzyl)-N'-(2-fluorobenzyl)succinamide trifluoroacetate Yield: 21 mg
HPLC analysis (220 nm): purity 77% (retention time: 3.596 min)
MASS (APCI$^+$): 568 (M+1)

EXAMPLE 42

N-[2-(3-aminomethylphenoxy)phenyl]-N-(4-tert-butylbenzyl)-N'-(2,6-difluorobenzyl)succinamide trifluoroacetate Yield: 24 mg
HPLC analysis (220 nm): purity 80% (retention time: 3.601 min)
MASS (APCI$^+$): 586 (M+1)

EXAMPLE 43

N-[2-(3-aminomethylphenoxy)phenyl]-N-(4-tert-butylbenzyl)-N'-(3,4-difluorobenzyl)succinamide trifluoroacetate Yield: 21 mg
HPLC analysis (220 nm): purity 72% (retention time: 3.640 min)
MASS (APCI$^+$): 586 (M+1)

EXAMPLE 44

N-[2-(3-aminomethylphenoxy)phenyl]-N-(4-tert-butylbenzyl)-N'-(2-trifluoromethylbenzyl)succinamide trifluoroacetate Yield: 23 mg
HPLC analysis (220 nm): purity 82% (retention time: 3.739 min)

EXAMPLE 45

N-[2-(3-aminomethylphenoxy)phenyl]-N-(4-tert-butylbenzyl)-N'-(4-methoxybenzyl)succinamide trifluoroacetate Yield: 20 mg
HPLC analysis (220 nm): purity 75% (retention time: 3.568 min)
MASS (APCI$^+$): 580 (M+1)

EXAMPLE 46

N-[2-(3-aminomethylphenoxy)phenyl]-N-(4-tert-butylbenzyl)-N'-[2-(2,4-dichlorophenethyl)]succinamide trifluoroacetate Yield: 23 mg
HPLC analysis (220 nm): purity 85% (retention time: 3.868 min)
MASS (APCI$^+$): 632 (M+1), 634 (M+3)

EXAMPLE 47

N-[2-(3-aminomethylphenoxy)phenyl]-N-(4-tert-butylbenzyl)-N'-(1-naphthylmethyl)succinamide trifluoroacetate Yield: 22 mg
HPLC analysis (220 nm): purity 86% (retention time: 3.741 min)
MASS (APCI$^+$): 600 (M+1)

EXAMPLE 48

N-[2-(3-aminomethylphenoxy)phenyl]-N-(4-tert-butylbenzyl)-N'-(1-indanyl)succinamide trifluoroacetate Yield: 22 mg
HPLC analysis (220 nm): purity 71% (retention time: 3.688 min)
MASS (APCI$^+$): 576 (M+1)

EXAMPLE 49

N-[2-(3-aminomethylphenoxy)phenyl]-N-(4-tert-butylbenzyl)-N'-(3-pyridylmethyl)succinamide trifluoroacetate Yield: 24 mg
HPLC analysis (220 nm): purity 78% (retention time: 2.963 min)
MASS (APCI$^+$): 551 (M+1)

EXAMPLE 50

N-[2-(3-aminomethylphenoxy)phenyl]-N-(4-tert-butylbenzyl)-N'-(1,2,3,4-tetrahydroisoquinolino)succinamide trifluoroacetate Yield: 22 mg
HPLC analysis (220 nm): purity 72% (retention time: 3.694 min)
MASS (APCI$^+$): 576 (M+1)

EXAMPLE 51

N-[2-(3-aminomethylphenoxy)phenyl]-N-(4-tert-butylbenzyl)-N'-(4-phenylpiperazino)succinamide trifluoroacetate Yield: 25 mg
HPLC analysis (220 nm): purity 81% (retention time: 3.436 min)
MASS (APCI$^+$): 605 (M+1)

EXAMPLE 52

N-[2-(3-aminomethylphenoxy)phenyl]-N-(4-tert-butylbenzyl)-N'-[2-(1-pyrrolidinoethyl)]succinamide trifluoroacetate Yield: 7.4 mg
HPLC analysis (220 nm): purity 99% (retention time: 3.004 min)
MASS (APCI$^+$): 557 (M+1)

EXAMPLE 53

N-[2-(3-aminomethylphenoxy)phenyl]-N-(1-naphthylmethyl)-N'-(2-fluorobenzyl)succinamide trifluoroacetate Yield: 19 mg
HPLC analysis (220 nm): purity 80% (retention time: 3.388 min)
MASS (APCI$^+$): 562 (M+1)

EXAMPLE 54

N-[2-(3-aminomethylphenoxy)phenyl]-N-(1-naphthylmethyl)-N'-(2,6-difluorobenzyl)succinamide trifluoroacetate Yield: 20 mg
HPLC analysis (220 nm): purity 80% (retention time: 3.390 min)
MASS (APCI$^+$): 580 (M+1)

EXAMPLE 55

N-[2-(3-aminomethylphenoxy)phenyl]-N-(1-naphthylmethyl)-N'-(3,4-difluorobenzyl)succinamide trifluoroacetate Yield: 20 mg
HPLC analysis (220 nm): purity 77% (retention time: 3.445 min)
MASS (APCI$^+$): 580 (M+1)

EXAMPLE 56

N-[2-(3-aminomethylphenoxy)phenyl]-N-(1-naphthylmethyl)-N'-(2-trifluoromethylbenzyl)succinamide trifluoroacetate Yield: 21 mg
HPLC analysis (220 nm): purity 74% (retention time: 3.544 min)
MASS (APCI$^+$): 612 (M+1)

EXAMPLE 57

N-[2-(3-aminomethylphenoxy)phenyl]-N-(1-naphthylmethyl)-N'-(4-methoxybenzyl)succinamide trifluoroacetate Yield: 19 mg
HPLC analysis (220 nm): purity 80% (retention time: 3.357 min)
MASS (APCI$^+$): 574 (M+1)

EXAMPLE 58

N-[2-(3-aminomethylphenoxy)phenyl]-N-(1-naphthylmethyl)-N'-[2-(2,4-dichlorophenethyl)]succinamide trifluoroacetate Yield: 21 mg
HPLC analysis (220 nm): purity 79% (retention time: 3.662 min)
MASS (APCI$^+$): 626 (M+1), 628 (M+3)

EXAMPLE 59

N-[2-(3-aminomethylphenoxy)phenyl]-N-(1-naphthylmethyl)-N'-(1-naphthylmethyl)succinamide trifluoroacetate Yield: 21 mg
HPLC analysis (220 nm): purity 76% (retention time: 3.554 min)
MASS (APCI$^+$): 594 (M+1)

EXAMPLE 60

N-[2-(3-aminomethylphenoxy)phenyl]-N-(1-naphthylmethyl)-N'-(1-indanyl)succinamide trifluoroacetate Yield: 21 mg
HPLC analysis (220 nm): purity 76% (retention time: 3.481 min)
MASS (APCI$^+$): 570 (M+1)

EXAMPLE 61

N-[2-(3-aminomethylphenoxy)phenyl]-N-(1-naphthylmethyl)-N'-(3-pyridylmethyl)succinamide trifluoroacetate Yield: 25 mg
HPLC analysis (220 nm): purity 76% (retention time: 2.723 min)
MASS (APCI$^+$): 587 (M+1)

EXAMPLE 62

N-[2-(3-aminomethylphenoxy)phenyl]-N-(1-naphthylmethyl)-N'-(1,2,3,4-tetrahydroisoquinolino)succinamide trifluoroacetate Yield: 23 mg
HPLC analysis (220 nm): purity 73% (retention time: 3.494 min)
MASS (APCI$^+$): 570 (M+1)

EXAMPLE 63

N-[2-(3-aminomethylphenoxy)phenyl]-N-(1-naphthylmethyl)-N'-(4-phenylpiperazino)succinamide trifluoroacetate Yield: 26 mg
HPLC analysis, (220 nm): purity 68% (retention time: 3.209 min)
MASS (APCI$^+$): 599 (M+1)

EXAMPLE 64

N-[2-(3-aminomethylphenoxy)phenyl]-N-(1-naphthylmethyl)-N'-[2-(1-pyrrolidinoethyl)]succinamide trifluoroacetate Yield: 24 mg
HPLC analysis (220 nm): purity 68% (retention time: 2.763 min)
MASS (APCI$^+$): 551 (M+1)

EXAMPLE 65

N-[2-(3-aminomethylphenoxy)phenyl]-N-(4-acetamidobenzyl)-N'-(2-fluorobenzyl)-succinamide trifluoroacetate Yield: 29 mg
HPLC analysis (220 nm): purity 76% (retention time: 2.899 min)
MASS (APCI$^+$): 569 (M+1)

EXAMPLE 66

N-[2-(3-aminomethylphenoxy)phenyl]-N-(4-acetamidobenzyl)-N'-(2,6-difluorobenzyl)succinamide trifluoroacetate Yield: 30 mg
HPLC analysis (220 nm): purity 75% (retention time: 2.903 min)
MASS (APCI$^+$): 587 (M+1)

EXAMPLE 67

N-[2-(3-aminomethylphenoxy)phenyl]-N-(4-acetamidobenzyl)-N'-(3,4-difluorobenzyl)succinamide trifluoroacetate Yield: 29 mg
HPLC analysis (220 nm): purity 76% (retention time: 2.976 min)
MASS (APCI$^+$): 587 (M+1)

EXAMPLE 68

N-[2-(3-aminomethylphenoxy)phenyl]-N-(4-acetamidobenzyl)-N'-(2-trifluoromethylbenzyl)succinamide trifluoroacetate Yield: 29 mg
HPLC analysis (220 nm): purity 75% (retention time: 3.100 min)
MASS (APCI$^+$): 619 (M+1)

EXAMPLE 69

N-[2-(3-aminomethylphenoxy)phenyl]-N-(4-acetamidobenzyl)-N'-(4-methoxybenzyl)succinamide trifluoroacetate Yield: 25 mg
HPLC analysis (220 nm): purity 75% (retention time: 2.865 min)
MASS (APCI$^+$): 581 (M+1)

EXAMPLE 70

N-[2-(3-aminomethylphenoxy)phenyl]-N-(4-acetamidobenzyl)-N'-[2-(2,4-dichlorophenethyl)]succinamide trifluoroacetate Yield: 30 mg
HPLC analysis (220 nm): purity 82% (retention time: 3.229 min)
MASS (APCI$^+$): 633 (M+1), 635 (M+3)

EXAMPLE 71

N-[2-(3-aminomethylphenoxy)phenyl]-N-(4-acetamidobenzyl)-N'-(1-naphthylmethyl)succinamide trifluoroacetate Yield: 29 mg
HPLC analysis (220 nm): purity 79% (retention time: 3.106 min)
MASS (APCI$^+$): 601 (M+1).

EXAMPLE 72

N-[2-(3-aminomethylphenoxy)phenyl]-N-(4-acetamidobenzyl)-N'-(1-indanyl)succinamide trifluoroacetate Yield: 21 mg
HPLC analysis (220 nm): purity 77% (retention time: 3.004 min)
MASS (APCI$^+$): 576 (M+1)

EXAMPLE 73

N-[2-(3-aminomethylphenoxy)phenyl]-N-(4-acetamidobenzyl)-N'-(3-pyridylmethyl)succinamide trifluoroacetate Yield: 28 mg
HPLC analysis (220 nm): purity 83% (retention time: 2.237 min)
MASS (APCI$^+$): 552 (M+1)

EXAMPLE 74

N-[2-(3-aminomethylphenoxy)phenyl]-N-(4-acetamidobenzyl)-N'-(1,2,3,4-tetrahydroisoquinolino)succinamide trifluoroacetate Yield: 27 mg
HPLC analysis (220 nm): purity 74% (retention time: 3.028 min)
MASS (APCI$^+$): 577 (M+1)

EXAMPLE 75

N-[2-(3-aminomethylphenoxy)phenyl]-N-(4-acetamidobenzyl)-N'-(4-phenylpiperazino)succinamide trifluoroacetate Yield: 32 mg
HPLC analysis (220 nm): purity 78% (retention time: 2.723 min)
MASS (APCI$^+$): 606 (M+1)

EXAMPLE 76

N-[2-(3-aminomethylphenoxy)phenyl]-N-(4-acetamidobenzyl)-N'-[2-(1-pyrrolidinoethyl)]succinamide trifluoroacetate Yield: 29 mg
HPLC analysis (220 nm): purity 74% (retention time: 2.283 min)
MASS (APCI$^+$): 558 (M+1)

EXAMPLE 77

N-[2-(3-aminomethylphenoxy)phenyl]-N-(4-cyanobenzyl)-N'-(2-fluorobenzyl)succinamide trifluoroacetate Yield: 9.5 mg
HPLC analysis (220 nm): purity 99% (retention time: 3.297 min)
MASS (APCI$^+$): 537 (M+1)

EXAMPLE 78

N-[2-(3-aminomethylphenoxy)phenyl]-N-(4-cyanobenzyl)-N'-(2,6-difluorobenzyl)succinamide trifluoroacetate Yield: 12 mg
HPLC analysis (220 nm): purity 99% (retention time: 3.297 min)
MASS (APCI$^+$): 555 (M+1)

EXAMPLE 79

N-[2-(3-aminomethylphenoxy)phenyl]-N-(4-cyanobenzyl)-N'-(3,4-difluorobenzyl)succinamide trifluoroacetate Yield: 7.6 mg
HPLC analysis (220 nm): purity 100% (retention time: 3.360 min)
MASS (APCI$^+$): 555 (M+1)

EXAMPLE 80

N-[2-(3-aminomethylphenoxy)phenyl]-N-(4-cyanobenzyl)-N'-(2-trifluoromethylbenzyl)succinamide trifluoroacetate Yield: 12 mg
HPLC analysis (220 nm): purity 91% (retention time: 3.481 min)
MASS (APCI$^+$): 587 (M+1)

EXAMPLE 81

N-[2-(3-aminomethylphenoxy)phenyl]-N-(4-cyanobenzyl)-N'-(2-methoxybenzyl)succinamide trifluoroacetate Yield: 8.5 mg
HPLC analysis (220 nm): purity 99% (retention time: 3.355 min)
MASS (APCI$^+$): 549 (M+1)

EXAMPLE 82

N-[2-(3-aminomethylphenoxy)phenyl]-N-(4-cyanobenzyl)-N'-[[2-(2,4-dichlorophenethyl)]succinamide trifluoroacetate Yield: 11 mg
HPLC analysis (220 nm): purity 97% (retention time: 3.614 min)
MASS (APCI$^+$): 601 (M+1), 603 (M+3)

EXAMPLE 83

N-[2-(3-aminomethylphenoxy)phenyl]-N-(4-cyanobenzyl)-N'-(1-naphthylmethyl)succinamide trifluoroacetate Yield: 11 mg
HPLC analysis (220 nm): purity 93% (retention time: 3.500 min)
MASS (APCI$^+$): 569 (M+1)

EXAMPLE 84

N-[2-(3-aminomethylphenoxy)phenyl]-N-(4-cyanobenzyl)-N'-(1-indanyl)succinamide trifluoroacetate Yield: 11 mg
HPLC analysis (220 nm): purity 100% (retention time: 3.412 min)
MASS (APCI$^+$): 545 (M+1)

EXAMPLE 85

N-[2-(3-aminomethylphenoxy)phenyl]-N-(4-cyanobenzyl)-N'-(2-pyridylmethyl)succinamide trifluoroacetate Yield: 8.8 mg
HPLC analysis (220 nm): purity 100% (retention time: 2.664 min)
MASS (APCI$^+$): 520 (M+1)

EXAMPLE 86

N-[2-(3-aminomethylphenoxy)phenyl]-N-(4-cyanobenzyl)-N'-(1,2,3,4-tetrahydroisoquinolino)succinamide trifluoroacetate Yield: 11 mg
HPLC analysis (220 nm): purity 99% (retention time: 3.438 min)
MASS (APCI$^+$): 545 (M+1)

EXAMPLE 87

N-[2-(3-aminomethylphenoxy)phenyl]-N-(4-cyanobenzyl)-N'-(4-phenylpiperazino)succinamide trifluoroacetate Yield: 12 mg
HPLC analysis (220 nm): purity 100% (retention time: 3.163 min)
MASS (APCI$^+$): 574 (M+1)

EXAMPLE 88

N-[2-(3-aminomethylphenoxy)phenyl]-N-(4-cyanobenzyl)-N'-[2-(1-pyrrolidinoethyl)]succinamide trifluoroacetate Yield: 8.7 mg
HPLC analysis (220 nm): purity 99% (retention time: 2.682 min)
MASS (APCI$^+$): 525 (M+1)

EXAMPLE 89

N-[2-(3-aminomethylphenoxy)phenyl]-N-(3,4,5-trimethoxybenzyl)-N'-(2-fluorobenzyl)succinamide trifluoroacetate Yield: 9.0 mg
HPLC analysis (220 nm): purity 98% (retention time: 3.331 min)
MASS (APCI$^+$): 601 (M+1)

EXAMPLE 90

N-[2-(3-aminomethylphenoxy)phenyl]-N-(3,4,5-trimethoxybenzyl)-N'-(2,6-difluorobenzyl)succinamide trifluoroacetate Yield: 10 mg
HPLC analysis (220 nm): purity 98% (retention time: 3.329 min)
MASS (APCI$^+$): 620 (M+1)

EXAMPLE 91

N-[2-(3-aminomethylphenoxy)phenyl]-N-(3,4,5-trimethoxybenzyl)-N'-(3,4-difluorobenzyl)succinamide trifluoroacetate Yield: 11 mg
HPLC analysis (220 nm): purity 97% (retention time: 3.369 min)
MASS (APCI$^+$): 620 (M+1)

EXAMPLE 92

N-[2-(3-aminomethylphenoxy)phenyl]-N-(3,4,5-trimethoxybenzyl)-N'-(2-trifluoromethylbenzyl)succinamide trifluoroacetate Yield: 8.7 mg.
HPLC analysis (220 nm): purity 99% (retention time: 3.509 min)
MASS (APCI$^+$): 652 (M+1)

EXAMPLE 93

N-[2-(3-aminomethylphenoxy)phenyl]-N-(3,4,5-trimethoxybenzyl)-N'-(2-methoxybenzyl)succinamide trifluoroacetate Yield: 3.9 mg
HPLC analysis (220 nm): purity 98% (retention time: 3.359 min)
MASS (APCI$^+$): 614 (M+1)

EXAMPLE 94

N-[2-(3-aminomethylphenoxy)phenyl]-N-(3,4,5-trimethoxybenzyl)-N'-[2-(2,4-dichlorophenethyl)]succinamide trifluoroacetate Yield: 9.6 mg
HPLC analysis (220 nm): purity 98% (retention time: 3.629 min)
MASS (APCI$^+$): 666 (M+1), 668 (M+3)

EXAMPLE 95

N-[2-(3-aminomethylphenoxy)phenyl]-N-(3,4,5-trimethoxybenzyl)-N'-(1-naphthylmethyl)succinamide trifluoroacetate Yield: 11 mg
HPLC analysis (220 nm): purity 96% (retention time: 3.511 min)
MASS (APCI$^+$): 634 (M+1)

EXAMPLE 96

N-[2-(3-aminomethylphenoxy)phenyl]-N-(3,4,5-trimethoxybenzyl)-N'-(1-indanyl)succinamide trifluoroacetate Yield: 6.4 mg
HPLC analysis (220 nm): purity 97% (retention time: 3.397 min)
MASS (APCI$^+$): 610 (M+1)

EXAMPLE 97

N-[2-(3-aminomethylphenoxy)phenyl]-N-(3,4,5-trimethoxybenzyl)-N'-(2-pyridylmethyl)succinamide trifluoroacetate Yield: 5.5 mg
HPLC analysis (220 nm): purity 99% (retention time: 2.666 min)
MASS (APCI$^+$): 585 (M+1)

EXAMPLE 98

N-[2-(3-aminomethylphenoxy)phenyl]-N-(3,4,5-trimethoxybenzyl)-N'-(1,2,3,4-tetrahydroisoquinolino)succinamide trifluoroacetate Yield: 5.9 mg
HPLC analysis (220 nm): purity 94% (retention time: 3.421 min)
MASS (APCI$^+$): 610 (M+1)

EXAMPLE 99

N-[2-(3-aminomethylphenoxy)phenyl]-N-(3,4,5-trimethoxybenzyl)-N'-(4-phenylpiperazino)succinamide trifluoroacetate Yield: 7.3 mg
HPLC analysis (220 nm): purity 100% (retention time: 3.152 min)
MASS (APCI$^+$): 639 (M+1)

EXAMPLE 100

N-[2-(3-aminomethylphenoxy)phenyl]-N-(3,4,5-trimethoxybenzyl)-N'-[2-(1-pyrrolidinoethyl)]succinamide trifluoroacetate Yield: 5.1 mg
HPLC analysis (220 nm): purity 98% (retention time: 2.721 min)
MASS (APCI$^+$): 591 (M+1)

EXAMPLE 101

N-[2-(3-aminomethylphenoxy)phenyl]-N-(2-fluorenylmethyl)-N'-(2-fluorobenzyl)succinamide trifluoroacetate Yield: 9.5 mg
HPLC analysis (220 nm): purity 99% (retention time: 3.774 min)
MASS (APCI$^+$): 600 (M+1)

EXAMPLE 102

N-[2-(3-aminomethylphenoxy)phenyl]-N-(2-fluorenylmethyl)-N'-(2,6-difluorobenzyl)succinamide trifluoroacetate Yield: 10 mg
HPLC analysis (220 nm): purity 99% (retention time: 3.775 min)
MASS (APCI$^+$): 618 (M+1)

EXAMPLE 103

N-[2-(3-aminomethylphenoxy)phenyl]-N-(2-fluorenylmethyl)-N'-(3,4-difluorobenzyl)succinamide trifluoroacetate Yield: 11 mg
HPLC analysis (220 nm): purity 100% (retention time: 3.882 min)
MASS (APCI$^+$): 618 (M+1)

EXAMPLE 104

N-[2-(3-aminomethylphenoxy)phenyl]-N-(2-fluorenylmethyl)-N'-(2-trifluoromethylbenzyl)succinamide trifluoroacetate Yield: 12 mg
HPLC analysis (220 nm): purity 99% (retention time: 3.902 min)
MASS (APCI$^+$): 650 (M+1)

EXAMPLE 105

N-[2-(3-aminomethylphenoxy)phenyl]-N-(2-fluorenylmethyl)-N'-(2-methoxybenzyl)succinamide trifluoroacetate Yield: 8.0 mg
HPLC analysis (220 nm): purity 99% (retention time: 3.794 min)
MASS (APCI$^+$): 612 (M+1)

EXAMPLE 106

N-[2-(3-aminomethylphenoxy)phenyl]-N-(2-fluorenylmethyl)-N'-[2-(2,4-dichlorophenethyl)]succinamide trifluoroacetate Yield: 13 mg
HPLC analysis (220 nm): purity 99% (retention time: 4.011 min)
MASS (APCI$^+$): 664 (M+1), 666 (M+3)

EXAMPLE 107

N-[2-(3-aminomethylphenoxy)phenyl]-N-(2-fluorenylmethyl)-N'-(1-naphthylmethyl)succinamide trifluoroacetate Yield: 8.6 mg
HPLC analysis (220 nm): purity 99% (retention time: 3.916 min)
MASS (APCI$^+$): 632 (M+1)

EXAMPLE 108

N-[2-(3-aminomethylphenoxy)phenyl]-N-(2-fluorenylmethyl)-N'-(1-indanyl)succinamide trifluoroacetate Yield: 11 mg
HPLC analysis (220 nm): purity 100% (retention time: 3.858 min)
MASS (APCI$^+$): 608 (M+1)

EXAMPLE 109

N-[2-(3-aminomethylphenoxy)phenyl]-N-(2-fluorenylmethyl)-N'-(2-pyridylmethyl)succinamide trifluoroacetate Yield: 13 mg
HPLC analysis (220 nm): purity 100% (retention time: 3.176 min)
MASS (APCI$^+$): 583 (M+1)

EXAMPLE 110

N-[2-(3-aminomethylphenoxy)phenyl]-N-(2-fluorenylmethyl)-N'-(1,2,3,4-tetrahydroisoquinolino)succinamide trifluoroacetate Yield: 11 mg
HPLC analysis (220 nm): purity 97% (retention time: 3.867 min)
MASS (APCI$^+$): 608 (M+1)

EXAMPLE 111

N-[2-(3-aminomethylphenoxy)phenyl]-N-(2-fluorenylmethyl)-N'-(4-phenylpiperazino)succinamide trifluoroacetate Yield: 11 mg
HPLC analysis (220 nm): purity 96% (retention time: 3.610 min)
MASS (APCI$^+$): 637 (M+1)

EXAMPLE 112

N-[2-(3-aminomethylphenoxy)phenyl]-N-(2-fluorenylmethyl)-N'-[2-(1-pyrrolidinoethyl)]succinamide trifluoroacetate Yield: 13 mg
HPLC analysis (220 nm): purity 100% (retention time: 3.179 min)
MASS (APCI$^+$): 589 (M+1)1

EXAMPLE 113

N-[2-(3-aminomethylphenoxy)phenyl]-N-[4-(2'-methylphenyl)benzyl]-N'-(2-fluorobenzyl)succinamide trifluoroacetate To a DMF (4 ml) suspension of N-(4-bromobenzyl)-N-[2-(3-Wang-carbonylaminomethyl)phenoxy]-N'-(2-fluorobenzyl)succinamic acid (50 mg), added were 2-methylphenylboronic acid (55 mg), tetrakis(triphenylphosphine) palladium(0) (6.3 mg) and aqueous 2 M sodium carbonate solution (0.28 ml). The mixture was stirred at 80° C. for 22 hours. The solvent was removed through filtration, and the resulting resin was washed with N,N-dimethylformamide, N,N-dimethylformamide/water (1/1 mixture), N,N-dimethylformamide, tetrahydrofuran and methanol three times each, and then dried under reduced pressure to give N-[2-(3-Wang-carbonylaminomethylphenoxy)phenyl]-N-[4-(2'-methylphenyl)benzyl]-N'-(2-fluorobenzyl)succinamide. The thus obtained resin was processed with trifluoroacetic acid/dichloromethane (3/1, 1 ml) to give N-[2-(3-aminomethylphenoxy)phenyl]-N-[4-(2'-methylphenyl)benzyl]-N'-(2-fluorobenzyl)succinamide trifluoroacetate (22 mg)

HPLC analysis (220 nm): purity 93% (retention time: 4.346 min)

MASS (APCI$^+$): 602 (M+1)

$^1$H-NMR (CDCl$_3$) δ: 2.22(3H,s), 2.30–2.40(4H,m), 4.03 (2H,s), 4.21(2H,t,J=6.6 Hz), 4.41(1H,d,J=14.2 Hz), 5.31 (1H,d,J=14.2 Hz), 6.90–7.40(20H,m)

The following compounds were produced in the same manner as in Example 113.

EXAMPLE 114

N-[2-(3-aminomethylphenoxy)phenyl]-N-[4-(2'-methylphenyl)benzyl]-N'-(2-trifluoromethylbenzyl)succinamide trifluoroacetate Yield: 23 mg HPLC analysis (220 nm): purity 83% (retention time: 4.449 min)

MASS (APCI$^+$): 652 (M+1)

$^1$H-NMR (CDCl$_3$) δ: 2.22(3H,s), 2.30–2.55(4H,m), 4.02 (2H,s), 4.34(2H,m), 4.39(1H,d,J=14.6 Hz), 5.32(1H,d, J=14.6 Hz), 6.85–7.70(20H,m)

EXAMPLE 115

N-[2-(3-aminomethylphenoxy)phenyl]-N-[4-(2'-methylphenyl)benzyl]-N'-(1-indanyl)succinamide trifluoroacetate Yield: 24 mg HPLC analysis (220 nm): purity 88% (retention time: 4.422 min)

MASS (APCI$^+$): 610 (M+1)

EXAMPLE 116

N-[2-(3-aminomethylphenoxy)phenyl]-N-[4-(2'-methylphenyl)benzyl]-N'-(4-phenylpiperazino)succinamide trifluoroacetate Yield: 28 mg HPLC analysis (220 nm): purity 81% (retention time: 3.423 min)

MASS (APCI$^+$): 639 (M+1)

EXAMPLE 117

N-[2-(3-aminomethylphenoxy)phenyl]-N-[4-(2'-methylphenyl)benzyl]-N'-(1,2,3,4-tetrahydroisoquinolino)succinamide trifluoroacetate Yield: 23 mg HPLC analysis (220 nm): purity 84% (retention time: 3.696 min)

MASS (APCI$^+$): 610 (M+1)

EXAMPLE 118

N-[2-(3-aminomethylphenoxy)phenyl]-N-[4-(2'-methylphenyl)benzyl]-N'-(2-fluorobenzyl)succinamide trifluoroacetate Yield: 1.8 mg HPLC analysis (220 nm): purity 98% (retention time: 4.220 min)

MASS (APCI$^+$): 618 (M+1)

EXAMPLE 119

N-[2-(3-aminomethylphenoxy)phenyl]-N-[4-(2'-methylphenyl)benzyl]-N'-(2-trifluoromethylbenzyl)succinamide trifluoroacetate Yield: 3.1 mg HPLC analysis (220 nm): purity 98% (retention time: 4.348 min)

MASS (APCI$^+$): 668 (M+1)

EXAMPLE 120

N-[2-(3-aminomethylphenoxy)phenyl]-N-[4-(2'-methylphenyl)benzyl]-N'-(1-indanyl)succinamide trifluoroacetate Yield: 3.3 mg HPLC analysis (220 nm): purity 100% (retention time: 4.305 min)

MASS (APCI$^+$): 626 (M+1)

EXAMPLE 121

N-[2-(3-aminomethylphenoxy)phenyl]-N-[4-(2'-methylphenyl)benzyl]-N'-(4-phenylpiperazino)succinamide trifluoroacetate Yield: 4.1 mg HPLC analysis (220 nm): purity 85% (retention time: 3.597 min)

MASS (APCI$^+$): 655 (M+1)

EXAMPLE 122

N-[2-(3-aminomethylphenoxy)phenyl]-N-[4-(2'-methoxyphenyl)benzyl]-N'-(1,2,3,4-tetrahydroisoquinolino) succinamide trifluoroacetate Yield: 3.3 mg HPLC analysis (220 nm): purity 89% (retention time: 3.329 min)

MASS (APCI$^+$): 626 (M+1)

EXAMPLE 123

N-[2-(3-aminomethylphenoxy)phenyl]-N-(4-(3'-thienyl)benzyl)-N'-(2-fluorobenzyl)succinamide trifluoroacetate Yield: 1.6 mg
HPLC analysis (220 nm): purity 100% (retention time: 4.216 min)
MASS (APCI$^+$): 594 (M+1)

EXAMPLE 124

N-[2-(3-aminomethylphenoxy)phenyl]-N-[4-(3'-thienyl)benzyl]-N'-(2-trifluoromethylbenzyl)succinamide trifluoroacetate Yield: 2.2 mg
HPLC analysis (220 nm): purity 100% (retention time: 4.346 min)
MASS (APCI$^+$): 644 (M+1)

EXAMPLE 125

N-[2-(3-aminomethylphenoxy)phenyl]-N-[4-(3'-thienyl)benzyl]-N'-(1-indanyl)succinamide trifluoroacetate Yield: 1.7 mg
HPLC analysis (220 nm): purity 99% (retention time: 4.289 min)
MASS (APCI$^+$): 602 (M+1)

EXAMPLE 126

N-[2-(3-aminomethylphenoxy)phenyl]-N-[4-(3'-thienyl)benzyl]-N'-(4-phenylpiperazino)succinamide trifluoroacetate Yield: 2.1 mg
HPLC analysis (220 nm): purity 92% (retention time: 3.268 min)
MASS (APCI$^+$): 631 (M+1)

EXAMPLE 127

N-[2-(3-aminomethylphenoxy)phenyl]-N-[4-(3'-thienyl)benzyl]-N'-(1,2,3,4-tetrahydroisoquinolino)succinamide trifluoroacetate Yield: 2.6 mg
HPLC analysis (220 nm): purity 100% (retention time: 3.539 min)
MASS (APCI$^+$): 602 (M+1)

EXAMPLE 128

N-[2-(3-aminomethylphenoxy)phenyl]-N-[4-(benzofuran-2'-yl)benzyl]-N'-(2-fluorobenzyl)succinamide trifluoroacetate Yield: 1.3 mg
HPLC analysis (220 nm): purity 99% (retention time: 4.408 min)
MASS (APCI$^+$): 628 (M+1)

EXAMPLE 129

N-[2-(3-aminomethylphenoxy)phenyl]-N-[4-(benzofuran-2'-yl)benzyl]-N'-(2-trifluoromethylbenzyl)succinamide trifluoroacetate Yield: 1.0 mg
HPLC analysis (220 nm): purity 98% (retention time: 4.513 min)
MASS (APCI$^+$): 678 (M+1)

EXAMPLE 130

N-[2-(3-aminomethylphenoxy)phenyl]-N-[4-(benzofuran-2'-yl)benzyl]-N'-(1-indanyl)succinamide trifluoroacetate Yield: 1.2 mg
HPLC analysis (220 nm): purity 98% (retention time: 4.479 min)
MASS (APCI$^+$): 636 (M+1)

EXAMPLE 131

N-[2-(3-aminomethylphenoxy)phenyl]-N-[4-(benzofuran-2'-yl)benzyl]-N'-(4-phenylpiperazino)succinamide trifluoroacetate Yield: 1.6 mg
HPLC analysis (220 nm): purity 99% (retention time: 3.528 min)
MASS (APCI$^+$): 665 (M+1)

EXAMPLE 132

N-[2-(3-aminomethylphenoxy)phenyl]-N-[4-(benzofuran-2'-yl)benzyl]-N'-(1,2,3,4-tetrahydroisoquinolino)succinamide trifluoroacetate Yield: 1.2 mg
HPLC analysis (220 mm): purity 99% (retention time: 3.776 min)
MASS (APCI$^+$): 636 (M+1)

EXAMPLE 133

N-[2-(3-aminomethylphenoxy)phenyl]-N-(4-(3'-trifluoromethylphenyl)benzyl)-N'-(2-fluorobenzyl)succinamide trifluoroacetate Yield: 23 mg
HPLC analysis (220 nm): purity 92% (retention time: 4.420 min)
MASS (APCI$^+$): 656 (M+1)

EXAMPLE 134

N-[2-(3-aminomethylphenoxy)phenyl]-N-[4-(3'-trifluoromethylphenyl)benzyl]-N'-(2-trifluoromethylbenzyl)succinamide trifluoroacetate Yield: 25 mg
HPLC analysis (220 nm): purity 91% (retention time: 4.534 min)
MASS (APCI$^+$): 706 (M+1)

EXAMPLE 135

N-[2-(3-aminomethylphenoxy)phenyl]-N-[4-(3'-trifluoromethylphenyl)benzyl]-N'-(1-indanyl)succinamide trifluoroacetate Yield: 26 mg
HPLC analysis (220 nm): purity 90% (retention time: 4.491 min)
MASS (APCI$^+$): 664 (M+1)

EXAMPLE 136

N-[2-(3-aminomethylphenoxy)phenyl]-N-[4-(3'-trifluoromethylphenyl)benzyl]-N'-(4-phenylpiperazino)succinamide trifluoroacetate Yield: 30 mg
HPLC analysis (220 nm): purity 81% (retention time: 3.527 min)
MASS (APCI$^+$): 693 (M+1)

EXAMPLE 137

N-[2-(3-aminomethylphenoxy)phenyl]-N-[4-(3'-trifluoromethylphenyl)benzyl]-N'-(1,2,3,4-tetrahydroisoquinolino)succinamide trifluoroacetate Yield: 11 mg
HPLC analysis (220 nm): purity 96% (retention time: 3.790 min)
MASS (APCI$^+$): 664 (M+1)

EXAMPLE 138

N-[2-(3-aminomethylphenoxy)phenyl]-N-[4-(4'-fluorophenyl)benzyl]-N'-(2-fluorobenzyl)succinamide trifluoroacetate Yield: 23 mg
HPLC analysis (220 nm): purity 93% (retention time: 4.293 min)
MASS (APCI$^+$): 606 (M+1)

EXAMPLE 139

N-[2-(3-aminomethylphenoxy)phenyl]-N-[4-(4'-fluorophenyl)benzyl]-N'-(2-trifluoromethylbenzyl)succinamide trifluoroacetate Yield: 23 mg
HPLC analysis (220 nm): purity 88% (retention time: 4.406 min)
MASS (APCI$^+$): 656 (M+1)

EXAMPLE 140

N-[2-(3-aminomethylphenoxy)phenyl]-N-[4-(4'-fluorophenyl)benzyl]-N'-(1-indanyl)succinamide trifluoroacetate Yield: 23 mg
HPLC analysis (220 nm): purity 87% (retention time: 4.365 min)
MASS (APCI$^+$): 614 (M+1)

EXAMPLE 141

N-[2-(3-aminomethylphenoxy)phenyl]-N-[4-(4'-fluorophenyl)benzyl]-N'-(4-phenylpiperazino)succinamide trifluoroacetate Yield: 28 mg
HPLC analysis (220 nm): purity 85% (retention time: 3.356 min)
MASS (APCI$^+$): 643 (M+1)

EXAMPLE 142

N-[2-(3-aminomethylphenoxy)phenyl]-N-[4-(4'-fluorophenyl)benzyl]-N'-(1,2,3,4-tetrahydroisoquinolino)succinamide trifluoroacetate Yield: 22 mg
HPLC analysis (220 nm): purity 80% (retention time: 3.634 min)
MASS (APCI$^+$): 614 (M+1)

EXAMPLE 143

N-[2-(3-aminomethylphenoxy)phenyl]-N-(4-(1'-naphthyl)benzyl)-N'-(2-fluorobenzyl)succinamide trifluoroacetate Yield: 21 mg
HPLC analysis (220 nm): purity 94% (retention time: 4.437 min)
MASS (APCI$^+$): 638 (M+1)

EXAMPLE 144

N-[2-(3-aminomethylphenoxy)phenyl]-N-[4-(1'-naphthyl)benzyl]-N'-(2-trifluoromethylbenzyl)succinamide trifluoroacetate Yield: 21 mg
HPLC analysis (220 nm): purity 94% (retention time: 4.540 min)
MASS (APCI$^+$): 688 (M+1)

EXAMPLE 145

N-[2-(3-aminomethylphenoxy)phenyl]-N-[4-(1'-naphthyl)benzyl]-N'-(1-indanyl)succinamide trifluoroacetate Yield: 23 mg
HPLC analysis (220 nm): purity 86% (retention time: 4.695 min)
MASS (APCI$^+$): 646 (M+1)

EXAMPLE 146

N-[2-(3-aminomethylphenoxy)phenyl]-N-[4-(1'-naphthyl)benzyl]-N'-(4-phenylpiperazino)succinamide trifluoroacetate Yield: 24 mg
HPLC analysis (220 nm): purity 89% (retention time: 3.547 min)
MASS (APCI$^+$): 675 (M+1)

EXAMPLE 147

N-[2-(3-aminomethylphenoxy)phenyl]-N-[4-(1'-naphthyl)benzyl]-N'-(1,2,3,4-tetrahydroisoquinolino)succinamide trifluoroacetate Yield: 22 mg
HPLC analysis (220 nm): purity 80% (retention time: 3.803 min)
MASS (APCI$^+$): 646 (M+1)

EXAMPLE 148

N-[2-(3-aminomethylphenoxy)phenyl]-N-[4-(4'-methoxyphenyl)benzyl]-N'-(2-fluorobenzyl)succinamide trifluoroacetate Yield: 5.4 mg
HPLC analysis (220 nm): purity 100% (retention time: 3.468 min)
MASS (APCI$^+$): 618 (M+1)

EXAMPLE 149

N-[2-(3-aminomethylphenoxy)phenyl]-N-[4-(4'-methoxyphenyl)benzyl]-N'-(2-trifluoromethylbenzyl)succinamide trifluoroacetate Yield: 5.3 mg
HPLC analysis (220 nm): purity 99% (retention time: 3.604 min)
MASS (APCI$^+$): 668 (M+1)

EXAMPLE 150

N-[2-(3-aminomethylphenoxy)phenyl]-N-[4-(4'-methoxyphenyl)benzyl]-N'-(1-indanyl)succinamide trifluoroacetate Yield: 6.7 mg
HPLC analysis (220 nm): purity 89% (retention time: 3.562 min)
MASS (APCI$^+$): 626 (M+1)

EXAMPLE 151

N-[2-(3-aminomethylphenoxy)phenyl]-N-[4-(4'-methoxyphenyl)benzyl]-N'-(4-phenylpiperazino)succinamide trifluoroacetate Yield: 6.4 mg
HPLC analysis (220 nm): purity 100% (retention time: 3.321 min)
MASS (APCI$^+$): 655 (M+1)

EXAMPLE 152

N-[2-(3-aminomethylphenoxy)phenyl]-N-[4-(4'-methoxyphenyl)benzyl]-N'-(1,2,3,4-tetrahydroisoquinolino)succinamide trifluoroacetate Yield: 8.3 mg
HPLC analysis (220 nm): purity 100% (retention time: 3.576 min)
MASS (APCI$^+$): 626 (M+1)

EXAMPLE 153

N-[2-(3-aminomethylphenoxy)phenyl]-N-(4-(3'-methoxyphenyl)benzyl)-N'-(2-fluorobenzyl)succinamide trifluoroacetate Yield: 1.4 mg
HPLC analysis (220 nm): purity 100% (retention time: 3.496 min)
MASS (APCI$^+$): 618 (M+1)

EXAMPLE 154

N-[2-(3-aminomethylphenoxy)phenyl]-N-[4-(3'-methoxyphenyl)benzyl]-N'-(2-trifluoromethylbenzyl)succinamide trifluoroacetate Yield: 1.7 mg
HPLC analysis (220 nm): purity 100% (retention time: 3.631 min)
MASS (APCI$^+$): 668 (M+1)

EXAMPLE 155

N-[2-(3-aminomethylphenoxy)phenyl]-N-[4-(3'-methoxyphenyl)benzyl]-N'-(1-indanyl)succinamide trifluoroacetate Yield: 1.4 mg
HPLC analysis (220 nm): purity 100% (retention time: 3.578 min)
MASS (APCI$^+$): 626 (M+1)

EXAMPLE 156

N-[2-(3-aminomethylphenoxy)phenyl]-N-[4-(3'-methoxyphenyl)benzyl]-N'-(4-phenylpiperazino)succinamide trifluoroacetate Yield: 1.6 mg
HPLC analysis (220 nm): purity 100% (retention time: 3.332 min)
MASS (APCI$^+$): 655 (M+1)

EXAMPLE 157

N-[2-(3-aminomethylphenoxy)phenyl]-N-[4-(3'-methoxyphenyl)benzyl]-N'-(1,2,3,4-tetrahydroisoquinolino)succinamide trifluoroacetate Yield: 1.5 mg
HPLC analysis (220 nm): purity 100% (retention time: 3.590 min)
MASS (APCI$^+$): 626 (M+1)

EXAMPLE 158

N-[2-(3-aminomethylphenoxy)phenyl]-N-[4-(3'-formylphenyl)benzyl]-N'-(2-fluorobenzyl)succinamide trifluoroacetate Yield: 13 mg
HPLC analysis (220 nm): purity 100% (retention time: 3.473 min)
MASS (APCI$^+$): 616 (M+1)

EXAMPLE 159

N-[2-(3-aminomethylphenoxy)phenyl]-N-[4-(3'-formylphenyl)benzyl]-N'-(2-trifluoromethylbenzyl)succinamide trifluoroacetate Yield: 13 mg
HPLC analysis (220 nm): purity 95% (retention time: 3.614 min)
MASS (APCI$^+$): 666 (M+1)

EXAMPLE 160

N-[2-(3-aminomethylphenoxy)phenyl]-N-[4-(3'-formylphenyl)benzyl]-N'-(1-indanyl)succinamide trifluoroacetate Yield: 11 mg
HPLC analysis (220 nm): purity 100% (retention time: 3.558 min)
MASS (APCI$^+$): 624 (M+1)

EXAMPLE 161

N-[2-(3-aminomethylphenoxy)phenyl]-N-[4-(3'-formylphenyl)benzyl]-N'-(4-phenylpiperazino)succinamide trifluoroacetate Yield: 11 mg
HPLC analysis (220 nm): purity 100% (retention time: 3.310 min)
MASS (APCI$^+$): 653 (M+1)

EXAMPLE 162

N-[2-(3-aminomethylphenoxy)phenyl]-N-[4-(3'-formylphenyl)benzyl]-N'-(1,2,3,4-tetrahydroisoquinolino)succinamide trifluoroacetate Yield: 12 mg
HPLC analysis (220 nm): purity 92% (retention time: 3.574 min)
MASS (APCI$^+$): 624 (M+1)

EXAMPLE 163

N-[2-(3-aminomethylphenoxy)phenyl]-N-[4-(4'-methylthiophenyl)benzyl]-N'-(2-fluorobenzyl)succinamide trifluoroacetate Yield: 5.2 mg
HPLC analysis (220 nm): purity 99% (retention time: 3.621 min)
MASS (APCI$^+$): 634 (M+1)

EXAMPLE 164

N-[2-(3-aminomethylphenoxy)phenyl]-N-[4-(4'-methylthiophenyl)benzyl]-N'-(2-trifluoromethylbenzyl)succinamide trifluoroacetate Yield: 2.9 mg
HPLC analysis (220 nm): purity 100% (retention time: 3.752 min)
MASS (APCI$^+$): 684 (M+1)

EXAMPLE 165

N-[2-(3-aminomethylphenoxy)phenyl]-N-[4-(4'-methylthiophenyl)benzyl]-N'-(1-indanyl)succinamide trifluoroacetate Yield: 3.7 mg
HPLC analysis (220 nm): purity 95% (retention time: 3.755 min)
MASS (APCI$^+$): 642 (M+1)

EXAMPLE 166

N-[2-(3-aminomethylphenoxy)phenyl]-N-[4-(4'-methylthiophenyl)benzyl]-N'-(4-phenylpiperazino)succinamide trifluoroacetate Yield: 2.7 mg
HPLC analysis (220 nm): purity 99% (retention time: 3.462 min)
MASS (APCI$^+$): 671 (M+1)

EXAMPLE 167

N-[2-(3-aminomethylphenoxy)phenyl]-N-[4-(4'-methylthiophenyl)benzyl]-N'-(1,2,3,4-tetrahydroisoquinolino)succinamide trifluoroacetate Yield: 2.8 mg
HPLC analysis (220 nm): purity 99% (retention time: 3.742 min)
MASS (APCI$^+$): 642 (M+1)

EXAMPLE 168

N-[2-(3-aminomethylphenoxy)phenyl]-N-[4-(2',5'-dichlorophenyl)benzyl]-N'-(2-fluorobenzyl)succinamide trifluoroacetate Yield: 11 mg
HPLC analysis (220 nm): purity 100% (retention time: 3.823 min)
MASS (APCI$^+$): 656 (M+1)

EXAMPLE 169

N-[2-(3-aminomethylphenoxy)phenyl]-N-[4-(2',5'-dichlorophenyl)benzyl]-N'-(2-trifluoromethylbenzyl)succinamide trifluoroacetate Yield: 11 mg
HPLC analysis (220 nm): purity 100% (retention time: 3.961 min)
MASS (APCI$^+$): 706 (M+1)

EXAMPLE 170

N-[2-(3-aminomethylphenoxy)phenyl]-N-[4-(2',5'-dichlorophenyl)benzyl]-N'-(1-indanyl)succinamide trifluoroacetate Yield: 9.1 mg
HPLC analysis (220 nm): purity 98% (retention time: 3.910 min)
MASS (APCI$^+$): 664 (M+1)

EXAMPLE 171

N-[2-(3-aminomethylphenoxy)phenyl]-N-[4-(2',5'-dichlorophenyl)benzyl]-N'-(4-phenylpiperazino)succinamide trifluoroacetate Yield: 9.3 mg
HPLC analysis (220 nm): purity 100% (retention time: 3.668 min)
MASS (APCI$^+$): 693 (M+1)

EXAMPLE 172

N-[2-(3-aminomethylphenoxy)phenyl]-N-[4-(2',5'-dichlorophenyl)benzyl]-N'-(1,2,3,4-tetrahydroisoquinolino)succinamide trifluoroacetate Yield: 8.7 mg
HPLC analysis (220 nm): purity 100% (retention time: 3.937 min)
MASS (APCI$^+$): 664 (M+1)

EXAMPLE 173

N-[2-(3-aminomethylphenoxy)phenyl]-N-(4-(3'-acetamidophenyl)benzyl]-N'-(2-fluorobenzyl)succinamide trifluoroacetate Yield: 28 mg
HPLC analysis (220 nm): purity 91% (retention time: 3.168 min)
MASS (APCI$^+$): 645 (M+1)

EXAMPLE 174

N-[2-(3-aminomethylphenoxy)phenyl]-N-[4-(3'-acetamidophenyl)benzyl]-N'-(2-trifluoromethylbenzyl)succinamide trifluoroacetate Yield: 25 mg
HPLC analysis (220 nm): purity 92% (retention time: 3.318 min)
MASS (APCI$^+$): 695 (M+1)

EXAMPLE 175

N-[2-(3-aminomethylphenoxy)phenyl]-N-[4-(3'-acetamidophenyl)benzyl]-N'-(1-indanyl)succinamide trifluoroacetate Yield: 13 mg
HPLC analysis (220 nm): purity 100% (retention time: 3.257 min)
MASS (APCI$^+$): 653 (M+1)

EXAMPLE 176

N-[2-(3-aminomethylphenoxy)phenyl]-N-[4-(3'-acetamidophenyl)benzyl]-N'-(4-phenylpiperazino)succinamide trifluoroacetate Yield: 10 mg
HPLC analysis (220 nm): purity 100% (retention time: 3.020 min)
MASS (APCI$^+$): 682 (M+1)

EXAMPLE 177

N-[2-(3-aminomethylphenoxy)phenyl]-N-[4-(3'-acetamidophenyl)benzyl]-N'-(1,2,3,4-tetrahydroisoquinolino)succinamide trifluoroacetate Yield: 20 mg
HPLC analysis (220 nm): purity 88% (retention time: 3.289 min)
MASS (APCI$^+$): 653 (M+1)

EXAMPLE 178

N-[2-(3-aminomethylphenoxy)phenyl]-N-[4-(2'-thienyl)benzyl]-N'-(2-fluorobenzyl)succinamide trifluoroacetate Yield: 1.1 mg
HPLC analysis (220 nm): purity 99% (retention time: 3.461 min)
MASS (APCI$^+$): 594 (M+1)

EXAMPLE 179

N-[2-(3-aminomethylphenoxy)phenyl]-N-[4-(2'-thienyl)benzyl]-N'-(2-trifluoromethylbenzyl)succinamide trifluoroacetate Yield: 1.3 mg
HPLC analysis (220 nm): purity 100% (retention time: 3.484 min)
MASS (APCI$^+$): 644 (M+1)

EXAMPLE 180

N-[2-(3-aminomethylphenoxy)phenyl]-N-[4-(2'-thienyl)benzyl]-N'-(1-indanyl)succinamide trifluoroacetate Yield: 1.1 mg
HPLC analysis (220 nm): purity 94% (retention time: 3.546 min)
MASS (APCI$^+$): 602 (M+1)

EXAMPLE 181

N-[2-(3-aminomethylphenoxy)phenyl]-N-[4-(2'-thienyl)benzyl]-N'-(4-phenylpiperazino)succinamide trifluoroacetate Yield: 2.3 mg
HPLC analysis (220 nm): purity 100% (retention time: 3.138 min)
MASS (APCI$^+$): 631 (M+1)

EXAMPLE 182

N-[2-(3-aminomethylphenoxy)phenyl]-N-[4-(2'-thienyl)benzyl]-N'-(1,2,3,4-tetrahydroisoquinolino)succinamide trifluoroacetate Yield: 1.2 mg
HPLC analysis (220 nm): purity 94% (retention time: 3.439 min)
MASS (APCI$^+$): 602 (M+1)

EXAMPLE 183

N-(2-fluorobenzyl)-4-[N'-[2-[3-(aminomethyl)phenoxy]-4-chlorophenyl]-N'-(9-oxo-9H-fluorene-2-carbonyl)]aminobutylamide hydrochloride (1) Aqueous 1 N sodium hydroxide solution (15 ml, 15 mmols) was added to a solution of ethyl 4-[2-[3-(tert-butoxycarbonylaminomethyl)phenoxy]-4-chlorophenyl] aminobutyrate (4.6 g, 10 mmols) in tetrahydrofuran (15 ml) and ethanol (15 ml). The resulting mixture was stirred at room temperature for 2 hours. Water was added to the reaction mixture, which was acidified with 1 N hydrochloric acid added thereto, and then extracted with ethyl acetate. The extract was washed with water, and then dried with anhydrous magnesium sulfate. This was concentrated under reduced pressure to give an amorphous solid of 4-[2-[3-(tert-butoxycarbonylaminomethyl)phenoxy]-4-chlorophenyl] aminobutyric acid (4.1 g, 95%).

Elemental Analysis for $C_{22}H_{27}N_2O_5Cl$:
Calcd.: C, 60.76; H, 6.26, N, 6.44
Found: C, 60.84; H, 6.30; N, 6.39
$^1$H-NMR (CDCl$_3$) δ: 1.44(9H,s), 1.86–1.99(2H,m), 2.38 (2H,t,J=6.8 Hz), 3.19(2H,t,J=6.6 Hz), 4.27(2H,s), 5.03(1H, bs), 5.45(1H,bs), 6.23(1H,bs), 6.63(1H,d,J=8.4 Hz), 6.81–6.87(2H,m), 6.95–7.03(3H,m), 7.25(1H,t,J=7.9 Hz)

(2) A mixture of 4-[2-[3-(tert-butoxycarbonylaminomethyl)phenoxy]-4-chlorophenyl]aminobutyric acid (3.9 g, 9 mmols), 2-fluorobenzylamine (1.2 ml, 11 mmols), diethyl cyanophosphate (1.5 ml, 11 mmols), triethylamine (1.5 ml, 11 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an oil of N-(2-fluorobenzyl)-4-[N'-[2-[3-(tert-butoxycarbonylaminomethyl) phenoxy]-4-chlorophenyl]aminobutylamide (2.8 g, 57%).

Elemental Analysis for $C_{29}H_{33}N_3O_4ClF$:
Calcd.: C, 64.26; H, 6.14; N, 7.75
Found: C, 64.14; H, 6.10; N, 7.68
$^1$H-NMR (CDCl$_3$) δ: 1.42(9H,s), 1.86–1.99(2H,m), 2.20 (2H,t,J=7.2 Hz), 3.17(2H,t,J=6.6 Hz), 4.25(2H,d,J=6.0 Hz), 4.43(2H,d,J=5.8 Hz), 4.94(1H,bs), 6.01(1H,bs), 6.60(2H,d, J=8.8 Hz), 6.79–6.86(3H,m), 6.95–7.12(4H,m), 7.21–7.33 (4H,m)

(3) A mixture of N-(2-fluorobenzyl)-4-[N'-[2-[3-(tert-butoxycarbonylaminomethyl)phenoxy]-4-chlorophenyl]aminobutylamide (0.6 g, 1.1 mmols), 9-fluorenone-2-carbonyl chloride (0.32 g, 1.3 mmols) and N,N-dimethylacetamide (20 ml) was stirred at room temperature for 2 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-(9-oxo-9H-fluorenone-2-carbonyl)]aminobutylamide (0.72 g, 87%).

Elemental Analysis for $C_{43}H_{39}N_3O_6ClF.1/2H_2O$:
Calcd.: C, 68.20; H, 5.32; N, 5.55
Found: C, 68.49; H, 5.35; N, 5.33

$^1$H-NMR (CDCl$_3$) δ: 1.42(9H,s), 1.96(2H,m), 2.37(2H, m), 3.86(1H,m), 4.01(1H,m), 4.22(2H,d,J=5.6 Hz), 4.50(2H, d,J=5.4 Hz), 5.20(1H,bs), 6.58(1H,s), 6.74(3H,m), 6.96–7.67(15H,m)

(4) A 2 N hydrochloric acid/ethyl acetate solution (10 ml) of N-(2-fluorobenzyl)-4-[N'-[2-[3-(tert-butoxycarbonylaminomethyl)phenoxy]-4-chlorophenyl]-N'-(9-oxo-9H-fluorenone-2-carbonyl)]aminobutylamide (0.59 g, 0.8 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-(9-oxo-9H-fluorenone-2-carbonyl)]aminobutylamide hydrochloride (0.35 g, 97%).

Elemental Analysis for $C_{38}H_{32}N_3O_4Cl_2F.1/2H_2O$:
Calcd.: C, 65.80; H, 4.80; N, 6.06
Found: C, 65.89; H, 4.89; N, 5.84
$^1$H-NMR (DMSO-d$_6$) δ: 1.84(2H,m), 2.30(2H,m), 3.47 (1H,m), 3.80(1H,m), 4.00(2H,m), 4.31(2H,d,J=4.4 Hz), 6.63 (1H,s), 6.87(1H,m), 7.16–7.83(16H,m), 8.52(3H,m)

EXAMPLE 184

N-(2-fluorobenzyl)-4-[N'-[2-[3-(aminomethyl)phenoxy]-4-chlorophenyl]-N'-[[4-(benzenesulfonylamino)phenyl]acetyl]]aminobutylamide hydrochloride (1) A mixture of ethyl 4-aminophenylacetate (3.0 g, 17 mmols), benzenesulfonyl chloride (3.0 g, 17 mmols) and N,N-dimethylacetamide (30 ml) was stirred at room temperature for 2 hours. The reaction mixture was cooled, poured into water, and extracted with ethyl acetate. The extract was washed with water and brine, and then dried with anhydrous magnesium sulfate. This was concentrated under reduced pressure. A 1 N sodium hydroxide solution (50 ml, 50 mmols) was added to a solution of the residue in tetrahydrofuran (50 ml) and ethanol (50 ml). The resulting mixture was stirred at 60° C. for 1 hour. Water was added to the reaction mixture, which was acidified with potassium hydrogensulfate added thereto, and then extracted with ethyl acetate. The extract was washed with water, and then dried with anhydrous magnesium sulfate. This was concentrated under reduced pressure, and the residue was crystallized from hexane/ethyl acetate to give a solid of 4-benzenesulfonylaminophenylacetic acid (3.1 g, 64%).

$^1$H-NMR (DMSO-d$_6$) δ: 3.45(2H,s), 7.00–7.13(4H,m), 7.49–7.64(3H,m), 7.76(2H,m), 10.26(1H,bs)

A tetrahydrofuran (15 ml) solution of 4-benzenesulfonylaminophenylacetic acid (0.35 g, 1.2 mmols), oxalyl chloride (0.30 g, 2.4 mmols) and N,N-dimethylformamide (0.3 ml) was stirred at room temperature for 1 hour. The reaction mixture was concentrated under reduced pressure, to which were added N-(2-fluorobenzyl)-4-[N7-[2-[3-(tert-butoxycarbonylaminomethyl)phenoxy]-4-chlorophenyl]]aminobutylamide (0.6 g, 1.1 mmols) and N,N-dimethylacetamide (10 ml). The resulting mixture was stirred at room temperature for 2 hours. This was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[[4-(benzenesulfonylamino)phenyl]acetyl]-N'-[2-[3-(tert-butoxycarbonylaminomethyl)phenoxy]-4-chlorophenyl]]aminobutylamide (0.56 g, 62%).

Elemental Analysis for $C_{43}H_{44}N_4O_7ClFS \cdot 1/2H_2O$:
Calcd.: C, 62.65; H, 5.50; N, 6.80
Found: C, 62.84; H, 5.41; N, 6.68
$^1$H-NMR (CDCl$_3$) δ: 1.43(9H,s), 1.85(2H,m), 2.26(2H,m), 3.41(2H,m), 3.65(1H,m), 3.80(1H,m), 4.26(2H,m), 4.42(2H,d,J=5.4 Hz), 5.21(1H,m), 6.68–7.51(19H,m), 7.71(2H,m), 7.92(1H,m)

(2) A 2N hydrochloric acid/ethyl acetate solution (2 ml) of N-(2-fluorobenzyl)-4-[N'-[[4-(benzenesulfonylamino)phenyl]acetyl]-N'-[2-[3-(tert-butoxycarbonylaminomethyl)phenoxy]-4-chlorophenyl]]aminobutylamide (0.29 g, 0.36 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[[4-(benzenesulfonylamino)phenyl]acetyl]]aminobutylamide hydrochloride (0.26 g, 96%).
Elemental Analysis for $C_{38}H_{37}N_4O_5Cl_2FS \cdot H_2O$:
Calcd.: C, 59.30; H, 5.11; N, 7.28
Found: C, 59.22; H, 4.93; N, 7.26
$^1$H-NMR (DMSO-d$_6$) δ: 1.67(2H,m), 2.16(2H,m), 3.31(2H,m), 3.46(1H,m), 3.70(1H,m), 4.03(2H,m), 4.26(2H,d,J=4.4 Hz), 6.81–7.60(18H,m), 7.76(2H,m), 8.39(1H,m), 8.51(2H,bs), 10.31(1H,s)

EXAMPLE 185

N-(2-fluorobenzyl)-4-[N'-[2-[3-(aminomethyl)phenoxy]-4-chlorophenyl]-N'-[(2-naphthyl)acetyl]]aminobutylamide hydrochloride (1) A mixture of N-(2-fluorobenzyl)-4-[N'-[2-[3-(tert-butoxycarbonylaminomethyl)phenoxy]-4-chlorophenyl]]aminobutylamide (0.5 g, 0.9 mmols), 2-naphthylacetyl chloride (0.38 mg, 1.8 mmols) and N,N-dimethylacetamide (15 ml) was stirred at room temperature for 2 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[(2-naphthyl)acetyl]-N'-[2-[3-(tert-butoxycarbonylaminomethyl)phenoxy]-4-chlorophenyl]]aminobutylamide (0.57 g, 87%).
Elemental Analysis for $C_{41}H_{41}N_3O_5ClF \cdot 1/4H_2O$:
Calcd.: C, 68.90, H, 5.85; N, 5.88
Found: C, 68.94; H, 5.96; N, 5.78
$^1$H-NMR (CDCl$_3$) δ: 1.43(9H,s), 1.84(2H,m), 2.25(2H,m), 3.67(2H,m), 3.74(2H,m), 4.19(2H,d,J=5.8 Hz), 4.44(2H,d,J=5.6 Hz), 5.02(1H,bs), 6.65–6.78(4H,m), 6.97–7.48(12H,m), 7.66–7.83(3H,m)

(2) A 2 N hydrochloric acid/ethyl acetate solution (2 ml) of N-(2-fluorobenzyl)-4-[N'-[(2-naphthyl)acetyl]-N'-[2-[3-(tert-butoxycarbonylaminomethyl)phenoxy]-4-chlorophenyl]]aminobutylamide (0.33 g, 0.46 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(2-naphthyl)acetyl]aminobutylamide hydrochloride (0.29 g, 95%).
Elemental Analysis for $C_{36}H_{34}N_3O_3Cl_2F \cdot 1/2H_2O$:
Calcd.: C, 65.95; H, 5.38; N, 6.41
Found: C, 66.13; H, 5.26; N, 6.41
$^1$H-NMR (DMSO-d$_6$) δ: 1.73(2H,m), 2.21(2H,m), 3.46(1H,m), 3.64(1H,m), 3.80(1H,m), 4.01(2H,m), 4.27(2H,d,J=5.0 Hz), 6.85(1H,m), 6.98–7.54(14H,m), 7.77–7.90(3H,m), 8.44(1H,m), 8.60(2H,bs)

EXAMPLE 186

N-(2-fluorobenzyl)-4-[N'-[2-[3-(aminomethyl)phenoxy]-4-chlorophenyl]-N'-[[4-(2-oxopyrrolidin-1-yl)phenyl]acetyl]]aminobutylamide hydrochloride (1) A mixture of ethyl 4-aminophenylacetate (2.0 g, 11 mmols), ethyl 4-bromobutanoate (8.7 g, 45 mmols), potassium carbonate (2.3 g, 17 mmols) and N,N-dimethylformamide (50 ml) was stirred at 60° C. for 24 hours. The reaction mixture was cooled, then poured into water, and extracted with ethyl acetate. The extract was washed with water and brine, and then dried with anhydrous magnesium sulfate. This was concentrated under reduced pressure, and the residue was purified through silica gel column chromatography to give an oil of ethyl 4-[4-(ethoxycarbonylmethyl)phenyl]aminobutanoate (2.4 g, 74%).
$^1$H-NMR (CDCl$_3$) δ: 1.25(6H,m), 1.94(2H,m), 2.41(2H,m), 3.16(2H,m), 3.48(2H,s), 3.70(1H,bs), 4.13(4H,m), 6.56(2H,d,J=8.6 Hz), 7.08(2H,d,J=8.6 Hz)

(2) A mixture in tetrahydrofuran (50 ml) of ethyl 4-[4-(ethoxycarbonylmethyl)phenyl]aminobutanoate (2.4 g. 8.3 mmols) and sodium hydride (oily) (0.5 g, 12 mmols) was stirred, while heated under reflux, for 18 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give a solid of ethyl [4-(2-oxopyrrolidin-1-yl)phenyl]acetate (1.2 g, 59%).
m.p. 63–65° C.
Elemental Analysis for $C_{14}H_{17}NO_3$:
Calcd.: C, 68.00; H, 6.93; N, 5.66
Found: C, 68.07; H, 6.69; N, 5.71
$^1$H-NMR (CDCl$_3$) δ: 1.24(3H,t,J=7.2 Hz), 2.16(2H,tt,J=7.0,8.0 Hz), 2.61(2H,t,J=8.0 Hz), 3.59(2H,s), 3.85(2H,t,J=7.0 Hz), 4.14(2H,q,J=7.2 Hz), 7.29(2H,d,J=8.4 Hz), 7.57(2H,d,J=8.4 Hz)

(3) Aqueous 1 N sodium hydroxide solution (10 ml, 10 mmols) was added to a solution of ethyl[4-(2-oxopyrrolidin-1-yl)phenyl]acetate (0.97 g, 3.9 mmols) in tetrahydrofuran (20 ml) and ethanol (20 ml). The resulting mixture was stirred at 60° C. for 1 hour. Water was added to the reaction mixture, which was acidified with potassium hydrogensulfate added thereto, and then extracted with ethyl acetate. The extract was washed with water, and then dried with anhydrous magnesium sulfate. This was concentrated under reduced pressure, and the residue was crystallized from hexane/ethanol to give a solid of [4-(2-oxopyrrolidin-1-yl)phenyl]acetic acid (0.5 g, 57%).
m.p. 171–172° C.
Elemental Analysis for $C_{12}H_{13}NO_3$:
Calcd.: C, 65.74; H, 5.98; N, 6.39
Found: C, 65.84; H, 5.74; N, 6.43
$^1$H-NMR (CDCl$_3$) δ: 2.05(2H,tt,J=7.0,8.0 Hz), 2.48(2H,t,J=8.4 Hz), 3.53(2H,s), 3.81(2H,t,J=7.0 Hz), 7.24(2H,d,J=8.4 Hz), 7.58(2H,d,J=8.4 Hz), 12.3(1H,s)

(4) A tetrahydrofuran (15 ml) solution of [4-(2-oxopyrrolidin-1-yl)phenyl]acetic acid (0.54 g, 2.4 mmols), oxalyl chloride (0.62 g, 4.9 mmols) and N,N-dimethylformamide (0.5 ml) was stirred at room temperature for 1 hour. The reaction mixture was concentrated under reduced pressure, to which were added N-(2-fluorobenzyl)-4-[N'-[2-[3-(tert-butoxycarbonylaminomethyl)phenoxy]-4-chlorophenyl]]aminobutylamide (0.66 g, 1.2 mmols) and N,N-dimethylacetamide (15 ml). The resulting mixture was stirred at room temperature for 5 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[[4-(2-oxopyrrolidin-1-yl)phenyl]acetyl]]aminobutylamide (0.47 g, 51%).

Elemental Analysis for $C_{41}H_{44}N_4O_6ClF$:

Calcd.: C, 66.25; H, 5.97; N, 7.54

Found: C, 66.01; H, 6.15; N, 7.30

$^1$H-NMR (CDCl$_3$) δ: 1.42(9H,s), 1.83(2H,m), 2.19(4H,m), 2.60(2H,m), 3.46(2H,m), 3.71(2H,m), 3.83(2H,m), 4.26 (2H,d,J=5.8 Hz), 4.44(2H,d,J=5.8 Hz), 5.33(1H,bs), 6.70 (1H,bs), 6.83–7.32(13H,m), 7.48(2H,m)

(5) A 2 N hydrochloric acid/ethyl acetate solution (2 ml) of N-(2-fluorobenzyl)-4-[N'-[2-[3-(tert-butoxycarbonylaminomethyl)phenoxy]-4-chlorophenyl]-N'-[[4-(2-oxopyrrolidin-1-yl)phenyl]acetyl]]aminobutylamide (0.28 g, 0.37 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[[4-(2-pyrrolidin-1-yl)phenyl]acetyl]]aminobutylamide hydrochloride (0.24 g, 94%).

Elemental Analysis for $C_{36}H_{37}N_4O_4Cl_2F.1/2H_2O$:

Calcd.: C, 62.79; H, 5.56; H, 8.14

Found: C, 62.93; H, 5.58; N, 8.16

$^1$H-NMR (DMSO-d$_6$) δ: 1.75(2H,m), 2.10(2H,m), 2.23 (2H,m), 2.54(2H,m), 3.46(4H,m), 3.84(2H,m), 4.08(2H,m), 4.31(2H,m), 6.91–7.06(15H,m), 8.47(1H,m), 8.61(2H,bs)

EXAMPLE 187

2-Fluorobenzyl 2-[N-[3-(aminomethyl)phenoxy]-4-chlorophenyl]-N-(4-phenylbenzoyl)]aminoethylcarbamate hydrochloride (1) A mixture of 3-[N-[2-[3-(tert-butoxycarbonylaminomethyl)phenoxy]-4-chlorophenyl]]-N-(4-phenylbenzoyl)]aminopropionic acid (0.8 g,-1.3 mmols), diphenylphosphorylazide (DPPA) (0.56 g, 2.0 mmols), triethylamine (0.17 g, 1.6 mmols) and N,N-dimethylformamide (5 ml) was stirred at room temperature for 1 hour. The reaction mixture was poured into water, and extracted with ethyl acetate. The extract was washed with water and brine, and then dried with anhydrous magnesium sulfate, and the solvent was evaporated away. Toluene (20 ml) was added to the residue, and the resulting mixture was stirred, while heated under reflux, for 3 hours. Next, 2-fluorobenzyl alcohol (0.42 g, 3.3 mmols) was added to the reaction mixture, and then further refluxed for 2 hours. This was cooled, then poured into water, and extracted with ethyl acetate. The extract was washed with water and brine, and then dried with anhydrous magnesium sulfate, and the solvent was evaporated away. The residue was purified through silica gel column chromatography to give an amorphous solid of 2-fluorobenzyl 2-[[N-[3-(tert-butoxycarbonylaminomethyl)phenoxy]-4-chlorophenyl]-N-(4-phenylbenzoyl)]aminoethylcarbamate (0.37 g, 38%).

Elemental Analysis for $C_{41}H_{39}N_3O_6ClF.1/2H_2O$:

Calcd.: C, 67.16; H, 5.50; N, 5.73

Found: C, 67.47; H, 5.66; N, 6.13

$^1$H-NMR (CDCl$_3$) δ: 1.43(9H,s), 3.51(2H,m), 4.00(1H, m), 4.17(3H,m), 4.88(1H,bs), 5.09(2H,m), 5.63(1H,bs), 6.47 (1H,m), 6.56(2H,m), 7.00–7.59(17H,m)

(2) A 2 N hydrochloric acid/ethyl acetate solution (4 ml) of 2-fluorobenzyl 2-[[N-[3-(tert-butoxycarbonylaminomethyl)phenoxy]-4-chlorophenyl]-N-(4-phenylbenzoyl)]aminoethylcarbamate (0.25 g, 0.34 mmols) was stirred at room temperature for 1 hour. The reaction mixture was concentrated under reduced pressure. The solid precipitated was taken out through filtration, and washed with ethyl ether to give an amorphous solid of 2-fluorobenzyl 2-[[N-[3-(aminomethyl)phenoxy]-4-chlorophenyl]-N-(4-phenylbenzoyl)]aminoethylcarbamate (0.22 g, 99%).

Elemental Analysis for $C_{36}H_{32}N_3O_4Cl_2F.1/4H_2O$:

Calcd.: C, 65.01; H, 4.93; N, 6.32

Found: C, 64.87; H, 5.00; N, 6.70

$^1$H-NMR (DMSO-d$_6$) δ: 3.32(1H,m), 3.52(1H,m), 4.04 (4H,m), 5.08(2H,s), 6.63(1H,s), 6.78(1H,m), 7.21–7.28(4H, m), 7.42–7.69(14H,m), 8.60(3H,m)

EXAMPLE 188

N-[2-[3-(aminomethyl)phenoxy]-4-chlorophenyl]-N-[2-(3-phenylbutyryl)aminoethyl]-4-phenylbenzamide hydrochloride (1) A mixture of 3-[N-[3-[3-(tert-butoxycarbonylaminomethyl)phenoxy]-4-chlorophenyl]]-N-(4-phenylbenzoyl)]aminopropionic acid (1.0 g, 1.7 mmols), diphenylphosphorylazide (DPPA) (0.73 g, 2.6 mmols), triethylamine (0.21 g, 2.1 mmols) and N,N-dimethylformamide (5 ml) was stirred at room temperature for 1 hour. The reaction mixture was poured into water, and extracted with ethyl acetate. The extract was washed with water and brine, and then dried with anhydrous magnesium sulfate, and the solvent was evaporated away. Toluene (20 ml) was added to the residue, and the resulting mixture was stirred, while heated under reflux, for 3 hours. Next, 9-fluorenyl methanol (0.33 g, 1.7 mmols) was added to the reaction mixture, and then further refluxed for 3 hours. This was cooled, then poured into water, and extracted with ethyl acetate. The extract was washed with water and brine, and then dried with anhydrous magnesium sulfate, and the solvent was evaporated away. The residue was purified through silica gel column chromatography to give an amorphous solid of 9H-fluoren-9-ylmethyl 2-[N-[2-[3-(tert-butoxycarbonylaminomethyl)phenoxy]-4-chlorophenyl]-N-(4-phenylbenzoyl)]aminoethylcarbamate (0.81 g, 61%).

Elemental Analysis for $C_{48}H_{44}N_3O_6Cl.H_2O$:

Calcd.: C, 70.97; H, 5.71; N, 5.17

Found: C, 71.03; H, 5.66; N, 6.48

$^1$H-NMR (CDCl$_3$) δ: 1.40(9H,s), 3.49(2H,m), 3.98(1H, m), 4.14(4H,m), 4.26(2H,m), 4.79(1H,bs), 5.80(1H,bs), 6.45 (1H,m), 6.57(2H,m), 7.00–7.58(19H,m), 7.75(2H,d)

(2) An N,N-dimethylformamide (10 ml) solution of 9H-fluoren-9-ylmethyl 2-[N-[2-[3-(tert-butoxycarbonylaminomethyl)phenoxy]-4-chlorophenyl]-N-(4-phenylbenzoyl)]aminoethylcarbamate (0.65 g, 0.82 mmols) and piperidine (0.5 ml) was stirred at room temperature for 1 hour. The reaction mixture was poured into water, and extracted with ethyl acetate. The extract was washed with brine, and then dried with anhydrous magnesium sulfate. This was concentrated under reduced pressure. Then, 3-phenyl-n-butyl chloride (0.3 g, 1.6 mmols) and N,N-dimethylacetamide (10 ml) were added to the residue. The resulting mixture was stirred at room temperature for 5,hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an amorphous solid of N-[2-[3-(tert-butoxycarbonylaminomethyl)phenoxy]-4-chlorophenyl]-N-[2-(3-phenylbutyryl)aminoethyl]-4-phenylbenzamide (0.1 g, 17%).

(3) A 2 N hydrochloric acid/ethyl acetate solution (4 ml) of N-[2-[3-(tert-butoxycarbonylaminomethyl)phenoxy]-4-chlorophenyl]-N-[2-(3-phenylbutyryl)aminoethyl]-4-phenylbenzamide (0.1 g, 0.14 mmols) was stirred at room temperature for 1 hour. The reaction mixture was concentrated under reduced pressure. The solid precipitated was taken out through filtration, and washed with ethyl ether to give an amorphous solid of N-[2-[3-(aminomethyl)phenoxy]-4-chlorophenyl]-N-[2-(3-phenylbutyryl)aminoethyl]-4-phenylbenzamide hydrochloride (0.087 g, 95%).
Elemental Analysis for $C_{38}H_{37}N_3O_3Cl_2 \cdot H_2O$:
Calcd.: C, 67.85; H, 5.84; N, 6.25
Found: C, 68.14; H, 5.75; N, 6.30
$^1$H-NMR (DMSO-$d_6$) δ: 1.16(3H,d,J=7.0 Hz), 2.33(2H, m), 3.15(2H,m), 3.50(1H,m), 3.91(1H,m), 4.03(2H,m), 4.40 (1H,m), 6.64(1H,bs), 7.20–7.68(19H,m), 8.16(1H,m), 8.52 (2H,bs)

EXAMPLE 189

N-[2-[3-(aminomethyl)phenoxy]-4-chlorophenyl]-N-[3-[(2-fluorophenylacetyl)amino]propyl]-4-phenylbenzamide hydrochloride (1) A mixture of 4-[N-[2-[3-(tert-butoxycarbonylaminomethyl)phenoxy]-4-chlorophenyl]]-N-(4-phenylbenzoyl)] aminobutanoic acid (0.88 g, 2.1 mmols), diphenylphosphorylazide (DPPA) (0.59 g, 2.2 mmols), triethylamine (0.22 g, 2.2 mmols) and N,N-dimethylformamide (10 ml) was stirred at room temperature for 1 hour. The reaction mixture was poured into water, and extracted with ethyl acetate. The extract was washed with water and brine, and then dried with anhydrous magnesium sulfate, and the solvent was evaporated away. Toluene (20 ml) was added to the residue, and the resulting mixture was stirred, while heated under reflux, for 3 hours. Next, 9-fluorenyl methanol (0.28 g, 1.4 mmols) was added to the reaction mixture, and then further refluxed for 12 hours. This was cooled, then poured into water, and extracted with ethyl acetate. The extract was washed with water and brine, and then dried with anhydrous magnesium sulfate, and the solvent was evaporated away. The residue was purified through silica gel column chromatography to give an amorphous solid of 9H-fluoren-9-ylmethyl 3-[N-[2-[3-(tert-butoxycarbonylaminomethyl)phenoxy]-4-chlorophenyl]-N-(4-phenylbenzoyl)] aminopropylcarbamate (0.66 g, 57%).
$^1$H-NMR (CDCl$_3$) δ: 1.43(9H,s), 1.77(2H,m), 3.38(2H, m), 3.81(1H,m), 4.17–4.26(4H,m), 4.36(2H,m), 4.87(1H, bs), 6.02(1H,m), 6.40(1H,m), 6.57(2H,m), 7.01–7.79(21H, m)

(2) An N,N-dimethylformamide (10 ml) solution of 9H-fluoren-9-ylmethyl 3-[N-[2-[3-(tert-butoxycarbonylaminomethyl)phenoxy]-4-chlorophenyl]-N-(4-phenylbenzoyl)] aminopropylcarbamate (0.65 g, 0.8 mmols) and piperidine (0.5 ml) was stirred at room temperature for 1 hour. The reaction mixture was poured into water, and extracted with ethyl acetate. The extract was washed with brine, and then dried with anhydrous magnesium sulfate. This was concentrated under reduced pressure. Then, 2-fluorophenylacetyl chloride (0.28 g, 1.6 mmols) and N,N-dimethylacetamide (10 ml) were added to the residue. The resulting mixture was stirred at room temperature for 5 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an amorphous solid of N-[2-[3-(tert-butoxycarbonylaminomethyl)phenoxy]-4-chlorophenyl]-N-[3-[(2-fluorophenyl)acetylamino]propyl]-4-phenylbenzamide (0.28 g, 48%).
Elemental Analysis for $C_{42}H_{41}N_3O_5ClF \cdot 1/2H_2O$:
Calcd.: C, 69.98; H, 5.79; N, 5.75
Found: C, 69.37; H, 5.84; N, 5.74
$^1$H-NMR (CDCl$_3$) δ: 1.43(9H,s), 1.73(2H,m), 3.62(2H,s), 3.72(1H,m), 3.85(1H,m), 4.13(1H,m), 4.20(2H,d,J=6.4 Hz), 4.91(1H,bs), 6.37(1H,d), 6.55(2H,m), 6.87(1H,bs), 6.99–7.59(17H,m)

(3) A 2 N hydrochloric acid/ethyl acetate solution (4 ml) of N-[2-[3-(tert-butoxycarbonylaminomethyl)phenoxy]-4-chlorophenyl]-N-[3-[(2-fluorophenyl)acetylamino]propyl]-4-phenylbenzamide (0.18 g, 0.25 mmols) was stirred at room temperature for 1 hour. The reaction mixture was concentrated under reduced pressure. The solid precipitated was taken out through filtration, and washed with ethyl ether to give an amorphous solid of N-[2-[3-(aminomethyl)phenoxy]-4-chlorophenyl]-N-[3-[(2-fluorophenylacetyl)amino] propyl]-4-phenylbenzamide hydrochloride (0.16 g, 95%).
Elemental Analysis for $C_{37}H_{34}N_3O_3Cl_2F \cdot 1/2H_2O$:
Calcd.: C, 66.57; H, 5.28; N, 6.29
Found: C, 66.77; H, 5.20; N, 6.24
$^1$H-NMR (DMSO-$d_6$) δ: 1.75(2H,m), 3.15(2H,m), 3.49 (2H,s), 3.81(2H,m), 4.02(2H,m), 6.58(1H,s), 6.69(1H,m), 7.09–7.68(18H,m), 8.25(1H,m), 8.54(2H,bs)

EXAMPLE 190

N-2-(fluorobenzyl)-4-[N'-[2-[3-[(1S)-1-aminoethyl] phenoxy]-4-chlorophenyl]-N'-(4-phenylbenzoyl)] aminobutylamide hydrochloride (1) A dichloromethane (50 ml) solution of boron tribromide (19 ml, 200 mmols) was dropwise added to a dichloromethane (100 ml) solution of (S)-1-(3-methoxyphenyl) ethylamine (10 g, 66 mmols) at −78° C. This was stirred at the temperature for 30 minutes, and then reacted at room temperature for 1 hour. Methanol was added to the reaction mixture to stop the reaction, and then the mixture was concentrated under reduced pressure. To the residue, added were tetrahydrofuran (200 ml), triethylamine (33.4 g, 330 mmols) and di-tert-butyl dicarbonate (14.4 g, 66 mmols). The resulting mixture was heated under reflux for 2 hours. This was cooled, then poured into water, and extracted with ethyl acetate. The extract was washed with 1 N hydrochloric acid, and brine, and then dried with anhydrous magnesium sulfate. This was concentrated under reduced pressure, and the residue was purified through silica gel column chromatography. An oil of tert-butyl(1S)-1-(3-hydroxyphenyl)ethylcarbamate (13.4 g, 85%) was obtained.
$^1$H-NMR (CDCl$_3$) δ: 1.42(9H,s), 1.45(3H,s), 4.72(1H,m), 4.81(1H,m), 5.92(1H,bs), 6.68–6.84(3H,m), 7.17(1H,m)

(2) A mixture of 4-chloro-2-fluoronitrobenzene (10.4 g, 59.2 mmols), tert-butyl(1S)-1-(3-hydroxyphenyl)ethylcarbamate (13.4 g, 56.5 mmols), potassium carbonate (9.4 g, 68 mmols) and N,N-dimethylformamide (150 ml) was stirred at 100° C. for 1 hour. The reaction mixture was cooled, poured into water, and extracted with ethyl acetate. The extract was washed with water and brine, and then dried with anhydrous magnesium sulfate, and the solvent was evaporated away. The residue was purified through silica gel column chromatography, and the resulting crystal was re-crystallized from hexane/ethyl acetate to give a crystal of tert-butyl(1S)-(-)-1-[3-(5-chloro-2-nitrophenoxy)phenyl]ethylcarbamate (15.7 g, 71%).

m.p. 94–96° C.

$[\alpha]_D^{24}$ −50° (C=0.5, MeOH)

Elemental Analysis for $C_{19}H_{21}N_2O_5Cl$:

Calcd.: C, 58.09; H, 5.39; N, 7.13

Found: C, 58.05; H, 5.29; N, 7.10

$^1$H-NMR (CDCl$_3$) δ: 1.41(12H,m), 4.79(2H,m), 6.93–7.42(6H,m), 7.94(1H,d)

(3) 5% carbon-palladium (1.1 g) was added to an ethyl acetate (50 ml) solution of tert-butyl(1S)-(-)-1-[3-(5-chloro-2-nitrophenoxy)phenyl]ethylcarbamate (3.5 g, 8.9 mmols). The resulting mixture was hydrogenated at room temperature under atmospheric pressure for 1 hour. The catalyst was removed through filtration, and the filtrate was concentrated under reduced pressure. The residue was purified through silica gel column chromatography to give an oil of tert-butyl (1S)-1-[3-(2-amino-5-chlorophenoxy)phenyl]ethylcarbamate (3.2 g, 99%).

$^1$H-NMR (CDCl$_3$) δ: 1.41(12H,m), 4.79(2H,m), 6.93–7.42(6H,m), 7.94(1H,d)

(4) A mixture of tert-butyl(1S)-1-[3-(2-amino-5-chlorophenoxy)phenyl]ethylcarbamate (3.2 g, 8.8 mmols), ethyl 4-bromobutyrate (14 g, 70 mmols), potassium carbonate (3.6 g, 26 mmols) and N,N-dimethylformamide (50 ml) was stirred at 80° C. for 48 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[N-[2-[3-[(1S)-1-tert-butoxycarbonylaminoethyl]phenoxy]-4-chlorophenyl]]aminobutyrate (2.8 g, 66%).

$^1$H-NMR (CDCl$_3$) δ: 1.24(3H,t,J=7.0 Hz), 1.41(12H,m), 1.95(2H,m), 2.38(2H,m), 3.19(2H,m), 4.10(2H,q,J=7.0 Hz), 14.22(1H,m), 4.79(2H,m), 6.64(1H,d), 6.75–6.85(2H,m), 6.95–7.07(3H,m), 7.28(1H,m)

(5) A mixture of ethyl 4-[N-[2-[3-[(1S)-1-tert-butoxycarbonylaminoethyl]phenoxy]-4-chlorophenyl]]aminobutyrate (2.8 g, 5.9 mmols), 4-phenylbenzoyl chloride (1.5 g, 7.1 mmols) and N,N-dimethylacetamide (50 ml) was stirred at room temperature for 3 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an oil of ethyl 4-[N-[2-[3-[(1S)-1-tert-butoxycarbonylaminoethyl]phenoxy]-4-chlorophenyl]-N-(4-phenylbenzoyl)]aminobutyrate (3.1 g, 80%).

Elemental Analysis for $C_{38}H_{41}N_2O_6Cl.1/2H_2O$:

Calcd.: C, 68.51; H, 6.35; N, 4.20

Found: C, 68.80; H, 6.63; N, 4.03

$^1$H-NMR (CDCl$_3$) δ: 1.25(3H,t,J=7.2 Hz), 1.34(3H,d,J=7.0 Hz), 1.40(9H,s), 2.00(2H,m), 2.46(2H,m), 3.88(1H,m), 4.06(1H,m), 4.11(2H,1,J=7.2 Hz), 4.76(2H,m), 6.44–6.53(2H,m), 6.66(1H,m), 6.96–7.59(13H,m)

(6) Aqueous 1 N sodium hydroxide solution (20 ml, 20 mmols) was added to a solution of ethyl 4-[N-[2-[3-[(1S)-1-tert-butoxycarbonylaminoethyl]phenoxy]-4-chlorophenyl]-N-(4-phenylbenzoyl)]aminobutyrate (2.8 g, 4.2 mmols) in tetrahydrofuran (50 ml) and ethanol (50 ml). The resulting mixture was stirred at 60° C. for 1 hour. This was poured into water, then acidified with potassium hydrogensulfate added thereto, and then extracted with ethyl acetate. The extract was washed with water, and then dried with anhydrous magnesium sulfate. This was concentrated under reduced pressure to give an amorphous solid of 4-[N-[2-[3-[(1S)-1-tert-butoxycarbonylaminoethyl]phenoxy]-4-chlorophenyl]-N-(4-phenylbenzoyl)]aminobutyric acid (2.7 g, 99%).

(7) A mixture of 4-[N-[2-[3-[(1S)-1-tert-butoxycarbonylaminoethyl]phenoxy]-4-chlorophenyl]-N-(4-phenylbenzoyl)]aminobutyric acid (0.8 g, 1.3 mmols), 2-fluorobenzylamine (0.25 g, 2.0 mmols), 1-ethyl-3-(3-dimethylaminopropyl)carbodiimide hydrochloride (WSC) (0.49 g, 2.6 mmols), 1-hydroxybenzotriazole monohydrate (HOBt) (0.35 g, 2.6 mmols) and N,N-dimethylformamide (10 ml) was stirred at room temperature for 6 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-[(1S)-1-tert-butoxycarbonylaminoethyl]phenoxy]-4-chlorophenyl]-N'-(4-phenylbenzoyl)]aminobutylamide (0.66 g, 70%).

$[\alpha]_D^{24}$ −29° (C=0.5, MeOH)

Elemental Analysis for $C_{43}H_{43}N_3O_5ClF.1/2H_2O$:

Calcd.: C, 69.30; H, 5.95; N, 5.64

Found: C, 69.57; H, 5.77; N, 5.63

$^1$H-NMR (CDCl$_3$) δ: 1.33(3H,d,H=6.8 Hz), 1.39(9H,s), 1.97(2H,m), 2.39(2H,m), 3.81(1H,m), 4.12(1H,m), 4.51 (2H,d,J=5.8 Hz), 4.67(1H,m), 4.83(1H,m), 6.43(1H,d), 6.52 (1H,s), 6.63(1H,d), 6.93(1H,bs), 6.98–7.59(17H,m)

(8) A 2 N hydrochloric acid/ethyl acetate solution (4 ml) of N-(2-fluorobenzyl)-4-[N'-[2-[3-[(1S)-1-tert-butoxycarbonylaminoethyl]phenoxy]-4-chlorophenyl]-N'-(4-phenylbenzoyl)]aminobutylamide (0.36 g, 0.51 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-[(1S)-1-aminoethyl]phenoxy]-4-chlorophenyl]-N'-(4-phenylbenzoyl))aminobutylamide hydrochloride (0.3 g, 87%).

$[\alpha]_D^{24}$ −0.1° (C=0.5, MeOH)

Elemental Analysis for $C_{38}H_{36}N_3O_3Cl_2F$:

Calcd.: C, 67.86; H, 5.39; N, 6.25

Found: C, 67.85; H, 5.43; N, 6.29

$^1$H-NMR (DMSO-d$_6$) δ: 1.48(3H,d,J=7.0 Hz), 1.83(2H,m), 2.27(2H,m), 3.77(2H,m), 4.29(2H,m), 4.37(1H,m), 6.59 (1H,s), 6.70(1H,bs), 7.11–7.68(18H,m), 8.44(1H,bs), 8.59 (2H,bs)

EXAMPLE 191

N-(2-fluorobenzyl)-4-[N'-[2-[3-(aminomethyl)phenoxy]-4-chlorophenyl]-N'-(9H-fluorene-1-carbonyl)] aminobutylamide hydrochloride (1) A mixture of N-(2-fluorobenzyl)-4-[N'-[2-[3-(tert-butoxycarbonylaminomethyl)phenoxy]-4-chlorophenyl]-]aminobutylamide (0.6 g, 1.1 mmols), 9H-fluorene-1-carbonyl chloride (0.51 g, 2.2 mmols) and N,N-dimethylacetamide (10 ml) was stirred at room temperature for 2 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-(9H-fluorene-1-carbonyl)]aminobutylamide (0.69 g, 84%).

Elemental Analysis for $C_{43}H_{41}N_3O_5ClF$:
Calcd.: C, 70.34; H, 5.63; N, 5.72
Found: C, 70.02; H, 5.66; N, 5.66
$^1$H-NMR (CDCl$_3$) δ: 1.43(9H,s), 2.01(2H,m), 2.46(2H, m), 3.52(1H,d,J=22.8 Hz), 3.75(3H,m), 4.10(1H,d,J=22.8 Hz), 4.30(2H,m), 4.54(2H,d,J=5.6 Hz), 5.82(1H,s), 6.43(2H, m), 6.78(1H,d), 6.95–7.43(13H,m), 7.22(2H,m)

(2) A 2 N hydrochloric acid/ethyl acetate solution (6 ml) of N-(2-fluorobenzyl)-4-[N'-[2-[3-(tert-butoxycarbonylaminomethyl)phenoxy]-4-chlorophenyl]-N'-(9H-fluorene-1-carbonyl)]aminobutylamide (0.39 g, 0.53 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-(9H-fluorene-1-carbonyl)]aminobutylamide (0.34 g, 95%).

Elemental Analysis for $C_{38}H_{34}N_3O_3Cl_2F·1/2H_2O$:
Calcd.: C, 67.16; H, 5.19; N, 6.18
Found: C, 67.13; H, 5.37; N, 6.05
$^1$H-NMR (DMSO-d$_6$) δ: 1.89(2H,m), 2.34(2H,m), 3.66–4.05(6H,m), 4.32(2H,d,J=5.6 Hz), 6.48(1H,s), 6.64(1H,m), 6.82(1H,s), 7.09–7.60(13H,m), 7.87(2H,m), 8.49(4H,m)

EXAMPLE 192

N-(2-fluorobenzyl)-4-[N'-[2-[3-(aminomethyl)phenoxy]-4-chlorophenyl]-N'-[4-(2-thiazolyl)benzoyl]]aminobutylamide hydrochloride (1) A mixture of 2-bromothiazole (0.9 ml, 10 mmols), 4-formylphenylboronic acid (1.65 g, 11 mmols), sodium carbonate (2.65 g, 25 mmols), toluene (150 ml), ethanol (30 ml) and water (30 ml) was stirred in an argon atmosphere at room temperature for 30 minutes. Tetrakis(triphenylphosphine)palladium(0) (0.58 mg, 0.5 mmols) was added thereto and heated under reflux for 15 hours. The reaction-mixture was cooled, poured into water, and extracted with ethyl acetate. The extract was washed with water and brine, then dried with anhydrous magnesium sulfate, and concentrated under reduced pressure. The residue was purified through silica gel column chromatography, and then recrystallized from ethyl acetate/hexane to give 4-(2-thiazolyl)benzaldehyde (1.4 g, 74%).

m.p. 91.5–92.5° C.
Elemental Analysis for $C_{10}H_7NOS$:
Calcd.: C, 63.47; H. 3.73; N, 7.40
Found: C, 63.67; H, 3.60; N, 7.316
$^1$H-NMR (CDCl$_3$) δ: 7.46(1H,d,J=3.2 Hz), 7.95–7.99(3H, m), 8.15(2H,d,J=8.2 Hz), 10.07(1H,s)

A mixture of 4-(2-thiazolyl)benzaldehyde (4.6 g, 24 mmol), sodium chlorite (5.5 g, 61 mmols), sodium dihydrogenphosphate (3.2 g, 27 mmols), 2-methyl-2-butene (8.6 g, 120 mmols), tert-butanol (40 ml), tetrahydrofuran (40 ml) and water (20 ml) was stirred at room temperature for 3 hours. The mixture was poured into 1 N hydrochloric acid, and the precipitate formed was taken out through filtration and dried. Thus was obtained a solid of 4-(2-thiazolyl)benzoic acid (4.0 g, 79%).

$^1$H-NMR (DMSO-d$_6$) δ: 7.89(1H,m), 8.00–8.06(5H,m)

A tetrahydrofuran (30 ml) solution of 4-(2-thiazolyl)benzoic acid (0.55 g, 2.7 mmols), oxalyl chloride (0.69 g, 5.4 mmols) and N,N-dimethylformamide (0.5 ml) was stirred at room temperature for 1 hour. The reaction mixture was concentrated under reduced pressure, to which were added N-(2-fluorobenzyl)-4-[N'-[2-[3-(tert-butoxycarbonylaminomethyl)phenoxy]-4-chlorophenyl]]aminobutylamide (0.49 g, 0.9 mmols) and N,N-dimethylacetamide (10 ml). The resulting mixture was stirred at room temperature for 5 hours. This was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[4-(2-thiazolyl)benzoyl]]aminobutylamide (0.31 g, 47%).

Elemental Analysis for $C_{39}H_{38}N_4O_5ClFS$:
Calcd.: C, 64.23; H, 5.25; N, 7.68
Found: C, 64.12; H, 5.62; N, 7.35
$^1$H-NMR (CDCl$_3$) δ: 1.41(9H,s), 1.95(2H,m), 2.37(2H, m), 3.81(1H,m), 4.14(3H,m), 4.50(2H,d,J=5.8 Hz), 5.32(1H, bs), 6.46(1H,s), 6.58(2H,m), 6.79(1H,bs), 6.98–7.42(11H, m), 7.76(2H,m), 7.87(1H,m)

(2) A 2 N hydrochloric acid/ethyl acetate solution (4 ml) of N-(2-fluorobenzyl)-4-[N'-[2-[3-(tert-butoxycarbonylaminomethyl)phenoxy]-4-chlorophenyl]-N'-[4-(2-thiazolyl)benzoyl]]aminobutylamide (0.2 g, 0.27 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[4-(2-thiazolyl)benzoyl]]aminobutylamide hydrochloride (0.17 g, 97%).

Elemental Analysis for $C_{34}H_{31}N_4O_3Cl_2FS·1.5H_2O$:
Calcd.: C, 58.96; H, 4.95; N, 8.09
Found: C, 58.79; H, 4.99; N, 7.89
$^1$H-NMR (DMSO-d$_6$) δ: 1.83(2H,m), 2.28(2H,m), 3.80(2H,m), 4.01(2H,m), 4.29(2H,d,J=5.6 Hz), 6.59(1H,s), 6.85(1H,m), 7.11–7.59(11H,m), 7.82–7.96(4H,m), 8.49(1H,m), 8.57(2H,bs)

EXAMPLE 193

N-(2-fluorobenzyl)-4-[N'-[2-[3-(aminomethyl)phenoxy]-4-chlorophenyl]-N'-[(4-trifluoromethylphenyl)acetyl]]aminobutylamide hydrochloride (1) A mixture of N-(2-fluorobenzyl)-4-[N'-[2-[3-(tert-butoxycarbonylaminomethyl)phenoxy]-4-chlorophenyl]]aminobutylamide (0.45 g, 0.83 mmols), (4-trifluoromethylphenyl)acetyl chloride (0.46 g, 2.1 mmols) and N,N-dimethylacetamide (10 ml) was stirred at room temperature for 5 hours. The reaction mixture was poured into water, and extracted with ethyl acetate. The extract was washed with aqueous 1 N sodium hydroxide solution and brine, and then dried with anhydrous magnesium sulfate. This was reduced under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[(4-trifluoromethylphenyl)acetyl]]aminobutylamide (0.49 g, 80%).

Elemental Analysis for $C_{38}H_{38}N_3O_5ClF_4 \cdot 1/2H_2O$:
Calcd.: C, 61.91; H, 5.33; N, 5.70
Found: C, 62.10; H, 5.52; N, 5.70
$^1$H-NMR (CDCl$_3$) δ: 1.42(9H,s), 1,84(2H,m), 2.24(2H,m), 3.54(2H,m), 3.72(2H,m), 4.27(2H,d,J=6.2 Hz), 4.43(2H,d,J=5.8 Hz), 5.16(1H,bs), 6.54(1H,m), 6.77–6.88(3H,m), 6.96–7.37(10H,m), 7.51(2H,d)

(2) A 2 N hydrochloric acid/ethyl acetate solution (6 ml) of N-(2-fluorobenzyl)-4-[N'-[2-[3-(tert-butoxycarbonylaminomethyl)phenoxy]-4-chlorophenyl]-N'-[(4-trifluoromethylphenyl)acetyl]]aminobutylamide (0.34 g, 0.46 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(4-trifluoromethylphenyl)acetyl]]aminobutylamide hydrochloride (0.3 g, 98%).

Elemental Analysis for $C_{33}H_{31}N_3O_3Cl_2F_4$:
Calcd.: C, 58.96; H, 4.95; N, 8.09
Found: C, 58.79; H, 4.99; N, 7.89
$^1$H-NMR (DMSO-d$_6$) δ: 1.71(2H,m), 2.20(2H,m), 3.46(1H,m), 3.55(2H,m), 3.80(1H,m), 4.04(2H,m), 4.26(2H,d,J=5.4 Hz), 6.88(1H,d), 7.07–7.65(14H,m), 8.46(1H,m), 8.64(3H,bs)

EXAMPLE 194

N-(2-fluorobenzyl)-4-[N'-[2-[3-(aminomethyl)phenoxy]-4-chlorophenyl]-N'-[(4-acetylaminophenoxy)acetyl]]aminobutylamide hydrochloride (1) A mixture of N-(2-fluorobenzyl)-4-[N'-[2-[3-(tert-butoxycarbonylaminomethyl)phenoxy]-4-chlorophenyl]]aminobutylamide (1.08 g, 2 mmols), chloroacetyl chloride (0.32 ml, 4 mmols), 4-dimethylaminopyridine (0.49 g, 4 mmols) and tetrahydrofuran (30 ml) was stirred at room temperature for 2 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-chloroacetyl]aminobutylamide (0.91 g, 74%).

Elemental Analysis for $C_{31}H_{34}N_3O_7Cl_2F \cdot 1/2H_2O$:
Calcd.: C, 59.33; H, 5.62; N, 6.70
Found: C, 59.40; H, 5.44; N, 6.68
$^1$H-NMR (CDCl$_3$) δ: 1.43(9H,s), 1.82–1.94(2H,m), 2.27(2H,t,J=6.8 Hz), 3.70–3.80(2H,m), 3.87(1H,d,J=13.4 Hz), 3.95(1H,d,J=13.4 Hz), 4.29(2H,d,J=4.4 Hz), 4.45(2H,d,J=6.0 Hz), 5.17(1H,bs), 6.47(1H,bs), 6.86–7.19(7H,m), 7.21–7.38(4H,m)

(2) A mixture of N-(2-fluorobenzyl)-4-[N'-[2-[3-(tert-butoxycarbonylaminomethyl)phenoxy]-4-chlorophenyl]-N'-chloroacetyl]aminobutylamide (0.5 g, 0.81 mmols), 4-acetamidophenol (0.12 g, 0.78 mmols), potassium carbonate (0.13 g, 0.94 mmols) and N,N-dimethylformamide (5 ml) was stirred at 60° C. for 24 hours. The reaction mixture was cooled, poured into water, and extracted with ethyl acetate. The extract was washed with water and brine, and then dried with anhydrous magnesium sulfate. This was concentrated under reduced pressure, and the residue was purified through silica gel column chromatography to give an amorphous solid of N-(2-fluorobenzyl)-4-[N'-[(4-acetylaminophenoxy)acetyl]-N'-[2-[3-(tert-butoxycarbonylaminomethyl)phenoxy]-4-chlorophenyl]]aminobutylamide (0.51 g, 89%).

Elemental Analysis for $C_{39}H_{42}N_4O_7ClF \cdot 1/4H_2O$:
Calcd.: C, 63.50; H, 5.81; N, 7.59
Found: C, 63.56; H, 5.93; N, 7.43
$^1$H-NMR (CDCl$_3$) δ: 1.41(9H,s), 1.86(2H,m), 2.11(3H,s), 2.24(2H,m), 3.75(2H,m), 4.28(2H,d,J=6.0 Hz), 4.43(2H,d,J=6.2 Hz), 4.45(2H,s), 5.45(1H,bs), 6.58(1H,m), 6.72–7.38(15H,m), 7.64(1H,bs)

(3) A 2 N hydrochloric acid/ethyl acetate solution (2 ml) of N-(2-fluorobenzyl)-4-[N'-[(4-acetylaminophenoxy)acetyl]-N'-[2-[3-(tert-butoxycarbonylaminomethyl)phenoxy]-4-chlorophenyl]]aminobutylamide (0.32 g, 0.43 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(4-acetylaminophenoxy)acetyl]]aminobutylamide hydrochloride (0.28 g, 98%).

Elemental Analysis for $C_{34}H_{35}N_4O_5Cl_2F \cdot 1/2H_2O$:
Calcd.: C, 60.18; H, 5.35; N, 8.26
Found: C, 60.01; H, 5.55; N, 8.00
$^1$H-NMR (DMSO-d$_6$) δ: 1.71(2H,m), 2.00(3H,s), 2.20(2H,m), 3.45(1H,m), 3.81(1H,m), 4.05(2H,m), 4.27(2H,d,J=5.6 Hz), 4.36(1H,d,J=15.2 Hz), 4.54(1H,d,J=15.2 Hz), 6.70(2H,d), 6.90(1H,d), 7.09–7.67(12H,m), 8.42(1H,m), 8.52(2H,bs), 9.95(1H,s)

EXAMPLE 195

N-(2-fluorobenzyl)-4-[N'-[2-[3-(aminomethyl)phenoxy]-4-chlorophenyl]-N'-[(2-oxo-benzo[1,3]oxathiol-6-yloxy)acetyl]]aminobutylamide hydrochloride (1) A mixture of N-(2-fluorobenzyl)-4-[N'-[2-[3-(tert-butoxycarbonylaminomethyl)phenoxy]-4-chlorophenyl]-N'-chloroacetyl]aminobutylamide (0.48 g, 0.78 mmols), 6-hydroxy-1,3-benzoxathiol-2-one (0.20 g, 1.2 mmol), potassium carbonate (0.13 g, 0.94 mmols) and N,N-dimethylformamide (5 ml) was stirred at 60° C. for 3 hours. The reaction mixture was cooled, poured into water, and extracted with ethyl acetate. The extract was washed with water and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[(2-oxo-benzo[1,3]oxathiol-6-yloxy)acetyl]]aminobutylamide (0.32 g, 54%).

Elemental Analysis for $C_{38}H_{37}N_3O_8ClFS$:
Calcd.: C, 60.84; H, 4.97; N, 5.60
Found: C, 60.67; H, 5.09; N, 5.31
$^1$H-NMR (CDCl$_3$) δ: 1.41(9H,s), 1.87(2H,m), 2.25(2H,m), 3.75(2H,m), 4.30(2H,d,J=6.4 Hz), 4.43(2H,d,J=5.6 Hz), 4.50(2H,m), 5.30(1H,bs), 6.35(1H,bs), 6.76–7.40(14H,m)

(2) A 2 N hydrochloric acid/ethyl acetate solution (2 ml) of N-(2-fluorobenzyl)-4-[N'-[2-[3-(tert-butoxycarbonylaminomethyl)phenoxy]-4-chlorophenyl]-N'-[(2-oxo-benzo[1,3]oxathiol-6-yloxy)acetyl]]aminobutylamide (0.23 g, 0.3 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4- chlorophenyl]-N'-[(2-oxo-benzo[1,3]oxathiol-6-yloxy)acetyl]]aminobutylamide hydrochloride (0.19 g, 92%).

Elemental Analysis for $C_{33}H_{30}N_3O_6Cl_2FS$:
Calcd.: C, 57.73; H, 4.40; N, 6.12
Found: C, 57.64; H, 4.54; N, 6.10
$^1$H-NMR (DMSO-$d_6$) δ: 1.72(2H,m), 2.21(2H,m), 3.40(1H,m), 3.79(1H,m), 4.05(2H,m), 4.27(2H,d,J=5.2 Hz), 4.47(1H,d,J=15.4 Hz), 4.68(1H,d,J=15.4 Hz), 6.80–7.71(14H,m), 8.43(1H,m), 8.55(3H,bs)

EXAMPLE 196

N-(2-fluorobenzyl)-4-[N'-[2-[3-(aminomethyl)phenoxy]-4-chlorophenyl]-N'-[(1H-indol-5-yloxy)acetyl]]aminobutylamide hydrochloride (1) A mixture of N-(2-fluorobenzyl)-4-[N'-[2-[3-(tert-butoxycarbonylaminomethyl)phenoxy]-4-chlorophenyl]-N'-chloroacetyl]aminobutylamide (0.57 g, 0.92 mmols), 5-hydroxyindole (0.18 g, 1.4 mmol), potassium carbonate (0.19 g, 1.4 mmols) and N,N-dimethylformamide (10 ml) was stirred at 60° C. for 8 hours. The reaction mixture was cooled, poured into water, and extracted with ethyl acetate. The extract was washed with water and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[(1H-indol-5-yloxy)acetyl]]aminobutylamide (0.47 g, 71%).

Elemental Analysis for $C_{39}H_{40}N_4O_6ClF.1/4H_2O$:
Calcd.: C, 65.08; H, 5.67; N, 7.78
Found: C, 65.14; H, 5.71; N, 7.50
$^1$H-NMR (CDCl$_3$) δ: 1.42(9H,s), 1.86(2H,m), 2.25(2H,m), 3.75(2H,m), 4.22(2H,d,J=5.4 Hz), 4.43(2H,d,J=6.2 Hz), 4.53(2H,s), 5.06(1H,bs), 6.32(1H,s), 6.55(1H,bs), 6.73–7.36(15H,m), 8.32(1H,bs)

(2) A 2 N hydrochloric acid/ethyl acetate solution (6 ml) of N-(2-fluorobenzyl)-4-[N'-[2-[3-(tert-butoxycarbonylaminomethyl)phenoxy]-4-chlorophenyl]-N'-[(1H-indol-5-yloxy)acetyl]]aminobutylamide (0.33 g, 0.46 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(1H-indol-5-yloxy)acetyl]]aminobutylamide hydrochloride (0.30 g, 99%).

Elemental Analysis for $C_{34}H_{33}N_4O_4Cl_2F$—$H_2O$:
Calcd.: C, 60.99; H, 5.27; N, 8.37
Found: C, 60.91; H, 5.15; N, 8.22
$^1$H-NMR (DMSO-$d_6$) δ: 1.73(2H,m), 2.22(2H,m), 3.44(1H,m), 3.79(1H,m), 4.03(3H,m), 4.26(2H,d,J=5.0 Hz), 4.53(2H,m), 6.84–7.72(16H,m), 8.54(4H,m), 10.68(1H,bs)

EXAMPLE 197

N-(2-fluorobenzyl)-4-[N'-[2-[3-(aminomethyl)phenoxy]-4-chlorophenyl]-N'-[(6-ethoxybenzothiazol-2-ylsulfanyl)acetyl]]aminobutylamide hydrochloride (1) A mixture of N-(2-fluorobenzyl)-4-[N'-[2-[3-(tert-butoxycarbonylaminomethyl)phenoxy]-4-chlorophenyl]-N'-chloroacetyl]aminobutylamide (0.67 g, 11.1 mmols), 6-ethoxy-2-mercaptobenzothiazole (0.34 g, 1.6 mmol), potassium carbonate (0.22 g, 1.6 mmols) and N,N-dimethylformamide (10 ml) was stirred at 60° C. for 12 hours. The reaction mixture was cooled, poured into water, and extracted with ethyl acetate. The extract was washed with water and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[(6-ethoxybenzothiazol-2-ylsulfanyl)acetyl]]aminobutylamide (0.38 g, 44%).

Elemental Analysis for $C_{40}H_{42}N_4O_6ClFS_2.1/2H_2O$:
Calcd.: C, 59.88; H, 5.40; N, 6.98
Found: C, 60.21; H, 5.44; N, 6.94
$^1$H-NMR (CDCl$_3$) δ: 1.42(9H,s), 1.43(3H,t,J=6.8 Hz), 1.87(2H,m), 2.28(2H,m), 3.77(2H,m), 3.95(1H,d,J=15.4 Hz), 4.05(2H,q,J=6.8 Hz), 4.17(1H,d,J=15.4 Hz), 4.26(2H,d,J=5.8 Hz), 4.42(2H,d,J=5.8 Hz), 5.12(1H,bs), 6.46(1H,bs), 6.85–7.37(13H,m), 7.60(1H,d)

(2) A 2 N hydrochloric acid/ethyl acetate solution (6 ml) of N-(2-fluorobenzyl)-4-[N'-[2-[3-(tert-butoxycarbonylaminomethyl)phenoxy]-4-chlorophenyl]-N'-[(6-ethoxybenzothiazol-2-ylsulfanyl)acetyl]]aminobutylamide (0.28 g, 0.36 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(6-ethoxybenzothiazol-2-ylsulfanyl)acetyl]]aminobutylamide hydrochloride (0.26 g, 99%).

Elemental Analysis for $C_{35}H_{35}N_4O_4Cl_2FS_2.2H_2O$:
Calcd.: C, 54.90; H, 5.13; N, 7.32
Found: C, 54.60; H, 5.13; N, 7.25
$^1$H-NMR (DMSO-$d_6$) δ: 1.34(3H,t,J=6.8 Hz), 1.72(2H,m), 2.21(2H,m), 3.46(1H,m), 3.80(1H,m), 3.98–4.10(5H,m), 4.20–4.28(3H,m), 6.88–7.71(14H,m), 8.44(1H,m), 8.62(1H,bs)

EXAMPLE 198

N-(2-fluorobenzyl)-4-[N'-[2-[4-(aminomethyl)phenylamino]phenyl]-N'-(4-phenylbenzoyl)]aminobutylamide hydrochloride (1) Tert-butyl(4-aminobenzyl) carbamate:
Di-tert-butyl dicarbonate (43.9 g, 199 mmols) was dropwise added to a tetrahydrofuran (400 ml) solution of 4-aminobenzylamine (24.3 g, 199 mmols) with the solution being stirred and cooled with ice. The resulting reaction mixture was further stirred at 0° C. for 1 hour. This was concentrated under reduced pressure, and the residue was diluted with ethyl acetate, then washed with water, and dried with anhydrous magnesium sulfate. The solvent was evaporated away under reduced pressure, and the residue was crystallized from hexane, and taken out through filtration. Thus was obtained a crystal of tert-butyl(4-aminobenzyl) carbamate (41.9 g, 94.8%).
m.p. 69–70° C.
$^1$H-NMR (CDCl$_3$) δ: 1.47(9H,s), 3.62(2H,bs), 4.19(2H,d,J=5.8 Hz), 4.73(1H,bs), 6.65(2H,d,J=8.6 Hz), 7.08(2H,d,J=8.6 Hz)

(2) Tert-butyl[4-(2-nitrophenylamino)benzyl]carbamate:
A mixture of tert-butyl(4-aminobenzyl) carbamate (89.2 g, 401 mmols), o-fluoronitrobenzene (56.7 g, 401 mmols) and potassium carbonate (55.4 g, 401 mmols) was stirred in a nitrogen atmosphere at 140° C. for 2 hours. The reaction mixture was cooled, diluted with ethyl acetate, and washed with water. This was dried with anhydrous magnesium sulfate, and concentrated under reduced pressure. The residue was purified through silica gel column chromatography to give a crystal of tert-butyl[4-(2-nitrophenylamino)benzyl]carbamate (36 g, 26%).

m.p. 121–123° C.
Elemental Analysis for $C_{18}H_{21}N_3O_4$:
Calcd.: C, 62.96; H, 6.16; N, 12.24
Found: C, 62.71; H, 6.05; N, 12.12
$^1$H-NMR (CDCl$_3$) δ: 1.49(9H,s), 4.34(2H,d,J=6 Hz), 4.92 (1H,bs), 6.78(1H,t,J=7.2 Hz), 7.18–7.37(6H,m), 8.21(1H,d, J=8.6 Hz), 9.47(1H,bs)

(3) Tert-butyl[4-(2-aminophenylamino)benzyl]carbamate:

10% carbon-palladium (4 g) was added to an ethanol solution of tert-butyl[4-(2-nitrophenylamino)benzyl]carbamate (36 g, 105 mmols). The resulting mixture was hydrogenated at room temperature under atmospheric pressure for 4 hours. The catalyst was removed through filtration, and the filtrate was concentrated under reduced pressure. The residual solid was recrystallized from hexane/ethyl acetate to give a crystal of tert-butyl[4-(2-aminophenylamino)benzyl]carbamate (29.5 g, 89.9%).

m.p. 117–119° C.
Elemental Analysis for $C_{18}H_{23}N_3O_2$:
Calcd.: C, 68.88; H, 7.40; N, 13.41
Found: C, 69.09; H, 7.55; N, 13.48
$^1$H-NMR (CDCl$_3$) δ: 1.46(9H,s), 3.78(2H,bs), 4.21(2H, d,J=5.4 Hz), 4.73(1H,bs), 5.19(1H,bs), 6.69–7.15(8H,m)

(4) Tert-butyl[4-[2-(4-biphenylmethylamino)phenylamino]benzyl]carbamate:

Acetic acid (5.4 ml, 94 mmols) was added to tert-butyl-[4-(2-aminophenylamino)benzyl]carbamate (29.5 g, 94.1 mmol) combined with an ethanol solution (500 ml) of 4-phenylaminobenzaldehyde. The resulting mixture was stirred at 0° C. for 30 minutes, to which was added sodium borocyanohydride (7.1 g, 117 mmols). Then, this was stirred at 0° C. for 1 hour and at room temperature for 30 minutes. The reaction mixture was poured into water, and extracted with ethyl acetate. The extract was washed with water, then dried with anhydrous magnesium sulfate, and concentrated under reduced pressure. The residue was purified through silica gel column chromatography to give an oil of tert-butyl [4-[2-(4-biphenylmethylamino)phenylamino]benzyl]carbamate (40.5 g, 90%).

$^1$H-NMR (CDCl$_3$) δ: 1.45(9H,s), 4.21(2H,d,J=5.4 Hz), 4.39(2H,s), 4.75(1H,bs), 5.12(1H,bs), 6.68–7.59(16H,m)

(5) A mixture of tert-butyl[4-(2-aminophenyl)amino]benzylcarbamate (4.2 g, 14 mmol), ethyl 4-bromobutyrate (7.7 ml, 54 mmols), potassium carbonate (2.1 g, 15 mmols) and N,N-dimethylformamide (30 ml) was stirred at 90° C. for 4 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[2-[4-(tert-butoxycarbonylaminomethyl)phenoxy]phenyl]aminobutyrate (4.8 g, 83%).

$^1$H-NMR (CDCl$_3$) δ: 1.23(3H,t,J=6.8 Hz), 1.45(9H,s), 1.82–1.98(2H,m), 2.36(2H,t,J=7.2 Hz), 3.18(2H,t,J=7.0 Hz), 4.07(2H,q,J=6.8 Hz), 4.11(2H,bs), 4.20(2H,d,J=5.6 Hz), 4.77(1H,bs), 5.09(1H,bs), 6.94–7.26(8H,m)

(6) 4-Phenylbenzoyl chloride (2.8 g, 13 mmols) was added, at 0° C., to a tetrahydrofuran (150 ml) solution of ethyl 4-[2-[4-(tert-butoxycarbonylaminomethyl)phenylamino]phenyl]aminobutyrate (5.0 g, 12 mmols) and 4-dimethylaminopyridine (1.6 g, 13 mmols). The reaction mixture was stirred at 0° C. for 30 minutes and at room temperature for 30 minutes, to which were again added 4-dimethylaminopyridine (1.6 g, 13 mmols) and 4-phenylbenzoyl chloride (2.8 g, 13 mmols) at 0° C. This was stirred at 0° C. for 30 minutes and at room temperature for 30 minutes, then poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[N-[2-[4-(tert-butoxycarbonylaminomethyl)phenylamino]phenyl]-N-(4-phenylbenzoyl)]aminobutyrate (3.1 g, 44%).

$^1$H-NMR (CDCl$_3$) δ: 1.17(3H,t,J=7.2 Hz), 1.45(9H,s), 1.78–1.98(2H,m), 2.33–2.42(2H,m), 3.10–3.30(2H,m), 4.07 (2H,q,J=7.2 Hz), 4.11(2H,d,J=5.8 Hz), 4.62(1H,bs), 4.88 (1H,bs), 6.47–7.66(17H,m)

(7) Aqueous 1 N sodium hydroxide solution (10 ml, 10 mmols) was added to a solution of ethyl 4-[N-[2-[4-(tert-butoxycarbonylaminomethyl)phenylamino]phenyl]-N-(4-phenylbenzoyl)]aminobutyrate (3.0 g, 4.9 mmols) in tetrahydrofuran (30 ml) and methanol (30 ml). The resulting mixture was stirred at 60° C. for 2 hours. To this were added water and potassium hydrogensulfate (1.4 g, 10 mmols). Then, this was extracted with ethyl acetate. The extract was washed with water, and then dried with anhydrous magnesium sulfate. This was concentrated under reduced pressure to give an oil of 4-[N-[2-[4-(tert-butoxycarbonylaminomethyl)phenylamino]phenyl]-N-(4-phenylbenzoyl)]aminobutyric acid (2.5 g, 87%).

$^1$H-NMR (CDCl$_3$) δ: 1.46(9H,s), 1.83–1.95(2H,m), 2.39 (2H,t,J=7.2 Hz), 3.18–3.36(2H,m), 4.19(2H,d,J=6.0 Hz), 4.79(1H,bs), 5.39(1H,bs), 6.78–7.60(17H,m)

(8) A mixture of 4-[N-[2-[4-(tert-butoxycarbonylaminomethyl)phenylamino]phenyl]-N-(4-phenylbenzoyl)]aminobutyric acid (0.50 g, 1.0 mmol), 2-fluorobenzylamine (0.23 ml, 2.0 mmols), diethyl cyanophosphate (0.30 ml, 2.0 mmols), triethylamine (0.28 ml, 2.0 mmols) and N,N-dimethylformamide (6 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to given an oil of N-(2-fluorobenzyl)-4-[N'-[2-[4-(tert-butoxycarbonylaminomethyl)phenylamino]phenyl]-N'-(4-phenylbenzoyl)]aminobutylamide (0.21 g, 31%).

$^1$H-NMR (CDCl$_3$) δ: 1.46(9H,s), 1.88–1.98(2H,m), 2.27 (2H,t,J=7.0 Hz), 3.25–3.51(2H,m), 4.20(2H,d,J=6.0 Hz), 4.44(2H,d,J=5.6 Hz), 4.82(1H,bs), 5.50(1H,bs), 6.70(1H,t, J=5.6 Hz), 6.81–7.75(21H,m)

(9) A 4 N hydrochloric acid/ethyl acetate solution (1 ml) was added to an ethyl acetate (1 ml) solution of N-(2-fluorobenzyl)-4-[N'-[2-[4-(tert-butoxycarbonylaminomethyl)phenylamino]phenyl]-N'-(4-phenylbenzoyl)]aminobutylamide (0.17 g, 0.25 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[4-(aminomethyl)phenylamino]phenyl]-N'-(4-phenylbenzoyl)]aminobutylamide dihydrochloride (0.13 g, 79%).

Elemental Analysis for $C_{37}H_{37}N_4O_2Cl_2F \cdot 0.4H_2O$:
Calcd.: C, 66.65; H, 5.71; N, 8.40
Found: C, 66.88; H, 5.98; N, 8.15

¹H-NMR (DMSO-d₆) δ: 1.99–2.12(2H,m), 2.41(2H,t, J=6.6 Hz), 3.77–3.87(2H,m), 4.18(2H,d,J=5.8 Hz), 4.28(2H, d,J=5.4 Hz), 4.70(2H,bs), 7.08–7.89(20H,m), 8.23(1H,d, J=8.0 Hz), 8.57(1H,t,J=5.8 Hz), 8.79(3H,bs)

EXAMPLE 199

N-[2-(2-fluorophenyl)ethyl]-3-[N'-[2-[3-(aminomethyl)phenoxy]-4-chlorophenyl]-N'-[(5-methyl-1,3,4-thiadiazol-2-ylsulfanyl)acetyl]]aminopropionamide hydrochloride (1) Aqueous 1 N sodium hydroxide solution (20 ml, 20 mmols) was added to a solution of ethyl 3-[2-[3-(tert-butoxycarbonylaminomethyl)phenoxy]-4-chlorophenyl] aminopropionate (2.5 g, 5.5 mmols) in tetrahydrofuran (40 ml) and ethanol (40 ml). The resulting mixture was stirred at 60° C. for 1 hour. To this were added water and potassium hydrogensulfate. Then, this was extracted with ethyl acetate. The extract was washed with water, and then dried with anhydrous magnesium sulfate. This was concentrated under reduced pressure to give an amorphous solid.

A mixture of the thus-obtained solid with 2-fluorophenethylamine (1.1 g, 8.2 mmols), 1-ethyl-3-(3-dimethylaminopropyl)carbodiimide hydrochloride (WSC) (2.1 g, 11 mmols), 1-hydroxybenzotriazole monohydrate (HOBt) (1.5 g, 11 mmols) and N,N-dimethylformamide (10 ml) was stirred at room temperature for 4 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an oil of N-[2-(2-fluorophenyl)ethyl]-3-[N'-[2-[3-(tert-butoxycarbonylaminomethyl)phenoxy]-4-chlorophenyl]]aminopropionamide (2.9 g, 98%).

(2) A mixture of N-[2-(2-fluorophenyl)ethyl]-3-[N'-[2-[3-(tert-butoxycarbonylaminomethyl)phenoxy]-4-chlorophenyl]]aminopropionamide (2.9 g, 5.4 mmols), bromoacetyl bromide (2.2 g, 11 mmols) and N,N-dimethylacetamide (10 ml) was stirred at room temperature for 1 hour. The reaction mixture was poured into water, and extracted with ethyl acetate. The extract was washed with brine, and then dried with anhydrous magnesium sulfate. This was concentrated under reduced pressure, and the residue was purified through column chromatography to give an oil of N-[2-(2-fluorophenyl)ethyl]-3-[N'-[2-[3-(tert-butoxycarbonylaminomethyl) phenoxy]-4-chlorophenyl]-N'-bromoacetyl]aminopropionamide (0.97 g, 27%).

Elemental Analysis for $C_{31}H_{34}N_3O_5BrClF·H_2O$:
Calcd.: C, 54.68; H, 5.33; N, 6.17
Found: C, 54.71; H, 5.38; N, 6.28
¹H-NMR (CDCl₃) δ: 1.44(9H,s), 2.49(2H,m), 2.83(2H, m), 3.46(2H,m), 3.69(2H,m), 3.84(1H,m), 3.97(1H,m), 4.30 (2H,d,J=6.5 Hz), 5.02(1H,bs), 6.20(1H,bs), 6.86–7.40(11H, m)

(3) A mixture of N-[2-(2-fluorophenyl)ethyl]-3-[N'-[2-[3-(aminomethyl)phenoxy]-4-chlorophenyl]-N'-bromoacetyl] aminopropionamide (0.94 g, 1.4 mmols), 2-methoxy-1,3,4-thiadiazole-5-thiol (0.18 g, 1.4 mmols), potassium carbonate (0.3 g, 2.1 mmols) and N,N-dimethylformamide (10 ml) was stirred at 60° C. for 1 hour. The reaction mixture was cooled, poured into water, and extracted with ethyl acetate. The extract was washed with water and brine, and then dried with anhydrous magnesium sulfate. This was concentrated under reduced pressure, and the residue was purified through silica gel column chromatography to give an amorphous solid of N-(2-fluorobenzyl)-3-[N'-[2-[3-(tert-butoxycarbonylaminomethyl)phenoxy]-4-chlorophenyl]-N'-[(5-methyl-1,3,4-thiadiazol-2-ylsulfanyl)acetyl]]aminopropionamide (0.49 g, 48%).

Elemental Analysis for $C_{34}H_{37}N_5O_5ClFS_2$:
Calcd.: C, 57.17; H, 5.22; N, 9.80
Found: C, 56.89; H, 5.43; N, 9.51
¹H-NMR (CDCl₃) δ: 1.42(9H,s), 2.42(1H,m), 2.52(1H, m), 2.69(3H,s), 2.83(2H,m), 3.47(2H,m), 3.80–4.17(4H,m), 4.30(2H,d,J=6.2 Hz), 5.34(1H,bs), 6.40(1H,m), 6.87–7.38 (11H,m)

(4) A 2 N hydrochloric acid/ethyl acetate solution (6 ml) of N-[2-(2-fluorophenyl)ethyl]-3-[N'-[2-[3-(tert-butoxycarbonylaminomethyl)phenoxy]-4-chlorophenyl]-N'-[(5-methyl-1,3,4-thiadiazol-2-ylsulfanyl)acetyl]]aminopropionamide (0.34 g, 0.47 mmols) was stirred at room temperature for 1 hour. The reaction mixture was concentrated under reduced pressure. The solid precipitated was taken out through filtration, and washed with ethyl ether to give an amorphous solid of N-[2-(2-fluorophenyl)ethyl]-3-[N'-[2-[3-(aminomethyl)phenoxy]-4-chlorophenyl]-N'-[(5-methyl-1,3,4-thiadiazol-2-ylsulfanyl)acetyl]]aminopropionamide hydrochloride (0.3 g, 97%).

Elemental Analysis for $C_{29}H_{30}N_5O_3Cl_2FS_2·H_2O$:
Calcd.: C, 52.09; H, 4.82; N, 10.47
Found: C, 52.27; H, 4.84; N, 10.40
¹H-NMR (DMSO-d₆) δ: 2.35(2H,m), 2.65(3H,s), 2.70 (2H,m), 3.22(2H,m), 3.66(1H,m), 3.88–4.13(5H,m), 6.88 (1H,d), 7.07–7.59(10H,m), 8.18(1H,m), 8.57(3H,bs)

EXAMPLE 200

N-(2-fluorobenzyl)-4-[N'-[2-[3-[(1S)-1-aminoethyl] phenoxy]-4-chlorophenyl]-N'-(9H-fluorene-2-carbonyl)]aminobutylamide hydrochloride (1) A mixture of N-(2-fluorobenzyl)-4-N'-[2-[3-[(1S)-1-tert-butoxycarbonylaminoethyl]phenoxy]-4-chlorophenyl]] aminobutylamide (0.56 g, 1 mmol), 9H-fluorene-2-carbonyl chloride (0.34 g, 1.5 mmols) and N,N-dimethylacetamide (10 ml) was stirred at room temperature for 6 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-[(1S)-1-tert-butoxycarbonylaminoethyl]phenoxy]-4-chlorophenyl]-N'-(9H-fluorene-2-carbonyl)]aminobutylamide (0.45 g, 59%).

$[\alpha]_D^{24}$ –27° (C=0.5, MeOH)
Elemental Analysis for $C_{44}H_{43}N_3O_5ClF$:
Calcd.: C, 70.62; H, 5.79; N, 5.62
Found: C, 70.44; H, 5.66; H, 5.49
¹H-NMR (CDCl₃) δ: 1.26(3H,m), 1.39(9H,s), 1.98(2H, m), 2.40(2H,m), 3.76(2H,s), 3.82(1H,m), 4.14(1H,m), 4.52 (2H,d,J=5.4 Hz), 4.53(1H,m), 6.41–6.64(3H,m), 6.98–7.35 (12H,m), 7.51–7.60(3H,m), 7.76(1H,d)

(2) A 4 N hydrochloric acid/ethyl acetate solution (3 ml) was added to an ethyl acetate (3 ml) solution of N-(2-fluorobenzyl)-4-[N'-[2-[3-[(1S)-1-tert-butoxycarbonylaminoethyl]phenoxy]-4-chlorophenyl]-N'-(9H-fluorene-2-carbonyl)]aminobutylamide (0.3 g, 0.4 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-

[3-[(1S)-1-aminoethyl]phenoxy]-4-chlorophenyl]-N'-(9H-fluorene-2-carbonyl)]aminobutylamide hydrochloride (0.27 g, 99%).

$[\alpha]_D^{24}$ +1.2° (C=0.5, MeOH)

Elemental Analysis for $C_{39}H_{36}N_3O_3Cl_2F \cdot 1/2H_2O$:

Calcd.: C, 67.53; H, 5.38; N, 6.06

Found: C, 67.37; H, 5.38; N, 5.95

$^1$H-NMR (DMSO-$d_6$) δ: 1.47(3H,d,J=5.8 Hz), 1.84(2H,m), 2.28(2H,m), 3.83(4H,m), 4.30(3H,m), 6.57(1H,br), 6.67(1H,m), 7.14–7.38(11H,m), 7.57(3H,m), 7.76(1H,d), 7.88(1H,d), 8.49(1H,m), 8.66(3H,bs)

EXAMPLE 201

N-(2-fluorobenzyl)-4-[N'-[2-[3-[(1S)-1-aminoethyl]phenoxy]-4-chlorophenyl]-N'-[[4-(benzenesulfonyl)aminophenyl]acetyl]]aminobutylamide hydrochloride (1) A mixture of N-(2-fluorobenzyl)-4-N'-[2-[3-[(1S)-1-tert-butoxycarbonylaminoethyl]phenoxy]-4-chlorophenyl]]aminobutylamide (0.54 g, 0.97 mmols), [4-(benzenesulfonyl)aminophenyl]acetyl chloride (0.39 g, 1.3 mmols) and N,N-dimethylacetamide (10 ml) was stirred at room temperature for 4 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[[4-(benzenesulfonyl)aminophenyl]acetyl]-N'-[2-[3-[(1S)-1-tert-butoxycarbonylaminoethyl]phenoxy]-4-chlorophenyl]]aminobutylamide (0.5 g, 62%).

$[\alpha]_D^{24}$ −24° (C=0.5, MeOH)

Elemental Analysis for $C_{44}H_{46}N_4O_7ClFS \cdot 1/2H_2O$:

Calcd.: C, 63.03; H, 5.65; N, 6.68

Found: C, 63.31; H, 5.84; N, 6.37

$^1$H-NMR (CDCl$_3$) δ: 1.39(12H,m), 1.87(2H,m), 2.26(2H,m), 3.72(2H,m), 3.63(1H,m), 4.44(2H,d,J=5.2 Hz), 4.68(1H,m), 5.08(1H,d), 6.65–7.52(20H,m), 7.72(2H,d)

(2) A 4 N hydrochloric acid/ethyl acetate solution (3 ml) was added to an ethyl acetate (3 ml) solution of N-(2-fluorobenzyl)-4-[N'-[2-[3-[(1S)-1-tert-butoxycarbonylaminoethyl]phenoxy]-4-chlorophenyl]-N'-[[4-(benzenesulfonyl)aminophenyl]acetyl]]aminobutylamide (0.33 g, 0.4 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-[(1S)-1-aminoethyl]phenoxy]-4-chlorophenyl]-N'-[[4-(benzenesulfonyl)aminophenyl]acetyl]]aminobutylamide hydrochloride (0.29 g, 96%).

$[\alpha]_D^{24}$ −2.8° (C=0.5, MeOH)

Elemental Analysis for $C_{39}H_{39}N_4O_5Cl_2FS \cdot 1.5H_2O$:

Calcd.: C, 59.09; H, 5.34; N, 7.07

Found: C, 59.33; H, 5.25; N, 6.91

$^1$H-NMR (DMSO-$d_6$) δ: 1.49(3H,d,J=4.0 Hz), 1.67(2H,m), 2.16(2H,m), 3.33(4H,m), 4.25(2H,d,J=5.6 Hz), 4.41(1H,m), 6.82–7.59(18H,m), 7.75(2H,m), 8.40(1H,m), 8.66(3H,bs), 10.32(1H,s)

EXAMPLE 202

N-(2-fluorobenzyl)-4-[N'-[2-[3-[(1S)-1-aminoethyl]phenoxy]-4-chlorophenyl]-N'-[(2'-methoxybiphenyl-4-yl)acetyl]]aminobutylamide hydrochloride (1) Concentrated sulfuric acid (10 ml) was added to an ethanol (300 ml) solution of 4-bromophenylacetic acid (25 g, 120 mmols), and heated under reflux for 15 hours. The reaction mixture was concentrated under reduced pressure, and the residue was poured into water with ice, and extracted with ethyl acetate. The extract was washed with water, and then dried with anhydrous magnesium sulfate. This was concentrated under reduced pressure to give an oil of ethyl 4-bromophenylacetate (28 g, 99%).

$^1$H-NMR (CDCl$_3$) δ: 1.25(3H,t,J=7.2 Hz), 3.56(2H,s), 4.15(2H,q,J=7.2 Hz), 7.14–7.20(2H,m), 7.42–7.49(2H,m)

A mixture of the resulting ethyl 4-bromophenylacetate (16 g, 66 mols) with 2-methoxyphenylboronic acid (10 g, 66 mmols), sodium carbonate (17.5 g, 165 mmols), toluene (50 ml, ethanol (50 ml) and water (50 ml) was stirred in an argon atmosphere at room temperature for 30 minutes. Tetrakis(triphenylphosphine)palladium(0) (1.9 g, 1.6 mmols) was added thereto, and heated under reflux for 15 hours. The reaction mixture was cooled, then poured into water, and extracted with ethyl acetate. The extract was washed with brine and water, then dried with anhydrous magnesium sulfate, and concentrated under reduced pressure. The residue was purified through silica gel column chromatography to give an oil of ethyl(2'-methoxy-4-biphenyl)acetate (17.3 g, 97%).

$^1$H-NMR (CDCl$_3$) δ: 1.27(3H,t,J=7.2 Hz), 3.65(2H,s), 3.81(3H,s), 4.17(2H,q,J=7.2 Hz), 6.96–7.06(2H,m), 7.26–7.35(4H,m), 7.49(2H,d,J=8.4 Hz)

Aqueous 1 N sodium hydroxide solution (70 ml, 70 mmols) was added to an ethanol (80 ml) solution of this ethyl (2'-methoxy-4-biphenyl)acetate (17.3 g, 64 mmols), and stirred at room temperature for 4 hours. The reaction mixture was concentrated under reduced pressure, water was added to the residue, which was then acidified with 1 N hydrochloric acid added thereto, and extracted with ethyl acetate. The extract was washed with brine, then dried with anhydrous magnesium sulfate, and concentrated under reduced pressure. This gave a solid of (2'-methoxy-4-biphenyl)acetic acid (14.7 g, 95%).

m.p. 174–176° C.

$^1$H-NMR (CDCl$_3$) δ: 3.69(2H,s), 3.80(3H,s), 6.96–7.05(2H,m), 7.25–7.35(4H,m), 7.51(2H,d,J=8.0 Hz)

A tetrahydrofuran (20 ml) solution of (2'-methoxy-4-biphenyl)acetic acid (0.39 g, 1.6 mmols), oxalyl chloride (0.41 g, 3.2 mmols) and N,N-dimethylformamide (0.3 ml) was stirred at room temperature for 1 hour. The reaction mixture was concentrated under reduced pressure, to which were added N-(2-fluorobenzyl)-4-[N'-[2-[3-[(1S)-1-tert-butoxycarbonylaminoethyl]phenoxy]-4-chlorophenyl]]aminobutylamide (0.6 g, 1.1 mmols) and N,N-dimethylacetamide (10 ml). The resulting mixture was stirred at room temperature for 3 hours. This was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-[(1S)-1-tert-butoxycarbonylaminoethyl]phenoxy]-4-chlorophenyl]-N'-[(2'-methoxybiphenyl-4-yl)acetyl]]aminobutylamide (0.74 g, 88%).

$[\alpha]_D^{24}$ −29° (C=0.5, MeOH)
Elemental Analysis for $C_{45}H_{47}N_3O_6ClF \cdot 1/2H_2O$:
Calcd.: C, 68.47; H, 6.13; N, 5.32
Found: C, 68.35; H, 6.08; N, 5.07
$^1$H-NMR (CDCl$_3$) δ: 1.38(12H,m), 1.86(2H,m), 2.27(2H, m), 3.54(2H,m), 3.74(2H,m), 3.79(3H,s), 4.46(2H,d,J=6.2 Hz), 4.69(1H,m), 4.96(1H,m), 6.74–7.50(20H,m)

(2) A 4 N hydrochloric acid/ethyl acetate solution (3 ml) was added to an ethyl acetate (3 ml) solution of N-(2-fluorobenzyl)-4-[N'-[2-[3-[(1S)-1-tert-butoxycarbonylaminoethyl]phenoxy]-4-chlorophenyl]-N'-[(2'-methoxybiphenyl-4-yl)acetyl]]aminobutylamide (0.35 g, 0.45 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-[(1S)-1-aminoethyl]phenoxy]-4-chlorophenyl]-N'-[(2'-methoxybiphenyl-4-yl)acetyl]]aminobutylamide hydrochloride (0.32 g, 99%).
$[\alpha]_D^{24}$ −1.0° (C=0.5, MeOH)
Elemental Analysis for $C_{40}H_{40}N_3O_4Cl_2F \cdot H_2O$:
Calcd.: C, 65.39; H, 5.76; N, 5.72
Found: C, 65.18; H, 5.73; N, 5.59
$^1$H-NMR (DMSO-d$_6$) δ: 1.50(3H,d,J=6.6 Hz), 1.73(2H, m), 2.20(2H,m), 3.47(2H,m), 3.71(2H,m), 3.75(3H,s), 4;27 (2H,d,J=5.2 Hz), 4.42(1H,m), 6.88–7.55(19H,m), 8.42(1H, m), 8.65(3H,bs)

EXAMPLE 203

N-[(1R)-1-indanyl]-4-[N'-[2-[3-[(1S)-1-aminoethyl]phenoxy]-4-chlorophenyl]-N'-(4-phenylbenzoyl)]aminobutylamide hydrochloride (1) A mixture of 4-[N-[2-[3-[(1S)-1-tert-butoxycarbonylaminoethyl]phenoxy]-4-chlorophenyl]-N-(4-phenylbenzoyl)]aminobutyric acid (0.71 g, 1.1 mmols), (R)-1-aminoindane (0.25 g, 1.9 mmols), 1-ethyl-3-(3-dimethylaminopropyl)carbodiimide hydrochloride (WSC) (0.44 g, 2.3 mmols), 1-hydroxybenzotriazole monohydrate (HOBt) (0.31 g, 2.3 mmols) and N,N-dimethylformamide (10 ml) was stirred at room temperature for 16 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[(R)-1-indanyl]-4-[N'-[2-[3-[(1S)-1-tert-butoxycarbonylaminoethyl]phenoxy]-4-chlorophenyl]-N'-(4-phenylbenzoyl)]aminobutylamide (0.67 g, 79%).
$[\alpha]_D^{24}$ +17° (C=0.5, MeOH)
Elemental Analysis for $C_{45}H_{46}N_3O_5Cl \cdot 1/2H_2O$:
Calcd.: C, 71.75; H, 6.29; N, 5.58
Found: C, 71.69; H, 6.52; H, 5.47
$^1$H-NMR (CDCl$_3$) δ: 1.32(3H,d), 1.38(9H,s), 1.85(1H,m), 2.02(2H,m), 2.39(2H,m), 2.50(1H,m), 2.88(2H,m), 3.85(1H,m), 4.09(1H,m), 4.17(1H,m), 4.87(1H,bs), 5.50(1H,m), 6.42–6.74(4H,m), 6.98–7.57(17H,m)

(2) A 4 N hydrochloric acid/ethyl acetate solution (3 ml) was added to an ethyl acetate (3 ml) solution of N-[(R)-1-indanyl]-4-[N'-[2-[3-[(1S)-1-tert-butoxycarbonylaminoethyl]phenoxy]-4-chlorophenyl]-N'-(4-phenylbenzoyl)]aminobutylamide (0.33 g, 0.44 mmols), and stirred at room temperature for 1 hour. The reaction mixture was concentrated under reduced pressure. The solid precipitated was taken out through filtration, and washed with ethyl ether to give an amorphous solid of N-[(1R)-1-indanyl]-4-[N'-[2-[3-[(1S)-1-aminoethyl]phenoxy]-4-chlorophenyl]-N'-(4-phenylbenzoyl)]aminobutylamide hydrochloride (0.3 g, 100%).
$[\alpha]_D^{24}$ +47° (C=0.5, MeOH)
Elemental Analysis for $C_{40}H_{39}N_3O_3Cl_2 \cdot 2H_2O$:
Calcd.: C, 67.03; H, 6.05; N, 5.86
Found: C, 67.14; H, 5.93; N. 5.81
$^1$H-NMR (DMSO-d$_6$) δ: 1.49(3H,d,J=6.6 Hz), 1.71–1.87 (3H,m), 2.25–2.37(3H,m), 2.85(2H,m), 3.87(2H,m), 4.38 (1H,m), 5.27(1H,m), 6.61(1H,s), 6.37(1H,m), 7.14–7.68(18H,m), 8.31(1H,d), 8.66(3H,bs)

EXAMPLE 204

N-(2-fluorobenzyl)-4-[N'-[2-[3-[(1R)-1-aminoethyl]phenoxy]-4-chlorophenyl]-N'-(4-phenylbenzoyl)]aminobutylamide hydrochloride (1) A dichloromethane (50 ml) solution of boron tribromide (19 ml, 200 mmols) was dropwise added to a dichloromethane (100 ml) solution of (R)-1-(3-methoxyphenyl)ethylamine (10 g, 66 mmols) at −78° C. This was stirred at the temperature for 30 minutes, and then reacted at room temperature for 1 hour. Methanol was added to the reaction mixture to stop the reaction, and then the mixture was concentrated under reduced pressure. To the residue, added were tetrahydrofuran (200 ml), triethylamine (33.8 g, 330 ml) and di-tert-butyl dicarbonate (14.5 g, 66 mmols). The resulting mixture was heated under reflux for 2 hours. This was cooled, then poured into water, and extracted with ethyl acetate. The extract was washed with 1 N hydrochloric acid, and brine, and then dried with anhydrous magnesium sulfate. This was concentrated under reduced pressure, and the residue was purified through silica gel column chromatography. An oil of tert-butyl(1R)-1-(3-hydroxyphenyl)ethylcarbamate (13.7 g, 87%) was obtained.
$^1$H-NMR (CDCl$_3$) δ: 1.42(9H,s), 1.46(3H,s), 4.71(1H,m), 4.90(1H,m), 6.68–6.81(3H,m), 6.94(1H,s), 7.14(1H,m)

(2) A mixture of 4-chloro-2-fluoronitrobenzene (10.6 g, 54 mmols), tert-butyl(1R)-1-(3-hydroxyphenyl)ethylcarbamate (13.7 g, 58 mmols), potassium carbonate (8.7 g, 63 mmols) and N,N-dimethylformamide (150 ml) was stirred at 100° C. for 1 hour. The reaction mixture was cooled, poured into water, and extracted with ethyl acetate. The extract was washed with water and brine, and then dried with anhydrous magnesium sulfate, and the solvent was evaporated away. The residue was purified through silica gel column chromatography, and the resulting crystal was re-crystallized from hexane/ethyl acetate to give a crystal of tert-butyl(1R)-(-)-1-[3-(5-chloro-2-nitrophenoxy)phenyl]ethylcarbamate (12.9 g, 60%).
m.p. 94–96° C.
$[\alpha]_D^{24}$ +50° (C=0.5, MeOH)
Elemental Analysis for $C_{19}H_{21}N_2O_5Cl$:
Calcd.: C, 58.09; H, 5.39; N, 7.13
Found: C,. 58.12; H, 5.42; N, 7.04
$^1$H-NMR (CDCl$_3$) δ: 1.41(12H,m), 4.80(2H,m), 6.93–7.42(6H,m), 7.93(1H,d)

(3) 5% carbon-palladium (1.I g) was added to an ethyl acetate (50 ml) solution of tert-butyl(1R)-(-)-1-[3-(5-chloro-2-nitrophenoxy)phenyl]ethylcarbamate (3.5 g, 8.9 mmols). The resulting mixture was hydrogenated at room temperature under atmospheric pressure for 1 hour. The catalyst was removed through filtration, and the filtrate was concentrated under reduced pressure. The residue was stirred with ethyl 4-bromobutyrate (7 g, 36 mmols), potassium carbonate (3.7 g, 27 mmols) and N,N-dimethylformamide (50 ml) at 80° C. for 72 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[N-[2-[3-[(1R)-1-tert-butoxycarbonylaminoethyl]phenoxy]-4-chlorophenyl]]aminobutyrate (2.4 g, 56%).

$^1$H-NMR (CDCl$_3$) δ: 1.24(3H,t,J=7.0 Hz), 1.41(12H,m), 1.93(2H,m), 2.37(2H,m), 3.19(2H,m), 4.11(2H,q,J=7.0 Hz), 4.21(1H,m), 4.79(2H,m), 6.61–7.32(7H,m)

(4) A mixture of ethyl 4-[N-[2-[3-[(1R)-1-tert-butoxycarbonylaminoethyl]phenoxy]-4-chlorophenyl]aminobutyrate (2.4 g, 5 mmols), 4-phenylbenzoyl chloride (1.6 g, 7.5 mmols) and N,N-dimethylacetamide (50 ml) was stirred at room temperature for 2 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an oil of ethyl 4-[N-[2-[3-[(1R)-1-tert-butoxycarbonylaminoethyl]phenoxy]-4-chlorophenyl]-N-(4-phenylbenzoyl)]aminobutyrate (2.8 g, 86%).

Elemental Analysis for C$_{38}$H$_{41}$N$_2$O$_6$Cl:
Calcd.: C, 69.45; H, 6.29; N, 4.26
Found: C, 69.22; H, 6.43; N, 4.20

$^1$H-NMR (CDCl$_3$) δ: 1.23(3H,t,J=7.0 Hz), 1.33(3H,m), 1.40(9H,s), 2.01(2H,m), 2.47(2H,m), 3.87(1H,m), 4.06(1H, m), 4.12(2H,q,J=7.0 Hz), 4.70(1H,m), 4.80(1H,bs), 6.44–6.53(2H,m), 6.67(1H,d), 6.97–7.59(13H,m)

(5) Aqueous 1 N sodium hydroxide solution (20 ml, 20 mmols) was added to a solution of ethyl 4-[N-[2-[3-[(1R)-1-tert-butoxycarbonylaminoethyl]phenoxy]-4-chlorophenyl]-N-(4-phenylbenzoyl)]aminobutyrate (2.5 g, 3.8 mmols) in tetrahydrofuran (20 ml) and ethanol (20 ml). The resulting mixture was stirred at 60° C. for 1 hour. This was poured into water, then acidified with potassium hydrogensulfate added thereto, and then extracted with ethyl acetate. The extract was washed with water, and then dried with anhydrous magnesium sulfate. This was concentrated under reduced pressure to give an amorphous solid of 4-[N-[2-[3-[(1R)-1-tert-butoxycarbonylaminoethyl]phenoxy]-4-chlorophenyl]-N-(4-phenylbenzoyl)]aminobutyric acid (2.4 g, 100%).

Elemental Analysis for C$_{36}$H$_{37}$N$_2$O$_6$Cl.1/2H$_2$O:
Calcd.: C, 67.76; H, 6.00; N, 4.39
Found: C, 67.76; H, 6.19; N, 4.28

$^1$H-NMR (CDCl$_3$) δ: 1.39(3H,m), 1.42(9H,s), 1.97(2H, m), 2.50(2H,m), 4.00(1H,m), 4.10(1H,m), 4.66(1H,m), 5.00 (1H,bs), 6.59–7.07(6H,m), 7.30–7.58(11H,m)

(6) A mixture of 4-[N-[2-[3-[(1R)-1-tert-butoxycarbonylaminoethyl]phenoxy]-4-chlorophenyl]-N-(4-phenylbenzoyl)]aminobutyric acid (1.0 g, 1.6 mmols), 2-fluorobenzylamine (0.3 g, 2.4 mmols), 1-ethyl-3-(3-dimethylaminopropyl)carbodiimide hydrochloride (WSC) (0.61 g, 3.2 mmols), 1-hydroxybenzotriazole monohydrate (HOBt) (0.43 g, 3.2 mmols) and N,N-dimethylformamide (10 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-[(1R)-1-tert-butoxycarbonylaminoethyl]phenoxy]-4-chlorophenyl]-N'-(4-phenylbenzoyl)]aminobutylamide (0.48 g, 41%).

[α]$_D^{24}$ +27° (C=0.5, MeOH)

Elemental Analysis for C$_{43}$H$_{43}$N$_3$O$_5$ClF.1/2H$_2$O:
Calcd.: C, 69.30; H, 5.95; N,. 5.64
Found: C, 69.60; H, 6.16; N, 5.62

$^1$H-NMR (CDCl$_3$) δ: 1.33(3H,d), 1.39(9H,s), 1.98(2H,m), 2.39(2H,m), 3.81(1H,m), 4.12(1H,m), 4.51(2H,d,J=5.8 Hz), 4.66(1H,m), 4.86(1H,bs), 6.43(1H,d), 6.45(1H,s), 6.63(1H, d), 6.91(1H,bs), 6.98–7.59(17H,m)

(7) A 4 N hydrochloric acid/ethyl acetate solution (3 ml) was added to an ethyl acetate (3 ml) solution of N-(2-fluorobenzyl)-4-[N'-[2-[3-[(1R)-1-tert-butoxycarbonylaminoethyl]phenoxy]-4-chlorophenyl]-N'-(4-phenylbenzoyl)]aminobutylamide (0.32 g, 0.48 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-[(1R)-1-aminoethyl]phenoxy]-4-chlorophenyl]-N'-(4-phenylbenzoyl)]aminobutylamide hydrochloride (0.3 g, 94%).

[α]$_D^{24}$ +0.1° (C=0.5, MeOH)

Elemental Analysis for C$_{38}$H$_{36}$N$_3$O$_3$Cl$_2$F.1/2H$_2$O:
Calcd.: C, 66.96; H, 5.47; N, 6.16
Found: C, 66.65; H, 5.44; N, 6.28

$^1$H-NMR (DMSO-d$_6$) δ: 1.49(3H,d,J=6.6 Hz), 1.83(2H, m), 2.27(2H,m), 3.78(2H,m), 4.29(2H,d,J=5.2 Hz), 4.43(1H, m), 6.59(1H,s), 6.59(1H,bs), 6.70(1H,m), 7.11–7.68(18H, m), 8.47(1H,m), 8.66(3H,bs)

EXAMPLE 205

N-[2-[3-[(1S)-1-aminoethyl]phenoxy]-4-chlorophenyl]-N-[3-[[[(2-fluorobenzyl)amino]carbonyl]amino] propyl]-4-phenylbenzamide hydrochloride (1) A mixture of 4-N-[2-[3-[(1S)-1-tert-butoxycarbonylaminoethyl]phenoxy]-4-chlorophenyl]-N-(4-phenylbenzoyl)]aminobutyric acid (1.0 g, 1.6 mmols), diphenylphosphorylazide (DPPA) (0.67 g, 2.4 mmols), triethylamine (0.2 g, 2.0 mmols) and N,N-dimethylformamide (10 ml) was stirred at room temperature for 6 hours. The reaction mixture was poured into water, and extracted with ethyl acetate. The extract was washed with brine and water, and then dried with anhydrous magnesium sulfate, and the solvent was evaporated away. Toluene (20 ml) was added to the residue, and the resulting mixture was heated under reflux for 3 hours. Next, 2-fluorobenzylamine (0.5 g, 4.0 mmols) was added to the reaction mixture, and further refluxed for 2 hours. This was cooled, poured into water, and extracted with ethyl acetate. The extract was washed with water and brine, and then dried with anhydrous magnesium sulfate, and the solvent was evaporated away. The residue was purified through silica gel column chromatography to give an amorphous solid of tert-butyl (1S)-1-[3-[2-[(4-phenylbenzoyl)[3-[[[(2-fluorobenzyl)amino]carbonyl]amino]propyl]amino]-5-chlorophenoxy]phenyl]ethylcarbamate (0.66 g, 55%).

[α]$_D^{24}$ −24° (C=0.5, MeOH)

Elemental Analysis for C$_{43}$H$_{44}$N$_4$O$_5$ClF.1/2H$_2$O:
Calcd.: C, 67.93; H, 5.97; N, 7.37
Found: C, 68.02; H, 5.98; N, 7.27

$^1$H-NMR (CDCl$_3$) δ: 1.31(3H,m), 1.37(9H,s), 1.76(2H, m), 3.36(2H,m), 3.77(1H,m), 4.17(1H,m), 4.43(2H,d,J=5.8 Hz), 4.66(1H,bs), 4.84(1H,m), 5.09(1H,m), 5.75(1H,m), 6.42(1H,m), 6.53–6.65(2H,m), 6.95–7.58(17H,m)

(2) A 4 N hydrochloric acid/ethyl acetate (3 ml) solution was added to an ethyl acetate (3 ml) solution of tert-butyl (1S)-1-[3-[2-[(4-phenylbenzoyl)[3-[[[(2-fluorobenzyl) amino]carbonyl]amino]propyl]amino]-5-chlorophenoxy] phenyl]ethylcarbamate (0.36 g, 0.48 mmols), and stirred at room temperature for 1 hour. The reaction mixture was concentrated under reduced pressure. The solid precipitated was taken out through filtration, and washed with ethyl ether to give an amorphous solid of N-[2-[3-[(1S)-1-aminoethyl]phenoxy]-4-chlorophenyl]-N-[3-[[[(2-fluorobenzyl)amino]carbonyl]amino]propyl]-4-phenylbenzamide hydrochloride (0.31 g, 95%).

$[\alpha]_D^{24}$ −2.1° (C=0.5, MeOH)

Elemental Analysis for $C_{38}H_{37}N_4O_3Cl_2F.1/2H_2O$:

Calcd.: C, 65.52; H, 5.50; N, 8.04

Found: C, 65.27; H, 5.57; N, 7.89

$^1$H-NMR (DMSO-$d_6$) δ: 1.49(3H,d,J=6.6 Hz), 1.69(2H,m), 3.11(2H,m), 3.81(2H,m), 4.25(2H,m), 4.40(1H,m), 6.29 (1H,m), 6.58(3H,m), 7.10–7.69(18H,m), 8.61(3H,bs)

EXAMPLE 206

N-[(R)-1-indanyl]-4-[N'-[2-[3-(aminomethyl)phenoxy]-4-chlorophenyl]-N'-(4-phenylbenzoyl)]aminobutylamide hydrochloride (1) A mixture of 4-[N-[2-[3-(tert-butoxycarbonylaminomethyl)phenoxy]-4-chlorophenyl]-N-(4-phenylbenzoyl)]aminobutyric acid (0.8 g, 1.3 mmols), (R)-1-aminoindane (0.32 g, 2.4 mmols), 1-ethyl-3-(3-dimethylaminopropyl)carbodiimide hydrochloride (WSC) (0.5 g, 2.6 mmols), 1-hydroxybenzotriazole monohydrate (HOBt) (0.35 g, 2.6 mmols) and N,N-dimethylformamide (10 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[(R)-1-indanyl]-4-[N'-[2-[3-(tert-butoxycarbonylaminomethyl)phenoxy]-4-chlorophenyl]-N'-(4-phenylbenzoyl)]aminobutylamide (0.79 g, 83%).

$[\alpha]_D^{24}$ +45° (C=0.5, MeOH)

Elemental Analysis for $C_{44}H_{44}N_3O_5Cl$:

Calcd.: C, 72.36; H, 6.07; N, 5.75

Found: C, 72.20; H, 6.06; N, 5.81

$^1$H-NMR (CDCl$_3$) δ: 1.42(9H,s), 1.88(1H,m), 2.00(2H,m), 2.37(2H,m), 2.56(1H,m), 2.88(2H,m), 3.84(1H,m), 4.10–4.19(3H,m), 4.98(1H,bs), 5.50(1H,m), 6.48(1H,bs), 6.56–6.62(3H,m), 7.04(2H,m), 7.18–7.58(15H,m)

(2) A 4 N hydrochloric acid/ethyl acetate solution (2 ml) was added to an ethyl acetate (2 ml) solution of N-[(R)-1-indanyl]-4-[N'-[2-[3-(tert-butoxycarbonylaminomethyl)phenoxy]-4-chlorophenyl]-N'-(4-phenylbenzoyl)]aminobutylamide (0.22 g, 0.31 mmols), and stirred at room temperature for 1 hour. The reaction mixture was concentrated under reduced pressure. The solid precipitated was taken out through filtration, and washed with ethyl ether to give an amorphous solid of N-[(R)-1-indanyl]-4-[N'-[2-[3-(aminomethyl)phenoxy]-4-chlorophenyl]-N'-(4-phenylbenzoyl)]aminobutylamide hydrochloride (0.2 g, 98%).

$[\alpha]_D^{24}$ +46° (C=0.5, MeOH)

Elemental Analysis for $C_{39}H_{37}N_3O_3Cl_2.1/2H_2O$:

Calcd.: C, 69.33; H, 5.67; N, 6.22

Found: C, 69.30; H, 5.81; N, 6.11

$^1$H-NMR (DMSO-$d_6$) δ: 1.70–1.91(3H,m), 2.24(2H,m), 2.31(1H,m), 2.82(2H,m), 3.79(2H,m), 4.10(2H,m), 5.27(1H,m), 6.62(1H,s), 6.76(1H,m), 7.15–7.68(18H,m), 8.29(1H,d), 8.46(2H,bs)

EXAMPLE 207

N-[(S)-1-indanyl]-4-[N'-[2-[3-(aminomethyl)phenoxy]-4-chlorophenyl]-N'-(4-phenylbenzoyl)]aminobutylamide hydrochloride (1) A mixture of 4-[N-[2-[3-(tert-butoxycarbonylaminomethyl)phenoxy]-4-chlorophenyl]-N-(4-phenylbenzoyl)]aminobutyric acid (0.5 g, 0.8 mmols), (S)-1-aminoindane (0.23 g, 1.7 mmols), 1-ethyl-3-(3-dimethylaminopropyl)carbodiimide hydrochloride (WSC) (0.31 g, 1.6 mmols), 1-hydroxybenzotriazole monohydrate (HOBt) (0.22 g, 1.6 mmols) and N,N-dimethylformamide (10 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[(S)-1-indanyl]-4-[N'-[2-[3-(tert-butoxycarbonylaminomethyl)phenoxy]-4-chlorophenyl]-N'-(4-phenylbenzoyl)]aminobutylamide (0.54 g, 91%).

$[\alpha]_D^{24}$ −38° (C=0.5, MeOH)

Elemental Analysis for $C_{44}H_{44}N_3O_5Cl$:

Calcd.: C, 72.36; H, 6.07; N, 5.75

Found: C, 72.10; H, 6.23; N, 5.57

$^1$H-NMR (CDCl$_3$) δ: 1.42(9H,s), 1.88(1H,m), 2.00(2H,m), 2.37(2H,m), 2.56(1H,m), 2.88(2H,m), 3.84(1H,m), 4.10–4.19(3H,m), 4.98(1H,bs), 5.50(1H,m), 6.48(1H,bs), 6.56–6.62(3H,m), 7.04(2H,m), 7.18–7.58(15H,m)

(2) A 4 N hydrochloric acid/ethyl acetate solution (2 ml) was added to an ethyl acetate (2 ml) solution of N-[(S)-1-indanyl]-4-[N'-[2-[3-(tert-butoxycarbonylaminomethyl)phenoxy]-4-chlorophenyl]-N'-(4-phenylbenzoyl)]aminobutylamide (0.22 g, 0.30 mmols), and stirred at room temperature for 1 hour. The reaction mixture was concentrated under reduced pressure. The solid precipitated was taken out through filtration, and washed with ethyl ether to give an amorphous solid of N-[(S)-1-indanyl]-4-[N'-[2-[3-(aminomethyl)phenoxy]-4-chlorophenyl]-N'-(4-phenylbenzoyl)]aminobutylamide hydrochloride (0.19 g, 97%).

$[\alpha]_D^{24}$ −51° (C=0.5, MeOH)

Elemental Analysis for $C_{39}H_{37}N_3O_3Cl_2.1/2H_2O$:

Calcd.: C, 69.33; H, 5.67; N, 6.22

Found: C, 69.34; H, 5.75; N, 6.21

$^1$H-NMR (DMSO-$d_6$) δ: 1.70–1.91(3H,m), 2.24(2H,m), 2.31(1H,m), 2.82(2H,m), 3.79(2H,m), 4.10(2H,m), 5.27(1H,m), 6.62(1H,s), 6.76(1H,m), 7.15–7.68(18H,m), 8.29(1H,d), 8.46(2H,bs)

EXAMPLE 208

N-[(R)-1-phenylethyl]-4-[N'-[2-[3-(aminomethyl)phenoxy]-4-chlorophenyl]-N'-(4-phenylbenzoyl)]aminobutylamide hydrochloride (1) A mixture of 4-[N-[2-[3-(tert-butoxycarbonylaminomethyl)phenoxy]-4-chlorophenyl]-N-(4-phenylbenzoyl)]aminobutyric acid (0.6 g, 0.97 mmols), (R)-1-phenylethylamine (0.25 g, 2.1 mmols), 1-ethyl-3-(3-dimethylaminopropyl)carbodiimide hydrochloride (WSC) (0.38 g, 2.0 mmols), 1-hydroxybenzotriazole monohydrate (HOBt) (0.26 g, 2.0 mmols) and N,N-dimethylformamide (10 ml) was stirred at room temperature for 6 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[(R)-1-phenylethyl]-4-[N'-[2-[3-(tert-butoxycarbonylaminomethyl)phenoxy]-4-chlorophenyl]-N'-(4-phenylbenzoyl)]aminobutylamide (0.68 g, 97%).

$[\alpha]_D^{24}$ +33° (C=0.5, MeOH)

Elemental Analysis for $C_{43}H_{44}N_3O_5Cl \cdot 1/2H_2O$:

Calcd.: C, 71.01; H, 6.24; N, 5.78

Found: C, 71.08; H, 6.15; N, 5.59

$^1$H-NMR (CDCl$_3$) δ: 1.43(9H,s), 1.52(3H,m), 1.92(2H, m), 2.33(2H,m), 3.80(1H,m), 4.10–4.17(3H,m), 4.93(1H, bs), 5.15(1H,m), 6.44(1H,m), 6.55–6.63(2H,m), 7.00–7.10 (3H,m), 7.15–7.48(14H,m), 7.54–7.59(2H,m)

(2) A 4 N hydrochloric acid/ethyl acetate solution (2 ml) was added to an ethyl acetate (2 ml) solution of N-[(R)-1-phenylethyl]-4-[N'-[2-[3-(tert-butoxycarbonylaminomethyl)phenoxy]-4-chlorophenyl]-N'-(4-phenylbenzoyl)]aminobutylamide (0.31 g, 0.43 mmols), and stirred at room temperature for 1 hour. The reaction mixture was concentrated under reduced pressure. The solid precipitated was taken out through filtration, and washed with ethyl ether to give an amorphous solid of N-[(R)-1-phenylethyl]-4-[N'-[2-[3-(aminomethyl)phenoxy]-4-chlorophenyl]-N'-(4-phenylbenzoyl)]aminobutylamide hydrochloride (0.24 g, 84%).

$[\alpha]_D^{24}$ +35° (C=0.5, MeOH)

Elemental Analysis for $C_{38}H_{37}N_3O_3Cl_2 \cdot 1/2H_2O$:

Calcd.: C, 68.77; H, 5.77; N, 6.33

Found: C, 68.48; H, 5.89; N, 6.31

$^1$H-NMR (DMSO-d$_6$) δ: 1.32(3H,d,J=7.0 Hz), 1.79(2H, m), 2.22(2H,m), 3.74(2H,m), 4.01(2H,m), 4.90(1H,m), 6.59 (1H,s), 6.69(1H,s), 7.12–7.68(19H,m), 8.40(3H,bs)

EXAMPLE 209

N-[(S)-1-phenylethyl]-4-[N'-[2-[3-(aminomethyl) phenoxy]-4-chlorophenyl]-N'-(4-phenylbenzoyl)] aminobutylamide hydrochloride (1) A mixture of 4-[N-[2-[3-(tert-butoxycarbonylaminomethyl)phenoxy]-4-chlorophenyl]-N-(4-phenylbenzoyl)]aminobutyric acid (0.45 g, 0.73 mmols), (S)-1-phenylethylamine (0.18 g, 1.5 mmols), 1-ethyl-3-(3-dimethylaminopropyl)carbodiimide hydrochloride (WSC) (0.29 g, 1.5 mmols), 1-hydroxybenzotriazole monohydrate (HOBt) (0.20 g, 1.5 mmols) and N,N-dimethylformamide (8 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[(S)-1-phenylethyl]-4-[N'-[2-[3-(tert-butoxycarbonylaminomethyl)phenoxy]-4-chlorophenyl]-N'-(4-phenylbenzoyl)]aminobutylamide (0.50 g, 94%).

$[\alpha]_D^{24}$ −27° (C=0.5, MeOH)

Elemental Analysis for $C_{43}H_{44}N_3O_5Cl$:

Calcd.: C, 71.90; H, 6.17; N, 5.85

Found: C, 71.70; H, 6.42; N, 5.69

$^1$H-NMR (CDCl$_3$) δ: 1.43(9H,s), 1.52(3H,m), 1.92(2H, m), 2.33(2H,m), 3.80(1H,m), 4.10–4.19(3H,m), 4.95(1H, bs), 5.15(1H,m), 6.44(1H,m), 6.55–6.63(2H,m), 7.00–7.10 (3H,m), 7.15–7.48(14H,m), 7.54–7.59(2H,m)

(2) A 4 N hydrochloric acid/ethyl acetate solution (2 ml) was added to an ethyl acetate (2 ml) solution of N-[(S)-1-phenylethyl]-4-[N'-[2-[3-(tert-butoxycarbonylaminomethyl) phenoxy]-4-chlorophenyl]-N'-(4-phenylbenzoyl)]aminobutylamide (0.31 g, 0.43 mmols), and stirred at room temperature for 1 hour. The reaction mixture was concentrated under reduced pressure. The solid precipitated was taken out through filtration, and washed with ethyl ether to give an amorphous solid of N-[(S)-1-phenylethyl]-4-[N'-[2-[3-(aminomethyl)phenoxy]-4-chlorophenyl]-N'-(4-phenylbenzoyl)]aminobutylamide hydrochloride (0.24 g, 84%).

$[\alpha]_D^{24}$ −34° (C=0.5, MeOH)

Elemental Analysis for $C_{38}H_{37}N_3O_3Cl_2$:

Calcd.: C, 69.72; H, 5.70; N, 6.42

Found: C, 69.33; H, 6.03; N, 6.23

$^1$H-NMR (DMSO-d$_6$) δ: 1.32(3H,d,J=7.0 Hz), 1.80(2H, m), 2.23(2H,m), 3.79(2H,m), 4.01(2H,m), 4.91(1H,m), 6.60 (1H,s), 6.74(1H,m), 7.14–7.69(19H,m), 8.50(3H,bs)

EXAMPLE 210

N-(2-fluorobenzyl)-4-[N'-[2-[3-(aminomethyl)phenoxy]-4-chlorophenyl]-N'-(5-bromo-2-furancarbonyl)]aminobutylamide hydrochloride (1) A mixture of ethyl 4-[N-[2-[3-(tert-butoxycarbonylaminomethyl)phenoxy]-4-chlorophenyl]]aminobutyrate (1.5 g, 3.2 mmols), 5-bromofurancarbonyl chloride (0.82 g, 3.9 mmols) and N,N-dimethylacetamide (15 ml) was stirred at room temperature for 5 hours. The reaction mixture was poured into water, and extracted with ethyl acetate. The extract was washed with brine, and then dried with anhydrous magnesium sulfate. This was concentrated under reduced pressure, and the residue was purified through silica gel column chromatography to give an amorphous solid of ethyl 4-[N-(5-bromo-2-furancarbonyl)-N-[2-[3-(tert-butoxycarbonylaminomethyl)phenoxy]-4-chlorophenyl]]aminobutyrate (1.7 g, 82%).

Elemental Analysis for $C_{29}H_{32}N_2O_7BrCl$:

Calcd.: C, 54.77; H, 5.07; N, 4.41

Found: C, 54.68; H, 5.04; N, 4.49

$^1$H-NMR (CDCl$_3$) δ: 1.22(3H,t,J=7.0 Hz), 1.45(9H,s), 1.96(2H,m), 2.43(2H,m), 3.86(2H,m), 4.10(2H,q,J=7.0 Hz), 4.28(2H,d,J=5.6 Hz), 4.96(1H,bs), 6.28(2H,m), 6.74–6.80 (3H,m), 7.10(2H,m), 7.21–7.34(2H,m)

(2) Aqueous 1 N sodium hydroxide solution (10 ml, 10 mmols) was added to a solution of ethyl 4-[N-(5-bromo-2-furancarbonyl)-N-[2-[3-(tert-butoxycarbonylaminomethyl) phenoxy]-4-chlorophenyl]]aminobutyrate (1.5 g, 2.3 mmols) in tetrahydrofuran (20 ml) and ethanol (20 ml). The resulting mixture was stirred at 60° C. for 1 hour. This was poured into water, acidified wit potassium hydrogensulfate added thereto, and extracted with ethyl acetate. The extract was washed with water, then dried with anhydrous magnesium sulfate, and concentrated under reduced pressure. A mixture of the resulting residue with 2-fluorobenzylamine (0.45 g, 3.6 mmols), 1-ethyl-3-(3-dimethylaminopropyl)carbodiimide hydrochloride (WSC) (0.89 g, 4.6 mmols), 1-hydroxybenzotriazole monohydrate (HOBt) (0.63 g, 4.6 mmols) and N,N-dimethylformamide (6 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-(5-bromo-2-furancarbonyl)-N'-[2-[3-(tert-butoxycarbonylaminomethyl)phenoxy]-4-chlorophenyl]]aminobutylamide (1.2 g, 74%).

Elemental Analysis for $C_{34}H_{34}N_3O_6BrClF$:

Calcd.: C, 57.11; H, 4.79; N, 5.88

Found: C, 57.06; H, 4.98; N, 6.02

¹H-NMR (CDCl₃) δ: 1.44(9H,s), 1.94(2H,m), 2.34(2H, m), 3.82(1H,m), 3.93(1H,m), 4.25(2H,d,J=5.6 Hz), 4.48(2H, d,J=5.8 Hz), 5.01(1H,bs), 6.25(2H,m), 6.69–6.78(4H,m), 6.98–7.36(8H,m)

(3) A 4 N hydrochloric acid/ethyl acetate solution (2 ml) was added to an ethyl acetate (2 ml) solution of N-(2-fluorobenzyl)-4-[N'-(5-bromo-2-furancarbonyl)-N'-[2-[3-(tert-butoxycarbonylaminomethyl)phenoxy]-4-chlorophenyl]]aminobutylamide (0.18 g, 0.25 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-(5-bromo-2-furancarbonyl)]aminobutylamide hydrochloride (0.11 g, 68%).

Elemental Analysis for $C_{29}H_{27}N_3O_4BrCl_2F$:
Calcd.: C, 53.48; H, 4.18; N, 6.45
Found: C, 53.65; H, 4.46; N, 6.30
¹H-NMR (DMSO-d₆) δ: 1.79(2H,m), 2.23(2H,m), 3.68 (1H,m), 3.79(1H,m), 4.01(2H,m), 4.28(2H,d,J=5.0 Hz), 6.27 (1H,bs), 6.62(1H,d,J=3.6 Hz), 6.80(1H,d), 6.85(1H,d,J=3.6 Hz), 7.11–7.59(9H,m), 8.42(3H,m)

EXAMPLE 211

N-(2-fluorobenzyl)-4-[N'-[2-[3-(aminomethyl)phenoxy]-4-chlorophenyl]-N'-(5-phenyl-2-furancarbonyl)]aminobutylamide hydrochloride (1) A mixture of N-(2-fluorobenzyl)-4-[N'-(5-bromo-2-furancarbonyl)-N'-[2-[3-(tert-butoxycarbonylaminomethyl)phenoxy]-4-chlorophenyl]]aminobutylamide (0.49 g, 0.68 mmols), phenylboronic acid (0.13 g, 1.0 mmols), sodium carbonate (0.24 g, 1.7 mmols), toluene (20 ml), ethanol (5 ml) and water (5 ml) was stirred in an argon atmosphere at room temperature for 10 minutes. Tetrakis(triphenylphosphine)palladium(0) (39 mg, 0.034 mmols) was added thereto, and heated under reflux for 12 hours. The reaction mixture was cooled, then poured into water, and extracted with ethyl acetate. The extract was washed with water and brine, then dried with anhydrous magnesium sulfate, and concentrated under reduced pressure. The residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-(5-phenyl-2-furancarbonyl)]aminobutylamide (0.43 g, 89%).

Elemental Analysis for $C_{40}H_{39}N_3O_6ClF$:
Calcd.: C, 67.46; H, 5.52; N, 5.90
Found: C, 67.25; H, 5.47; N, 5.86
¹H-NMR (CDCl₃) δ: 1.42(9H,s), 1.97(2H,m), 2.38(2H, m), 3.85(1H,m), 4.04(1H,m), 4.06(2H,d,J=5.8 Hz), 4.50(2H, d,J=5.8 Hz), 4.80(1H,bs), 6.60–6.66(3H,m), 6.82(2H,m), 6.98–7.38(14H,m)

(2) A 4 N hydrochloric acid/ethyl acetate solution (2 ml) was added to an ethyl acetate (2 ml) solution of N-(2-fluorobenzyl)-4-[N'-[2-[3-(tert-butoxycarbonylaminomethyl)phenoxy]-4-chlorophenyl]-N'-(5-phenyl-2-furancarbonyl)]aminobutylamide (0.28 g, 0.39 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-(5-phenyl-2-furancarbonyl)]aminobutylamide hydrochloride (0.24 g, 95%).

Elemental Analysis for $C_{35}H_{32}N_3O_4Cl_2F$:
Calcd.: C, 64.82; H, 4.97; N, 6.48
Found: C, 64.81; H, 5.08; N, 6.25
¹H-NMR (DMSO-d₆) δ: 1.87(2H,m), 2.25(2H,m), 3.70 (1H,m), 3.91(3H,m), 4.28(2H,d,J=5.6 Hz), 6.72(1H,m), 6,87 (2H,m), 7.01–7.42(14H,m), 7.65(1H,d), 8.42(3H,m)

EXAMPLE 212

N-(2-fluorobenzyl)-4-[N'-[2-[3-(aminomethyl)phenoxy]-4-chlorophenyl]-N'-[(2-methoxyphenyl)-2-furancarbonyl]]aminobutylamide hydrochloride (1) A mixture of N-(2-fluorobenzyl)-4-[N'-(5-bromo-2-furancarbonyl)-N'-[2-[3-(tert-butoxycarbonylaminomethyl)phenoxy]-4-chlorophenyl]]aminobutylamide (0.42 g, 0.59 mmols), 2-methoxyphenylboronic acid (0.13 g, 0.88 mmol), sodium carbonate (0.2 g, 1.5 mmols), toluene (20 ml), ethanol (5 ml) and water (5 ml) was stirred in an argon atmosphere at room temperature for 10 minutes. Tetrakis (triphenylphosphine)palladium(0) (34 mg, 0.029 mmols) was added thereto, and heated under reflux for 12 hours. The reaction mixture was cooled, poured into water, and extracted with ethyl acetate. The extract was washed with water and brine, then dried with anhydrous magnesium sulfate, and concentrated under reduced pressure. The residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[(2-methoxyphenyl)-2-furancarbonyl]]aminobutylamide (0.39 g, 89%).

Elemental Analysis for $C_{41}H_{41}N_3O_7ClF$:
Calcd.: C, 66.35; H, 5.57; N, 5.66
Found: C, 66.05; H, 5.47; N, 5.52
¹H-NMR (CDCl₃) δ: 1.42(9H,s), 1.97(2H,m), 2.38(2H, m), 3.84(1H,m), 3.92(3H,s), 4.02(2H,d,J=5.2 Hz), 4.03(1H, m), 4.50(2H,d,J=5.6 Hz), 4.82(1H,bs), 6.49(1H,s), 6.66(1H, m), 6.78–7.37(16H,m)

(2) A 4 N hydrochloric acid/ethyl acetate solution (2 ml) was added to an ethyl acetate (2 ml) solution of N-(2-fluorobenzyl)-4-[N'-[2-[3-(tert-butoxycarbonylaminomethyl)phenoxy]-4-chlorophenyl]-N'-[(2-methoxyphenyl)-2-furancarbonyl]]aminobutylamide (0.25 g, 0.34 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(2-methoxyphenyl)-2-furancarbonyl]]aminobutylamide hydrochloride (0.19 g, 82%).

Elemental Analysis for $C_{36}H_{34}N_3O_5Cl_2F$:
Calcd.: C, 63.72; H, 5.05; N, 6.19
Found: C, 63.69; H, 5.23; N, 6.20
¹H-NMR (DMSO-d₆) δ: 1.83(2H,m), 2.26(2H,m), 3.70 (1H,m), 3.84(3H,m), 3.90(3H,s), 4.28(2H,d,J=4.4 Hz), 6.70 (1H,m), 6.82–6.93(5H,m), 7.08–7.42(10H,m), 7.64(1H,d), 8.45(3H,m)

EXAMPLE 213

N-(2-fluorobenzyl)-4-[N'-[(4-acetylaminophenyl)acetyl]-N'-[2-[3-(aminomethyl)phenoxy]-4-chlorophenyl]]aminobutylamide hydrochloride (1) A mixture of ethyl 4-amionophenylacetate (5.0 g, 28 mmols), acetyl chloride (2.6 g, 34 mmols) and N,N-dimethylacetamide (30 ml) was stirred at room temperature for 30 minutes. The reaction mixture was cooled, poured into water, and extracted with ethyl acetate. The extract was washed with water and brine, and then dried with anhydrous magnesium sulfate. This was concentrated under reduced pressure. To a solution of the residue in tetrahydrofuran (100 ml) and ethanol (100 ml), added was aqueous 1 N sodium hydroxide solution (90 ml, 90 mmols). The resulting mixture was stirred at 60° C. for 1 hour. Water was added to this, which was then acidified with potassium hydrogensulfate added thereto, and extracted with ethyl acetate. The extract was washed with water, and then dried with anhydrous magnesium sulfate. This was concentrated under reduced pressure, and the residue was crystallized from hexane/ethyl acetate to give a solid of 4-acetamidophenylacetic acid (3.8 g, 71%).

$^1$H-NMR (DMSO-$d_6$) δ: 2.03(3H,s), 3.49(2H,s), 7.71(2H, d,J=8.6 Hz), 7.51(2H,d,J=8.6 Hz), 9.91(1H,s)

A tetrahydrofuran (30 ml) solution of 4-acetamidophenylacetic acid (1.0 g, 5.2 mmols), oxalyl chloride (1.3 g, 10 mmols) and N,N-dimethylformamide (0.5 ml) was stirred at room temperature for 1 hour. The reaction mixture was concentrated under reduced pressure, to which were added ethyl 4-[N-[2-[3-(tert-butoxycarbonylaminomethyl)phenoxy]-4-chlorophenyl]]aminobutyrate (1.2 g, 2.6 mmols) and N,N-dimethylacetamide (40 ml). The resulting mixture was stirred at room temperature for 24 hours. This was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N'-[(4-acetylaminophenyl)acetyl]-N-[2-[3-(tert-butoxycarbonylaminomethyl)phenoxy]-4-chlorophenyl]]aminobutyrate (1.1 g, 67%).

Elemental Analysis for $C_{34}H_{40}N_3O_7Cl$:
Calcd.: C, 63.99; H, 6.32; N, 6.58
Found: C, 63.80; H, 6.32; N, 6.63

$^1$H-NMR (CDCl$_3$) δ: 1.20(3H,t,J=7.2 Hz), 1.46(9H,s), 1.84(2H,m), 2.34(2H,m), 2.16(3H,s), 3.48(2H,s), 3.51(1H, m), 3.91(1H,m), 4.07(2H,q,J=7.2 Hz), 4.27(2H,m), 5.20(1H, bs), 6.70(2H,m), 6.82–7.18(6H,m), 7.27–7.38(3H,m), 8.00 (1H,bs)

(2) Aqueous 1 N sodium hydroxide solution (8 ml, 8 mmols) was added to a solution of ethyl 4-[N'-[(4-acetylaminophenyl)acetyl]-N-[2-[3-(tert-butoxycarbonylaminomethyl)phenoxy]-4-chlorophenyl]]aminobutyrate (0.91 g, 1.4 mmols) in tetrahydrofuran (10 ml) and ethanol (10 ml). The resulting mixture was stirred at 60° C. for 1 hour. Water was added to this, which was then acidified with potassium hydrogensulfate added thereto, and extracted with ethyl acetate. The extract was washed with water, then dried with anhydrous magnesium sulfate, and concentrated under reduced pressure. A mixture of the residue with 2-fluorobenzylamine (0.30 g, 2.4 mmols), 1-ethyl-3-(3-dimethylaminopropyl)carbodiimide hydrochloride (WSC) (0.55 g, 2.9 mmols), 1-hydroxybenzotriazole monohydrate (HOBt) (0.39 g, 2.9 mmols) and N,N-dimethylformamide (10 ml) was stirred at room temperature for 24 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[(4-acetylaminophenyl) acetyl]-N'-[2-[3-(tert-butoxycarbonylaminomethyl)phenoxy]-4-chlorophenyl]]aminobutylamide (0.88 g, 86%).

Elemental Analysis for $C_{39}H_{42}N_4O_6ClF$:
Calcd.: C, 65.31; H, 5.90; N, 7.81
Found: C, 65.21; H, 5.82; N, 7.86

$^1$H-NMR (CDCl$_3$) δ: 1.45(9H,s), 1.83(2H,m), 2.15(3H,s), 2.22(2H,m), 3.46(2H,s), 3.63(1H,m), 3.78(1H,m), 4.25(2H, m), 4.44(2H,d,J=6.0 Hz), 5.26(1H,bs), 6.68–7.38(16H,m), 7.99(1H,bs)

(3) A 4 N hydrochloric acid/ethyl acetate solution (4 ml) was added to an ethyl acetate (4 ml) solution of N-(2-fluorobenzyl)-4-[N'-[(4-acetylaminophenyl)acetyl]-N'-[2-[3-(tert-butoxycarbonylaminomethyl)phenoxy]-4-chlorophenyl]]aminobutylamide (0.59 g, 0.82 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[(4-acetylaminophenyl)acetyl]-N'-[2-[3-(aminomethyl) phenoxy]-4-chlorophenyl]]aminobutylamide hydrochloride (0.53 g, 99%).

Elemental Analysis for $C_{34}H_{35}N_4O_4Cl_2F·1/4H_2O$:
Calcd.: C, 62.05; H, 5.44; N, 8.51
Found: C, 62.07; H, 5.55; N, 8.26

$^1$H-NMR (DMSO-$d_6$) δ: 1.70(2H,m), 2.02(3H,s), 2.19 (2H,m), 3.39(2H,s), 3.76(1H,m), 4.05(3H,m), 4.28(2H,m), 6.83–7.45(15H,m), 8.41(1H,bs), 8.54(2H,bs), 10.05(1H,bs)

EXAMPLE 214

N-(2-fluorobenzyl)-4-[N'-[2-[3-(aminomethyl)phenoxy]-4-chlorophenyl]-N'-[4-(benzenesulfonylamino)benzoyl]]aminobutylamide hydrochloride (1) A mixture of N-(2-fluorobenzyl)-4-[N'-[2-[3-(tert-butoxycarbonylaminomethyl)phenoxy]-4-chlorophenyl]]aminobutylamide (1.1 g, 2.0 mmols), 4-nitrobenzoyl chloride (0.49 g, 2.6 mmols) and N,N-dimethylacetamide (20 ml) was stirred at room temperature for 1 hour. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[4-(nitrobenzoyl)] aminobutylamide (1.3 g, 89%).

Elemental Analysis for $C_{36}H_{36}N_4O_7ClF·1/2H_2O$:
Calcd.: C, 61.76; H, 5.33; N, 8.00
Found: C, 62.08; H, 5.48; N, 7.90

$^1$H-NMR (CDCl$_3$) δ: 1.43(9H,s), 1.98(2H,m), 2.35(2H, m), 3.86(1H,m), 4.01(1H,m), 4.24(2H,d,J=6.2 Hz), 4.48(2H, d,J=5.8 Hz), 5.14(1H,bs), 6.98–7.35(8H,m), 7.51(2H,d, J=8.8 Hz), 8.06(2H,d,J=8.8 Hz)

(2) 5% carbon-palladium (0.21 g) was added to an ethyl acetate (15 ml) solution of N-(2-fluorobenzyl)-4-[N'-[2-[3-(tert-butoxycarbonylaminomethyl)phenoxy]-4-chlorophenyl]-N'-[4-(nitrobenzoyl)]aminobutylamide (0.7 g, 1.0 mmol). The resulting mixture was hydrogenated at room temperature under atmospheric pressure for 1 hour. The catalyst was removed through filtration, and the filtrate was concentrated under reduced pressure. The residue was dissolved in N,N-dimethylacetamide (10 ml), to which was added benzenesulfonyl chloride (0.45 g, 2.6 mmols). The resulting mixture was stirred at room temperature for 4 hours, then poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-(2-fluorobenzyl)-4-[N'-[4-(benzenesulfonylamino)benzoyl]-N'-[2-[3-(tert-butoxycarbonylaminomethyl)phenoxy]-4-chlorophenyl]]aminobutylamide (0.57 g, 70%).

Elemental Analysis for $C_{42}H_{42}N_4O_7ClFS \cdot 1/2H_2O$:
Calcd.: C, 62.25; H, 5.35; N, 6.91
Found: C, 62.37; H, 5.25; N, 6.70
$^1$H-NMR (CDCl$_3$) δ: 1.45(9H,s), 1.95(2H,m), 2.36(2H,m), 3.69(1H,m), 4.12(3H,m), 4.49(2H,d,J=5.4 Hz), 5.20(1H,bs), 5.92(1H,bs), 6.50–6.59(2H,m), 6.89–7.53(16H,m), 7.71(2H,d), 8.09(1H,bs)

(3) A 4 N hydrochloric acid/ethyl acetate solution (2 ml) was added to an ethyl acetate (2 ml) solution of N-(2-fluorobenzyl)-4-[N'-[2-[3-(tert-butoxycarbonylaminomethyl)phenoxy]-4-chlorophenyl-N'-[4-(benzenesulfonylamino)benzoyl]]aminobutylamide (0.33 g, 0.41 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[4-(benzenesulfonylamino)benzoyl]]aminobutylamide hydrochloride (0.30 g, 99%).

Elemental Analysis for $C_{37}H_{35}N_4O_5Cl_2FS \cdot 1/2H_2O$:
Calcd.: C, 59.52; H, 4.86; N, 7.50
Found: C, 59.36; H, 5.09; N, 7.20
$^1$H-NMR (DMSO-d$_6$) δ: 1.76(2H,m), 2.21(2H,m), 3.67(2H,m), 3.99(2H,m), 4.27(2H,d,J=5.6 Hz), 6.51(2H,m), 6.95–7.75(18H,m), 8.47(3H,m), 10.60(1H,s)

EXAMPLE 215

N-(1,2,3,4-tetrahydronaphthalen-1-yl)-4-[N'-[2-[3-(aminomethyl)phenoxy]-4-chlorophenyl]-N'-(4-phenylbenzoyl)]aminobutylamide hydrochloride (1) A mixture of 4-[N-[2-[3-(tert-butoxycarbonylaminomethyl)phenoxy]-4-chlorophenyl-N-(4-phenylbenzoyl)]aminobutyric acid (0.5 g, 0.81 mmols), 1,2,3,4-tetrahydro-1-naphthylamine hydrochloride (0.22 g, 1.2 mmols), 1-ethyl-3-(3-dimethylaminopropyl)carbodiimide hydrochloride (WSC) (0.32 g, 1.6 mmols), 1-hydroxybenzotriazole monohydrate (HOBt) (0.22 g, 1.6 mmols), triethylamine (0.15 g, 1.5 mmols) and N,N-dimethylformamide (8 ml) was stirred at room temperature for 6 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(1,2,3,4-tetrahydronaphthalen-1-yl)-4-[N'-[2-[3-(tert-butoxycarbonylaminomethyl)phenoxy]-4-chlorophenyl]-N'-(4-phenylbenzoyl)]aminobutylamide (0.58 g, 96%).

Elemental Analysis for $C_{45}H_{46}N_3O_5Cl \cdot 1/2H_2O$:
Calcd.: C, 71.75; H, 6.29; N, 5.58
Found: C, 71.70; H, 6.31; N, 5.59
$^1$H-NMR (CDCl$_3$) δ: 1.42(9H,s), 1.83(1H,m), 2.00(2H,m), 2.36(2H,m), 2.76(2H,m), 3.81(1H,m), 4.07(1H,m), 4.19(2H,m), 4.99(1H,bs), 5.22(1H,m), 6.48–6.63(4H,m), 7.00–7.58(17H,m)

(2) A 4 N hydrochloric acid/ethyl acetate solution (3 ml) was added to an ethyl acetate (3 ml) solution of N-(1,2,3,4-tetrahydronaphthalen-1-yl)-4-[N'-[2-[3-(tert-butoxycarbonylaminomethyl)phenoxy]-4-chlorophenyl]-N'-(4-phenylbenzoyl)]aminobutylamide (0.30 g, 0.41 mmols), and stirred at room temperature for 1 hour. The reaction mixture was concentrated under reduced pressure. The solid precipitated was taken out through filtration, and washed with ethyl ether to give an amorphous solid of N-(1,2,3,4-tetrahydronaphthalen-1-yl)-4-[N'-[2-[3-(aminomethyl)phenoxy]-4-chlorophenyl]-N'-(4-phenylbenzoyl)]aminobutylamide hydrochloride (0.26 g, 94%).

Elemental Analysis for $C_{40}H_{39}N_3O_3Cl_2 \cdot 1/2H_2O$:
Calcd.: C, 69.66; H, 5.85; N, 6.09
Found: C, 69.32; H, 5.75; N, 5.98
$^1$H-NMR (DMSO-d$_6$) δ: 1.68(2H,m), 1.84(4H,m), 2.24(2H,m), 2.73(2H,m), 3.80(2H,m), 4.01(2H,m), 4.96(1H,m), 6.62(1H,s), 6.77(1H,m), 7.10–7.68(18H,m), 8.28(1H,d), 8.44(2H,bs)

EXAMPLE 216

N-[[3-(aminomethyl)phenoxy]-4-chlorophenyl]-N-[2-[[[(2-fluorobenzyl)amino]carbonyl]amino]ethyl]-9H-fluorene-2-carboxamide hydrochloride (1) A mixture of ethyl 3-[N-[2-[3-(tert-butoxycarbonylaminomethyl)phenoxy]-4-chlorophenyl]]aminopropionate (1.8 g, 4.1 mmols), 9H-fluorene-2-carbonyl chloride (1.2 g, 5.3 mmols) and N,N-dimethylacetamide (20 ml) was stirred at room temperature for 4 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 3-[N-[2-[3-(tert-butoxycarbonylaminomethyl)phenoxy]-4-chlorophenyl]-N-(9H-fluorene-2-carbonyl)]aminopropionate (1.8 g, 68%).

Elemental Analysis for $C_{37}H_{37}N_2O_6Cl \cdot 1/2H_2O$:
Calcd.: C, 68.35; H, 5.89; N, 4.31
Found: C, 68.62; H, 6.13; N, 4.15
$^1$H-NMR (CDCl$_3$) δ: 1.25(3H,t,J=7.0 Hz), 1.44(9H,s), 2.73(1H,m), 2.85(1H,m), 3.71(2H,m), 4.03–4.17(5H,m), 4.23(1H,m), 4.71(1H,bs), 6.52(3H,m), 6.95–7.76(11H,m)

(2) Aqueous 1 N sodium hydroxide solution (12 ml, 12 mmols) was added to a solution of ethyl 3-[N-[2-[3-(tert-butoxycarbonylaminomethyl)phenoxy]-4-chlorophenyl]-N-(9H-fluorene-2-carbonyl)]aminopropionate (1.6 g, 2.4 mmols) in tetrahydrofuran (30 ml) and ethanol (30 ml). The resulting mixture was stirred at 60° C. for 1 hour. The reaction mixture was poured into water, then acidified with potassium hydrogensulfate added thereto, and extracted with ethyl acetate. The extract was washed with water, then dried with anhydrous magnesium sulfate, and concentrated under reduced pressure. An amorphous solid of 3-[N-[2-[3-(tert-butoxycarbonylaminomethyl)phenoxy]-4-chlorophenyl]-N-(9H-fluorene-2-carbonyl)]aminopropionic acid (1.4 g, 96%) was obtained.

Elemental Analysis for $C_{35}H_{33}N_2O_6Cl \cdot 5/4H_2O$:
Calcd.: C, 66.14; H, 5.63; N, 4.41
Found: C, 66.35; H, 5.64; N, 4.02
$^1$H-NMR (CDCl$_3$) δ: 1.43(9H,s), 2.84(2H,m), 3.73(2H,m), 4.10(3H,m), 4.28(1H,m), 4.80(1H,bs), 6.48–6.55(3H,m), 6.97–7.76(12H,m)

(3) A mixture of 3-[N-[2-[3-(tert-butoxycarbonylaminomethyl)phenoxy]-4-chlorophenyl]-N-(9H-fluorene-2-carbonyl)]aminopropionic acid (0.6 g, 0.98 mmols), diphenylphosphorylazide (DPPA) (0.4 g, 1.5 mmols), triethylamine (0.12 g, 1.2 mmols) and N,N-dimethylformamide (5 ml) was stirred at room temperature for 1 hour. The reaction mixture was poured into water, and extracted with ethyl acetate. The extract was washed with water and brine, and dried with anhydrous magnesium sulfate, and the solvent was evaporated away. Toluene (20 ml) was added to the residue, and the resulting mixture was stirred, while heated under reflux, for 3 hours. Next, 2-fluorobenzylamine (0.39 g, 3.1 mmols) and triethylamine (0.36 g, 3.6 mmols) were added to the reaction mixture, and further refluxed for 2 hours. Then, this was cooled, poured into water, and extracted with ethyl acetate. The extract was washed with water and brine, and dried with anhydrous magnesium sulfate, and the solvent was evaporated away. The residue was purified through silica gel column chromatography to give an amorphous solid of tert-butyl 3-[2-[(4-phenylbenzoyl)[3-[[[(2-fluorobenzyl)amino]carbonyl]amino]propyl]amino]-5-chlorophenoxy]benzylcarbamate (0.4 g, 55%).

Elemental Analysis for $C_{42}H_{40}N_4O_5ClF \cdot 1/2H_2O$:
Calcd.: C, 67.78; H, 5.55; N, 7.53
Found: C, 67.68; H, 5.65; H, 7.31
$^1$H-NMR (CDCl$_3$) δ: 1.41(9H,s), 3.45(1H,m), 3.56(1H, m), 3.70(2H,m), 4.00–4.14(4H,m), 4.36(2H,m), 5.02(1H, m), 5.20(1H,bs), 5.65(1H,bs), 6.53(3H,m), 6.92–7.53(14H, m), 7.75(1H,m)

(4) A 4 N hydrochloric acid/ethyl acetate solution (2 ml) was added to an ethyl acetate (2 ml) solution of tert-butyl 3-[2-[(4-phenylbenzoyl)[3-[[[(2-fluorobenzyl)amino]carbonyl]amino]propyl]amino]-5-chlorophenoxy]benzylcarbamate (0.29 g, 0.39 mmols), and stirred at room temperature for 1 hour. The reaction mixture was concentrated under reduced pressure. The solid precipitated was taken out through filtration, and washed with ethyl ether to give an amorphous solid of N-[[3-(aminomethyl)phenoxy]-4-chlorophenyl]-N-[2-[[[(2-fluorobenzyl)amino]carbonyl]amino]ethyl]-9H-fluorene-2-carboxamide hydrochloride (0.26 g, 100%).

Elemental Analysis for $C_{37}H_{33}N_4O_3Cl_2F \cdot H_2O$:
Calcd.: C, 64.44; H, 5.12; N, 8.12
Found: C, 64.59; H, 5.12; N, 7.89
$^1$H-NMR (DMSO-d$_6$) δ: 3.32(2H,m), 3.58(1H,m), 3.98 (5H,m), 4.26(2H,s), 6.62(1H,bs), 6.77(1H,bs), 7.15–7.37 (12H,m), 7.57–7.91(5H,m), 8.46(3H,bs)

EXAMPLE 217

N-[[3-(aminomethyl)phenoxy]-4-chlorophenyl]-N-[2-[[[2-[(2-fluorophenyl)ethyl]amino]carbonyl]amino]ethyl]-9H-fluorene-2-carboxamide hydrochloride (1) A mixture of 3-[N-[2-[3-(tert-butoxycarbonylaminomethyl)phenoxy]-4-chlorophenyl]-N-(9H-fluorene-2-carbonyl)]aminopropionic acid (0.69 g, 1.1 mmols), diphenylphosphorylazide (DPPA) (0.48 g, 1.8 mmols), triethylamine (0.14 g, 1.4 mmols) and N,N-dimethylformamide (5 ml) was stirred at room temperature for 1 hour. The reaction mixture was poured into water, and extracted with ethyl acetate. The extract was washed with water and brine, and dried with anhydrous magnesium sulfate, and the solvent was evaporated away. Toluene (20 ml) was added to the residue, and the resulting mixture was stirred, while heated under reflux, for 3 hours. Next, 2-fluorophenethylamine (0.40 g, 2.8 mmols) and triethylamine (0.29 g, 2.8 mmols) were added to the reaction mixture, and further refluxed for 2 hours. Then, this was cooled, poured into water, and extracted with ethyl acetate. The extract was washed with water and brine, and dried with anhydrous magnesium sulfate, and the solvent was evaporated away. The residue was purified through silica gel column chromatography to give an amorphous solid of tert-butyl 3-[2-[(4-phenylbenzoyl)[3-[[[2-[(2-fluorophenyl)ethyl]amino]carbonyl]amino]propyl]amino]-5-chlorophenoxy]benzylcarbamate (0.55 g, 65%).

Elemental Analysis for $C_{43}H_{42}N_4O_5ClF \cdot 1/2H_2O$:
Calcd.: C, 68.11; H, 5.72; N, 7.39
Found: C, 68.17; H, 5.68; N, 7.31
$^1$H-NMR (CDCl$_3$) δ: 1.42(9H,s), 2.78(2H,m), 3.36(2H, m), 3.48(2H,m), 3.73(2H,d,J=5.0 Hz), 4.01–4.14(4H,m), 4.81(1H,bs), 5.04(1H,m), 5.45(1H,m), 6.53(3H,m), 6.94–7.42(11H,m), 7.55(3H,m), 7.75(1H,m)

(2) A 4 N hydrochloric acid/ethyl acetate solution (2 ml) was added to an ethyl acetate (2 ml) solution of tert-butyl 3-[2-[(4-phenylbenzoyl)[3-[[[2-[(2-fluorophenyl)ethyl]amino]carbonyl]amino]propyl]amino]-5-chlorophenoxy]benzylcarbamate (0.35 g, 0.46 mmols), and stirred at room temperature for 1 hour. The reaction mixture was concentrated under reduced pressure. The solid precipitated was taken out through filtration, and washed with ethyl ether to give an amorphous solid of N-[[3-(aminomethyl)phenoxy]-4-chlorophenyl]-N-[2-[[[2-[(2-fluorophenyl)ethyl]amino]carbonyl]amino]ethyl]-9H-fluorene-2-carboxamide hydrochloride (0.31 g, 98%).

Elemental Analysis for $C_{38}H_{35}N_4O_3Cl_2F \cdot 2H_2O$:
Calcd.: C, 63.25; H, 5.45; N, 7.76
Found: C, 63.10; H, 5.17; N, 7.53
$^1$H-NMR (DMSO-d$_6$) δ: 2.72(2H,m), 3.23(4H,m), 3.85 (2H,s), 3.98(2H,m), 4.52(2H,m), 6.62(1H,s), 6.77(1H,m), 7.10–7.37(12H,m), 7.60(3H,m), 7.78(1H,d), 7.90(1H,d), 8.46(3H,bs)

EXAMPLE 218

N-(2-trifluoromethylbenzyl)-4-[N'-[2-[3-(aminomethyl)phenoxy]-4-chlorophenyl]-N'-(4-phenylbenzoyl)]aminobutylamide hydrochloride (1) A mixture of 4-[N-[2-[3-(tert-butoxycarbonylaminomethyl)phenoxy]-4-chlorophenyl]-N-(4-phenylbenzoyl)]aminobutyric acid (0.45 g, 0.73 mmols), 2-trifluorobenzylamine (0.27 g, 1.5 mmols), 1-ethyl-3-(3-dimethylaminopropyl)carbodiimide hydrochloride (WSC) (0.29 g, 1.5 mmols), 1-hydroxybenzotriazole monohydrate (HOBt) (0.2 g, 1.5 mmols) and N,N-dimethylformamide (8 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-trifluoromethylbenzyl)-4-[N'-[2-[3-(tert-butoxycarbonylaminomethyl)phenoxy]-4-chlorophenyl]-N'-(4-phenylbenzoyl)]aminobutylamide (0.45 g, 80%).

Elemental Analysis for $C_{43}H_{41}N_3O_5ClF_3$:
Calcd.: C, 66.88; H, 5.35; N, 5.44
Found: C, 66.73; H, 5.37; N, 5.23
$^1$H-NMR (CDCl$_3$) δ: 1.42(9H,s), 1.98(2H,m), 2.41(2H, m), 3.85(1H,m), 4.16(1H,m), 4.20(2H,d,J=5.2 Hz), 4.65(2H, d,J=5.2 Hz), 4.98(1H,bs), 4.57(1H,m), 6.59(2H,d), 6.86(1H, m), 7.01–7.09(2H,m), 7.18–7.66(15H,m)

(2) A 4 N hydrochloric acid/ethyl acetate solution (2 ml) was added to an ethyl acetate (2 ml) solution of N-(2-trifluoromethylbenzyl)-4-[N'-[2-[3-(tert-butoxycarbonylaminomethyl)phenoxy]-4-chlorophenyl]-N'-(4-phenylbenzoyl)]aminobutylamide (0.24 g, 0.31 mmols), and stirred at room temperature for 1 hour. The reaction mixture was concentrated under reduced pressure. The solid precipitated was taken out through filtration, and washed with ethyl ether to give an amorphous solid of N-(2-trifluoromethylbenzyl)-4-[N'-[2-[3-(aminomethyl)phenoxy]-4-chlorophenyl]-N'-(4-phenylbenzoyl)]aminobutylamide hydrochloride (0.21 g, 96%).

Elemental Analysis for $C_{38}H_{34}N_3O_3Cl_2F_3 \cdot 1/2H_2O$:

Calcd.: C, 63.60; H, 4.92; N, 5.86

Found: C, 63.73; H, 4.87; N, 5.60

$^1$H-NMR (DMSO-$d_6$) δ: 1.88(2H,m), 2.34(2H,m), 3.80 (2H,m), 4.01(2H,m), 4.44(2H,m), 6.60(1H,s), 6.73(2H,m), 7.17–7.24(2H,m), 7.38–7.73(15H,m), 8.53(3H,m)

EXAMPLE 219

N-(2-fluorobenzyl)-4-[N'-[2-[3-(aminomethyl)phenoxy]-4-chlorophenyl]-N'-[4-(benzoylamino)benzoyl]]aminobutylamide hydrochloride (1) A mixture of ethyl 4-[N-[2-[3-(tert-butoxycarbonylaminomethyl)phenoxy]-4-chlorophenyl]]aminobutyrate (3.0 g, 6.5 mmols), 4-nitrobenzoyl chloride (1.8 g, 9.8 mmols), 4-dimethylaminopyridine (1.2 g, 9.8 mmols) and tetrahydrofuran (60 ml) was stirred at room temperature for 12 hours. The reaction mixture was concentrated, poured into water, and extracted with ethyl acetate. The extract was washed with brine, and then dried with anhydrous magnesium sulfate. This was concentrated under reduced pressure, and the residue was purified through silica gel column chromatography to give an amorphous solid of ethyl 4-[N-[2-[3-(tert-butoxycarbonylaminomethyl)phenoxy]-4-chlorophenyl]-N-[4-(nitrobenzoyl)]aminobutyrate (1.9 g, 48%).

Elemental Analysis for $C_{31}H_{34}N_3O_8Cl$:

Calcd.: C, 60.83; H, 5.60; N, 6.87

Found: C, 60.78; H, 5.72; N, 6.76

$^1$H-NMR (CDCl$_3$) δ: 1.24(3H,t,J=7.4 Hz), 1.44(9H,s), 1.98(2H,m), 2.45(2H,m), 3.89(1H,m), 3.97(1H,m), 4.12 (12H,q,J=7.4 Hz), 4.27(2H,d,J=6.0 Hz), 5.03(1H,bs), 6.57–6.68(3H,m), 6.97–7.34(4H,m), 7.51(2H,d,J=8.8 Hz), 8.07(2H,d,J=8.8 Hz)

(2) 5% carbon-palladium (0.23 g) was added to an ethyl acetate (50 ml) solution of ethyl 4-[N-[2-[3-(tert-butoxycarbonylaminomethyl)phenoxy]-4-chlorophenyl]-N-[4-(nitrobenzoyl)]aminobutyrate (0.82 g, 1.3 mmol). The resulting mixture was hydrogenated at room temperature under atmospheric pressure for 1 hour. The catalyst was removed through filtration, and the filtrate was concentrated under reduced pressure. The residue was dissolved in tetrahydrofuran (20 ml), to which were added benzoyl chloride (0.4 g, 2.9 mmols) and 4-dimethylaminopyridine (0.33 g, 2.7 mmols). The resulting mixture was stirred at room temperature for 12 hours, then poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N-[4-(benzoylamino)benzoyl)-[N-[2-[3-(tert-butoxycarbonylaminomethyl)phenoxy]-4-chlorophenyl]]aminobutyrate (0.85 g, 91%).

Elemental Analysis for $C_{38}H_{40}N_3O_7Cl$:

Calcd.: C, 66.51; H, 5.88; N, 6.12

Found: C, 66.55; H, 6.18; N, 5.84

$^1$H-NMR (CDCl$_3$) δ: 1.24(3H,t,J=7.0 Hz), 1.42(9H,s), 1.99(2H,m), 2.47(2H,m), 3.71(1H,m), 4.13(3H,m), 4.15(2H,d), 5.23(1H,bs), 5.94(1H,s), 6.51(1H,s), 6.79(1H, m), 7.03(2H,m), 7.25–7.35(4H,m), 7.41–7.54(5H,m), 7.94 (2H,d), 8.71(1H,bs)

(3) Aqueous 1 N sodium hydroxide solution (5 ml, 5 mmols) was added to a solution of ethyl 4-[N-[4-(benzoylamino)benzoyl)-[N-[2-[3-(tert-butoxycarbonylaminomethyl)phenoxy]-4-chlorophenyl]]aminobutyrate (0.73 g, 1.1 mmols) in tetrahydrofuran (10 ml) and ethanol (10 ml). The resulting mixture was stirred at 60° C. for 2 hours. This was poured into water, then acidified with potassium hydrogensulfate added thereto, and extracted with ethyl acetate. The extract was washed with water, then dried with anhydrous magnesium sulfate, and concentrated under reduced pressure to give an amorphous solid (690 mg). A mixture of this amorphous solid (0.4 g, 0.61 mmols) with 2-fluorobenzylamine (0.16 g, 1.3 mmols), 1-ethyl-3-(3-dimethylaminopropyl)carbodiimide hydrochloride (WSC) (0.23 g, 1.2 mmols), 1-hydroxybenzotriazole monohydrate (HOBt) (0.17 g, 1.2 mmols) and N,N-dimethylformamide (6 ml) was stirred at room temperature for 24 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[4-(benzoylamino)benzoyl]]aminobutylamide (0.36 g, 78%).

Elemental Analysis for $C_{43}H_{42}N_4O_6ClF \cdot 1/2H_2O$:

Calcd.: C, 66.70; H, 5.60; N, 7.24

Found: C, 66.81; H, 5.75; N, 6.87

$^1$H-NMR (CDCl$_3$) δ: 1.42(9H,s), 1.94(2H,m), 2.38(2H, m), 3.68(1H,m), 4.13(2H,d,J=4.8 Hz), 4.20(1H,m), 4.51(2H, d,J=5.8 Hz), 5.26(1H,bs), 5.90(1H,s) 6.51(1H,s), 6.72(1H, d), 6.99–7.09(5H,m), 7.19–7.54(11H,m), 7.93(2H,d), 9.10 (1H,bs)

(4) A 4 N hydrochloric acid/ethyl acetate solution (2 ml) was added to an ethyl acetate (2 ml) solution of N-(2-fluorobenzyl)-4-[N'-[2-[3-(tert-butoxycarbonylaminomethyl)phenoxy]-4-chlorophenyl]-N'-[4-(benzoylamino)benzoyl]]aminobutylamide (0.17 g, 0.22 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[4-(benzoylamino)benzoyl]]aminobutylamide hydrochloride (0.14 g, 91%).

Elemental Analysis for $C_{38}H_{35}N_4O_4Cl_2F \cdot 1/2H_2O$:

Calcd.: C, 64.23; H, 5.11; N, 7.88

Found: C, 64.46; H, 5.09; N, 7.88

$^1$H-NMR (DMSO-$d_6$) δ: 1.82(2H,m), 2.25(2H,m), 3.73 (2H,m), 4.03(2H,m), 4.30(2H,m), 6.61(1H,s), 6.80(1H,m), 7.08–7.72(16H,m), 7.97(2H,d), 8.45(3H,m), 10.44(1H,bs)

EXAMPLE 220

N-(2-fluorobenzyl)-4-[N'-[2-[3-(aminomethyl)phenoxy]-4-chlorophenyl]-N'-[4-(methanesulfonylamino)benzoyl]]aminobutylamide hydrochloride (1) 5% carbon-palladium (0.23 g) was added to an ethyl acetate (50 ml) solution of ethyl 4-[N-[2-[3-(tert-butoxycarbonylaminomethyl)phenoxy]-4-chlorophenyl]-N-[4-(nitrobenzoyl)]aminobutyrate (0.82 g, 1.3 mmol). The resulting mixture was hydrogenated at room temperature under atmospheric pressure for 2 hours. The catalyst was removed through filtration, and the filtrate was concentrated under reduced pressure. The residue was dissolved in tetrahydrofuran (20 ml), to which were added methanesulfonyl chloride (0.64 g, 5.8 mmols) and 4-dimethylaminopyridine (0.66 g, 5.4 mmols). The resulting mixture was stirred at room temperature for 12 hours and at 50° C. for 12 hours, then poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N-[2-[3-(tert-butoxycarbonylaminomethyl)phenoxy]-4-chlorophenyl]-N-[4-(methanesulfonylamino)benzoyl]]aminobutyrate (0.50 g, 56%).

Elemental Analysis for $C_{32}H_{38}N_3O_8ClS$:
Calcd.: C, 58.22; H, 5.80; N, 6.36
Found: C, 58.13; H, 6.02; N, 6.12
$^1$H-NMR (CDCl$_3$) δ: 1.24(3H,t,J=7.2 Hz), 1.45(9H,s), 1.97(2H,m), 2.46(2H,m), 2.96(3H,s), 3.70(1H,m), 4.11(2H, q,J=7.2 Hz), 4.14(3H,m), 5.13(1H,bs), 5.99(1H,s), 6.57(1H, s), 6.74(1H,m), 7.02–7.07(4H,m), 7.24–7.32(4H,m), 7.73 (1H,bs)

(2) Aqueous 1 N sodium hydroxide solution (5 ml, 5 mmols) was added to a solution of ethyl 4-[N-[2-[3-(tert-butoxycarbonylaminomethyl)phenoxy]-4-chlorophenyl]-N-[4-(methanesulfonylamino)benzoyl]]aminobutyrate (0.42 g, 0.64 mmols) in tetrahydrofuran (5 ml) and ethanol (5 ml). The resulting mixture was stirred at 60° C. for 1 hour. This was poured into water, then acidified with potassium hydrogensulfate added thereto, and extracted with ethyl acetate. The extract was washed with water, then dried with anhydrous magnesium sulfate, and concentrated under reduced pressure. A mixture of the residue with 2-fluorobenzylamine (0.14 g, 1.1 mmols), 1-ethyl-3-(3-dimethylaminopropyl)carbodiimide hydrochloride (WSC) (0.2 g, 1.1 mmols), 1-hydroxybenzotriazole monohydrate (HOBt) (0.14 g, 1.1 mmols) and N,N-dimethylformamide (5 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-[4-(methanesulfonylamino)benzoyl]]aminobutylamide (0.32 g, 74%).

Elemental Analysis for $C_{37}H_{40}N_4O_7ClFS$:
Calcd.: C, 60.11; H, 5.45; N, 7.58
Found: C, 59.93; H, 5.49; N, 7.76
$^1$H-NMR (CDCl$_3$) δ: 1.44(9H,s), 1.94(2H,m), 2.38(2H, m), 2.95(3H,s), 3.69(1H,m), 4.15(2H,d,J=6.2 Hz), 4.17(1H, m), 4.51(2H,d,J=5.8 Hz), 5.20(1H,bs), 6.03(1H,s), 6.56(1H, s), 6.67(1H,m), 6.90(1H,m), 6.98–7.12(6H,m), 7.20–7.38 (6H,m), 7.97(1H,bs)

(3) A 4 N hydrochloric acid/ethyl acetate solution (2 ml) was added to an ethyl acetate (2 ml) solution of N-(2-fluorobenzyl)-4-[N'-[2-[3-(tert-butoxycarbonylaminomethyl)phenoxy]-4-chlorophenyl]-N'-[4-(methanesulfonylamino)benzoyl]]aminobutylamide (0.20 g, 0.27 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[4-(methanesulfonylamino)benzoyl]]aminobutylamide hydrochloride (0.15 g, 82%).

Elemental Analysis for $C_{32}H_{33}N_4O_5Cl_2FS \cdot 1/2H_2O$:
Calcd.: C, 56.14; H, 5.01; N, 8.18
Found: C, 56.29; H, 5.09; N, 8.07
$^1$H-NMR (DMSO-d$_6$) δ: 1.78(2H,m), 2.23(2H,m), 3.03 (3H,s), 3.75(2H,m), 4.00(2H,m), 4.28(2H,d,J=4.0 Hz), 6.59 (1H,s), 6.72(1H,m), 7.04–7.54(13H,m), 8.46(3H,m), 10.08 (1H,s)

EXAMPLE 221

N-[[3-(aminomethyl)phenoxy]-4-chlorophenyl]-N-[2-[[(2-fluorobenzyl)aminocarbonyl]amino]ethyl]-4-phenylbenzamide hydrochloride (1) A mixture of 3-[N-[2-[3-(tert-butoxycarbonylaminomethyl)phenoxy]-4-chlorophenyl]-N-(4-phenylbenzoyl)]aminopropionic acid (1.1 g, 1.8 mmols), diphenylphosphorylazide (DPPA) (0.68 g, 2.5 mmols), triethylamine (0.24 g, 2.4 mmols) and N,N-dimethylformamide (10 ml) was stirred at room temperature for 1 hour. The reaction mixture was poured into water, and extracted with ethyl acetate. The extract was washed with water and brine, and dried with anhydrous magnesium sulfate, and the solvent was evaporated away. Toluene (20 ml) was added to the residue, and the resulting mixture was stirred, while heated under reflux, for 3 hours. Next, 2-fluorobenzylamine (0.40 g, 3.2 mmols) and triethylamine (0.4 g, 4.0 mmols) were added to the reaction mixture, and further refluxed for 2 hours. Then, this was cooled, poured into water, and extracted with ethyl acetate. The extract was washed with water and brine, and dried with anhydrous magnesium sulfate, and the solvent was evaporated away. The residue was purified through silica gel column chromatography to give an amorphous solid of tert-butyl 3-[2-[(4-phenylbenzoyl)[3-[[(2-fluorobenzyl)aminocarbonyl]amino]propyl]amino]-5-chlorophenoxy]benzylcarbamate (0.88 g, 68%).

Elemental Analysis for $C_{41}H_{40}N_4O_5ClF$:
Calcd.: C, 68.09; H, 5.57; N, 7.75
Found: C, 67.96; H, 5.69; N, 7.67
$^1$H-NMR (CDCl$_3$) δ: 1.41(9H,s), 3.43(1H,m), 3.55(1H, m), 4.01(2H,m), 4.20(2H,d,J=5.2 Hz), 4.35(2H,d,J=5.8 Hz), 5.17(1H,m), 5.22(2H,bs), 5.62(1H,m), 6.50–6.56(2H,m), 6.67(1H,s), 6.93–7.58(17H,m)

(2) A 4 N hydrochloric acid/ethyl acetate solution (3 ml) was added to an ethyl acetate (3 ml) solution of tert-butyl 3-[2-[(4-phenylbenzoyl)[3-[[(2-fluorobenzyl)aminocarbonyl]amino]propyl]amino]-5-chlorophenoxy]benzylcarbamate (0.38 g, 0.53 mmols), and stirred at room temperature for 1 hour. The reaction mixture was concentrated under reduced pressure. The solid precipitated was taken out through filtration, and washed with ethyl ether to give an amorphous solid of N-[[3-(aminomethyl)phenoxy]-4-chlorophenyl]-N-[2-[[(2-fluorobenzyl)aminocarbonyl]amino] ethyl]-4-phenylbenzamide hydrochloride (0.32 g, 92%).

Elemental Analysis for $C_{36}H_{33}N_4O_3Cl_2F \cdot 1/2H_2O$:
Calcd.: C, 64.67; H, 5.13; N, 8.38
Found: C, 64.32; H, 5.16; N, 8.36
$^1$H-NMR (DMSO-d$_6$) δ: 3.31(2H,m), 3.57(1H,m), 3.95 (1H,m), 4.01(2H,m), 4.25(2H,m), 6.45(1H,bs), 6.64(1H,s), 6.77(1H,m), 7.10–7.69(18H,m), 8.46(3H,bs)

EXAMPLE 222

N-[2-(2-fluorophenyl)ethyl]-3-[N'-[2-[3-(aminomethyl)phenoxy]-4-chlorophenyl]-N'-(4-phenylbenzoyl)]aminopropanamide hydrochloride (1) A mixture of 3-[N-[2-[3-(tert-butoxycarbonylaminomethyl)phenoxy]-4-chlorophenyl]-N-(4-phenylbenzoyl)]aminopropionic acid (0.50 g, 0.83 mmols), 2-fluorophenethylamine (0.24 g, 1.7 mmols), 1-ethyl-3-(3-dimethylaminopropyl)carbodiimide hydrochloride (WSC) (0.24 g, 1.3 mmols), 1-hydroxybenzotriazole monohydrate (HOBt) (0.17 g, 1.3 mmols) and N,N-dimethylformamide (8 ml) was stirred at room temperature for 6 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[2-(2-fluorophenyl)ethyl]-4-[N'-[2-[3-(tert-butoxycarbonylaminomethyl)phenoxy]-4-chlorophenyl]-N'-(4-phenylbenzoyl)]aminopropionamide (0.58 g, 96%).

Elemental Analysis for $C_{42}H_{41}N_3O_5Cl \cdot H_2O$:
Calcd.: C, 69.94; H, 6.01; N, 5.83
Found: C, 69.70; H, 5.80; N, 5.88
$^1$H-NMR (CDCl$_3$) δ: 1.43(9H,s), 2.55(1H,m), 2.67(1H, m), 2.84(2H,m), 3.48(2H,m), 4.07(1H,m), 4.21(2H,d,J=6.2 Hz), 4.22(1H,m), 4.93(1H,bs), 6.48(2H,m), 6.60(2H,m), 6.97–7.59(17H,m)

(2) A 4 N hydrochloric acid/ethyl acetate solution (2 ml) was added to an ethyl acetate (2 ml) solution of N-[2-(2-fluorophenyl)ethyl]-4-[N'-[2-[3-(tert-butoxycarbonylaminomethyl)phenoxy]-4-chlorophenyl]-N'-(4-phenylbenzoyl)]aminopropionamide (0.23 g, 0.32 mmols), and stirred at room temperature for 1 hour. The reaction mixture was concentrated under reduced pressure. The solid precipitated was taken out through filtration, and washed with ethyl ether to give an amorphous solid of N-[2-(2-fluorophenyl)ethyl]-3-[N'-[2-[3-(aminomethyl)phenoxy]-4-chlorophenyl]-N'-(4-phenylbenzoyl)]aminopropanamide hydrochloride (0.13 g, 63%).

Elemental Analysis for $C_{37}H_{34}N_3O_3Cl_2F_2$:
Calcd.: C, 67.48; H, 5.20; N, 6.38
Found: C, 67.32; H, 5.32; N, 6.37
$^1$H-NMR (DMSO-d$_6$) δ: 2.42(2H,m), 2.73(2H,m), 3.24 (2H,m), 4.02(4H,m), 6.60(1H,s), 6.79(1H,m), 7.12–7.68(18H,m), 8.21(1H,bs), 8.50(2H,bs)

EXAMPLE 223

N-[2-(1H-indol-3-yl)-1-methylethyl]-3-[N'-[2-[3-(aminomethyl)phenoxy]-4-chlorophenyl]-N'-(4-phenylbenzoyl)]aminopropanamide hydrochloride (1) A mixture of 3-[N-[2-[3-(tert-butoxycarbonylaminomethyl)phenoxy]-4-chlorophenyl]-N-(4-phenylbenzoyl)]aminopropionic acid (0.50 g, 0.83 mmols), α-methyltryptamine (0.22 g, 1.3 mmols), 1-ethyl-3-(3-dimethylaminopropyl)carbodiimide hydrochloride (WSC) (0.24 g, 1.3 mmols), 1-hydroxybenzotriazole monohydrate (HOBt) (0.17 g, 1.3 mmols) and N,N-dimethylformamide (8 ml) was stirred at room temperature for 9 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[2-(1H-indol-3-yl)-1-methylethyl]-3-[N'-[2-[3-(tert-butoxycarbonylaminomethyl)phenoxy]-4-chlorophenyl]-N'-(4-phenylbenzoyl)]aminopropionamide (0.42 g, 66%).

Elemental Analysis for $C_{45}H_{45}N_4O_5Cl \cdot 1/2H_2O$:
Calcd.: C, 70.53; H, 6.05; N, 7.31
Found: C, 70.47; H, 5.98; N, 7.07
$^1$H-NMR (CDCl$_3$) δ: 1.15(3H,m), 1.43(9H,s), 2.50(1H, m), 2.63(1H,m), 2.90(2H,m), 4.03(1H,m), 4.19(2H,d,J=5.8 Hz), 4.31(1H,m), 4.94(1H,bs), 6.42(2H,m), 6.57(2H,m), 6.95–7.69(18H,m), 8.31(1H,bs)

(2) A 4 N hydrochloric acid/ethyl acetate solution (2 ml) was added to an ethyl acetate (2 ml) solution of N-[2-(1H-indol-3-yl)-1-methylethyl]-3-[N'-[2-[3-(tert-butoxycarbonylaminomethyl)phenoxy]-4-chlorophenyl]-N'-(4-phenylbenzoyl)]aminopropionamide (0.26 g, 0.34 mmols), and stirred at room temperature for 1 hour. The reaction mixture was concentrated under reduced pressure. The solid precipitated was taken out through filtration, and washed with ethyl ether to give an amorphous solid of N-[2-(1H-indol-3-yl)-1-methylethyl]-3-[N'-[2-[3-(aminomethyl)phenoxy]-4-chlorophenyl]-N'-(4-phenylbenzoyl)]aminopropanamide hydrochloride (0.23 g, 96%).

Elemental Analysis for $C_{40}H_{38}N_4O_3Cl_2 \cdot 1/2H_2O$:
Calcd.: C, 68.37; H, 5.59; N, 7.97
Found: C, 67.99; H, 5.88; N, 7.67
$^1$H-NMR (DMSO-d$_6$) δ: 1.01(3H,d,J=6.6 Hz), 2.41(2H, m), 2.66(1H,m), 2.84(1H,m), 3.71–4.05(6H,m), 6.60(1H,s), 6.79(1H,m), 6.92–7.19(5H,m), 7.32–7.68(14H,m), 8.04(1H, bs), 8.48(2H,bs), 10.86(1H,bs)

EXAMPLE 224

N-(2-fluorobenzyl)-4-[N'-[2-[3-(aminomethyl)phenoxy]-4-chlorophenyl]-N'-(9H-fluorene-2-carbonyl)]aminobutylamide hydrochloride (1) A mixture of ethyl 4-[N-[2-[3-(tert-butoxycarbonylaminomethyl)phenoxy]-4-chlorophenyl]]aminobutyrate (2.0 g, 4.3 mmols), 9H-fluorene-2-carbonyl chloride (1.2 g, 5.2 mmols) and N,N-dimethylacetamide (40 ml) was stirred at room temperature for 4 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N-[2-[3-(tert-butoxycarbonylaminomethyl)phenoxy]-4-chlorophenyl]-N-(9H-fluorene-2-carbonyl)]aminobutyrate (2.1 g, 75%).

Elemental Analysis for $C_{38}H_{39}N_2O_6Cl$:
Calcd.: C, 69.66; H, 6.00; N, 4.28
Found: C, 69.72; H, 5.89; N, 4.05
$^1$H-NMR (CDCl$_3$) δ: 1.24(3H,t,J=7.2 Hz), 1.44(9H,s), 2.00(2H,m), 2.47(2H,m), 3.72(2H,m), 3.82(1H,m), 4.01–4.17(5H,m), 4.85(1H,bs), 6.46–6.55(3H,m), 6.98–7.42 (7H,m), 7.55(3H,m), 7.76(1H,m)

(2) Aqueous 1 N sodium hydroxide solution (15 ml, 15 mmols) was added to a solution of ethyl 4-[N-[2-[3-(tert-butoxycarbonylaminomethyl)phenoxy]-4-chlorophenyl]-N-(9H-fluorene-2-carbonyl)]aminobutyrate (2.0 g, 3.1 mmols) in tetrahydrofuran (20 ml) and ethanol (20 ml). The resulting mixture was stirred at 60° C. for 1 hour. This was poured into water, acidified with potassium hydrogensulfate added thereto, and then extracted with ethyl acetate. The extract was washed with water, then dried with anhydrous magnesium sulfate, and concentrated under reduced pressure to give an amorphous solid (1.9 g, 100%). A mixture of the thus-obtained amorphous solid (0.8 g, 1.3 mmols) with 2-fluorobenzylamine (0.35 g, 2.8 mmols), 1-ethyl-3-(3-dimethylaminopropyl)carbodiimide hydrochloride (WSC) (0.49 g, 2.6 mmols), 1-hydroxybenzotriazole monohydrate (HOBt) (0.26 g, 1.9 mmols) and N,N-dimethylformamide (10 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-(tert-butoxycarbonylaminomethyl)phenoxy]-4-chlorophenyl]-N'-(9H-fluorene-2-carbonyl)]aminobutylamide (0.72 g, 77%).

Elemental Analysis for $C_{43}H_{41}N_3O_5ClF$:
Calcd.: C, 70.34; H, 5.63; N, 5.72
Found: C, 70.44; H, 5.50; N, 6.00
$^1$H-NMR (CDCl$_3$) δ: 1.42(9H,s), 1.96(2H,m), 2.38(2H,m), 3.72(2H,m), 3.79(1H,m), 4.07(2H,d,J=4.8 Hz), 4.09(1H,m), 4.51(2H,d,J=5.4 Hz), 4.80(1H,bs), 6.43–6.53(3H,m), 6.98–7.38(12H,m), 7.54(3H,m), 7.75(1H,m)

(3) A 4 N hydrochloric acid/ethyl acetate solution (3 ml) was added to an ethyl acetate (3 ml) solution of N-(2-fluorobenzyl)-4-[N'-[2-[3-(tert-butoxycarbonylaminomethyl)phenoxy]-4-chlorophenyl]-N'-(9H-fluorene-2-carbonyl)]aminobutylamide (0.35 g, 0.53 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-(9H-fluorene-2-carbonyl)]aminobutylamide hydrochloride (0.31 g, 98%).

Elemental Analysis for $C_{38}H_{34}N_3O_3Cl_2F.1/2H_2O$:
Calcd.: C, 67.16; H, 5.19; N, 6.18
Found: C, 67.08; H, 5.44; N, 6.22
$^1$H-NMR (DMSO-d$_6$) δ: 1.84(2H,m), 2.29(2H,m), 3.75–4.09(6H,m), 4.30(2H,m), 6.59(1H,s), 6.72(1H,m), 7.13–7.37(11H,m), 7.57(3H,m), 7.78(1H,d), 7.90(1H,m), 8.54(3H,m)

EXAMPLE 225

N-(3,4-difluorophenyl)-4-[N'-[2-[3-(aminomethyl)phenoxy]-4-chlorophenyl]-N'-(9H-fluorene-2-carbonyl)]aminobutylamide hydrochloride (1) Aqueous 1 N sodium hydroxide solution (15 ml, 15 mmols) was added to a solution of ethyl 4-[N-[2-[3-(tert-butoxycarbonylaminomethyl)phenoxy]-4-chlorophenyl]-N-(9H-fluorene-2-carbonyl)]aminobutyrate (2.0 g, 3.1 mmols) in tetrahydrofuran (20 ml) and ethanol (20 ml). The resulting mixture was stirred at 60° C. for 1 hour. This was poured into water, acidified with potassium hydrogensulfate added thereto, and then extracted with ethyl acetate. The extract was washed with water, then dried with anhydrous magnesium sulfate, and concentrated under reduced pressure to give an amorphous solid (1.9 g, 100%). A mixture of the thus-obtained amorphous solid (0.8 g, 1.3 mmols) with 3,4-difluoroaniline (0.38 g, 2.9 mmols), 1-ethyl-3-(3-dimethylaminopropyl)carbodiimide hydrochloride (WSC) (0.49 g, 2.6 mmols), 1-hydroxybenzotriazole monohydrate (HOBt) (0.26 g, 1.9 mmols) and N,N-dimethylformamide (10 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(3,4-difluorophenyl)-4-[N'-[2-[3-(tert-butoxycarbonylaminomethyl)phenoxy]-4-chlorophenyl]-N'-(9H-fluorene-2-carbonyl)]aminobutylamide (0.58 g, 62%).

Elemental Analysis for $C_{42}H_{38}N_3O_5ClF_2$:
Calcd.: C, 68.33; H, 5.19; N, 5.69
Found: C, 68.28; H, 5.33; N, 5.63
$^1$H-NMR (CDCl$_3$) δ: 1.43(9H,s), 2.05(2H,m), 2.47(1H,m), 2.64(1H,m), 3.74(2H,d), 3.83(1H,m), 4.08(2H,d,J=4.6 Hz), 4.37(1H,m), 4.69(1H,bs), 6.38–6.42(2H,m), 6.55(1H,m), 7.00–7.85(14H,m), 9.92(1H,s)

(2) A 4 N hydrochloric acid/ethyl acetate solution (2 ml) was added to an ethyl acetate (2 ml) solution of N-(3,4-difluorophenyl)-4-[N'-[2-[3-(tert-butoxycarbonylaminomethyl)phenoxy]-4-chlorophenyl]-N'-(9H-fluorene-2-carbonyl)]aminobutylamide (0.3 g, 0.41 mmols), and stirred at room temperature for 1 hour. The reaction mixture was concentrated under reduced pressure. The solid precipitated was taken out through filtration, and washed with ethyl ether to give an amorphous solid of N-(3,4-difluorophenyl)-4-[N'-[2-[3-(aminomethyl)phenoxy]-4-chlorophenyl]-N'-(9H-fluorene-2-carbonyl)]aminobutylamide hydrochloride (0.26 g, 93%).

Elemental Analysis for $C_{37}H_{31}N_3O_3Cl_2F_2$:
Calcd.: C, 65.88; H, 4.63; N, 6.23
Found: C, 65.86; H, 5.01; N, 6.39
$^1$H-NMR (DMSO-d$_6$) δ: 1.90(2H,m), 2.49(2H,m), 3.83(2H,s), 3.79(2H,m), 3.98(2H,m), 6.59(1H,s), 6.76(1H,bs), 7.15–7.44(9H,m), 7.57–7.64(3H,m), 7.75–7.92(3H,m), 8.46(2H,bs), 10.43(1H,s)

EXAMPLE 226

N-(2-fluorobenzyl)-4-[N'-[2-[3-(1-amino-1-methylethyl)phenoxy]-4-chlorophenyl]-N'-(4-phenylbenzoyl)]aminobutylamide hydrochloride (1) Bromomethylmagnesium (3 M diethyl ether solution) (24 ml, 72 mmols) was dropwise added to a diethyl ether (200 ml) solution of 3-methoxyacetophenone (10 g, 67 mmols) at room temperature. After the addition, the mixture was stirred at room temperature for 1 hour. Saturated aqueous ammonia was added to the reaction mixture, which was then extracted with ethyl acetate. The extract was washed with brine, and then dried with anhydrous magnesium sulfate. This was concentrated under reduced pressure to give an oil of 2-(3-methoxyphenyl)propan-2-ol (11 g, 98%).

$^1$H-NMR (CDCl$_3$) δ: 1.56(6H,s), 3.80(3H,s), 6.77(1H,m), 7.01–7.06(2H,m), 7.25(1H,m)

(2) Boron trifluoride-diethyl ether complex (11.2 g, 78.9 mmols) was dropwise added to a toluene (100 ml) solution of 2-(3-methoxyphenyl)propan-2-ol (10.9 g, 65.6 mmols) and trimethylsilylazide (8.3 g, 72 mmols), at room temperature. The resulting mixture was stirred at room temperature for 20 hours. The reaction mixture was poured into water, and extracted with ethyl acetate. The extract was washed with brine, and then dried with anhydrous magnesium sulfate. This was concentrated under reduced pressure to give an oil of 1-(1-azido-1-methylethyl)-3-methoxybenzene (12.5 g, 100%).

$^1$H-NMR (CDCl$_3$) δ: 1.62 (6H,s), 3.83(3H,s), 6.83(1H,m), 7.00–7.05(2H,m), 7.28(1H,m)

(3) A mixture of 1-(1-azido-1-methylethyl)-3-methoxybenzene (34.1 g, 178 mmols), Raney nickel (100 g) and ethanol (300 ml) was stirred at room temperature for 24 hours. The catalyst was removed through decantation, and the resulting supernatant was concentrated under reduced pressure. 1 N hydrochloric acid was added to the residue, which was then washed with diethyl ether. After neutralized, the aqueous layer was made alkaline with sodium hydroxide added thereto, and extracted with ethyl acetate. The extract was washed with brine, and then dried with anhydrous magnesium sulfate. This was concentrated under reduced pressure to give an oil of 1-(3-methoxyphenyl)-1-methylethylamine (17.9 g, 60%).

$^1$H-NMR (CDCl$_3$) δ: 1.49(6H,s), 1.68(2H,s), 3.82(3H,s), 6.77(1H,m), 7.06–7.10(2H,m), 7.27(1H,m)

(4) A dichloromethane (150 ml) solution of 1 N boron trifluoride was dropwise added to a dichloromethane (50 ml) solution of 1-(3-methoxyphenyl)-1-methylethylamine (8.12 g, 49.1 mmols), at −78° C. This was stirred at the temperature for 30 minutes, and then reacted at room temperature for 1 hour. Methanol was added to the reaction mixture to stop the reaction, and the mixture was then concentrated under reduced pressure. To the residue, added were tetrahydrofuran (100 ml), triethylamine (14.9 g, 147 mmols) and di-tert-butyl dicarbonate (10.7 g, 49 mmols). The resulting mixture was heated under reflux for 2 hours. This was cooled, then poured into water, and extracted with ethyl acetate. The extract was washed with brine, and then dried with anhydrous magnesium sulfate. This was concentrated under reduced pressure, and the residue was purified through silica gel column chromatography. An oil of tert-butyl[1-(3-hydroxyphenyl)-1-methylethyl]carbamate (8.5 g, 68%) was obtained.

$^1$H-NMR (CDCl$_3$) δ: 1.39(9H,bs), 1.59(6H,s), 5.00(1H,s), 6.00(1H,bs), 6.65(1H,m), 6.86–6.93(2H,m), 7.15(1H,m)

(5) A mixture of 4-chloro-2-fluoronitrobenzene (2.57 g, 14.6 mmols), tert-butyl[1-(3-hydroxyphenyl)-1-methylethyl]carbamate (3.21 g, 12.8 mmols), potassium carbonate (2.02 g, 14.6 mmols) and N,N-dimethylformamide (20 ml) was stirred at 100° C. for 2 hours. The reaction mixture was cooled, then poured into water, and extracted with ethyl acetate. The extract was washed with water and brine, and then dried with anhydrous magnesium sulfate, and the solvent was evaporated away. The residue was purified through silica gel column chromatography to give a crystal of tert-butyl[1-[3-(5-chloro-2-nitrophenoxy)phenyl]-1-methylethyl]carbamate (3.6 g, 69%).

m.p. 87–88° C.

Elemental Analysis for C$_{20}$H$_{23}$N$_3$O$_5$Cl:
Calcd.: C, 59.04; H, 5.70; N, 6.89
Found: C, 59.21; H, 5.84; N, 6.79

$^1$H-NMR (CDCl$_3$) δ: 1.34(9H,bs), 1.62(6H,s), 4.95(1H, bs), 6.93(2H,m), 7.08–7.17(2H,m), 7.30–7.42(2H,m), 7.92 (1H,d)

(6) 5% carbon-palladium (1.0 g) was added to an ethyl acetate (100 ml) solution of tert-butyl[1-[3-(5-chloro-2-nitrophenoxy)phenyl]-1-methylethyl]carbamate (3.3 g, 8.1 mmols). The resulting mixture was hydrogenated at room temperature under atmospheric pressure for 3 hours. The catalyst was removed through filtration, and the filtrate was concentrated under reduced pressure. The residue was purified through silica gel column chromatography to give an amorphous solid of tert-butyl[1-[3-(2-amino-5-chlorophenoxy)phenyl]-1-methylethyl]carbamate (2.7 g, 89%).

$^1$H-NMR (CDCl$_3$) δ: 1.37(9H,bs), 1.61(6H,s), 3.50(2H, bs), 4.94(1H,bs), 6.70–6.94(4H,m), 7.07–7.32(3H,m)

(7) A mixture of tert-butyl[1-[3-(2-amino-5-chlorophenoxy)phenyl]-1-methylethyl]carbamate (2.5 g, 6.62 mmols), ethyl 4-bromobutyrate (9.0 g, 46 mmols), potassium carbonate (2.7 g, 20 mmols) and N,N-dimethylformamide (20 ml) was stirred at 80° C. for 24 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[N-[2-[3-(1-tert-butoxycarbonylamino-1-methylethyl)phenoxy]-4-chlorophenyl]]aminobutyrate (1.6 g, 49%).

$^1$H-NMR (CDCl$_3$) δ: 1.26(3H,t), 1.36(9H,bs), 1.61(6H,s), 1.94(2H,m), 2.39(2H,m), 3.20(2H,m), 4.12(2H,q), 4.25(1H, m), 4.94(1H,bs), 6.60–7.31(7H,m)

(8) A mixture of ethyl 4-[N-[2-[3-(1-tert-butoxycarbonylamino-1-methylethyl)phenoxy]-4-chlorophenyl]]aminobutyrate (1.4 g, 2.8 mmols), 4-phenylbenzoyl chloride (0.72 g, 3.3 mmols) and N,N-dimethylacetamide (20 ml) was stirred at room temperature for 2 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N-[2-[3-(1-tert-butoxycarbonylamino-1-methylethyl)phenoxy]-4-chlorophenyl]-N-(4-phenylbenzoyl)]aminobutyrate (1.6 g, 88%).

Elemental Analysis for C$_{39}$H$_{43}$N$_2$O$_6$Cl.1/2H$_2$O:
Calcd.: C, 68.86; H, 6.52; N, 4.12
Found: C, 68.74; H, 6.55; N, 3.82

$^1$H-NMR (CDCl$_3$) δ: 1.26(3H,t,J=7.4 Hz), 1.29(9H,bs), 1.52(6H,d), 2.02(2H,m), 2.48(2H,m), 3.89(1H,m), 4.07(1H, m), 4.12(2H,q,J=7.4 Hz), 4.84(1H,bs), 6.50(2H,m), 6.71 (1H,bs), 6.97(1H,m), 7.20–7.61(12H,m)

(9) Aqueous 1 N sodium hydroxide solution (10 ml, 10 mmols) was added to a solution of ethyl 4-[N-[2-[3-(1-tert-butoxycarbonylamino-1-methylethyl)phenoxy]-4-chlorophenyl]-N-(4-phenylbenzoyl)]aminobutyrate (1.4 g, 2.1 mmols) in tetrahydrofuran (50 ml) and ethanol (50 ml). The resulting mixture was stirred at 60° C. for 1 hour. This was poured into water, acidified with potassium hydrogensulfate added thereto, and extracted with ethyl acetate. The extract was washed with water, and then dried with anhydrous magnesium sulfate. This was concentrated under reduced pressure to give an amorphous solid of 4-[N-[2-[3-(1-tert-butoxycarbonylamino-1-methylethyl)phenoxy]-4-chlorophenyl]-N-(4-phenylbenzoyl)]aminobutyric acid (1.3 g, 97%).

Elemental Analysis for C$_{37}$H$_{39}$N$_2$O$_6$Cl.1/2H$_2$O:
Calcd.: C, 68.14; H, 6.18; N, 4.30
Found: C, 68.36; H, 6.32; N, 4.31

$^1$H-NMR (CDCl$_3$) δ: 1.29(9H,bs), 1.56(6H,d), 2.00(2H, m), 2.52(2H,m), 3.98–4.20(2H,m), 5.00(1H,bs), 6.06(1H, bs), 6.54(1H,s), 6.94(1H,bs), 7.22–7.58(14H,m)

(10) A mixture of 4-[N-[2-[3-(1-tert-butoxycarbonylamino-1-methylethyl)phenoxy]-4-chlorophenyl]-N-(4-phenylbenzoyl)]aminobutyric acid (0.5 g, 0.78 mmols), 2.-fluorobenzylamine (0.19 g, 1.5 mmols), 2-ethyl-3-(3-dimethylaminopropyl)carbodiimide hydrochloride (WSC) (0.30 g, 1.6 mmols), 1-hydroxybenzotriazole monohydrate (0.21 g, 1.6 mmols) and N,N-dimethylformamide (10 ml) was stirred at room temperature for 12 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[3-(1-tert-butoxycarbonylamino-1-methylethyl)phenoxy]-4-chlorophenyl]-N'-(4-phenylbenzoyl)]aminobutylamide (0.49 g, 84%).

Elemental Analysis for C$_{44}$H$_{45}$N$_3$O$_6$Cl.1/2H$_2$O:
Calcd.: C, 69.60; H, 6.11; N, 5.53
Found: C, 69.84; H, 6.13; N, 5.63

¹H-NMR (CDCl₃) δ: 1.33(9H,bs), 1.51(6H,d), 1.98(2H, m), 2.41(2H,m), 3.85(1H,m), 4.15(1H,m), 4.52(2H,d,J=5.2 Hz), 4.85(1H,bs), 6.41(1H,bs), 6.50(1H,s), 6.69(1H,s), 6.98–7.60(18H,m)

(11) A 4 N hydrochloric acid/ethyl acetate solution (2 ml) was added to an ethyl acetate (2 ml) solution of N-(2-fluorobenzyl)-4-[N'-[2-[3-(1-tert-butoxycarbonylamino-1-methylethyl)phenoxy]-4-chlorophenyl]-N'-(4-phenylbenzoyl)]aminobutylamide (0.32 g, 0.43 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(1-amino-1-methylethyl)phenoxy]-4-chlorophenyl]-N'-(4-phenylbenzoyl)]aminobutylamide hydrochloride (0.29 g, 99%).

Elemental Analysis for $C_{39}H_{38}N_3O_3Cl_2F \cdot 1/2H_2O$:
Calcd.: C, 67.34; H, 5.65; N, 6.04
Found: C, 67.10; H, 5.84; N, 5.94
¹H-NMR (DMSO-d₆) δ: 1.61(6H,s), 1.84(2H,m), 2.29 (2H,m), 3.79(2H,m) 4.30(2H,d,J=4.8 Hz), 6.56(1H,s), 6.68 (1H,d), 7.11–7.69(17H,m), 8.47(1H,m), 8.78(3H,m)

EXAMPLE 227

N-[2-[3-(aminomethyl)phenoxy]-4-chlorophenyl]-N-[3-[[[(2-fluorobenzyl)amino]carbonyl]amino]propyl]-4-phenylbenzamide hydrochloride (1) A mixture of 4-[N-[2-[3-(tert-butoxycarbonylaminomethyl)phenoxy]-4-chlorophenyl-N-(4-phenylbenzoyl)]aminobutyric acid (0.92 g, 1.5 mmols), diphenylphosphorylazide (DPPA) (0.39 ml, 1.8 mmols), triethylamine (0.25 ml, 1.8 mmols) and N,N-dimethylformamide (10 ml) was stirred at 0° C. for 1 hour. The reaction mixture was poured into water, and extracted with ethyl acetate. The extract was washed with water and brine, and dried with anhydrous magnesium sulfate, and the solvent was evaporated away. Toluene (20 ml) was added to the residue, and the resulting mixture was stirred, while heated under reflux, for 1 hour. Next, 2-fluorobenzylamine (0.25 ml, 1.8 mmols) and triethylamine (0.25 ml, 1.8 mmols) were added to the reaction mixture, and further refluxed for 12 hours. Then, this was cooled, poured into water, and extracted with ethyl acetate. The extract was washed with water and brine, and dried with anhydrous magnesium sulfate, and the solvent was evaporated away. The residue was purified through silica gel column chromatography to give an amorphous solid of tert-butyl 3-[2-[(4-phenylbenzoyl)[3-[[[(2-fluorobenzyl)amino]carbonyl]amino]propyl]amino]-5-chlorophenoxy]benzylcarbamate (0.76 g, 69%).

Elemental Analysis for $C_{42}H_{42}N_4O_5ClF \cdot 1/2H_2O$:
Calcd.: C, 67.60; H, 5.81; N, 7.51
Found: C, 67.72; H, 5.73; H, 7.52
¹H-NMR (CDCl₃) δ: 1.41(9H,m), 1.72–1.80(2H,m), 3.34 (2H,bs), 3.70–3.80(1H,m), 4.19(2H,d,J=6.4 Hz), 4.43(2H,d, J=4.8 Hz), 4.97–5.03(2H,m), 5.75(2H,m), 5.75(1H,bs), 6.42 (1H,d,J=7.6 Hz), 6.58(2H,d,J=7.8 Hz), 6.95–7.17(4H,m), 7.19–7.26(4H,m), 7.32–7.48(8H,m), 7.53–7.58(2H,m)

(2) A 4 N hydrochloric acid/ethyl acetate solution (5 ml) was added to an ethyl acetate (5 ml) solution of tert-butyl 3-[2-[(4-phenylbenzoyl)[3-[[[(2-fluorobenzyl)amino]carbonyl]amino]propyl]amino]-5-chlorophenoxy]benzylcarbamate (0.66 g, 0.9 mmols), and stirred at room temperature for 1 hour. The reaction mixture was concentrated under reduced pressure. The solid precipitated was taken out through filtration, and washed with ethyl ether to give an amorphous solid of N-[2-[3-(aminomethyl)phenoxy]-4-chlorophenyl]-N-[3-[[[(2-fluorobenzyl)amino]carbonyl]amino]propyl]-4-phenylbenzamide hydrochloride (0.54 g, 90%).

Elemental Analysis for $C_{37}H_{35}N_4O_3Cl_2F \cdot 1/2H_2O$:
Calcd.: C, 65.10; H, 5.32; N, 8.21
Found: C, 64.92; H, 5.32; N, 8.32
¹H-NMR (DMSO-d₆) δ: 1.69(2H,t,J=6.6 Hz), 3.10(2H, bs), 3.81(2H,bs), 4.01(2H,s), 4.25(2H,s), 4.46(1H,bs), 6.57–6.68(2H,m), 7.13–7.68(18H,m), 8.51(3H,bs)

EXAMPLE 228

N-[2-[3-(aminomethyl)phenoxy]-4-chlorophenyl]-N-[3-[[[(2-fluorophenyl)amino]carbonyl]amino]propyl]-4-phenylbenzamide hydrochloride (1) A mixture of 4-[N-[2-[3-(tert-butoxycarbonylaminomethyl)phenoxy]-4-chlorophenyl]-N-(4-phenylbenzoyl)]aminobutyric acid (0.92 g, 1.5 mmols), diphenylphosphorylazide (DPPA) (0.39 ml, 1.8 mmols), triethylamine (0.25 ml, 1.8 mmols) and N,N-dimethylformamide (10 ml) was stirred at 0° C. for 1 hour. The reaction mixture was poured into water, and extracted with ethyl acetate. The extract was washed with water and brine, and dried with anhydrous magnesium sulfate, and the solvent was evaporated away. Toluene (20 ml) was added to the residue, and the resulting mixture was stirred, while heated under reflux, for 1 hour. Next, 2-fluoroaniline (0.17 ml, 1.8 mmols) and triethylamine (0.25 ml, 1.8 mmols) were added to the reaction mixture, and further refluxed for 12 hours. Then, this was cooled, poured into water, and extracted with ethyl acetate. The extract was washed with water and brine, and dried with anhydrous magnesium sulfate, and the solvent was evaporated away. The residue was purified through silica gel column chromatography to give an amorphous solid of tert-butyl 3-[2-[(4-phenylbenzoyl)[3-[[[(2-fluorophenyl)amino]carbonyl]amino]propyl]amino]-5-chlorophenoxy]benzylcarbamate (0.81 g, 75%).

Elemental Analysis for $C_{41}H_{40}N_4O_5ClF \cdot 1/2H_2O$:
Calcd.: C, 67.25; H, 5.64; N, 7.65
Found: C, 67.24; H, 5.43; N, 7.57
¹H-NMR (CDCl₃) δ: 1.42(9H,m), 1.82(2H,bs), 3.41(2H, bs), 3.74–3.81(1H,m), 4.18–4.22(3H,m), 4.99(1H,bs), 6.21 (1H,bs), 6.46(1H,d,J=7.6 Hz), 6.60(2H,d,J=9.4 Hz), 6.86–7.11(6H,m), 7.18–7.48(9H,m), 7.54–7.59(2H,m), 8.14 (1H,t,J=8.5 Hz)

(2) In the same manner as in (2) in Example 227, an amorphous solid of N-[2-[3-(aminomethyl)phenoxy]-4-chlorophenyl]-N-[3-[[[(2-fluorophenyl)amino]carbonyl]amino]propyl]-4-phenylbenzamide hydrochloride was obtained from tert-butyl 3-[2-[(4-phenylbenzoyl)[3-[[[(2-fluorophenyl)amino]carbonyl]amino]propyl]amino]-5-chlorophenoxy]benzylcarbamate.

Elemental Analysis for $C_{36}H_{33}N_4O_3Cl_2F \cdot 1/2H_2O$:
Calcd.: C, 64.67; H, 5.13; N, 8.38
Found: C, 64.72; H, 4.96; N, 8.44
¹H-NMR (DMSO-d₆) δ: 1.75(2H,t,J=6.8 Hz), 3.19(2H,s), 3.92(2H,s), 4.02(2H,s), 6.56–6.63(2H,m), 6.89–7.95(2H,m), 7.02–7.20(3H,m), 7.34–7.49(7H,m), 7.56–7.66(5H,m), 8.13 (1H,d,J=8.3 Hz), 8.46(3H,bs)

EXAMPLE 229

N-(2-fluorobenzyl)-4-[N'-[4-(acetamido)benzoyl]-N'-[2-[3-(aminobutyl)phenoxy]-4-chlorophenyl]] aminobutylamide hydrochloride (1) A mixture of ethyl 4-[N-[2-[3-(tert-butoxycarbonylaminomethyl)phenoxy]-4-chlorophenyl]]aminobutyrate (2.3 g, 5.0 mmols), 4-(acetamido)benzoyl chloride (2.0 g, 10 mmols), 4-dimethylaminopyridine (1.2 g, 10 mmols) and tetrahydrofuran (20 ml) was stirred at room temperature for 5 hours. The reaction mixture was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N-[2-[3-(tert-butoxycarbonylaminomethyl)phenoxy]-4-chlorophenyl]-N-[4-(acetamido)benzoyl]]aminobutyrate (1.7 g, 54%).

Elemental Analysis for $C_{33}H_{38}N_3O_7Cl.1/4H_2O$:
Calcd.: C, 63.05; H, 6.17; N, 6.68
Found: C, 62.98; H, 5.94; N, 6.78
$^1$H-NMR (CDCl$_3$) δ: 1.23(3H,t,J=7.2 Hz), 1.45(9H,s), 1.93–2.03(2H,m), 2.14(3H,s), 2.46(2H,t,J=7.2 Hz), 3.67–3.75(1H,m), 4.06–4.18(5H,m), 5.24(1H,bs), 5.92(1H,bs), 6.51(1H,s), 6.72–6.95(1H,m), 7.02(2H,d,J=8.2 Hz), 7.20–7.33(6H,m), 8.40(1H,bs)

(2) Aqueous 1 N sodium hydroxide solution (5 ml, 5 mmols) was added to a solution of ethyl 4-N-[2-[3-(tert-butoxycarbonylaminomethyl)phenoxy]-4-chlorophenyl]-N-[4-(acetamido)benzoyl]]aminobutyrate (1.6 g, 2.5 mmols) in tetrahydrofuran (10 ml) and ethanol (10 ml). The resulting mixture was stirred at room temperature for 2 hours. The reaction mixture was poured into water, then acidified with 1 N hydrochloric acid added thereto, and extracted with ethyl acetate. The extract was washed with water, and then dried with anhydrous magnesium sulfate. This was concentrated under reduced pressure to give an amorphous solid of 4-[N-[4-(acetamido)benzoyl]-N-[2-[3-(tert-butoxycarbonylaminomethyl)phenoxy]-4-chlorophenyl]]aminobutyric acid (1.5 g, 99%).

Elemental Analysis for $C_{31}H_{34}N_3O_7Cl$:
Calcd.: C, 62.46; H, 5.75; N, 7.05
Found: C, 62.48; H, 5.90; N, 7.00
$^1$H-NMR (CDCl$_3$) δ: 1.44(9H,s), 1.86–1.98(2H,m), 2.13(3H,s), 2.50(1H,bs), 3.75(1H,bs), 4.07–4.17(3H,m), 5.31(1H,bs), 5.99(1H,bs), 6.34(1H,bs), 6.55(2H,s), 6.58–6.74(1H,m), 6.93–7.03(3H,m), 7.24–7.41(4H,m), 8.44(1H,bs)

(3) A mixture of 4-[N-[4-(acetamido)benzoyl]-N-[2-[3-(tert-butoxycarbonylaminomethyl)phenoxy]-4-chlorophenyl]]aminobutyric acid (0.72 g, 1.2 mmols), 2-fluorobenzylamine (0.17 ml, 1.5 mmols), diethyl cyanophosphate (0.21 ml, 1.5 mmols), triethylamine (0.21 ml, 1.5 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4'-[N-[4-(acetamido)benzoyl]-N'-[2-[3-(tert-butoxycarbonylaminomethyl)phenoxy]-4-chlorophenyl]]aminobutylamide (0.76 g, 91%).

Elemental Analysis for $C_{38}H_{40}N_4O_6ClF.1/2H_2O$:
Calcd.: C, 64.08; H, 5.80; N, 7.87
Found: C, 64.05; H, 5.81; N, 7.75
$^1$H-NMR (CDCl$_3$) δ: 1.45(9H,s), 1.90–1.93(2H,m), 2.14(3H,s), 2.31–2.45(2H,m), 3.63(1H,m), 4.00–4.18(3H,m), 4.50(2H,d,J=5.4 Hz), 5.28(1H,bs), 5.88(1H,bs), 6.50(1H,bs), 6.67–6.71(1H,m), 7.00–7.11(4H,m), 7.19–7.38(9H,m), 8.50(1H,bs)

(4) A 4 N hydrochloric acid/ethyl acetate solution (5 ml) was added to an ethyl acetate (5 ml) solution of N-(2-fluorobenzyl)-4'-[N-[4-(acetamido)benzoyl]-N'-[2-[3-(tert-butoxycarbonylaminomethyl)phenoxy]-4-chlorophenyl]] aminobutylamide (0.63 g, 0.9 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4'-[N-[4-(acetamido)benzoyl]-N'-[2-[3-(aminomethyl)phenoxy]-4-chlorophenyl]]aminobutylamide hydrochloride (0.44 g, 77%).

Elemental Analysis for $C_{33}H_{33}N_4O_4Cl_2F.1/2H_2O$:
Calcd.: C, 61.11; H, 5.28; N, 8.63
Found: C, 60.75; H, 5.32; N, 8.42
$^1$H-NMR (DMSO-d$_6$) δ: 1.73–1.83(2H,m), 2.05(3H,s), 2.24(2H,t,J=7.0 Hz), 3.59–3.76(2H,m), 4.00(2H,s), 4.28(2H,d,J=4.8 Hz), 6.58(1H,s), 6.74–6.76(1H,m), 7.00–7.52(13H,m), 8.42–8.45(3H,m), 10.23(1H,s)

EXAMPLE 230

N-[2-[3-(aminomethyl)phenoxy]phenyl]-N-[4-[(2-fluorobenzoyl)amino]butyl]-4-phenylbenzamide hydrochloride (1) A mixture of 5-[N-[2-[3-(tert-butoxycarbonylaminomethyl)phenoxy]-4-chlorophenyl]-N-(4-phenylbenzoyl)]aminopentanoic acid (2.5 g, 4 mmols), diphenylphosphorylazide (DPPA) (0.86 ml, 4 mmols), triethylamine (0.56 ml, 4 mmols) and N,N-dimethylformamide (10 ml) was stirred at room temperature for 1 hour. The reaction mixture was poured into water, and extracted with ethyl acetate. The extract was washed with water and brine, and then dried with anhydrous magnesium sulfate, and the solvent was evaporated away. Toluene (20 ml) was added to the residue, and the resulting mixture was stirred, while heated under reflux, for 1 hour. Next, benzyl alcohol was added to the reaction mixture, and further refluxed for 12 hours. This was cooled, then poured into water, and extracted with ethyl acetate. The extract was washed with water and brine, and then dried with anhydrous magnesium sulfate, and the solvent was evaporated away. The residue was purified through silica gel column chromatography to give an amorphous solid of tert-butyl 3-[2-[(4-phenylbenzoyl)[3-[[(benzyloxycarbonyl]amino]butyl]amino]-5-chlorophenoxy]benzylcarbamate (1.3 g, 45%).

Elemental Analysis for $C_{43}H_{44}N_3O_6Cl.1/2H_2O$:
Calcd.: C, 69.48; H, 6.10; N, 5.65
Found: C, 69.62; H, 6.04; N, 5.92
$^1$H-NMR (CDCl$_3$) δ: 1.42(9H,m), 1.63(4H,bs), 3.20–3.23(2H,m), 3.76–3.80(1H,m), 3.92–4.07(1H,m), 4.19(2H,s), 5.01(1H,bs), 5.07(2H,s), 5.10(1H,bs), 6.47(1H,d,J=7.2 Hz), 6.62(2H,d,J=16.0 Hz), 6.97–7.07(2H,m), 7.18–7.47(14H,m), 7.54–7.58(3H,m)

(2) 5% carbon-palladium (0.4 g) was added to a mixture of tert-butyl 3-[2-[(4-phenylbenzoyl)[3-[[(benzyloxycarbonyl]amino]butyl]amino]-5-chlorophenoxy]benzylcarbamate (0.66 g, 0.9 mmols) in ethyl acetate (10 ml) and tetrahydrofuran (10 ml). The resulting mixture was hydrogenated at room temperature under atmospheric pressure. The catalyst was removed through filtration, and the filtrate was concentrated under reduced pressure. The residue was dissolved in tetrahydrofuran (10 ml), to which were added 2-fluorobenzoyl chloride (0.15 ml, 1.2 mmols) and triethylamine (0.17 ml, 1.2 mmols). The resulting mixture was stirred at room temperature for 1 hour, then poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of N-[2-[3-(tert-butoxycarbonylaminomethyl)phenoxy]phenyl]-N-[4-[(2-fluorobenzoyl)amino]butyl]-4-phenylbenzamide (0.16 g, 25%).

Elemental Analysis for $C_{42}H_{42}N_3O_5F \cdot 1/2H_2O$:
Calcd.: C, 72.40; H, 6.22; N, 6.03
Found: C, 72.29; H, 6.16; N, 5.68
$^1$H-NMR (CDCl$_3$) δ: 1.42(9H,s), 1.75(4H,bs), 3.49(2H,bs), 3.88(1H,bs), 4.07(1H,bs), 4.17(1H,bs), 5.06(1H,bs), 6.49(1H,brd,J=7.4 Hz), 6.65(1H,s), 6.82(1H,bs), 6.98–7.56 (17H,m), 8.00–8.099(1H,m)

(3) A 4 N hydrochloric acid/ethyl acetate solution (5 ml) was added to an ethyl acetate (5 ml) solution of N-[2-[3-(tert-butoxycarbonylaminomethyl)phenoxy]phenyl]-N-[4-[(2-fluorobenzoyl)amino]butyl]-4-phenylbenzamide (0.13 g, 0.18 mmols), and stirred at room temperature for 1 hour. The reaction mixture was concentrated under reduced pressure. The solid precipitated was taken out through filtration, and washed with ethyl ether to give an amorphous solid of N-[2-[3-(aminomethyl)phenoxy]phenyl]-N-[4-[(2-fluorobenzoyl)amino]butyl]-4-phenylbenzamide hydrochloride (0.07 g, 64%).

Elemental Analysis for $C_{37}H_{35}N_3O_3ClF \cdot 1/2H_2O$:
Calcd.: C, 70.19; H, 5.73; N, 6.64
Found: C, 69.79; H, 5.55; N, 6.51
$^1$H-NMR (DMSO-d$_6$) δ: 1.69(4H,bs), 3.23(2H,bs), 3.80 (2H,bs), 3.99(2H,bs), 6.61–6.69(2H,m), 7.09–7.64(19H,m), 8.31(2H,bs)

EXAMPLE 231

N-[2-(2-fluorophenyl)ethyl]-2-[N'-[2-[3-(aminomethyl)phenoxy]-4-chlorophenyl]-N'-(4-phenylbenzoyl)]aminoacetamide hydrochloride (1) A mixture of 2-[N-[2-[3-(tert-butoxycarbonylaminomethyl)phenoxy]-4-chlorophenyl]-N-(4-phenylbenzoyl)]aminobutyric acid (0.59 g, 1 mmol), 2-(2-fluorophenyl)ethylamine (0.16 ml, 1.2 mmols), diethyl cyanophosphate (0.17 ml, 1.2 mmols), triethylamine (0.17 ml, 1.2 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-[2-(2-fluorophenyl)ethyl]-2-[N'-[2-[3-(aminomethyl)phenoxy]-4-chlorophenyl]-N'-(4-phenylbenzoyl)]aminoacetamide (0.57 g, 81%).

Elemental Analysis for $C_{41}H_{39}N_3O_5ClF$:
Calcd.: C, 69.53; H, 5.55; N, 5.93
Found: C, 69.36; H, 5.62; N, 5.94
$^1$H-NMR (CDCl$_3$) δ: 1.43(9H,s), 2.84–2.89(2H,m), 3.48–3.56(2H,m), 4.18(2H,d,J=4.8 Hz), 4.47(2H,d,J=3.0 Hz), 4.86(1H,bs), 6.32(1H,brd,J=7.6 Hz), 6.47–6.51(2H,m), 6.90–7.24(9H,m), 7.33–7.49(6H,m), 7.54–7.60(3H,m)

(2) A 4 N hydrochloric acid/ethyl acetate solution (5 ml) was added to an ethyl acetate (5 ml) solution of N-[2-(2-fluorophenyl)ethyl]-2-[N'-[2-[3-(aminomethyl)phenoxy]-4-chlorophenyl]-N'-(4-phenylbenzoyl)]aminoacetamide (0.5 g, 0.7 mmols), and stirred at room temperature for 1 hour. The reaction mixture was concentrated under reduced pressure. The solid precipitated was taken out through filtration, and washed with ethyl ether to give N-[2-(2-fluorophenyl)ethyl]-2-[N'-[2-[3-(aminomethyl)phenoxy]-4-chlorophenyl]-N'-(4-phenylbenzoyl)]aminoacetamide hydrochloride (0.4 g, 89%).

Elemental Analysis for $C_{36}H_{32}N_3O_3Cl_2F \cdot H_2O$:
Calcd.: C, 66.62; H, 5.05; N, 6.47
Found: C, 66.66; H, 5.06; N, 6.45
$^1$H-NMR (DMSO-d$_6$) δ: 2.73–2.81(2H,m), 3.31–3.39(2H,m), 3.85(1H,d,J=16.3 Hz), 4.02(2H,s), 4.70 (1H,d,J=16.3 Hz), 6.68(1H,s), 6.77–6.81(2H,m), 7.12–7.69 (18H,m), 8.26(1H,bs), 8.42(2H,bs)

EXAMPLE 232

N-[3-(3-indolyl)-2-propyl]-2-[N'-[2-[3-(aminomethyl)phenoxy]-4-chlorophenyl]-N'-(4-phenylbenzoyl)]aminoacetamide hydrochloride (1) In the same manner as in (1) in Example 231, N-[3-(3-indolyl)-2-propyl]-2-[N'-[2-[3-(tert-butoxycarbonylaminomethyl)phenoxy]-4-chlorophenyl]-N'-(4-phenylbenzoyl)]aminoacetamide was obtained from 2-[N-[2-[[3-(tert-butoxycarbonylaminomethyl)phenoxy]-4-chlorophenyl]-N-(4-phenylbenzoyl)]aminoacetic acid and α-methyltryptamine.

Elemental Analysis for $C_{44}H_{44}N_4O_5ClF \cdot H_2O$:
Calcd.: C, 69.42; H, 5.96; N, 7.36
Found: C, 69.69; H, 5.90; N, 7.08
$^1$H-NMR (CDCl$_3$) δ: 1.17(3H,d,J=6.0 Hz), 1.44(9H,s), 2.95(2H,d,J=5.4 Hz), 4.07–4.17(2H,m), 4.38–4.44(3H,m), 4.79(1H,bs), 6.39–6.49(3H,m), 6.74(1H,bs), 6.85–7.11(8H, m), 7.28–7.58(1H,m), 8.31(1H,bs)

(2) In the same manner as in (2) in Example 231, an amorphous solid of N-[3-(3-indolyl)-2-propyl]-2-[N'-[2-[3-(1-aminomethyl)phenoxy]-4-chlorophenyl]-N'-(4-phenylbenzoyl)]aminoacetamide hydrochloride was obtained from N-[3-(3-indolyl)-2-propyl]-2-[N'-[2-[3-(tert-butoxycarbonylaminomethyl)phenoxy]-4-chlorophenyl]-N'-(4-phenylbenzoyl)]aminoacetamide.

Elemental Analysis for $C_{39}H_{36}N_4O_3Cl_2F \cdot 1/2H_2O$:
Calcd.: C, 68.02; H, 5.42; N, 8.14
Found: C, 67.98; H, 5.54; N, 8.08
$^1$H-NMR (DMSO-d$_6$) δ: 1.06(3H,d,J=7.0 Hz), 2.65–2.95 (2H,m), 3.67–3.81(1H,m), 4.02(2H,s), 4.03–4.13(1H,m), 4.74(1H,d,J=14.6 Hz), 6.68–6.76(2H,m), 6.93–7.11(6H,m), 7.32–7.68(13H,m), 8.02–8.06(1H,m), 8.50(2H,bs)

EXAMPLE 233

N-[[4-(2-methoxyphenyl)-1-piperazinyl]carbonylmethyl]-N-[2-[3-(aminomethyl)phenoxy]-4-chlorophenyl]-4-phenylbenzamide dihydrochloride (1) In the same manner as in (1) in Example 231, an amorphous solid of N-[[4-(2-methoxyphenyl)-1-piperazinyl]carbonylmethyl]-N-[2-[3-(tert-butoxycarbonylaminomethyl)phenoxy]-4-chlorophenyl]-4-phenylbenzamide was obtained from 2-N-[2-[3-(tert-butoxycarbonylaminomethyl) phenoxy]-4-chlorophenyl]-N-(4-phenylbenzoyl)]aminoacetic acid and 4-(2-methoxyphenyl)piperazine.

Elemental Analysis for $C_{44}H_{45}N_4O_6ClF \cdot 1/2H_2O$:
Calcd.: C, 68.60; H, 6.02; N, 7.27
Found: C, 68.41; H, 5.99; N, 7.04
$^1$H-NMR (CDCl$_3$) δ: 1.44(9H,s), 3.07(4H,bs), 3.74(4H, bs), 3.88(3H,s), 4.03(1H,d,J=16.6 Hz), 4.27(2H,d,J=6.2 Hz), 4.88(1H,bs), 5.33(1H,d,J=16.6 Hz), 6.64–6.66(2H,m), 6.79(1H,s), 6.87–7.11(6H,m), 7.24–7.58(11H,m)

(2) In the same manner as in (2) in Example 231, an amorphous solid of N-[[4-(2-methoxyphenyl)-1-piperazinyl]carbonylmethyl]-N-[2-[3-(aminomethyl)phenoxy]-4-chlorophenyl]-4-phenylbenzamide dihydrochloride was obtained from N-[[4-(2-methoxyphenyl)-1-piperazinyl]carbonylmethyl]-N-[2-[3-(tert-butoxycarbonylaminomethyl)phenoxy]-4-chlorophenyl]-4-phenylbenzamide.

Elemental Analysis for $C_{39}H_{39}N_4O_4Cl_3 \cdot 1/2H_2O$:
Calcd.: C, 63.03; H, 5.43; N, 7.54
Found: C, 63.15; H, 5.42; N, 7.45
$^1$H-NMR (DMSO-d$_6$) δ: 3.23–3.46(4H,m), 3.80–3.90(7H,m), 4.04(2H,s), 4.33(1H,d,J=16.4 Hz), 5.15(1H,d,J=16.4 Hz), 6.68(1H,s), 6.84–6.88(1H,m), 6.98–7.06(1H,m), 7.17–7.68(17H,m), 8.61(2H,bs)

EXAMPLE 234

N-(2-fluorobenzyl)-4-[N'-[2-[3-(aminomethyl)phenoxy]-4-chlorophenyl]-N'-[[1-(benzyloxy)carbonyl-4-piperidinyl]carbonyl]]aminobutylamide hydrochloride (1) A diethyl ether (50 ml) solution of benzyl chloroformate (36 g, 0.21 mols) was dropwise added to an aqueous solution (200 ml) of isonipecotic acid (25 g, 0.19 mols) and sodium hydrogencarbonate (49 g, 0.58 mols) with stirring at room temperature. After the addition, this was further stirred at room temperature for 15 hours. The reaction mixture was acidified with concentrated hydrochloric acid added thereto, and then extracted with ethyl acetate. The extract was washed with brine, then dried with anhydrous magnesium sulfate, and concentrated under reduced pressure. The residue was crystallized from isopropyl ether/hexane, and taken out through filtration. A colorless crystal of N-benzyloxycarbonylisonipecotic acid (36 g, 71%) was obtained.
m.p. 79–80° C.
$^1$H-NMR (CDCl$_3$) δ: 1.57–1.77(2H,m), 1.90–1.96(2H, m), 2.45–2.59(1H,m), 3.89–3.03(2H,m), 4.06–4.13(2H,m), 5.13(2H,s), 7.30–7.39(5H,m)

A tetrahydrofuran (100 ml) solution of N-benzyloxycarbonylisonipecotic acid (7.9 g, 30 mmols), oxalyl chloride (5.0 g, 39 mmols) and N,N-dimethylformamide (0.5 ml) was stirred at room temperature for 1 hour. The reaction mixture was concentrated under reduced pressure, to which were added ethyl 4-[N-2-[3-(tert-butoxycarbonylaminomethyl)phenoxy]-4-chlorophenyl]]aminobutyrate (6.9 g, 15 mmols), 4-dimethylaminopyridine (3.7 g, 30 mmols) and tetrahydrofuran (50 ml). The resulting mixture was stirred at room temperature for 12 hours. This was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an oil of ethyl 4-N-[[1-(benzyloxy)carbonyl-4-piperidinyl]carbonyl]-N-[2-[3-(tert-butoxycarbonylaminomethyl)phenoxy]-4-chlorophenyl]]aminobutyrate (7.4 g, 70%).

Elemental Analysis for $C_{38}H_{46}N_3O_8Cl \cdot 1/2H_2O$:
Calcd.: C, 63.63; H, 6.60; N, 5.86
Found: C, 63.86; H, 6.70; N, 5.99
$^1$H-NMR (CDCl$_3$) δ: 1.20(3H,t,J=7.0 Hz), 1.43(9H,s), 1.60–1.90(6H,m), 2.29–2.37(3H,m), 2.59–2.65(1H,m), 3.59–3.80(2H,m), 4.07(2H,d,J=7.0 Hz), 4.09–4.17(2H,m), 4.30(2H,d,J=5.8 Hz), 5.05(1H,bs), 5.10(2H,s), 6.83–6.92(3H,m), 7.08–7.17(3H,m), 7.27–7.38(6H,m)

(2) Aqueous 1 N sodium hydroxide solution (5 ml, 5 mmols) was added to a solution of ethyl 4-N-[[1-(benzyloxy)carbonyl-4-piperidinyl]carbonyl]-N-[2-[3-(tert-butoxycarbonylaminomethyl)phenoxy]-4-chlorophenyl]]aminobutyrate (1.8 g, 2.5 mmols) in tetrahydrofuran (10 ml) and ethanol (10 ml). The resulting mixture was stirred at room temperature for 2 hours. This was poured into water, then acidified with 1 N hydrochloric acid added thereto, and extracted with ethyl acetate. The extract was washed with water, and then dried with anhydrous magnesium sulfate. This was concentrated under reduced pressure to give an amorphous solid of 4-N-[[1-(benzyloxy)carbonyl-4-piperidinyl]carbonyl]-N-[2-[3-(tert-butoxycarbonylaminomethyl)phenoxy]-4-chlorophenyl]]aminobutyric acid (1.7 g, 98%).

Elemental Analysis for $C_{36}H_{42}N_3O_8Cl \cdot 1/2H_2O$:
Calcd.: C, 62.74; H, 6.29, N, 6.10
Found: C, 62.72; H, 6.30; N, 6.19
$^1$H-NMR (CDCl$_3$) δ: 1.43(9H,s), 1.65–1.85(6H,m), 2.34–2.41(3H,m), 2.64(1H,bs), 3.33(1H,bs), 3.73–3.81(2H, m), 3.95(1H,bs), 4.21(2H,bs), 5.11(2H,s), 5.19(1H,bs), 6.68(1H,bs), 6,87–6.91(2H,m), 7.04–7.15(3H,m), 7.29–7.38(6H,m)

(3) A mixture of 4-N-[[1-(benzyloxy)carbonyl-4-piperidinyl]carbonyl]-N-[2-[3-(tert-butoxycarbonylaminomethyl)phenoxy]-4-chlorophenyl]]aminobutyric acid (0.68 g, 1 mmol), 2-fluorobenzylamine (0.14 ml, 1.2 mmols), diethyl cyanophosphate (0.17 ml, 1.2 mmols), triethylamine (0.17 ml, 1.2 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[[1-(benzyloxy)carbonyl-4-piperidinyl]carbonyl]-N'-[2-[3-(tert-butoxycarbonylaminomethyl)phenoxy]-4-chlorophenyl]]aminobutylamide (0.72 g, 92%).

Elemental Analysis for $C_{43}H_{48}N_4O_7ClF \cdot 1/2H_2O$:
Calcd.: C, 64.86; H, 6.20; H, 7.04
Found: C, 65.06; H, 6.04; N, 7.16
$^1$H-NMR (CDCl$_3$) δ: 1.41(9H,s), 1.58–1.86(8H,m), 2.13–2.33(2H,m), 2.59–2.66(1H,m), 3.59–3.78(2H,m), 4.07–4.17(2H,m), 4.28(2H,d,J=6.4 Hz), 4.45(2H,d,J=5.8 Hz), 5.10(1H,bs), 6.66(1H,bs), 6.83–6.90(3H,m), 6.97–7.37(13H,m)

(4) A 4 N hydrochloric acid/ethyl acetate solution (5 ml) was added to an ethyl acetate (5 ml) solution of N-(2-fluorobenzyl)-4-[N'-[[1-(benzyloxy)carbonyl-4-piperidinyl]carbonyl]-N'-[2-[3-(tert-butoxycarbonylaminomethyl)phenoxy]-4-chlorophenyl]]aminobutylamide (0.63 g, 0.8 mmols), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[[(1-benzyloxy)carbonyl-4-piperidinyl]carbonyl]]aminobutylamide hydrochloride (0.52 g, 91%).

Elemental Analysis for $C_{38}H_{41}N_4O_5Cl_2F \cdot 1/2H_2O$:
Calcd.: C, 62.30; H, 5.78; N, 7.65
Found: C, 62.09; H, 5.73; N, 7.97

¹H-NMR (DMSO-d₆) δ: 1.44–1.73(5H,m), 2.17(2H,t, J=7.3 Hz), 2.36(1H,bs), 2.69(1H,bs), 3.40–3.50(1H,m), 3.65–3.75(1H,m), 3.92–4.05(2H,m), 4.27(2H,s), 4.48(2H,s), 5.05(2H,s), 6.91(1H,d,J=2.2 Hz), 6.99–7.18(2H,m), 7.25–7.54(13H,m), 8.38(1H,bs), 8.52(2H,bs)

EXAMPLE 235

N-(2-fluorobenzyl)-4-[N'-[2-[3-(aminomethyl)phenoxy]phenyl]-N'-[[1-benzoyl-4-piperidinyl]carbonyl]]aminobutylamide hydrochloride (1) 5% carbon-palladium (0.3 g) was added to a solution of ethyl 4-[N-[[1-(benzyloxy)carbonyl-4-piperidinyl]carbonyl]-N-[2-[3-(tert-butoxycarbonylaminomethyl)phenoxy]-4-chlorophenyl]]aminobutyrate (1.42 g, 2 mmols) in ethyl acetate (10 ml) and tetrahydrofuran (10 ml). The resulting mixture was hydrogenated at room temperature under atmospheric pressure. The catalyst was removed through filtration, and the filtrate was concentrated under reduced pressure. The residue was dissolved in tetrahydrofuran (10 ml), to which were added benzoyl chloride (0.35 ml, 3 mmols) and triethylamine (0.42 ml, 3 mmols). The resulting mixture was stirred at room temperature for 1 hour. This was poured into water, and extracted with ethyl acetate. The extract was washed with brine, and then dried with anhydrous magnesium sulfate. This was concentrated under reduced pressure, and the residue was purified through silica gel column chromatography to give an amorphous solid of ethyl 4-[N-[(1-benzoyl-4-piperidinyl)carbonyl]-N-[2-[3-(tert-butoxycarbonylaminomethyl)phenoxy]phenyl]]aminobutyrate (0.54 g, 40%).

Elemental Analysis for C₃₇H₄₅N₃O₇.1/2H₂O:
Calcd.: C, 68.08; H, 7.10; N, 6.44
Found: C, 68.02; H, 6.97; N, 6.36
¹H-NMR (CDCl₃) δ: 1.20(3H,t,J=7.2 Hz), 1.42(9H,s), 1.66–1.91(6H,m), 2.33(2H,t,J=7.6 Hz), 2.37–2.85(3H,m), 3.64–3.76(3H,m), 4.07(2H,d,J=7.2 Hz), 4.28(2H,d,J=5.4 Hz), 4.61(1H,bs), 5.05(1H,bs), 6.83–7.41(11H,m)

(2) In the same manner as in (2) in Example 234, an amorphous solid of 4-[N-[(1-benzoyl-4-piperidinyl)carbonyl]-N-[2-[3-(tert-butoxycarbonylaminomethyl)phenoxy]phenyl]]aminobutyric acid was obtained from ethyl 4-[N-[(1-benzoyl-4-piperidinyl)carbonyl]-N-[2-[3-(tert-butoxycarbonylaminomethyl)phenoxy]phenyl]]aminobutyrate.

Elemental Analysis for C₃₅H₄₁N₃O₇.H₂O:
Calcd.: C, 66.33; H, 6.84; N, 6.63
Found: C, 66.46; H, 6.80; N, 6.49
¹H-NMR (CDCl₃) δ: 1.42(9H,s), 1.81(6H,bs), 2.34–2.47(3H,m), 2.71(2H,bs), 3.32(1H,bs), 3.72(2H,bs), 4.26(2H,bs), 4.63(1H,bs), 5.15(1H,bs), 6.85–6.99(3H,m), 7.17–7.42(8H,m)

(3) In the same manner as in (3) in Example 234, an amorphous solid of N-(2-fluorobenzyl)-4-[N'-[(1-benzoyl-4-piperidinyl)carbonyl]-N'-[2-[3-(tert-butoxycarbonylaminomethyl)phenoxy]phenyl]]aminobutylamide was obtained from 4-[N-[(1-benzoyl-4-piperidinyl)carbonyl]-N-[2-[3-(tert-butoxycarbonylaminomethyl)phenoxy]phenyl]]aminobutyric acid.

Elemental Analysis for C₄₂H₄₇N₄O₆F.H₂O:
Calcd.: C, 68.09; H, 6.67; N, 7.56
Found: C, 67.81; H, 6.45; N, 7.75
¹H-NMR (CDCl₃) δ: 1.40(9H,s), 1.52–1.94(6H,m), 2.15–2.28(2H,m), 2.43–2.52(2H,m), 2.73(1H,bs), 3.61–3.82(2H,m), 4.04–4.19(1H,m), 4.25(2H,d,J=4.8 Hz), 4.46(2H,d, J=5.6 Hz), 4.59(1H,bs), 5.16(1H,bs), 6.75–7.41(15H,m)

(4) In the same manner as in (4) in Example 234, an amorphous solid of N-(2-fluorobenzyl)-4-[N'-[2-[3-(aminomethyl)phenoxy]phenyl]-N'-[[1-benzoyl-4-piperidinyl]carbonyl]]aminobutylamide hydrochloride was obtained from N-(2-fluorobenzyl)-4-[N'-[(1-benzoyl-4-piperidinyl)carbonyl]-N'-[2-[3-(tert-butoxycarbonylaminomethyl)phenoxy]phenyl]]aminobutylamide.

Elemental Analysis for C₃₇H₄₀N₄O₄ClF.H₂O:
Calcd.: C, 65.62; H, 6.25; N, 8.27
Found: C, 65.35; H, 5.98; N, 8.46
¹H-NMR (DMSO-d₆) δ: 1.28–1.76(6H,m), 2.16(2H,t, J=8.0 Hz), 2.23(1H,bs), 2.78(1H,bs), 3.28–3.46(1H,m), 3.67–3.74(2H,m), 4.01(2H,s), 4.26(2H,s), 4.35(1H,bs), 6.98–7.44(16H,m), 8.35(2H,bs)

EXAMPLE 236

N-(2-fluorobenzyl)-4-[N'-[2-[3-(aminomethyl)phenoxy]-4-chlorophenyl]-N'-[[1-benzenesulfonyl-4-piperidinyl]carbonyl]]aminobutylamide hydrochloride (1) 5% carbon-palladium (0.3 g) was added to a solution of ethyl 4-[N-[[1-(benzyloxy)carbonyl-4-piperidinyl]carbonyl]-N-[2-[3-(tert-butoxycarbonylaminomethyl)phenoxy]-4-chlorophenyl]]aminobutyrate (1.42 g, 2 mmols) in ethyl acetate (10 ml) and tetrahydrofuran (10 ml). The resulting mixture was hydrogenated at room temperature under atmospheric pressure. The catalyst was removed through filtration, and the filtrate was concentrated under reduced pressure. The residue was dissolved in tetrahydrofuran (10 ml), to which were added benzenesulfonyl chloride (0.38 ml, 3 mmols) and triethylamine (0.42 ml, 3 mmols). The resulting mixture was stirred at room temperature for 1 hour. This was poured into water, and extracted with ethyl acetate. The extract was washed with brine, and then dried with anhydrous magnesium sulfate. This was concentrated under reduced pressure, and the residue was purified through silica gel column chromatography to give an amorphous solid of ethyl 4-[N-[(1-benzenesulfonyl-4-piperidinyl)carbonyl]-N-[2-[3-(tert-butoxycarbonylaminomethyl)phenoxy]-4-chlorophenyl]]aminobutyrate (1.2 g, 81%).

Elemental Analysis for C₃₆H₄₄N₃O₈ClS:
Calcd.: C, 60.54; H, 6.21; N, 5.88
Found: C, 60.53; H, 6.20; N, 5.99
¹H-NMR (CDCl₃) δ: 1.20(3H,t,J=7.2 Hz), 1.44(9H,s), 1.61–1.86(6H,m), 2.07–2.34(5H,m), 3.57–3.78(4H,m), 4.06 (2H,d,J=7.2 Hz), 4.28(2H,d,J=5.8 Hz), 5.06(1H,bs), 6.77–6.87(3H,m), 7.04–7.16(3H,m), 7.28–7.36(1H,m), 7.49–7.60(3H,m), 7.72–7.77(2H,m)

(2) In the same manner as in (2) in Example 234, an amorphous solid of 4-[N-[(1-benzenesulfonyl-4-piperidinyl)carbonyl]-N-[2-[3-(tert-butoxycarbonylaminomethyl)phenoxy]4-chlorophenyl]]aminobutyric acid was obtained from ethyl 4-[N-[(1-benzenesulfonyl-4-piperidinyl)carbonyl]-N-[2-[3-(tert-butoxycarbonylaminomethyl)phenoxy]-4-chlorophenyl]]aminobutyrate.

Elemental Analysis for C₃₄H₄₀N₃O₇ClS.1/2H₂O:
Calcd.: C, 58.74; H, 5.94; N, 6.04
Found: C, 68.81; H, 5.78; N, 5.74
¹H-NMR (CDCl₃) δ: 1.43(9H,s), 1.69–1.98(6H,m), 2.11–2.35(5H,m), 3.25(1H,bs), 3.72–3.78(2H,m), 4.05(2H, bs), 4.24(2H,bs), 5.11(1H,bs), 6.84(2H,d,J=8.0 Hz), 6.86–7.20(5H,m), 7.29–7.37(1H,m), 7.47–7.63(3H,m), 7.71–7.76(2H,m)

(3) In the same manner as in (3) in Example 234, an amorphous solid of N-(2-fluorobenzyl)-4-[N'-[(1-benzenesulfonyl-4-piperidinyl)carbonyl]-N'-[2-[3-(tert-butoxycarbonylaminomethyl)phenoxy]phenyl]]aminobutylamide was obtained from 4-[N-[(1-benzenesulfonyl-4-piperidinyl)carbonyl]-N-[2-[3-(tert-butoxycarbonylaminomethyl)phenoxy]4-chlorophenyl]]aminobutyric acid.

Elemental Analysis for $C_{41}H_{46}N_4O_7ClFS.1/2H_2O$:
Calcd.: C, 61.37; H, 5.90; N, 6.98
Found: C, 61.48; H, 5.87; N, 7.12
$^1$H-NMR (CDCl$_3$) δ: 1.43(9H,s), 1.63–1.96(6H,m), 2.02–2.27(5H,m), 3.59–3.80(4H,m), 4.25(2H,d,J=5.8 Hz), 4.44(2H,d,J=5.6 Hz), 5.17(1H,bs), 6.58(1H,bs), 6.76–6.85 (3H,m), 6.98–7.12(5H,m), 7.16–7.34(3H,m), 7.47–7.59(3H, m), 7.71–7.75(2H,m)

(4) In the same manner as in (4) in Example 234, an amorphous solid of N-(2-fluorobenzyl)-4-[N'-[2-[3-(aminomethyl)phenoxy]-4-chlorophenyl]-N'-[(1-benzenesulfonyl-4-piperidinyl)carbonyl]]aminobutylamide hydrochloride was obtained from N-(2-fluorobenzyl)-4-[N'-[(1-benzenesulfonyl-4-piperidinyl)carbonyl]-N'-[2-[3-(tert-butoxycarbonylaminomethyl)phenoxy]-4-chlorophenyl]] aminobutylamide.

Elemental Analysis for $C_{36}H_{39}N_4O_5Cl_2FS.1/2H_2O$:
Calcd.: C, 58.53; H, 5.46; N, 7.58
Found: C, 58.79; H, 5.64; N, 7.77
$^1$H-NMR (DMSO-d$_6$) δ: 1.46–1.68(6H,m), 2.11–2.18(5H, m), 3.32–3.73(4H,m), 4.01(2H,s), 4.36(2H,s), 6.84(1H,d, J=2.2 Hz), 7.04–7.59(12H,m), 7.63–7.71(3H,m), 8.32–8.47 (3H,m)

EXAMPLE 237

N-(2-fluorobenzyl)-4-[N'-[2-[3-(aminomethyl)phenoxy]-4-chlorophenyl]-N'-[(4-biphenyl)carbamoyl]] aminobutylamide hydrochloride (1) A mixture of 4-phenylbenzoic acid (2.0 g, 10 mmols), diphenylphosphorylazide (DPPA) (4.1 g, 15 mmols), triethylamine (1.2 g, 12 mmols) and N,N-dimethylformamide (5 ml) was stirred at room temperature for 1 hour. The reaction mixture was poured into water, and extracted with ethyl acetate. The extract was washed with water and brine, and then dried with anhydrous magnesium sulfate, and the solvent was evaporated away. Toluene (20 ml) was added to the residue, and the resulting mixture was stirred, while heated under reflux, for 3 hours. To this were added ethyl 4-[N-[2-[3-(tert-butoxycarbonylaminomethyl)phenoxy]-4-chlorophenyl]]aminobutyrate (2.31 g, 5 mmols) and 4-dimethylaminopyridine (1.22 g, 10 mmols), and the resulting mixture was stirred, while heated under reflux, for 5 hours. This was poured into water, and extracted with ethyl acetate. The extract was washed with aqueous 1 N sodium hydroxide solution and brine, and then dried with anhydrous magnesium sulfate. This was concentrated under reduced pressure, and the residue was purified through silica gel column chromatography to give an amorphous solid of ethyl 4-[N-[(4-biphenyl)carbamoyl]-N-[2-[3-(tert-butoxycarbonylaminomethyl)phenoxy]-4-chlorophenyl]]aminobutyrate (2.2 g, 67%).

Elemental Analysis for $C_{37}H_{40}N_3O_6Cl$:
Calcd.: C, 67.52; H, 6.13; N, 6.38
Found: C, 67.30; H, 5.96; H, 6.57
$^1$H-NMR (CDCl$_3$) δ: 1.22(3H,t,J=7.1 Hz), 1.42(9H,s), 1.84–1.98(2H,m), 2.41(2H,t,J=7.5 Hz), 3.74(2H,t,J=7.0 Hz), 4.10(2H,q,J=7.1 Hz), 4.24(2H,d,J=4.4 Hz), 4.93(1H, bs), 6.45(1H,s), 6.89–6.95(3H,m), 7.08(1H,d,J=7.6 Hz), 7.17(1H,dd,J=2.2,8.4 Hz), 7.29–7.58(11H,m)

(2) Aqueous 1 N sodium hydroxide solution (6 ml, 6 mmols) was added to a solution of ethyl 4-[N-[(4-biphenyl) carbamoyl]-N-[2-[3-(tert-butoxycarbonylaminomethyl)phenoxy]-4-chlorophenyl]]aminobutyrate (2.0 g, 3 mmols) in tetrahydrofuran (5 ml) and ethanol (5 ml). The resulting mixture was stirred at room temperature for 2 hours. The reaction mixture was poured into water, acidified with 1 N hydrochloric acid added thereto, and extracted with ethyl acetate. The extract was washed with water, and then dried with anhydrous magnesium sulfate. This was concentrated under reduced pressure to give an amorphous solid of 4-[N-[(4-biphenyl)carbamoyl]-N-[2-[3-(tert-butoxycarbonylaminomethyl)phenoxy]-4-chlorophenyl]]aminobutyric acid (1.85 g, 98%).

Elemental Analysis for $C_{35}H_{36}N_3O_6Cl.1/2H_2O$:
Calcd.: C, 65.77; H, 5.83; N, 6.57
Found: C, 65.83; H, 5.82; N, 6.52
$^1$H-NMR (CDCl$_3$) δ: 1.43(9H,s), 1.82–1.96(2H,m), 2.44 (2H,bs), 3.78(2H,bs), 4.24(2H,d,J=4.4 Hz), 5.09(1H,bs), 6.35(1H,bs), 6.89–7.05(3H,m), 7.18(1H,dd,J=2.2,8.6 Hz), 7.28–7.58(13H,m)

(3) A mixture of 4-[N-[(4-biphenyl)carbamoyl]-N-[2-[3-(tert-butoxycarbonylaminomethyl)phenoxy]-4-chlorophenyl]]aminobutyric acid (0.95 g, 1.5 mmols), 2-fluorobenzylamine (0.21 ml, 1.8 mmols), diethyl cyanophosphate (0.25 ml, 1.8 mmols), triethylamine (0.25 ml, 1.8 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[(4-biphenyl)carbamoyl]-N'-[2-[3-(tert-butoxycarbonylaminomethyl)phenoxy]-4-chlorophenyl]]aminobutylamide (0.82 g, 75%).

Elemental Analysis for $C_{42}H_{42}N_4O_5ClF.1/2H_2O$:
Calcd.: C, 67.60; H, 5.81; N, 7.51
Found: C, 67.94; H, 5.67; N, 7.73
$^1$H-NMR (CDCl$_3$) δ: 1.41(9H,s), 1.85–1.95(2H,m), 2.34 (2H,t,J=6.5 Hz), 3.77(2H,t,J=6.6 Hz), 4.23(2H,d,J=5.8 Hz), 4.48(2H,d,J=6.0 Hz), 5.00(1H,bs), 6.68(1H,bs), 6.76(1H, bs), 6.87–6.98(2H,m), 7.01–7.58(18H,m)

(4) A 4 N hydrochloric acid/ethyl acetate solution (5 ml) was added to an ethyl acetate (5 ml) solution of N-(2-fluorobenzyl)-4-[N'-[(4-biphenyl)carbamoyl]-N'-[2-[3-(tert-butoxycarbonylaminomethyl)phenoxy]-4-chlorophenyl]] aminobutylamide (0.74 g, 1 mmol), and stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[2-[3-(aminomethyl)phenoxy]-4-chlorophenyl]-N'-[(4-biphenyl) carbamoyl]]aminobutylamide hydrochloride (0.61 g, 91%).

Elemental Analysis for $C_{37}H_{35}N_4O_3Cl_2F.1/2H_2O$:
Calcd.: C, 65.10; H, 5.32; N, 8.21
Found: C, 65.06; H, 5.27; N, 8.10
$^1$H-NMR (DMSO-d$_6$) δ: 1.70–1.79(2H,m), 2.20–2.27(2H,m), 3.62(2H,s), 3.97(2H,s), 4.30(2H,s), 6.92 (1H,d,J=2.2 Hz), 7.08–7.19(3H,m), 7.25–7.52(15H,m), 7.61 (2H,d,J=7.2 Hz), 8.32–8.52(3H,m)

EXAMPLE 238

N-(2-fluorobenzyl)-4-[N'-[2-[3-(aminomethyl)phenoxy]-4-chlorophenyl]-N'-[[4-(2-methoxyphenyl)-1-piperazinyl]acetyl]]aminobutylamide trihydrochloride (1) In the same manner as in (2) in Example 194, an amorphous solid of N-(2-fluorobenzyl)-4-[N'-[2-[3-(tert-butoxycarbonylaminomethyl)phenoxy]-4-chlorophenyl]-N'-[[4-(2-methoxyphenyl)-1-piperazinyl]acetyl]aminobutylamide was obtained from N-(2-fluorobenzyl)-4-[N'-[2-[3-(tert-butoxycarbonylaminomethyl)phenoxy]-4-chlorophenyl]-N'-chloroacetyl]aminobutylamide and 4-(2-methoxyphenyl)piperazine.

Elemental Analysis for $C_{42}H_{49}N_5O_6ClF.1/2H_2O$:
Calcd.: C, 64.40; H, 6.43; N, 8.94
Found: C, 64.45; H, 6.25; N, 8.94
$^1$H-NMR (CDCl$_3$) δ: 1.43(9H,s), 1.81–1.85(4H,m), 2.23–2.28(2H,m), 2.57–2.72(4H,m), 3.05(3H,s), 3.06–3.08 (2H,m), 3.68–3.78(2H,m), 3.84(2H,s), 4.29(2H,d,J=6.0 Hz), 4.47(2H,d,J=5.8 Hz), 5.16(1H,bs), 6.83–7.38(16H,m)

(2) In the same manner as in (3) in Example 194, an amorphous solid of N-(2-fluorobenzyl)-4-[N'-[2-[3-(aminomethyl)phenoxy]-4-chlorophenyl]-N'-[[4-(2-methoxyphenyl)-1-piperazinyl]acetyl]aminobutylamide trihydrochloride was obtained from N-(2-fluorobenzyl)-4-[N'-[2-[3-(tert-butoxycarbonylaminomethyl)phenoxy]-4-chlorophenyl]-N'-[[4-(2-methoxyphenyl)-1-piperazinyl]acetyl]aminobutylamide.

Elemental Analysis for $C_{37}H_{44}N_5O_4Cl_4F.1/2H_2O$:
Calcd.: C, 56.07; H, 5.72; N, 8.84
Found: C, 56.22; H, 5.74; N, 8.85
$^1$H-NMR (DMSO-d$_6$) δ: 1.76(2H,t,J=7.0 Hz), 2.26(2H,t, J=7.5 Hz), 3.11–3.63(11H,m), 3.79(2H,s), 3.86–3.97(2H, m), 4.05(2H,s), 4.27(2H,s), 6.88–7.71(8H,m), 7.27–7.54(6H,m), 7.65(1H,d,J=8.4 Hz), 8.54(1H,bs), 8.73 (2H,bs)

EXAMPLE 239

N-(2-fluorobenzyl)-4-[N'-[2-[3-(aminomethyl)phenoxy]-4-chlorophenyl]-N'-[(3,4-dihydro-1H-isoquinolyl)acetyl]]aminobutylamide dihydrochloride (1) In the same manner as in (2) in Example 194, an amorphous solid of N-(2-fluorobenzyl)-4-[N'-[2-[3-(tert-butoxycarbonylaminomethyl)phenoxy]-4-chlorophenyl]-N'-[(3,4-dihydro-1H-isoquinolyl)acetyl]]aminobutylamide was obtained from N-(2-fluorobenzyl)-4-[N'-[2-[3-(tert-butoxycarbonylaminomethyl)phenoxy]-4-chlorophenyl]-N'-chloroacetyl]aminobutylamide and 3,4-dihydro-1H-isoquinoline.

Elemental Analysis for $C_{40}H_{44}N_4O_5ClF.1/2H_2O$:
Calcd.: C, 66.33; H, 6.26; N, 7.74
Found: C, 66.45; H, 5.96; N, 7.78
$^1$H-NMR (CDCl$_3$) δ: 1.43(9H,s), 1.78–1.89(2H,m), 2.23–2.36(2H,m), 2.72–2.88(4H,m), 3.18(2H,d,J=1.6 Hz), 3.67(2H,s), 3.72–3.78(2H,m), 4.25(2H,d,J=6.2 Hz), 4.46 (2H,d,J=5.8 Hz), 5.08(1H,bs), 6.81–6.84(3H,m), 6.93–7.34 (12H,m)

(2) In the same manner as in (3) in Example 194, an amorphous solid of N-(2-fluorobenzyl)-4-[N'-[2-[3-(aminomethyl)phenoxy]-4-chlorophenyl]-N'-[(3,4-dihydro-1H-isoquinolyl)acetyl]]aminobutylamide dihydrochloride was obtained from N-(2-fluorobenzyl)-4-[N'-[2-[3-(tert-butoxycarbonylaminomethyl)phenoxy]-4-chlorophenyl]-N'-[(3,4-dihydro-1H-isoquinolyl)acetyl]]aminobutylamide.

Elemental Analysis for $C_{35}H_{38}N_4O_3Cl_3F.1/2H_2O$:
Calcd.: C, 60.31; H, 5.64; N, 8.04
Found: C, 60.31; H, 5.83; N, 8.30
$^1$H-NMR (DMSO-d$_6$) δ: 1.73–1.80(2H,m), 2.26(2H,t, J=7.4 Hz), 2.90–3.17(2H,m), 3.43–3.67(4H,m), 3.85–4.00 (2H,m), 4.05(2H,s), 4.28(2H,s), 4.48–4.56(2H,m), 6.86(1H, s), 7.09–7.68(14H,m), 8.51(1H,bs), 8.72(2H,bs)

EXAMPLE 240

N-(2-fluorobenzyl)-4-[N'-[2-[3-(aminomethyl)phenoxy]-4-chlorophenyl]-N'-[[spiro(1H-indene-1,4'-piperidin)-1'-yl]acetyl]]aminobutylamide dihydrochloride (1) In the same manner as in (2) in Example 194, an amorphous solid of N-(2-fluorobenzyl)-4-[N'-[2-[3-(tert-butoxycarbonylaminomethyl)phenoxy]-4-chlorophenyl]-N'-[[spiro(1H-indene-1,4'-piperidin)-1'-yl]acetyl]]aminobutylamide was obtained from N-(2-fluorobenzyl)-4-[N'-[2-[3-(tert-butoxycarbonylaminomethyl)phenoxy]-4-chlorophenyl]-N'-chloroacetyl]aminobutylamide and spiro (1H-indene-1,4'-piperidine).

Elemental Analysis for $C_{44}H_{48}N_4O_5ClF.1/2H_2O$:
Calcd.: C, 68.07; H, 6.36; N, 7.22
Found: C, 68.34; H, 6.14; N, 7.08
$^1$H-NMR (CDCl$_3$) δ: 1.42(9H,s), 1.89–1.98(4H,m), 2.11–2.50(6H,m), 2.88–3.08(2H,m), 3.14(2H,s), 3.65–3.84 (2H,m), 4.29(2H,d,J=6.2 Hz), 4.47(2H,d,J=5.6 Hz), 5.14 (1H,bs), 6.72(1H,d,J=5.7 Hz), 6.79(1H,d,J=5.7 Hz), 6.89–6.94(3H,m), 7.01–7.38(12H,m)

(2) In the same manner as in (3) in Example 194, an amorphous solid of N-(2-fluorobenzyl)-4-[N'-[2-[3-(aminomethyl)phenoxy]-4-chlorophenyl]-N'-[[spiro(1H-indene-1,4'-piperidin)-1'-yl]acetyl]]aminobutylamide dihydrochloride was obtained from N-(2-fluorobenzyl)-4-[N'-[2-[3-(tert-butoxycarbonylaminomethyl)phenoxy]-4-chlorophenyl]-N'-[[spiro(1H-indene-1,4'-piperidin)-1'-yl] acetyl]]aminobutylamide.

Elemental Analysis for $C_{39}H_{42}N_4O_3Cl_3F.3/2H_2O$:
Calcd.: C, 61.06; H, 5.91; N, 7.30
Found: C, 61.16; H, 5.93; N, 7.45
$^1$H-NMR (DMSO-d$_6$) δ: 1.17–1.32(2H,m), 1.74–1.79(2H,m), 2.23–2.28(2H,m), 2.51–2.74(2H,m), 3.39–3.54(4H,m), 3.89–4.05(4H,m), 4.28(2H,s), 6.85–6.90 (2H,s), 7.10–7.56(13H,m), 7.63–7.68(2H,m), 8.51(1H,bs), 8.74(2H,bs)

EXAMPLE 241

N-(2-fluorobenzyl)-4-[N'-[2-[3-(aminomethyl)phenoxy]-4-chlorophenyl]-N'-[[4-(2-oxo-2,3-dihydro-1H-benzimidazol-1-yl)-1-piperazinyl]acetyl]]aminobutylamide dihydrochloride (1) In the same manner as in (2) in Example 194, an amorphous solid of N-(2-fluorobenzyl)-4-[N'-[2-[3-(tert-butoxycarbonylaminomethyl)phenoxy]-4-chlorophenyl]-N'-[[4-(2-oxo-2,3-dihydro-1H-benzimidazol-1-yl)-1-piperazinyl]acetyl]]aminobutylamide was obtained from N-(2-fluorobenzyl)-4-[N'-[2-[3-(tert-butoxycarbonylaminomethyl)phenoxy]-4-chlorophenyl]-N'-chloroacetyl]aminobutylamide and 4-(2-oxo-2,3-dihydro-1H-benzimidazol-1-yl)-1-piperazine.

Elemental Analysis for $C_{43}H_{48}N_6O_6ClF.H_2O$:
Calcd.: C, 63.19; H, 6.17; N, 10.28
Found: C, 63.45; H, 6.00; N, 10.39

¹H-NMR (CDCl₃) δ: 1.43(9H,s), 1.65–1.89(8H,m), 2.27–2.48(4H,m), 3.01–3.10(3H,m), 3.76(2H,s), 4.29(2H,d, J=6.2 Hz), 4.47(2H,d,J=5.6 Hz), 5.25(1H,bs), 6.79(1H,bs), 6.89–7.39(15H,m), 9.11(1H,bs)

(2) In the same manner as in (3) in Example 194, an amorphous solid of N-(2-fluorobenzyl)-4-[N'-[2-[3-(aminomethyl)phenoxy]-4-chlorophenyl]-N'-[[4-(2-oxo-2,3-dihydro-1H-benzimidazol-1-yl)-1-piperazinyl]acetyl]]aminobutylamide dihydrochloride was obtained from N-(2-fluorobenzyl)-4-[N'-[2-[3-(tert-butoxycarbonylaminomethyl)phenoxy]-4-chlorophenyl]-N'-[[4-(2-oxo-2,3-dihydro-1H-benzimidazol-1-yl)-1-piperazinyl]acetyl]]aminobutylamide.

Elemental Analysis for $C_{38}H_{42}N_6O_4Cl_3F \cdot H_2O$:
Calcd.: C, 57.76; H, 5.61; N, 10.64
Found: C, 57.50; H, 5.75; N, 10.65
¹H-NMR (DMSO-d₆) δ: 1.77–1.91(4H,m), 2.12–2.28(2H,m), 2.74–2.89(2H,m), 3.39–3.58(4H,m), 3.79–3.87(4H,m), 4.08(2H,s), 4.28(2H,s), 4.55(1H,bs), 6.86 (1H,d,J=2.2 Hz), 7.01–7.67(14H,m), 8.49(1H,bs), 8.72(2H, bs)

EXAMPLE 242

N-(2-fluorobenzyl)-4-[N'-[2-[3-(aminomethyl)phenoxy]-4-chlorophenyl]-N'-[(4-biphenyloxy)acetyl]]aminobutylamide hydrochloride (1) In the same manner as in (2) in Example 194, an amorphous solid of N-(2-fluorobenzyl)-4-[N'-[(4-biphenyloxy)acetyl]-N'-[2-[3-(tert-butoxycarbonylaminomethyl)phenoxy]-4-chlorophenyl]]aminobutylamide was obtained from N-(2-fluorobenzyl)-4-[N'-[2-[3-(tert-butoxycarbonylaminomethyl)phenoxy]-4-chlorophenyl]-N'-chloroacetyl]aminobutylamide and 4-phenylphenol.

Elemental Analysis for $C_{43}H_{43}N_3O_6ClF$:
Calcd.: C, 68.65; H, 5.76; N, 5.59
Found: C, 68.54; H, 5.60; N, 5.50
¹H-NMR (CDCl₃) δ: 1.41(9H,s), 1.85–1.92(2H,m), 2.28 (2H,t,J=6.7 Hz), 3.67–3.88(2H,m), 4.27(2H,d,J=4.2 Hz), 4.44(2H,d,J=5.4 Hz), 4.53(2H,d,J=2.0 Hz), 5.13(1H,bs), 6.52(1H,bs), 6.84–7.54(20H,m)

(2) In the same manner as in (3) in Example 194, an amorphous solid of N-(2-fluorobenzyl)-4-[N'-[2-[3-(aminomethyl)phenoxy]-4-chlorophenyl]-N'-[(4-biphenyloxy)acetyl]]aminobutylamide hydrochloride was obtained from N-(2-fluorobenzyl)-4-[N'-[(4-biphenyloxy)acetyl]-N'-[2-[3-(tert-butoxycarbonylaminomethyl)phenoxy]-4-chlorophenyl]]aminobutylamide.

Elemental Analysis for $C_{38}H_{36}N_3O_4Cl_2F \cdot 1/2H_2O$:
Calcd.: C, 65.42; H, 5.35; N, 6.02
Found: C, 65.78; H, 5.31; N, 6.01
¹H-NMR (DMSO-d₆) δ: 1.69–1.75(2H,m), 2.21(2H,t, J=8.4 Hz), 3.54–3.85(2H,m), 4.02(2H,s), 4.27(2H,s), 4.46 (1H,d,J=15.1 Hz), 4.63(1H,d,J=15.1 Hz), 6.85–6.92(3H,m), 7.11–7.59(16H,m), 7.67(1H,d,J=8.8 Hz), 8.39(2H,bs)

EXAMPLE 243

N-(2-fluorobenzyl)-4-[N'-[2-[3-(aminomethyl)phenoxy]-4-chlorophenyl]-N'-(1-naphthalenesulfonyl)]aminobutylamide hydrochloride (1) A mixture of ethyl 4-[2-[3-(tert-butoxycarbonylaminomethyl)phenoxy]-4-chlorophenyl]aminobutyrate (2.3 g, 5.0 mmols), 4-dimethylaminopyridine (1.2 g, 10 mmols), 1-naphthalenesulfonyl chloride (2.3 g, 10 mmols) and tetrahydrofuran (20 ml) was stirred at 60° C. for 72 hours, and the reaction mixture was poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[N-(1-naphthalenesulfonyl)-N-[2-[3-(tert-butoxycarbonylaminomethyl)phenoxy]-4-chlorophenyl]]aminobutyrate (2.3 g, 71%).

Elemental Analysis for $C_{34}H_{37}N_2O_7ClS \cdot 1/2H_2O$:
Calcd.: C, 61.67; H, 5.78; N, 4.23
Found: C, 61.90; H, 5.62; H, 4.32
¹H-NMR (CDCl₃) δ: 1.22(3H,t,J=7.0 Hz), 1.47(9H,s), 1.76–1.90(2H,m), 2.41(2H,t,J=7.3 Hz), 3.80(2H,bs), 4.07 (2H,q,J=7.0 Hz), 4.18(2H,d,J=5.8 Hz), 4.82(1H,bs), 6.08 (1H,s), 6.21(1H,d,J=7.8 Hz), 6.46(1H,d,J=2.2 Hz), 6.97–7.16(3H,m), 7.39–7.54(4H,m), 7.86(1H,d,J=7.4 Hz), 8.01(1H,d,J=8.4 Hz), 8.14(1H,dd,J=2.2,7.4 Hz), 8.49(1H,d, J=8.8 Hz)

(2) In the same manner as in (3) in Example 6, an amorphous solid of 4-[N-[2-[3-(tert-butoxycarbonylaminomethyl)phenoxy]-4-chlorophenyl-N-(1-naphthalenesulfonyl)]aminobutyric acid was obtained from ethyl 4-[N-[2-[3-(tert-butoxycarbonylaminomethyl)phenoxy]-4-chlorophenyl-N-(1-naphthalenesulfonyl)]aminobutyrate.

Elemental Analysis for $C_{32}H_{33}N_2O_7ClS$:
Calcd.: C, 61.48; H, 5.32; N, 4.48
Found: C, 61.16; H, 5.35; N, 4.41
¹H-NMR (CDCl₃) δ: 1.40(9H,s), 1.85–1.95(2H,m), 2.41 (2H,bs), 3.72(1H,bs), 4.14(2H,bs), 5.06(1H,bs), 5.86(1H,d, J=8.0 Hz), 6.07–6.28(1H,m), 6.46(1H,s), 6.63–6.87(2H,m), 7.08(2H,s), 7.40–7.54(4H,m), 7.91(1H,bs), 8.05(1H,d,J=8.6 Hz), 8.16(1H,d,J=7.4 Hz), 8.44(1H,d,J=8.8 Hz)

(3) In the same manner as in (4) in Example 6, an amorphous solid of N-(2-fluorobenzyl)-4-[N'-[2-[3-(tert-butoxycarbonylaminomethyl)phenoxy]-4-chlorophenyl-N'-(1-naphthalenesulfonyl)]aminobutylamide was obtained from 4-[N-[2-[3-(tert-butoxycarbonylaminomethyl)phenoxy]-4-chlorophenyl-N-(1-naphthalenesulfonyl)]aminobutyric acid.

Elemental Analysis for $C_{39}H_{39}N_3O_6ClF$:
Calcd.: C, 63.97; H, 5.37; N, 5.74
Found: C, 63.77; H, 5.39; N, 5.60
¹H-NMR (CDCl₃) δ: 1.46(9H,s), 1.83(2H,t,J=7.0 Hz), 2.35(2H,t,J=7.0 Hz), 3.72–3.78(2H,m), 4.17(2H,d,J=2.2 Hz), 4.47(2H,d,J=5.8 Hz), 4.87(1H,bs), 6.09–6.15(2H,m), 6.15–6.27(1H,s), 6.49(1H,d,J=2.2 Hz), 6.96–7.55(10H,m), 7.87(1H,d,J=7.4 Hz), 8.02(1H,d,J=8.6 Hz), 8.08(1H,dd, J=1.2,7.4 Hz), 8.46(1H,d,J=8.6 Hz)

(4) In the same manner as in (5) in Example 6, an amorphous solid of N-(2-fluorobenzyl)-4-[N'-[2-[3-(aminomethyl)phenoxy]-4-chlorophenyl-N'-(1-naphthalenesulfonyl)]aminobutylamide hydrochloride was obtained from N-(2-fluorobenzyl)-4-[N'-[2-[3-(tert-butoxycarbonylaminomethyl)phenoxy]-4-chlorophenyl-N'-(1-naphthalenesulfonyl)]aminobutylamide.

Elemental Analysis for $C_{34}H_{32}N_3O_4Cl_2FS \cdot 1/2H_2O$:
Calcd.: C, 60.27; H, 4.91; N, 6.20
Found: C, 60.48; H, 4.90; N, 6.07
¹H-NMR (DMSO-d₆) δ: 1.62–1.71(2H,m), 2.21(2H,t, J=5.4 Hz), 3.66(2H,s), 3.93(2H,s), 4.25(2H,d,J=4.6 Hz), 6.28–6.31(1H,m), 6.51(1H,d,J=1.2 Hz), 6.80(1H,s), 7.07–7.40(7H,m), 7.50–7.66(4H,m), 8.06–8.13(2H,m), 8.25 (1H,d,J=8.0 Hz), 8.30–8.50(4H,m)

EXAMPLE 244

N-(2-fluorobenzyl)-4-[N'-[4-chloro-2-[4-(1-piperazinyl)phenoxy]phenyl]-N'-(4-phenylbenzoyl)]aminobutylamide hydrochloride (1) In the same manner as in (1) in Example 198, 1-(4-hydroxyphenyl)piperazine was processed to give 4-(4-tert-butoxycarbonylpiperazin-1-yl)phenol.

$^1$H-NMR (CDCl$_3$) δ: 1.49(9H,s), 2.95–3.00(2H,m), 3.55–3.60(2H,m), 6.03(1H,bs), 6.74–6.97(4H,m)

A mixture of 4-chloro-2-fluoronitrobenzene (2.63 g, 15 mmols), 4-(4-tert-butoxycarbonylpiperazin-1-yl)phenol (4.18 g, 15 mmols), potassium carbonate (2.07 g, 15 mmols) and N,N-dimethylformamide (50 ml) was stirred at 100° C. for 12 hours. The reaction mixture was cooled, poured into water, and extracted with ethyl acetate. The extract was washed with water, and then dried with anhydrous magnesium sulfate, and the solvent was evaporated away. The residue was purified through silica gel column chromatography to give a crystal of tert-butyl 4-[4-(5-chloro-2-nitrophenoxy)phenyl]piperazine-1-carboxylate (5.8 g, 89%).

m.p. 124–125° C.

Elemental Analysis for C$_{21}$H$_{24}$N$_3$O$_5$Cl:
Calcd.: C, 58.13; H, 5.58; N, 9.68
Found: C, 57.98; H, 5.57; N, 9.56

$^1$H-NMR (CDCl$_3$) δ: 1.49(9H,s), 3.11–3.16(4H,m), 3.58–3.63(4H,m), 6.87(1H,d,J=2.2 Hz), 6.93–7.05(4H,m), 7.08(1H,dd,J=2.2,8.8 Hz), 7.90(1H,d,J=8.8 Hz)

(2) 5% carbon-palladium (1.3 g) was added to an ethyl acetate (100 ml) solution of tert-butyl 4-[4-(5-chloro-2-nitrophenoxy)phenyl]piperazine-1-carboxylate (5.64 g, 13 mmols). The resulting mixture was hydrogenated at room temperature under atmospheric pressure. The catalyst was removed through filtration, and the filtrate was concentrated under reduced pressure. The residue was purified through silica gel column chromatography to give a crystal of tert-butyl 4-[4-(2-amino-5-chlorophenoxy)phenyl]piperazine-1-carboxylate (4.0 g, 76%).

m.p. 95–96° C.

$^1$H-NMR (CDCl$_3$) δ: 1.49(9H,s), 3.02–3.10(4H,m), 3.56–3.61(4H,m), 3.84(2H,bs), 6.68–6.72(2H,m), 6.77–6.93(5H,m)

(3) A mixture of tert-butyl 4-[4-(2-amino-5-chlorophenoxy)phenyl]piperazine-1-carboxylate (3.8 g, 9.5 mmols), ethyl 4-bromobutyrate (2.7 ml, 19 mmols), potassium carbonate (1.3 g, 9.5 mmols) and N,N-dimethylformamide (30 ml) was stirred at 60° C. for 72 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 4-[2-[4-(4-tert-butoxycarbonyl-1-piperazinyl)phenoxy]-4-chlorophenyl]aminobutyrate (3.5 g, 71%).

Elemental Analysis for C$_{27}$H$_{36}$N$_3$O$_5$Cl:
Calcd.: C, 62.60; H, 7.00; N, 8.11
Found: C, 62.55; H, 7.20; N, 7.85

$^1$H-NMR (CDCl$_3$) δ: 1.24(3H,t,J=7.0 Hz), 1.49(9H,s), 1.88–2.02(2H,m), 2.40(2H,t,J=7.1 Hz), 3.03–3.25(6H,m), 3.56–3.61(4H,m), 4.12(2H,q,J=7.0 Hz), 4.29(1H,bs), 6.55–6.76(2H,m), 6.85–7.06(5H,m)

(4) 4-Phenylbenzoyl chloride (2.2 g, 10 mmols) was added to a tetrahydrofuran (30 ml) solution of ethyl 4-[2-[4-(4-tert-butoxycarbonyl-1-piperazinyl)phenoxy]-4-chlorophenyl]aminobutyrate (3.4 g, 6.5 mmols) and 4-dimethylaminopyridine (1.6 g, 13 mmols). The resulting mixture was stirred at room temperature for 5 hours, then poured into water, and extracted with ethyl acetate. The extract was washed with water, and then dried with anhydrous magnesium sulfate. This was concentrated under reduced pressure, and the residue was purified through silica gel column chromatography to give an amorphous solid of ethyl 4-[N-[2-[4-(4-tert-butoxycarbonyl-1-piperazinyl)]phenoxy]-4-chlorophenyl]-N-(4-phenylbenzoyl)]aminobutyrate (3.4 g, 74%).

Elemental Analysis for C$_{40}$H$_{44}$N$_3$O$_6$Cl:
Calcd.: C, 68.80; H, 6.35; N, 6.02
Found: C, 69.03; H, 6.36; N, 6.00

$^1$H-NMR (CDCl$_3$) δ: 1.24(3H,t,J=7.0 Hz), 1.49(9H,s), 2.00(2H,t,J=7.5 Hz), 2.48(2H,t,J=7.5 Hz), 3.01–3.10(4H,m), 3.55–3.60(4H,m), 3.80–3.90(1H,m), 4.06–4.13(1H,m), 4.11(2H,q,J=7.0 Hz), 6.48–6.57(3H,m), 6.79–6.85(2H,m), 6.93–7.05(1H,m), 7.21–7.48(8H,m), 7.51–7.58(2H,m)

(5) Aqueous 1 N sodium hydroxide solution (9 ml, 9 mmols) was added to a solution of ethyl 4-[N-[2-[4-(4-tert-butoxycarbonyl-1-piperazinyl)]phenoxy]-4-chlorophenyl]-N-(4-phenylbenzoyl)]aminobutyrate (3.1 g, 4.5 mmols) in tetrahydrofuran (10 ml) and ethanol (10 ml). The resulting mixture was stirred at room temperature for 2 hours. Water was added to this, which was then acidified with 1 N hydrochloric acid added thereto, and extracted with ethyl acetate. The extract was washed with water, and then dried with anhydrous magnesium sulfate. This was concentrated under reduced pressure to give a crystal of 4-[N-[2-[4-(4-tert-butoxycarbonyl-1-piperazinyl)]phenoxy]-4-chlorophenyl]-N-(4-phenylbenzoyl)]aminobutyric acid (2.9 g, 96%).

m.p. 192–193° C.

Elemental Analysis for C$_{38}$H$_{40}$N$_3$O$_6$Cl:
Calcd.: C, 68.10; H, 6.02; N, 6.27
Found: C, 68.39; H, 6.11; N, 6.06

$^1$H-NMR (CDCl$_3$) δ: 1.48(9H,s), 1.95–2.04(2H,m), 2.51–2.56(2H,m), 2.51–2.56(2H,m), 3.01–3.09(4H,m), 3.54–3.59(4H,m), 3.80–3.89(1H,m), 4.07–4.21(1H,m), 6.50–6.55(3H,m), 6.78–7.07(1H,m), 7.22–7.58(10H,m)

(6) A mixture of 4-[N-[2-[4-(4-tert-butoxycarbonyl-1-piperazinyl)]phenoxy]-4-chlorophenyl]-N-(4-phenylbenzoyl)]aminobutyric acid (1.3 g, 2.0 mmols), 2-fluorobenzylamine (0.27 ml, 2.4 mmols), diethyl cyanophosphate (0.33 ml, 2.4 mmols), triethylamine (0.33 ml, 2.4 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-4-[N'-[2-[4-(4-tert-butoxycarbonyl-1-piperazinyl)]phenoxy]-4-chlorophenyl]-N'-(4-phenylbenzoyl)]aminobutylamide (1.4 g, 90%).

Elemental Analysis for C$_{45}$H$_{46}$N$_4$O$_6$ClF:
Calcd.: C, 69.53; H, 5.96; N, 7.21
Found: C, 69.50; H, 6.22; N, 7.12

$^1$H-NMR (CDCl$_3$) δ: 1.49(9H,s), 1.94–2.01(2H,m), 2.40–2.44(2H,m), 3.01–3.09(4H,m), 3.55–3.60(4H,m), 3.71–3.88(1H,m), 4.14–4.27(1H,m), 4.53(2H,d,J=5.8 Hz), 6.46–6.53(3H,m), 6.77–6.84(2H,m), 6.94–7.59(16H,m)

(7) A 2H hydrochloric acid/ethyl acetate solution (10 ml) of N-(2-fluorobenzyl)-4-[N'-[2-[4-(4-tert-butoxycarbonyl-1-piperazinyl)]phenoxy]-4-chlorophenyl]-N'-(4-phenylbenzoyl)]aminobutylamide (1.2 g, 1.5 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-4-[N'-[4-chloro-2-[4:-(1-piperazinyl)phenoxy]phenyl]-N'-(4-phenyl-benzoyl)]aminobutylamide hydrochloride (1.0 g, 90%).

Elemental Analysis for $C_{40}H_{40}N_4O_3Cl_3F \cdot H_2O$:
Calcd.: C, 62.54; H, 5.51; N, 7.29
Found: C, 62.82; H, 5.75; N, 7.24

$^1$H-NMR (DMSO-$d_6$) δ: 1.85–1.88(2H,m), 2.25–2.32(2H,m), 3.23(4H,bs), 3.37(4H,bs), 3.82(2H,s), 4.30(2H,s), 6.40(1H,s), 6.67–6.71(2H,m), 6.98–7.67(17H, m), 8.40(1H,bs), 9.43(1H,bs)

EXAMPLE 245

N-(2-fluorobenzyl)-2-[N'-[2-[3-(aminomethyl)phenoxy]-4-chlorophenyl]-N'-(4-phenylbenzoyl)]aminoacetamide hydrochloride (1) A mixture of tert-butyl[3-(2-amino-5-chlorophenoxy) benzylcarbamate (5.2 g, 15 mmols), ethyl bromoacetate (3.3 ml, 30 mmols), potassium carbonate (2.1 g, 15 mmols) and N,N-dimethylformamide (30 ml) was stirred at 60° C. for 12 hours. The reaction mixture was cooled, poured into water, and extracted with ethyl acetate. The extract was washed with water, and then dried with anhydrous magnesium sulfate. This was concentrated under reduced pressure, and the residue was purified through silica gel column chromatography to give an oil of ethyl 2-[2-[3-(tert-butoxycarbonylaminomethyl)phenoxy]-4-chlorophenyl]aminoacetate (4.3 g, 66%).

Elemental Analysis for $C_{22}H_{27}N_2O_5Cl$:
Calcd.: C, 60.76; H, 6.26; N, 6.44
Found: C, 60.50; H, 6.24; N, 6.33

$^1$H-NMR(CDCl$_3$) δ: 1.28(3H,t,J=7.1 Hz), 1.45(9H,s), 3.91(2H,s), 4.22(2H,q,J=7.1 Hz), 4.29(2H,d,J=6.2 Hz), 4.78(1H,bs), 4.94(1H,bs), 6.52(1H,d,J=8.4 Hz), 6.78(1H,d,J=2.6 Hz), 6.81–7.05(4H,m), 7.29(1H,t,J=7.8 Hz)

(2) 4-Phenylbenzoyl chloride (1.7 g, 8 mmols) was added to a tetrahydrofuran (30 ml) solution of ethyl 2-[2-[3-(tert-butoxycarbonylaminomethyl)phenoxy]-4-chlorophenyl] aminoacetate (1.7 g, 4.0 mmols) and 4-dimethylaminopyridine (0.98 g, 8 mmols). The resulting mixture was stirred at room temperature for 3 hours, then poured into water, and extracted with ethyl acetate. The extract was washed with water, and then dried with anhydrous magnesium sulfate. This was concentrated under reduced pressure, and the residue was purified through silica gel column chromatography to give an amorphous solid of ethyl 2-[N-[2-[3-(tert-butoxycarbonylaminomethyl)phenoxy]-4-chlorophenyl]-N-(4-phenylbenzoyl)]aminoacetate (1.3 g, 53%).

Elemental Analysis for $C_{35}H_{35}N_2O_6Cl \cdot 1/2H_2O$:
Calcd.: C, 67.35; H, 5.81; N, 4.49
Found: C, 67.40; H, 5.93; N, 4.59

$^1$H-NMR (CDCl$_3$) δ: 1.30(3H,t,J=7.2 Hz), 1.44(9H,s), 4.00–4.23(3H,m), 4.28(2H,d,J=5.4 Hz), 4.84–5.06(2H,m), 6.67–6.73(2H,m), 6.83(1H,s), 6.91–6.95(1H,m), 7.11(1H,d, J=8.4 Hz), 7.27–7.48(9H,m), 7.55–7.60(2H,m)

(3) Aqueous 1 N sodium hydroxide solution (4 ml, 4 mmols) was added to a solution of ethyl 2-[N-[2-[3-(tert-butoxycarbonylaminomethyl)phenoxy]-4-chlorophenyl]-N-(4-phenylbenzoyl)]aminoacetate (1.2 g, 2.0 mmols) in tetrahydrofuran (5 ml) and ethanol (5 ml). The resulting mixture was stirred at room temperature for 2 hours. Water was added to the reaction mixture, which was then acidified with 1 N hydrochloric acid added thereto, and extracted with ethyl acetate. The extract was washed with water, and then dried with anhydrous magnesium sulfate. This was concentrated under reduced pressure to give an amorphous solid of 2-[N-[2-[3-(tert-butoxycarbonylaminomethyl)phenoxy]-4-chlorophenyl]-N-(4-phenylbenzoyl)]aminoacetic acid (1.1 g, 92%).

Elemental Analysis for $C_{35}H_{31}N_2O_6Cl \cdot 1/2H_2O$:
Calcd.: C, 66.29; H, 5.43; N, 4.69
Found: C, 66.08; H, 5.51; N, 4.67

$^1$H-NMR (CDCl$_3$) δ: 1.43(9H,s), 4.27(2H,d,J=5.6 Hz), 4.50(2H,bs), 4.90(1H,bs), 4.99(1H,bs), 6.68(2H,s), 6.81(1H, s), 6.92(1H,d,J=8.4 Hz), 7.09(1H,d,J=7.8 Hz), 7.26–7.48 (9H,m), 7.54–7.59(2H,m)

(4) A mixture of 2-[N-[2-[3-(tert-butoxycarbonylaminomethyl)phenoxy]-4-chlorophenyl]-N-(4-phenylbenzoyl)]aminoacetic acid (0.30 g, 0.5 mmols), 2-fluorobenzylamine (0.07 ml, 0.6 mmols), diethyl cyanophosphate (0.08 ml, 0.6 mmols), triethylamine (0.08 ml, 0.6 mmols) and N,N-dimethylformamide (10 ml) was stirred at room temperature for 2 hours. The reaction mixture was poured into water, and extracted with ethyl acetate. The extract was washed with water, and then dried with anhydrous magnesium sulfate. This was concentrated under reduced pressure, and the residue was purified through silica gel column chromatography to give an amorphous solid of N-(2-fluorobenzyl)-2-[N'-[2-[3-(tert-butoxycarbonylaminomethyl)phenoxy]-4-chlorophenyl]-N'-(4-phenylbenzoyl)]aminoacetamide (0.29 g, 85%).

Elemental Analysis for $C_{40}H_{37}N_3O_5ClF \cdot 1/2H_2O$:
Calcd.: C, 68.32; H, 5.45; N, 5.98
Found: C, 68.54; H, 5.28; N, 5.91

$^1$H-NMR (CDCl$_3$) δ: 1.43(9H,s), 4.15(2H,d,J=6.8 Hz), 4.51(4H,bs), 4.82(1H,bs), 6.29(1H,d,J=8.0 Hz), 6.42(1H,s), 6.54(1H,d,J=1.8 Hz), 6.96–7.09(3H,m), 7.13–7.48(13H,m), 7.54–7.59(2H,m)

(5) A 2 N hydrochloric acid/ethyl acetate solution (10 ml) of N-(2-fluorobenzyl)-2-[N'-[2-[3-(tert-butoxycarbonylaminomethyl)phenoxy]-4-chlorophenyl]-N'-(4-phenylbenzoyl)] aminoacetamide (0.15 g, 0.35 mmols) was stirred at room temperature for 1 hour. The reaction mixture was concentrated under reduced pressure. The solid precipitated was taken out through filtration, and washed with ethyl ether to give an amorphous solid of N-(2-fluorobenzyl)-2-[N'-[2-[3-(aminomethyl)phenoxy]-4-chlorophenyl]-N'-(4-phenylbenzoyl)]aminoacetamide hydrochloride (0.15 g, 68%).

Elemental Analysis for $C_{35}H_{30}N_3O_3Cl_2F \cdot 1/2H_2O$:
Calcd.: C, 65.73; H, 4.89; N, 6.57
Found: C, 65.44; H, 4.96; N, 6.48

$^1$H-NMR (DMSO-$d_6$) δ: 3.99–4.15(3H,m), 4.38(2H,s), 4.72(1H,d,J=16.4 Hz), 6.68(1H,s), 6.82(1H,d,J=7.0 Hz), 7.14–7.50(15H,m), 7.59–7.69(3H,m), 8.44(2H,bs), 8.66(1H,bs)

The pharmaceutical effects of the compounds of the invention are described concretely hereinunder, which, however, are not limitative. Regarding the genetic engineering with *Escherichia coli*, herein referred to are the methods described in Molecular Cloning (T. Maniatis, et al., 1989).

(1) Cloning of Human Somatostatin Receptor Protein Sub-Type 1 (SSTR1) DNA:

Based on the known base sequence of human SSTR1 cDNA (Proc. Natl. Acad. Sci., USA, Vol. 89, pp. 251–255, 1992), DNA oligomers S1-1 and S1-2 were produced. The sequence of S1-1 is 5'-GGTCGACCTCAGCTAGGATGT-TCCCCAATG-3' (sequence No. 1); and that of S1-2 is 5'-GGTCGACCCGGGCTCAGAGCGTCGTGAT-3' (sequence No. 2). The template used is a human chromosomal DNA (Clonetec's catalogue No. CL6550-1). 25 pmols of the DNA oligomer was added to 0.5 ng of the DNA, and subjected to polymerase chain reaction with 2.5 units of Pfu DNA polymerase (from Stratagene) added thereto. Regarding the composition of the reaction mixture, referred to were the manufacturer's instructions for the product, Pfu DNA polymerase. The reaction needed 35 cycles, one cycle comprising 94° C. for 1 minute, 63° C. for 1 minute and 75° C. for 2 minutes. The reaction mixture was subjected to 1% agarose gel electrophoresis, which showed specific amplification of the intended size (about 1.2 kb) DNA fragment. The DNA fragment was recovered from the agarose gel in an ordinary manner, and linked to pUC118 cleaved at the HincII site. This was transformed into competent cells, Escherichia coli JM109. The transformed cells having the DNA fragment-containing plasmid were selected through screening, and the base sequence of the insert DNA fragment therein was analyzed by the use of an automatic base sequence analyzer, ALF DNA Sequencer (from Pharmacia) in which was used a fluorescent dye. The data confirmed that the amino acid sequence of the DNA fragment estimated from the base sequence thereof is entirely the same as that described in the above-mentioned reference.

(2) Construction of Expression Plasmid for Human Somatostatin Receptor Protein Sub-Type 1 (SSTR1) DNA:

For the expression vector in CHO (Chinese hamster ovary) cells, used was pAKKO-111. pAKKO-111 was constructed as follows: A 1.4 kb DNA fragment containing an SPα promoter and a poly A-addition signal was obtained from pTB1417 described in Japanese Patent Laid-Open No. 076385/1993, through HindIII and ClaI processing. A 4.5 kb DNA fragment containing a dihydrofolate reductase (DHFR) gene was obtained from pTB348 (Biochem. Biophys. Res. Commun., 128, pp. 256–264, 1985), through ClaI and SalI processing. These DNA fragments were blunted with T4 polymerase to thereby have blunt ends, and were ligated together with a T4 ligase to construct a pAKKO-111 plasmid. Next, 5 μg of the human SSTR1 DNA fragment-having plasmid that had been prepared in the previous step (1) was digested with a restriction enzyme SalI, and then subjected to 1% agarose gel electrophoresis to recover the 1.2 kb DNA fragment coding for human SSTR1. Then, 1 μg of the expression vector pAKKO-111 (5.5 kb) was digested with SalI to form a cloning site for human SSTR1 DNA fragment insertion thereinto. The expression vector fragment and the 1.2 kb DNA fragment were ligated with a T4 DNA ligase, and the reaction mixture was introduced into cells of E. coli JM109 according to a calcium chloride method. From the thus-transformed cells, obtained was an expression plasmid pA1-11-SSTR1 having a human SSTR1 DNA fragment inserted thereinto in the stream direction of the promoter therein. The transformant is referred to as E. coli JM109/pA-1-11-SSTR1.

(3) Transduction of Human Somatostatin Receptor Protein Sub-Type 1 (SSTR1) DNA into CHO (dhfr⁻) Cells and Expression Thereof in the Cells:

$1 \times 10^6$ CHO (dhfr⁻) cells were incubated for 24 hours in a 10% fetal calf serum-containing HAM F12 medium in a 8 cm-φ laboratory dish. Into these cells, introduced was 10 μg of the human SSTR1 cDNA expression plasmid 1, pA-1-11-SSTR1 that had been prepared in the previous step (2), according to a calcium phosphate method (using Pharmacia's Cell Phect Transition Kit). After 24 hours, the medium was substituted with a 10% dialyzed fetal calf serum-containing DMEM medium, on which the cells forming colonies (these are DHFR⁺ cells) were selected. The thus-selected single cells were separately cloned according to a limiting dilution-culture method, and their somatostatin receptor protein activity was determined according to the method mentioned below. The human SSTR cDNA-expressing cell strain was diluted with an incubation buffer (50 mM tris-HCl, 1 mM EDTA, 5 mM magnesium chloride, 0.1% BSA, 0.2 mg/ml bacitracin, 10 μl/ml leupeptin, 1 μl/ml pepstatin, 200 units/ml aprotinin, pH, 7.5) to have a controlled cell number of $2 \times 10^4$ cells/200 μl. The cell dilution was put into a plurality of 200 μl tubes. 2 μl/tube of 5 nM [$^{125}$I]-somatostatin-14 (2000 Ci/mmol, from Amersham) was added to some tubes, in which the cells were incubated at 25° C. for 60 minutes. To measure the non-specific binding site (NSB), 2 μl/tube of somatostatin-14 ($10^{-4}$ M) was added to the other tubes, in which the cells were also incubated. A washing buffer (50 mM tris-HCl, 1 mM EDTA, 5 mM magnesium chloride, pH 7.5) (1.5 ml) was added to each tube, and the liquid in each tube was filtered through a GF/F glass fiber filter (from Whatman), which was then washed with the same buffer (1.5 ml). The [$^{125}$I]radiation of the filter was measured with a γ-counter. Through the process, the somatostatin-binding cell strain, SSTR1-8-3 was selected.

(4) Cloning of Human Somatostatin Receptor Protein Sub-Type 2 (SSTR2) DNA:

Based on the known base sequence of human SSTR2 cDNA (Proc. Natl. Acad. Sci., USA, Vol. 89, pp. 251–255, 1992), DNA oligomers PT-1 and PT-2 were produced. The sequence of PT-1 is 5'-GGTCGACACCATGGACATG-GCGGATGA-3' (sequence No. 3); and that of PT-2 is 5'-GGTCGACAGTTCAGATACTGGTTTGG-3' (sequence No. 4). The template used is a human pituitary cDNA (Clonetec's catalogue No. 7173-1). 25 pmols of the DNA oligomer was added to 1 ng of the cDNA, and subjected to polymerase chain reaction with 2.5 units of Taq DNA polymerase (from Takara Shuzo) added thereto. Regarding the composition of the reaction mixture, referred to were the manufacturer's instructions for the product, Taq DNA polymerase. The reaction needed 30 cycles, one cycle comprising 94° C. for 30 seconds, 52° C. for 20 seconds and 72° C. for 60 seconds. The reaction mixture was subjected to 1% agarose gel electrophoresis, which showed specific amplification of the intended size (about 1.1 kb) DNA fragment. The DNA fragment was recovered from the agarose gel in an ordinary manner, and linked to pUC118 cleaved at the HincII site. This was transformed into competent cells, E. coli JM109. The transformed cells (two strains, No. 5 and No. 7) having the DNA fragment-containing plasmid were selected through screening, and the base sequence of the insert DNA fragment therein was analyzed by the use of an automatic base sequence analyzer, 373A DNA Sequencer (from Applied Biosystems) in which was used a fluorescent dye. The data confirmed one point mutation in the sequence of the 770 base fragment between SalI-BstPI in the cells of the strain No. 5, and one point mutation in the sequence of the 360 base fragment between BstPI-SalI in the cells of the strain No. 7. The fragment of the cell strain No. 5 from which the BstPI-SalI fragment had been removed and the fragment of the cell strain No. 7 from which the BstPI-SalI fragment had been removed were purified through agarose electrophoresis, and these were ligated to construct a plasmid. The base sequence of the insert DNA fragment in this plasmid was identified, and it was entirely the same as that described in the above-mentioned reference.

(5) Construction of Expression Plasmid for Human Somatostatin Receptor Protein Sub-Type 2 (SSTR2) DNA:

For the expression vector in CHO (Chinese hamster ovary) cells, used was the pAKKO-111 described in the above (2). 5 μl of the human SSTR2 cDNA fragment-having plasmid that had been prepared in the previous step (4) was digested with a restriction enzyme SalI, and then subjected to 1% agarose gel electrophoresis to recover the 1.1 kb DNA fragment coding for human SSTR2. Then, 1 μl of the expression vector pAKKO-111 (5.5 kb) was digested with SalI to form a cloning site for human SSTR2 DNA fragment insertion thereinto. The expression vector fragment and the 1.1 kb DNA fragment were ligated with a T4 DNA ligase, and the reaction mixture was introduced into cells of E. coli JM109 according to a calcium chloride method. From the thus-transformed cells, obtained was an expression plasmid pAC01 having a human SSTR2 DNA fragment inserted thereinto in the stream direction of the promoter therein. The transformant is referred to as E. coliJM109/pAC01.

(6) Transduction of Human Somatostatin Receptor Protein Sub-Type 2 (SSTR2) DNA into CHO (dhfr⁻) Cells and Expression Thereof in the Cells:

1×10⁶ CHO (dhfr⁻) cells were incubated for 24 hours in a 10% fetal calf serum-containing HAM F12 medium in a 8 cm-φ laboratory dish. Into these cells, introduced was 10 μg of the human SSTR2 cDNA expression plasmid, pAC01 that had been prepared in the previous step (5), according to a calcium phosphate method (using Pharmacia's Cell Phect Transition Kit). After 24 hours, the medium was substituted with a 10% dialyzed fetal calf serum-containing DMEM medium, on which the cells forming colonies (these are DHFR⁺ cells) were selected. The thus-selected single cells were separately cloned according to a limiting dilution-culture method, and the somatostatin-binding cell strain, SSTR2-HS5-9 was selected from them.

(7) Cloning of Human Somatostatin Receptor Protein Sub-Type 3 (SSTR3) DNA:

Based on the known base sequence of human SSTR3 cDNA (Mol. Endocrinol., Vol. 6, pp. 2136–2142, 1992), DNA oligomers S3-1 and S3-2 were produced. The sequence of S3-1 is 5'-GGTCGACCTCAACCATGGACAT-GCTTCATC-3' (sequence No. 5); and that of S3-2 is 5'-GGTCGACTTTCCCCAGGCCCCTACAGGTA-3' (sequence No. 6). The template used is a human chromosomal DNA (Clonetec's catalogue No. CL6550-1). 25 pmols of the DNA oligomer was added to 0.5 ng of the DNA, and subjected to polymerase chain reaction with 2.5 units of Pfu DNA polymerase (from Stratagene) added thereto. Regarding the composition of the reaction mixture, referred to were the manufacturer's instructions for the product, Pfu DNA polymerase. The reaction needed 35 cycles, one cycle comprising 94° C. for 1 minute, 63° C. for 1 minute and 75° C. for 2 minutes. The reaction mixture was subjected to 1% agarose gel electrophoresis, which showed specific amplification of the intended size (about 1.3 kb) DNA fragment. The amino acid sequence of the DNA fragment estimated from the base sequence thereof is entirely the same as that described in the above-mentioned reference.

(8) Construction of Expression Plasmid for Human Somatostatin Receptor Protein Sub-Type 3 (SSTR3) DNA:

For the expression vector in CHO cells, used was the pAKKO-111 described in the above (2). 5 μg of the human SSTR3 DNA fragment-having plasmid that had been prepared in the previous step (7) was digested with a restriction enzyme SalI, and then subjected to 1% agarose gel electrophoresis to recover the 1.3 kb DNA fragment coding for human SSTR3. Then, 1 μg of the expression vector pAKKO-111 (5.5 kb) was digested with SalI to form a cloning site for human SSTR3 DNA fragment insertion thereinto. The expression vector fragment and the 1.3 kb DNA fragment were ligated with a T4 DNA ligase, and the reaction mixture was introduced into cells of E. coli JM109 according to a calcium chloride method. From the thus-transformed cells, obtained was an expression plasmid pA1-11-SSTR3 having a human SSTR3 DNA fragment inserted thereinto in the stream direction of the promoter therein. The transformant is referred to as E. coli JM109/pA-1-11-SSTR3.

(9) Transduction of Human Somatostatin Receptor Protein Sub-Type 3 (SSTR3) DNA into CHO (dhfr⁻) Cells and Expression Thereof in the Cells 1×10⁶ CHO (dhfr⁻) cells were incubated for 24 hours in a 10% fetal calf serum-containing HAM F12 medium in a 8 cm-φ laboratory dish. Into these cells, introduced was 10 μg of the human SSTR3 DNA expression plasmid, pA-1-11-SSTR3 that had been prepared in the previous step (5), according to a calcium phosphate method. After 24 hours, the medium was substituted with a 10% dialyzed fetal calf serum-containing DMEM medium, on which the cells forming colonies (these are DHFR⁺ cells) were selected. The thus-selected single cells were separately cloned according to a limiting dilution-culture method, and their somatostatin receptor protein expression ability was measured through binding assay of above (3). Through the process, the somatostatin-binding cell strain, SSTR3-15-19 was selected.

(10) Cloning of Human Somatostatin Receptor Protein Sub-Type 4 (SSTR4) DNA:

Based on the known base sequence of human SSTR4 DNA (Proc. Natl. Acad. Sci., USA, Vol. 90, pp. 4196–4200, 1993), DNA oligomers S4-1 and S4-2 were produced. The sequence of S4-1 is 5'-GGCTCGAGTCACCATGAGCGC-CCCCTCG-3' (sequence No. 7); and that of S4-2 is 5'-GGGCTCGAGCTCCTCAGAAGGTGGTGG-3' (sequence No. 8). The template used is a human chromosomal DNA (Clonetec's catalogue No. CL6550-1). 25 pmols of the DNA oligomer was added to 0.5 ng of the DNA, and subjected to polymerase chain reaction with 2.5 units of Pfu DNA polymerase (from Stratagene) added thereto. Regarding the composition of the reaction mixture, referred to were the manufacturer's instructions for the product, Pfu DNA polymerase. The reaction needed 35 cycles, one cycle comprising 94° C. for 1 minute, 66° C. for 1 minute and 75° C. for 2 minutes. The reaction mixture was subjected to 1% agarose gel electrophoresis, which showed specific amplification of the intended size (about 1.2 kb) DNA fragment. The base sequence of the DNA fragment was confirmed according to the method described in the above (1), and the amino acid sequence of the DNA fragment estimated from the base sequence thereof is entirely the same as that described in the above-mentioned reference.

(11) Construction of Expression Plasmid for Human Somatostatin Receptor Protein Sub-Type 4 (SSTR4) DNA:

For the expression vector in CHO cells, used was the pAKKO-111 described in the above (2). 5 μg of the human SSTR4 DNA fragment-having plasmid that had been prepared in the previous step (10) was digested with a restriction enzyme XhoI, and then subjected to 1% agarose gel electrophoresis to recover the 1.2 kb DNA fragment coding for human SSTR4. Then, 1 μg of the expression vector pAKKO-111 (5.5 kb) was digested with SalI to form a cloning site for human SSTR4 DNA fragment insertion thereinto. The expression vector fragment and the 1.2 kb DNA fragment were ligated with a T4 DNA ligase, and the reaction mixture was introduced into cells of E. coli JM109 according to a calcium chloride method. From the thus-transformed cells, obtained was an expression plasmid pA1-

11-SSTR4 having a human SSTR4 DNA fragment inserted thereinto in the stream direction of the promoter therein. The transformant is referred to as E. coli JM109/pA-1-11-SSTR4.

(12) Transduction of Human Somatostatin Receptor Protein Sub-Type 4 (SSTR4) DNA into CHO (dhfr⁻) Cells and Expression Thereof in the Cells:

$1\times10^6$ CHO (dhfr⁻) cells were incubated for 24 hours in a 10% fetal calf serum-containing HAM F12 medium in a 8 cm-φ laboratory dish. Into these cells, introduced was 10 μg of the human SSTR4 DNA expression plasmid, pA-1-11-SSTR4 that had been prepared in the previous step (8), according to a calcium phosphate method. After 24 hours, the medium was substituted with a 10% dialyzed fetal calf serum-containing DMEM medium, on which the cells forming colonies (these are DHFR⁺ cells) were selected. The thus-selected single cells were separately cloned according to a limiting dilution-culture method, and their somatostatin receptor protein expression ability was measured through binding assay of above (3). Through the process, the somatostatin-binding cell strain, SSTR4-1-2 was selected.

(13) Cloning of Human Somatostatin Receptor Protein Sub-Type 5 (SSTR5) DNA:

Based on the known base sequence of human SSTR5 cDNA (Biochem. Biophys. Res. Commun., Vol. 195, pp. 844–852, 1993), DNA oligomers S5-1 and S5-2 were produced. The sequence of S5-1 is 5'-GGTCGACCACCATG-GAGCCCCTGTTCCC-3' (sequence No. 9); and that of S5-2 is 5'-CCGTCGACACTCTCACAGCTTGCTGG-3' (sequence No. 10). The template used is a human chromosomal DNA (Clonetec's catalogue No. CL6550-1). 25 pmols of the DNA oligomer was added to 0.5 ng of the DNA, and subjected to polymerase chain reaction with 2.5 units of Pfu DNA polymerase (from Stratagene) added thereto. Regarding the composition of the reaction mixture, referred to were the manufacturer's instructions for the product, Pfu DNA polymerase. The reaction needed 35 cycles, one cycle comprising 94° C. for 1 minute, 66° C. for 1 minute and 75° C. for 2 minutes. The reaction mixture was subjected to 1% agarose gel electrophoresis, which showed specific amplification of the intended size (about 1.1 kb) DNA fragment. The base sequence of the DNA fragment was confirmed according to the method described in the above (1), and the amino acid sequence of the DNA fragment estimated from the base sequence thereof is entirely the same as that described in the above-mentioned reference.

(14) Construction of Expression Plasmid for Human Somatostatin Receptor Protein Sub-Type 5 (SSTR5) DNA:

For the expression vector in CHO cells, used was the pAKKO-111 described in the above (2). 5 μg of the human SSTR5 DNA fragment-having plasmid that had been prepared in the previous step (13) was digested with a restriction enzyme SalI, and then subjected to 1% agarose gel electrophoresis to recover the 1.1 kb DNA fragment coding for human SSTR5. Then, 1 μg of the expression vector pAKKO-111 (5.5 kb) was digested with SalI to form a cloning site for human SSTR5 DNA fragment insertion thereinto. The expression vector fragment and the 1.1 kb DNA fragment were ligated with a T4 DNA ligase, and the reaction mixture was introduced into cells of E. coli JM109 according to a calcium chloride method. From the thus-transformed cells, obtained was an expression plasmid pA1-11-SSTR5 having a human SSTR5 DNA fragment inserted thereinto in the stream direction of the promoter therein. The transformant is referred to as E. coli JM109/pA-1-11-SSTR5.

(15) Transduction of Human Somatostatin Receptor Protein Sub-Type 5 (SSTR5) DNA into CHO (dhfr⁻) Cells and Expression Thereof in the Cells:

$1\times10^6$ CHO (dhfr⁻) cells were incubated for 24 hours in a 10% fetal calf serum-containing HAM F12 medium in a 8 cm-φ laboratory dish. Into these cells, introduced was 10 μg of the human SSTR5 cDNA expression plasmid, pA-1-11-SSTR5 that had been prepared in the previous step (14), according to a calcium phosphate method. After 24 hours, the medium was substituted with a 10% dialyzed fetal calf serum-containing DMEM medium, on which the cells forming colonies (these are DHFR⁺ cells) were selected. The thus-selected single cells were separately cloned according to a limiting dilution-culture method, and their somatostatin receptor protein expression ability was measured through binding assay of above (3). Through the process, the somatostatin-binding cell strain, SSTR5-32-4 was selected.

Experiment 1: Preparation of Human Somatostatin Receptor-Containing CHO Cell Membrane Fraction $10^9$ cells of any of the human somatostatin receptor-expressing CHO cell strain, SSTR1-8-3, SSTR2-HS5-9, SSTR3-15-19, SSTR4-1-2 or SSTR5-32-4 were floated in a 5 mM EDTA-containing, phosphate-buffered physiological saline (PBS-EDTA), which was then centrifuged. To the resulting cell pellets, added was 10 ml of a buffer for cell homogenization (10 mM NaHCO₃, 5 mM EDTA, pH=7.5). This was homogenized in a polytron homogenizer. The resulting homogenate was centrifuged (400×g, 15 minutes), and the supernatant was centrifuged (100,000×g, 1 hour) to give a precipitate of the cell membrane fraction. The precipitate was suspended in 2 ml of an assay buffer (25 ml tris-HCl, 1 ml EDTA, 0.1% BSA (bovine serum albumin), 0.25 ml PMSF, 1 μg/ml pepstatin, 20 μg/ml leupeptin, 10 μg/ml phosphramidone, pH=7.5), and centrifuged (100,000× g, 1 hour). The membrane fraction thus recovered as the precipitate was again suspended in 20 ml of the assay buffer, and stored in a plurality of vials at −80° C. Before use, it was thawed.

Experiment 2: Determination of ¹²⁵I-Somatostatin Binding Inhibition

The membrane fraction prepared in Experiment 1 was diluted with the assay buffer to be 3 μg/ml, and put into a plurality of tubes. Each tube contained 173 μl of the dilution. A compound to be tested was dissolved in DMSO. 2 μl of the DMSO solution of the compound, and 25 μl of 200 pM radiation-labeled somatostatin (¹²⁵I-somatostatin, from Amersham) were both added to each tube. To measure the maximum binding, prepared was a reaction mixture containing 2 μl of DMSO and 25 μl of 200 pM ¹²⁵I-somatostatin. To measure the non-specific binding, prepared was a reaction mixture containing 2 μl of 100 μM somatostatin dissolved in DMSO and 25 μl of 200 pM ¹²⁵I-somatostatin. These were separately reacted at 25° C. for 60 minutes, and then filtered under suction through a polyethylenimine-processed Whatman glass filter (GF-B). The ¹²⁵I-somatostatin radiation activity having remained on the filter was measured with a γ-counter. The percent maximum binding (PBM, %) of each test compound was obtained according to the following formula:

$$PBM = (B - NSB)/(B_0 - NSB) \times 100$$

wherein PBM indicates percent maximum binding of the test compound; B indicates the radiation activity with the compound added; $B_0$ indicates the maximum binding radiation activity; and NSB indicates the non-specific binding radiation activity.

The concentration of the test compound was varied, and the percent maximum binding of every case was obtained. From the data, obtained was the 50% binding inhibition concentration ($IC_{50}$) of the test compound through Hill plotting.

The reactivity ($IC_{50}$, μM) of all the compounds mentioned below on the human somatostatin receptor measured according to the method mentioned above was not higher than 10 μM.

Compound of Example 1
Compound of Example 2
Compound of Example 3
Compound of Example 4
Compound of Example 5
Compound of Example 6
Compound of Example 7
Compound of Example 8
Compound of Example 9
Compound of Example 10
Compound of Example 11
Compound of Example 12
Compound of Example 13
Compound of Example 14
Compound of Example 15
Compound of Example 19
Compound of Example 20
Compound of Example 22
Compound of Example 23
Compound of Example 24
Compound of Example 26
Compound of Example 27
Compound of Example 29
Compound of Example 30
Compound of Example 31
Compound of Example 32
Compound of Example 33
Compound of Example 34
Compound of Example 35
Compound of Example 36
Compound of Example 37
Compound of Example 38
Compound of Example 39
Compound of Example 40
Compound of Example 41
Compound of Example 42
Compound of Example 43
Compound of Example 44
Compound of Example 45
Compound of Example 46
Compound of Example 47
Compound of Example 48
Compound of Example 49
Compound of Example 50
Compound of Example 51
Compound of Example 52
Compound of Example 53
Compound of Example 54
Compound of Example 55
Compound of Example 56
Compound of Example 57
Compound of Example 58
Compound of Example 59
Compound of Example 60
Compound of Example 61
Compound of Example 62
Compound of Example 63
Compound of Example 64
Compound of Example 65
Compound of Example 66
Compound of Example 67
Compound of Example 68
Compound of Example 69
Compound of Example 70
Compound of Example 71
Compound of Example 72
Compound of Example 74
Compound of Example 75
Compound of Example 76
Compound of Example 77
Compound of Example 79
Compound of Example 80
Compound of Example 82
Compound of Example 83
Compound of Example 84
Compound of Example 86
Compound of Example 87
Compound of Example 89
Compound of Example 90
Compound of Example 92
Compound of Example 93
Compound of Example 94
Compound of Example 95
Compound of Example 96
Compound of Example 98
Compound of Example 99
Compound of Example 101
Compound of Example 102
Compound of Example 103
Compound of Example 104
Compound of Example 105
Compound of Example 106
Compound of Example 107
Compound of Example 108
Compound of Example 109
Compound of Example 110
Compound of Example 111
Compound of Example 112
Compounds of Example 113 to Example 245

INDUSTRIAL APPLICABILITY

The compounds (I) or their salts of the invention have an excellent somatostatin receptor function-regulating effect, and are not toxic. Therefore, they are useful for safe medicines for preventing and treating the somatostatin receptor function-regulating effect-associated disorders.

The invention claimed is:

1. A Compound of the following formula, or a salt thereof:

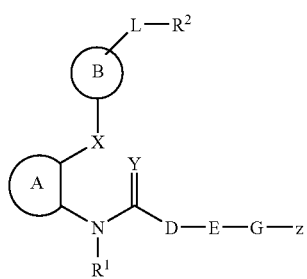

(I)

wherein Ring A represents an optionally-substituted benzene ring;

Ring B represents an optionally-substituted benzene or cycloalkane ring;

Z represents an optionally-substituted cyclic hydrocarbon group or an optionally-substituted heterocyclic group;

$R^1$ represents a hydrogen atom, an optionally-substituted hydrocarbon group, or an acyl group;

$R^2$ represents an optionally-substituted amino group;

D is an optionally substituted $C_{1-6}$ alkylene group;

E represents —CON($R^a$)—
   wherein $R^a$ represents a hydrogen atom or an optionally-substituted $C_{1-6}$ alkyl group;

G represents an optionally substituted $C_{1-6}$ alkylene group;

L represents an alkylene group optionally having from 1 to 5 substituents selected from;
   (i) a $C_{1-6}$ alkyl group,
   (ii) a halogeno-$C_{1-6}$ alkyl group,
   (iii) a phenyl group,
   (iv) a benzyl group,
   (v) an optionally-substituted amino group,
   (vi) an optionally-substituted hydroxy group, and
   (vii) a carbamoyl or thiocarbamoyl group optionally substituted by:
      <1> a $C_{1-6}$ alkyl group,
      <2> an optionally-substituted phenyl group, or
      <3> an optionally-substituted heterocyclic group;

X represents an oxygen atom or an optionally-oxidized sulfur atom; and

Y represents two hydrogen atoms.

2. A Compound as claimed in claim 1, wherein L is an alkylene group optionally substituted by a $C_{1-6}$ alkyl group.

3. A Compound as claimed in claim 1, wherein L is a $C_{1-6}$ alkylene group.

4. A Compound as claimed in claim 1, wherein $R^2$ is (1) an unsubstituted amino group, or (2) an amino group optionally having one or two substituents selected from (i) a benzyl group, (ii) a $C_{1-6}$ alkyl group optionally substituted by an amino or phenyl group, (iii) a (mono- or di-$C_{1-6}$ alkyl)-carbamoyl or -thiocarbamoyl group, (iv) a $C_{1-6}$ alkoxy-carbonyl group, (v) a $C_{1-6}$ alkyl-sulfonyl group, (vi) a piperidylcarbonyl group, and (vii) a $C_{1-6}$ alkyl-carbonyl group optionally substituted by a halogen atom or an amino group.

5. A Compound as claimed in claim 1, wherein $R^2$ is an unsubstituted amino group.

6. A Compound as claimed in claim 1, wherein B is an optionally-substituted benzene ring.

7. A Compound as claimed in claim 1, wherein X is an oxygen atom.

8. A Compound as claimed in claim 1, wherein $R^1$ is an acyl group.

9. A Compound of the following formula, or a salt thereof

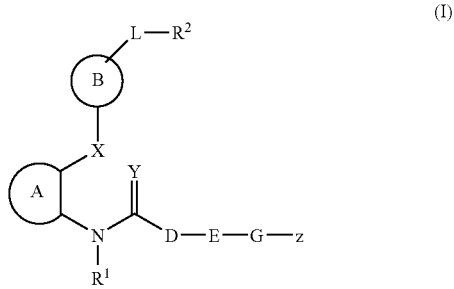

(I)

wherein Ring A is an optionally-substituted benzene ring;
Ring B is a benzene or cyclohexane ring optionally substituted by a $C_{1-6}$ alkoxy group;
Z is a $C_{6-14}$ aryl, $C_{3-10}$ cycloalkyl, piperidyl, thienyl, furyl, pyridyl, thiazolyl, indanyl or indolyl group optionally having from 1 to 3 substituents selected from a halogen atom, a formyl group, a halogeno-$C_{1-6}$ alkyl group, a $C_{1-6}$ alkoxy group, a $C_{1-6}$ alkyl-carbonyl group, an oxo group and a pyrrolidinyl group;
D is a $C_{1-6}$ alkylene group;
G is a $C_{1-6}$ alkylene group optionally having a phenylene group and optionally substituted by a phenyl group;
$R^1$ is (a) a hydrogen atom, (b) a $C_{1-6}$ alkyl, $C_{2-6}$ alkenyl, $C_{6-14}$ aryl or $C_{7-14}$ aralkyl group optionally substituted by substituent(s) selected from
  (1) a halogen atom,
  (2) a nitro group,
  (3) an amino group optionally substituted by one or two substituents selected from a $C_{1-6}$ alkyl-carbonyl group, a $C_{6-14}$ aryl-carbonyl group, a $C_{1-6}$ alkyl group, a $C_{1-6}$ alkyloxy-carbonyl group, a $C_{7-14}$ aralkyloxy-carbonyl group, a $C_{1-6}$ alkyl-sulfonyl group and a $C_{6-14}$ aryl-sulfonyl group,
  (4) (i) a $C_{1-6}$ alkyl group optionally substituted by a hydroxy group, a $C_{1-6}$ alkyl-carbonyl group, a $C_{6-14}$ aryl-carbonyl group, a carboxyl group or a $C_{1-6}$ alkoxy-carbonyl group, (ii) a phenyl group optionally substituted by a hydroxy group, (iii) a benzoyl group, or (iv) a hydroxy group optionally substituted by a mono- or di-$C_{1-6}$ alkylamino-carbonyl group,
  (5) a $C_{3-6}$ cycloalkyl group,
  (6) a phenyl group optionally substituted by a hydroxy group or a halogeno-$C_{1-6}$ alkyl group, and
  (7) a thienyl group, a furyl group, a thiazolyl group, an indanyl group, an indolyl or a benzyloxycarbonylpiperidyl group, or (c) an acyl group;
$R^2$ is (1) an unsubstituted amino group, or (2) an amino group optionally having one or two substituents selected from
  (i) a benzyl group,
  (ii) a $C_{1-6}$ alkyl group optionally substituted by an amino or phenyl group,
  (iii) a mono- or di-$C_{1-6}$ alkyl-carbamoyl or -thiocarbamoyl group,
  (iv) a $C_{1-6}$ alkoxy-carbonyl group,
  (v) a $C_{1-6}$ alkyl-sulfonyl group,
  (vi) a piperidylcarbonyl group, and
  (vii) a $C_{1-6}$ alkyl-carbonyl group optionally substituted by a halogen atom or an amino group;
X represents an oxygen atom or an optionally-oxidized sulfur atom; and
Y represents two hydrogen atoms;
E is —CON($R^a$)—
  wherein $R^a$ is a hydrogen atom or a $C_{1-6}$ alkyl group; and
L is a $C_{1-6}$ alkylene group optionally substituted by a $C_{1-6}$ alkyl group.

10. A Compound as claimed in claim 1, wherein Z is a phenyl group optionally substituted by a halogen atom; D is a $C_{1-6}$ alkylene group; G is a $C_{1-6}$ alkylene group; $R^1$ is (a) a $C_{1-6}$ alkyl or $C_{7-14}$ aralkyl group optionally substituted by substituent(s) selected from (1) a hydroxy group, (2) a phenyl group, (3) a thienyl, furyl, thiazolyl, indanyl, indolyl or benzyloxycarbonylpiperidyl group, and (4) an amino group optionally substituted by a $C_{1-6}$ alkyl-carbonyl, $C_{6-14}$ aryl-carbonyl, $C_{1-6}$ alkyl-sulfonyl or $C_{6-14}$ aryl-sulfonyl group, or (b) an acyl group; $R^2$ is an unsubstituted amino group; L is a $C_{1-6}$ alkylene group.

11. A method for producing a compound according to claim 1, or a salt thereof, which comprises reacting a compound of a formula (IIa):

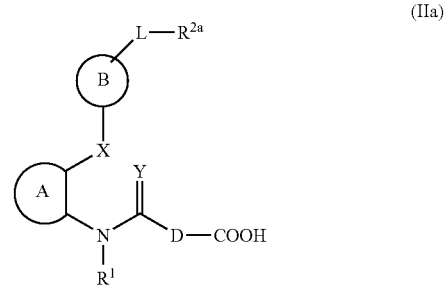

(IIa)

wherein $R^{2a}$ represents an optionally-protected, optionally-substituted amino group; and the other symbols A, B, X, Y, L, $R^1$ and D have the same meanings as in claim 1, or its salt with a compound of a formula (III):

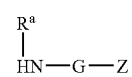

(III)

wherein the symbols G, Z and $R^a$ have the same meanings as in claim 1, or its salt to give a compound of a formula (Ia-a):

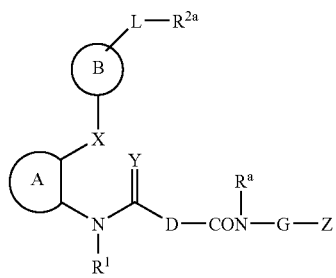

(Ia-a)

wherein the symbols A, B, X, Y, L, D, G, Z, $R^1$, $R^{2a}$ and $R^a$ have the same meanings as, in claim 1, or its salt, optionally followed by de-protecting it.

12. A pharmaceutical composition comprising:
a compound of the following formula, or a salt thereof:

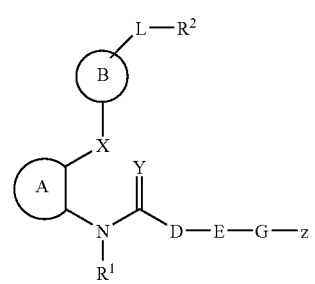

(I)

wherein Ring A represents an optionally-substituted benzene ring;
Ring B represents an optionally-substituted benzene or cycloalkane ring;
Z represents an optionally-substituted; cyclic hydrocarbon group or an optionally substituted heterocyclic group;
$R^1$ represents a hydrogen atom, an optionally-substituted hydrocarbon group, or an acyl group;
$R^2$ represents an optionally-substituted amino group;
D is an optionally substituted $C_{1-6}$ alkylene group;
E represents —CON($R^a$)—
  wherein $R^a$ represents a hydrogen atom or an optionally-substituted $C_{1-6}$ alkyl group;
G represents an optionally substituted $C_{1-6}$ alkylene group;
L represents an alkylene group optionally having from 1 to 5 substituents selected from;
  (i) a $C_{1-6}$ alkyl group,
  (ii) a halogeno-$C_{1-6}$ alkyl group,
  (iii) a phenyl group,
  (iv) a benzyl group,
  (v) an optionally-substituted amino group,
  (vi) an optionally-substituted hydroxy group, and
  (vii) a carbamoyl or thiocarbamoyl group optionally substituted by:
    <1> a $C_{1-6}$ alkyl group,
    <2> an optionally-substituted phenyl group, or
    <3> an optionally-substituted heterocyclic group;
X represents an oxygen atom or an optionally-oxidized sulfur atom; and
Y represents two hydrogen atoms;
and a pharmaceutically acceptable carrier.

13. A method for treating diabetes comprising administering a pharmaceutically effective amount of a compound of the following formula or a salt thereof

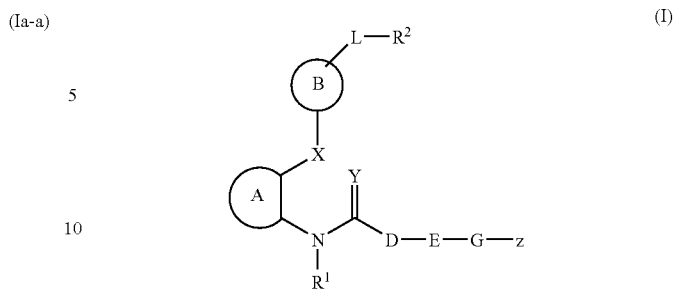

(I)

wherein Ring A represents an optionally-substituted benzene ring;
Ring B represents an optionally-substituted benzene or cycloalkane ring;
Z represents an optionally-substituted; cyclic hydrocarbon group or an optionally substituted heterocyclic group;
$R^1$ represents a hydrogen atom, an optionally-substituted hydrocarbon group, or an acyl group;
$R^2$ represents an optionally-substituted amino group;
D is an optionally substituted $C_{1-6}$ alkylene group;
E represents —CON($R^a$)—
  wherein $R^a$ represents a hydrogen atom or an optionally-substituted $C_{1-6}$ alkyl group;
G represents an optionally substituted $C_{1-6}$ alkylene group;
L represents an alkylene group optionally having from 1 to 5 substituents selected from;
  (i) a $C_{1-6}$ alkyl group,
  (ii) a halogeno-$C_{1-6}$ alkyl group,
  (iii) a phenyl group,
  (iv) a benzyl group,
  (v) an optionally-substituted amino group,
  (vi) an optionally-substituted hydroxy group, and
  (vii) a carbamoyl or thiocarbamoyl group optionally substituted by:
    <1> a $C_{1-6}$ alkyl group,
    <2> an optionally-substituted phenyl group, or
    <3> an optionally-substituted heterocyclic, group;
X represents an oxygen atom or an optionally-oxidized sulfur atom; and
Y represents two hydrogen atoms;
to a mammal in need thereof.

14. A method for treating obesity comprising administering a pharmaceutically effective amount of a compound of the following formula or a salt thereof

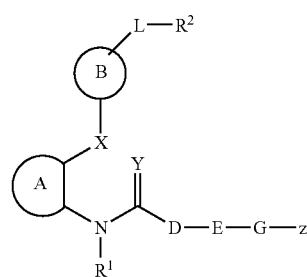

(I)

wherein Ring A represents an optionally-substituted benzene ring;

Ring B represents an optionally-substituted benzene or cycloalkane ring;

Z represents an optionally-substituted; cyclic hydrocarbon group or an optionally substituted heterocyclic group;

$R^1$ represents a hydrogen atom, an optionally-substituted hydrocarbon group, or an acyl group;

$R^2$ represents an optionally-substituted amino group;

D is an optionally substituted $C_{1-6}$ alkylene group;

E represents —CON($R^a$)—
  wherein $R^a$ represents a hydrogen atom or an optionally-substituted $C_{1-6}$ alkyl group;

G represents an optionally substituted $C_{1-6}$ alkylene group;

L represents an alkylene group optionally having from 1 to 5 substituents selected from;
  (i) a $C_{1-6}$ alkyl group,
  (ii) a halogeno-$C_{1-6}$ alkyl group,
  (iii) a phenyl group,
  (iv) a benzyl group,
  (v) an optionally-substituted amino group,
  (vi) an optionally-substituted hydroxy group, and
  (vii) a carbamoyl or thiocarbamoyl group optionally substituted by:
    <1> a $C_{1-6}$ alkyl group,
    <2> an optionally-substituted phenyl group, or
    <3> an optionally-substituted heterocyclic, group;

X represents an oxygen atom or an optionally-oxidized sulfur atom; and

Y represents two hydrogen atoms;

to a mammal in need thereof.

15. A compound of the following formula, or a salt thereof:

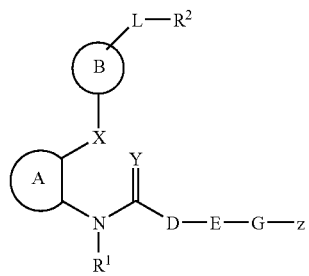

(I)

wherein Ring A represents a benzene ring substituted with halogen;

Ring B represents a benzene or cycloalkane ring;

Z represents a halogenated cyclic hydrocarbon group;

$R^1$ represents an acyl group substituted with an optionally substituted hydrocarbon group;

$R^2$ represents an optionally-substituted amino group;

D is methylene, ethylene, propylene or butylene;

E represents —CON($R^a$)—
  wherein $R^a$ represents a hydrogen atom;

G is methylene or ethylene;

L is methylene or ethylene;

X represents an oxygen atom or a sulfur atom; and

Y represents two hydrogen atoms.

16. N-(2-fluorobenzyl)-4-[N'-[2-(3-aminomethylphenoxy)-4-chlorophenyl]-N'-(4-phenylbenzoyl)]aminobutylamide or a salt thereof.

17. A method for treating diabetes comprising administering a pharmaceutically effective amount of N-(2-fluorobenzyl)-4-[N'-[2-(3-aminomethylphenoxy)-4-chlorophenyl]-N'-(4-phenylbenzoyl)]aminobutylamide or a salt thereof to a mammal in need thereof.

18. A method for treating obesity comprising administering a pharmaceutically effective amount of N-(2-fluorobenzyl)-4-[N'-[2-(3-aminomethylphenoxy)-4-chlorophenyl]-N'-(4-phenylbenzoyl)]aminobutylamide or a salt thereof to a mammal in need thereof.

* * * * *

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
ggtcgacctc agctaggatg ttccccaatg                             30

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
ggtcgacccg ggctcagagc gtcgtgat                               28

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
ggtcgacacc atggacatgg cggatgag                               28

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
ggtcgacagt tcagatactg gtttgg                                 26

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
ggtcgacctc aaccatggac atgcttcatc                             30

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
ggtcgacttt ccccaggccc ctacaggta                              29

<210> SEQ ID NO 7
<211> LENGTH: 28

```
-continued

<212> TYPE: DNA
<213> ORGANISM: Artificial Sequence
<220> FEATURE:
<223> OTHER INFORMATION: primer

<400> SEQUENCE: 7
ggctcgagtc accatgagcg cccctcg                                              28

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
gggctcgagc tcctcagaag gtggtgg                                              27

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
ggtcgaccac catggagccc ctgttccc                                             28

<210> SEQ ID NO 10
<211> LENGTH: 26
<212> TYPE: DNA
<213> ORGANISM: Artificial Sequence
<220> FEATURE:
<223> OTHER INFORMATION: primer

<400> SEQUENCE: 10
ccgtcgacac tctcacagct tgctgg                                               26
```